US012268579B2

(12) United States Patent
LaVon et al.

(10) Patent No.: US 12,268,579 B2
(45) Date of Patent: Apr. 8, 2025

(54) BEAMED ELASTOMERIC LAMINATE PERFORMANCE AND ZONES

(71) Applicant: The Procter & Gamble Company, Cincinnati, OH (US)

(72) Inventors: Gary D. LaVon, Liberty Township, OH (US); Bret D. Seitz, West Chester, OH (US); Kaoru Ishihara, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1067 days.

(21) Appl. No.: 17/194,371

(22) Filed: Mar. 8, 2021

(65) Prior Publication Data

US 2021/0282979 A1    Sep. 16, 2021

Related U.S. Application Data

(60) Provisional application No. 62/989,059, filed on Mar. 13, 2020.

(51) Int. Cl.
*A61F 13/15* (2006.01)
*A61F 13/49* (2006.01)
(Continued)

(52) U.S. Cl.
CPC .. *A61F 13/15699* (2013.01); *A61F 13/49012* (2013.01); *A61F 13/4963* (2013.01); *A61F 13/53* (2013.01); *A61F 2013/1591* (2013.01)

(58) Field of Classification Search
CPC .......... A61F 13/00; A61F 13/10; A61F 13/15; A61F 13/156; A61F 13/156; A61F 13/15601; A61F 13/1569; A61F 13/15699; A61F 13/40; A61F 13/49; A61F 13/49; A61F 13/4901; A61F 13/49012;
(Continued)

(56) References Cited

U.S. PATENT DOCUMENTS

| 3,113,225 | A | 12/1963 | Kleesattel et al. |
| 3,508,722 | A | 4/1970 | Kohl |

(Continued)

FOREIGN PATENT DOCUMENTS

| CA | 2158790 | 3/1996 |
| CN | 1276196 | 6/1999 |

(Continued)

OTHER PUBLICATIONS

3D Nonwovens Developments for textured nonwovens; Detlef Frey; http://web.archive.org/web/20170919080326/https://www.reicofil.com/en/pages/3d_nonwovens, Sep. 19, 2017.
(Continued)

*Primary Examiner* — Michele Kidwell
(74) *Attorney, Agent, or Firm* — Charles R. Matson

(57) ABSTRACT

Elastomeric laminates of the present disclosure may comprise closely spaced (e.g., Average-Strand-Spacing less than 4 mm), fine elastomeric strands (Average-Dtex less than 400), and laminates may be deformed via MD activation and/or aperturing. Further, the laminates of the present disclosure may comprise elastomeric strands having different polymer compositions. The laminates of the present disclosure may be used for disposable absorbent article components (including pant belts).

10 Claims, 67 Drawing Sheets

(51) Int. Cl.
*A61F 13/496* (2006.01)
*A61F 13/53* (2006.01)

(58) Field of Classification Search
CPC .......... A61F 13/49015; A61F 13/49017; A61F 13/49019; A61F 13/4902; B29C 65/00; B29C 65/40; B29C 65/48; B29C 66/00; B29C 66/30; B29C 66/34; B29C 66/344; B29C 66/80; B29C 66/83; B29C 66/834; B29C 66/8341; B29C 66/83411; B32B 5/00; B32B 5/04; D04H 3/00; D04H 3/10; D04H 3/12
See application file for complete search history.

(56) References Cited

U.S. PATENT DOCUMENTS

| | | |
|---|---|---|
| 3,562,041 A | 2/1971 | Robertson |
| 3,575,782 A | 4/1971 | Hansen |
| 3,733,238 A | 5/1973 | Long et al. |
| 3,860,003 A | 1/1975 | Buell |
| 4,333,979 A | 6/1982 | Sciaraffa et al. |
| 4,525,905 A | 7/1985 | Bogucki-Land |
| 4,610,678 A | 9/1986 | Weisman et al. |
| 4,640,859 A | 2/1987 | Hansen et al. |
| 4,657,539 A | 4/1987 | Hasse |
| 4,673,402 A | 6/1987 | Weisman et al. |
| 4,695,278 A | 9/1987 | Lawson |
| 4,704,115 A | 11/1987 | Buell |
| 4,741,941 A | 5/1988 | Englebert et al. |
| 4,795,454 A | 1/1989 | Dragoo |
| 4,834,735 A | 5/1989 | Alemany et al. |
| 4,854,984 A | 8/1989 | Ball et al. |
| 4,888,231 A | 12/1989 | Angstadt |
| 4,909,803 A | 3/1990 | Aziz et al. |
| 4,940,464 A | 7/1990 | Van Gompel et al. |
| 4,984,584 A | 1/1991 | Hansen et al. |
| 5,003,676 A | 4/1991 | McFalls |
| 5,060,881 A | 10/1991 | Bogucki-Land |
| 5,092,861 A | 3/1992 | Nomura et al. |
| 5,110,403 A | 5/1992 | Ehlert |
| 5,167,897 A | 12/1992 | Weber et al. |
| 5,246,433 A | 9/1993 | Hasse et al. |
| 5,334,289 A | 8/1994 | Trokhan et al. |
| 5,342,341 A | 8/1994 | Igaue et al. |
| 5,360,420 A | 11/1994 | Cook et al. |
| 5,393,360 A | 2/1995 | Bridges et al. |
| 5,413,849 A | 5/1995 | Austin et al. |
| 5,514,523 A | 5/1996 | Trokhan et al. |
| 5,531,729 A | 7/1996 | Coles et al. |
| 5,562,646 A | 10/1996 | Goldman et al. |
| 5,569,234 A | 10/1996 | Buell et al. |
| 5,575,874 A | 11/1996 | Griesbach, III et al. |
| 5,599,335 A | 2/1997 | Goldman et al. |
| 5,599,420 A | 2/1997 | Yeo et al. |
| 5,628,097 A | 5/1997 | Benson et al. |
| 5,643,588 A | 7/1997 | Roe et al. |
| 5,643,653 A | 7/1997 | Griesbach, III et al. |
| 5,669,894 A | 9/1997 | Goldman et al. |
| 5,674,216 A | 10/1997 | Buell et al. |
| 5,702,551 A | 12/1997 | Huber et al. |
| 5,775,380 A | 7/1998 | Roelstraete et al. |
| 5,858,504 A | 1/1999 | Steven |
| 5,887,322 A | 3/1999 | Hartzheim et al. |
| 5,895,623 A | 4/1999 | Trokhan et al. |
| 5,897,545 A | 4/1999 | Kline et al. |
| 5,916,661 A | 6/1999 | Benson et al. |
| 5,957,908 A | 9/1999 | Kline et al. |
| 5,964,973 A | 10/1999 | Heath et al. |
| 5,968,025 A | 10/1999 | Roe et al. |
| 6,036,796 A | 3/2000 | Halbert et al. |
| 6,043,168 A | 3/2000 | Colman et al. |
| 6,107,537 A | 8/2000 | Elder et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson et al. |
| 6,139,941 A | 10/2000 | Jankevics et al. |
| 6,153,209 A | 11/2000 | Vega et al. |
| 6,248,195 B1 | 6/2001 | Schmitz |
| 6,291,039 B1 | 9/2001 | Combe et al. |
| 6,319,239 B1 | 11/2001 | Daniels et al. |
| 6,361,638 B2 | 3/2002 | Takai et al. |
| 6,383,431 B1 | 5/2002 | Dobrin et al. |
| 6,395,957 B1 | 5/2002 | Chen et al. |
| 6,410,129 B2 | 6/2002 | Zhang et al. |
| 6,426,444 B2 | 7/2002 | Roe et al. |
| 6,508,641 B1 | 1/2003 | Kubik |
| 6,545,197 B1 | 4/2003 | Muller et al. |
| 6,554,815 B1 | 4/2003 | Umebayashi |
| 6,586,652 B1 | 7/2003 | Roe et al. |
| 6,617,016 B2 | 9/2003 | Zhang et al. |
| 6,627,787 B1 | 9/2003 | Roe et al. |
| 6,632,504 B1 | 10/2003 | Gillespie et al. |
| 6,645,330 B2 | 11/2003 | Pargass et al. |
| 6,673,418 B1 | 1/2004 | DeOlivera et al. |
| 6,676,054 B2 | 1/2004 | Heaney et al. |
| 6,790,798 B1 | 9/2004 | Suzuki et al. |
| 6,821,301 B2 | 11/2004 | Azuse et al. |
| 6,825,393 B2 | 11/2004 | Roe et al. |
| 6,861,571 B1 | 3/2005 | Roe et al. |
| 7,008,685 B2 | 3/2006 | Groitzsch et al. |
| 7,118,558 B2 | 10/2006 | Wu et al. |
| 7,465,367 B2 | 12/2008 | Day |
| 7,569,039 B2 | 8/2009 | Matsuda et al. |
| 7,582,348 B2 | 9/2009 | Ando et al. |
| 7,642,398 B2 | 1/2010 | Järpenberg et al. |
| 7,708,849 B2 | 5/2010 | McCabe |
| 7,777,094 B2 | 8/2010 | Mori et al. |
| 7,861,756 B2 | 1/2011 | Jenquin et al. |
| 7,878,447 B2 | 2/2011 | Hartzheim |
| 7,901,393 B2 | 3/2011 | Matsuda et al. |
| 7,905,446 B2 | 3/2011 | Hartzheim |
| 7,954,213 B2 | 6/2011 | Mizutani et al. |
| 8,093,161 B2 | 1/2012 | Bansal et al. |
| 8,143,177 B2 | 3/2012 | Noda et al. |
| 8,186,296 B2 | 5/2012 | Brown et al. |
| 8,226,625 B2 | 7/2012 | Turner et al. |
| 8,277,430 B2 | 10/2012 | Tabor et al. |
| 8,308,706 B2 | 11/2012 | Fukae |
| 8,377,554 B2 | 2/2013 | Martin et al. |
| 8,388,594 B2 | 3/2013 | Turner et al. |
| 8,440,043 B1 | 5/2013 | Schneider et al. |
| 8,551,608 B2 | 10/2013 | Kawakami et al. |
| 8,585,666 B2 | 11/2013 | Weisman et al. |
| 8,647,319 B2 | 2/2014 | Een et al. |
| 8,729,332 B2 | 5/2014 | Takahashi et al. |
| 8,778,127 B2 | 7/2014 | Schneider et al. |
| 8,853,108 B2 | 10/2014 | Ahoniemi et al. |
| 8,906,275 B2 | 12/2014 | Davis et al. |
| 8,939,957 B2 | 1/2015 | Raycheck et al. |
| 9,005,392 B2 | 4/2015 | Schneider et al. |
| 9,039,855 B2 | 5/2015 | Schneider et al. |
| 9,050,213 B2 | 6/2015 | LaVon et al. |
| 9,156,648 B2 | 10/2015 | Yamamoto |
| 9,168,182 B2 | 10/2015 | Hargett et al. |
| 9,198,804 B2 | 12/2015 | Nakamura et al. |
| 9,226,861 B2 | 1/2016 | LaVon et al. |
| 9,248,054 B2 | 2/2016 | Brown et al. |
| 9,265,672 B2 | 2/2016 | Brown et al. |
| 9,295,590 B2 | 3/2016 | Brown et al. |
| 9,370,775 B2 | 6/2016 | Harvey et al. |
| 9,440,043 B2 | 9/2016 | Arora et al. |
| 9,453,303 B2 | 9/2016 | Aberg et al. |
| 9,539,735 B2 | 1/2017 | Ferguson et al. |
| 9,732,454 B2 | 8/2017 | Davis et al. |
| 9,758,339 B2 | 9/2017 | Yanez, Jr. et al. |
| 9,795,520 B2 | 10/2017 | Kaneko et al. |
| 9,877,876 B2 | 1/2018 | Huang et al. |
| 10,190,244 B2 | 1/2019 | Ashraf et al. |
| 10,596,045 B2 | 3/2020 | Koshijima et al. |
| 10,792,194 B2 | 10/2020 | Hohm et al. |
| 11,000,420 B2 * | 5/2021 | LaVon .............. A61F 13/15593 |
| 11,147,718 B2 * | 10/2021 | LaVon .................... B29C 65/48 |

(56) References Cited

U.S. PATENT DOCUMENTS

| | | |
|---|---|---|
| 11,311,427 B2 | 4/2022 | Kline et al. |
| 11,547,613 B2 * | 1/2023 | Ashraf ............... A61F 13/4902 |
| 11,660,235 B2 | 5/2023 | Schneider et al. |
| 12,161,539 B2 * | 12/2024 | Ashraf ............. A61F 13/15764 |
| 2001/0030014 A1 | 10/2001 | Kwok |
| 2001/0056268 A1 | 12/2001 | Mizutani et al. |
| 2002/0046802 A1 | 4/2002 | Tachibana et al. |
| 2002/0072723 A1 | 6/2002 | Ronn et al. |
| 2002/0103469 A1 | 8/2002 | Chen et al. |
| 2002/0134067 A1 | 9/2002 | Heaney et al. |
| 2002/0153271 A1 | 10/2002 | McManus et al. |
| 2002/0177829 A1 | 11/2002 | Fell et al. |
| 2003/0044585 A1 | 3/2003 | Taylor et al. |
| 2003/0070780 A1 | 4/2003 | Chen et al. |
| 2003/0087056 A1 | 5/2003 | Ducker et al. |
| 2003/0093045 A1 | 5/2003 | Jensen |
| 2003/0119404 A1 | 6/2003 | Belau et al. |
| 2003/0125687 A1 | 7/2003 | Gubernick et al. |
| 2003/0144643 A1 | 7/2003 | Järpenberg et al. |
| 2003/0203162 A1 | 10/2003 | Christopher et al. |
| 2003/0233082 A1 | 12/2003 | Kline et al. |
| 2004/0006323 A1 | 1/2004 | Hall et al. |
| 2004/0059309 A1 | 3/2004 | Nortman |
| 2004/0097895 A1 | 5/2004 | Busam et al. |
| 2004/0122411 A1 | 6/2004 | Hancock-cooke |
| 2004/0133180 A1 | 7/2004 | Mori et al. |
| 2004/0158212 A1 | 8/2004 | Ponomarenko et al. |
| 2004/0158217 A1 | 8/2004 | Wu et al. |
| 2004/0219854 A1 | 11/2004 | Groitzsch et al. |
| 2004/0230171 A1 | 11/2004 | Ando et al. |
| 2005/0013975 A1 | 1/2005 | Brock et al. |
| 2005/0107764 A1 | 5/2005 | Matsuda et al. |
| 2005/0148971 A1 | 7/2005 | Kuroda et al. |
| 2005/0230037 A1 | 10/2005 | Jenquin et al. |
| 2006/0047260 A1 | 3/2006 | Ashton et al. |
| 2006/0069373 A1 | 3/2006 | Schlinz et al. |
| 2006/0087053 A1 | 4/2006 | O'Donnell et al. |
| 2006/0105075 A1 | 5/2006 | Otsubo |
| 2006/0189954 A1 | 8/2006 | Kudo et al. |
| 2006/0228969 A1 | 10/2006 | Erdman |
| 2006/0270302 A1 | 11/2006 | Ando et al. |
| 2007/0026753 A1 | 2/2007 | Neely et al. |
| 2007/0045143 A1 | 3/2007 | Clough et al. |
| 2007/0045144 A1 | 3/2007 | Wheeler et al. |
| 2007/0131335 A1 | 6/2007 | Zhou et al. |
| 2007/0141311 A1 | 6/2007 | Mleziva et al. |
| 2007/0179466 A1 | 8/2007 | Tremblay et al. |
| 2007/0218245 A1 | 9/2007 | Schneider et al. |
| 2008/0149292 A1 | 6/2008 | Scherb |
| 2008/0161768 A1 | 7/2008 | Baba et al. |
| 2008/0287897 A1 | 11/2008 | Guzman et al. |
| 2009/0177176 A1 | 7/2009 | Saito |
| 2009/0204093 A1 | 8/2009 | Vasic et al. |
| 2009/0312730 A1 | 12/2009 | LaVon et al. |
| 2010/0022151 A1 | 1/2010 | Malowaniec |
| 2010/0036346 A1 | 2/2010 | Hammons |
| 2010/0048072 A1 | 2/2010 | Kauschke |
| 2010/0075103 A1 | 3/2010 | Miyamoto |
| 2010/0076394 A1 | 3/2010 | Hayase et al. |
| 2010/0248575 A1 | 9/2010 | Malz |
| 2010/0307668 A1 | 12/2010 | Lange et al. |
| 2011/0092943 A1 | 4/2011 | Bishop et al. |
| 2011/0118689 A1 | 5/2011 | Een et al. |
| 2011/0120897 A1 | 5/2011 | Takahashi |
| 2011/0250378 A1 | 10/2011 | Eaton et al. |
| 2012/0004633 A1 | 1/2012 | Marcelo et al. |
| 2012/0015156 A1 | 1/2012 | Abrams |
| 2012/0061015 A1 | 3/2012 | LaVon et al. |
| 2012/0061016 A1 | 3/2012 | LaVon et al. |
| 2012/0095429 A1 | 4/2012 | Kobayashi et al. |
| 2012/0271267 A1 | 10/2012 | Love et al. |
| 2012/0277713 A1 | 11/2012 | Raycheck et al. |
| 2012/0323206 A1 | 12/2012 | McMorrow et al. |
| 2013/0032656 A1 | 2/2013 | Yamamoto |
| 2013/0072887 A1 | 3/2013 | LaVon et al. |
| 2013/0102982 A1 | 4/2013 | Nakano et al. |
| 2013/0112584 A1 | 5/2013 | Gaspari et al. |
| 2013/0139960 A1 | 6/2013 | Maruyama et al. |
| 2013/0171421 A1 | 7/2013 | Weisman et al. |
| 2013/0199696 A1 | 8/2013 | Schneider et al. |
| 2013/0199707 A1 | 8/2013 | Schneider |
| 2013/0211356 A1 | 8/2013 | Nishikawa et al. |
| 2013/0211363 A1 | 8/2013 | LaVon et al. |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0261589 A1 | 10/2013 | Fujkawa et al. |
| 2013/0306226 A1 | 11/2013 | Zink et al. |
| 2014/0000794 A1 | 1/2014 | Hamilton et al. |
| 2014/0005621 A1 | 1/2014 | Roe et al. |
| 2014/0018759 A1 | 1/2014 | Jayasinghe et al. |
| 2014/0041797 A1 | 2/2014 | Schneider |
| 2014/0107605 A1 | 4/2014 | Schroer, Jr. et al. |
| 2014/0127460 A1 | 5/2014 | Xu et al. |
| 2014/0148773 A1 | 5/2014 | Brown et al. |
| 2014/0234575 A1 | 8/2014 | Mitsuno et al. |
| 2014/0235127 A1 | 8/2014 | DeJesus et al. |
| 2014/0257231 A1 | 9/2014 | Wang et al. |
| 2014/0276517 A1 | 9/2014 | Chester et al. |
| 2014/0288521 A1 | 9/2014 | Wade et al. |
| 2014/0296815 A1 | 10/2014 | Takken et al. |
| 2014/0302286 A1 | 10/2014 | Okuda et al. |
| 2014/0305570 A1 | 10/2014 | Matsunaga et al. |
| 2014/0324009 A1 | 10/2014 | Lee et al. |
| 2014/0343525 A1 | 11/2014 | Roh et al. |
| 2014/0377506 A1 | 12/2014 | Eckstein et al. |
| 2014/0377513 A1 | 12/2014 | Galie et al. |
| 2015/0083309 A1 | 3/2015 | Long et al. |
| 2015/0126956 A1 | 5/2015 | Raycheck et al. |
| 2015/0136893 A1 | 5/2015 | Koskol |
| 2015/0164708 A1 | 6/2015 | Hashimoto et al. |
| 2015/0173967 A1 | 6/2015 | Kreuzer et al. |
| 2015/0230995 A1 | 8/2015 | Kaneko et al. |
| 2015/0245958 A1 | 9/2015 | Chmielewski et al. |
| 2015/0257941 A1 | 9/2015 | Eckstein et al. |
| 2015/0282999 A1 | 10/2015 | Arizti et al. |
| 2015/0320612 A1 | 11/2015 | Seitz et al. |
| 2015/0320613 A1 | 11/2015 | Seitz et al. |
| 2015/0320619 A1 | 11/2015 | Seitz et al. |
| 2015/0320620 A1 | 11/2015 | Seitz et al. |
| 2015/0320622 A1 | 11/2015 | Seitz et al. |
| 2015/0328056 A1 | 11/2015 | Een et al. |
| 2015/0351972 A1 | 12/2015 | Bing-Wo |
| 2016/0058624 A1 | 3/2016 | Hohm et al. |
| 2016/0058627 A1 | 3/2016 | Barnes et al. |
| 2016/0067119 A1 | 3/2016 | Weisman et al. |
| 2016/0100989 A1 | 4/2016 | Seitz et al. |
| 2016/0100997 A1 | 4/2016 | Seitz et al. |
| 2016/0106633 A1 | 4/2016 | Nagata et al. |
| 2016/0129661 A1 | 5/2016 | Arora et al. |
| 2016/0136009 A1 | 5/2016 | Weisman et al. |
| 2016/0228305 A1 | 8/2016 | Gualtieri et al. |
| 2016/0331600 A1 | 11/2016 | Polidori et al. |
| 2017/0000660 A1 | 1/2017 | Wade |
| 2017/0014281 A1 | 1/2017 | Xie et al. |
| 2017/0027774 A1 | 2/2017 | Ashraf et al. |
| 2017/0029993 A1 | 2/2017 | Ashraf et al. |
| 2017/0029994 A1 | 2/2017 | Ashraf et al. |
| 2017/0056256 A1 | 3/2017 | Smith et al. |
| 2017/0065461 A1 | 3/2017 | Schneider |
| 2017/0079852 A1 | 3/2017 | Fujima et al. |
| 2017/0119595 A1 | 5/2017 | Carla et al. |
| 2017/0191198 A1 | 7/2017 | Ashraf et al. |
| 2017/0258650 A1 | 9/2017 | Rosati et al. |
| 2017/0319403 A1 | 11/2017 | Bewick-Sonntag et al. |
| 2017/0348163 A1 | 12/2017 | Lakso et al. |
| 2018/0092784 A1 | 4/2018 | Wade et al. |
| 2018/0140473 A1 | 5/2018 | Koshijima et al. |
| 2018/0168874 A1 | 6/2018 | LaVon et al. |
| 2018/0168875 A1 | 6/2018 | LaVon et al. |
| 2018/0168876 A1 | 6/2018 | LaVon et al. |
| 2018/0168877 A1 | 6/2018 | Schneider et al. |

(56) References Cited

U.S. PATENT DOCUMENTS

| | | |
|---|---|---|
| 2018/0168878 A1 | 6/2018 | Schneider et al. |
| 2018/0168879 A1 | 6/2018 | Schneider et al. |
| 2018/0168880 A1 | 6/2018 | Schneider et al. |
| 2018/0168885 A1 | 6/2018 | Zink, II et al. |
| 2018/0168887 A1 | 6/2018 | LaVon et al. |
| 2018/0168888 A1 | 6/2018 | Zink, II et al. |
| 2018/0168889 A1 | 6/2018 | LaVon et al. |
| 2018/0168890 A1 | 6/2018 | LaVon et al. |
| 2018/0168891 A1 | 6/2018 | Wise et al. |
| 2018/0168892 A1 | 6/2018 | LaVon et al. |
| 2018/0168893 A1 | 6/2018 | Ashraf et al. |
| 2018/0169964 A1 | 6/2018 | Schneider et al. |
| 2018/0170026 A1 | 6/2018 | Schneider et al. |
| 2018/0170027 A1 | 6/2018 | Schneider et al. |
| 2018/0214318 A1 | 8/2018 | Ashraf et al. |
| 2018/0214321 A1 | 8/2018 | Ashraf et al. |
| 2018/0216269 A1 | 8/2018 | Ashraf et al. |
| 2018/0216270 A1 | 8/2018 | Ashraf et al. |
| 2018/0216271 A1 | 8/2018 | Ashraf et al. |
| 2018/0333311 A1 | 11/2018 | Maki et al. |
| 2019/0003079 A1 | 1/2019 | Ashraf et al. |
| 2019/0003080 A1 | 1/2019 | Ashraf et al. |
| 2019/0070041 A1 | 3/2019 | Schneider et al. |
| 2019/0070042 A1 | 3/2019 | LaVon et al. |
| 2019/0112737 A1 | 4/2019 | Ashraf et al. |
| 2019/0246196 A1 | 8/2019 | Han et al. |
| 2019/0254881 A1 | 8/2019 | Ishikawa et al. |
| 2019/0298586 A1 | 10/2019 | Ashraf et al. |
| 2019/0298587 A1 | 10/2019 | Ashraf et al. |
| 2019/0374392 A1 | 12/2019 | Ninomiya et al. |
| 2019/0374404 A1 | 12/2019 | Ninomiya et al. |
| 2020/0155370 A1 | 5/2020 | Ohtsubo |
| 2020/0155371 A1 | 5/2020 | Ohtsubo et al. |
| 2020/0206040 A1 | 7/2020 | Andrews et al. |
| 2020/0214901 A1 | 7/2020 | Andrews et al. |
| 2020/0298545 A1 | 9/2020 | Andrews et al. |
| 2023/0190540 A1 | 6/2023 | Barnes et al. |

FOREIGN PATENT DOCUMENTS

| | | | |
|---|---|---|---|
| CN | 1461634 A | | 12/2003 |
| CN | 1685099 | | 10/2005 |
| CN | 1937979 A | | 3/2007 |
| CN | 101746057 | | 6/2010 |
| CN | 105997351 | | 10/2016 |
| CN | 110035728 A | | 7/2019 |
| CN | 114392052 A | | 4/2022 |
| EP | 0989218 | | 3/2000 |
| EP | 1305248 | | 5/2003 |
| EP | 1452157 | | 9/2004 |
| EP | 1473148 | | 11/2004 |
| EP | 1393701 | | 7/2013 |
| EP | 3056176 | | 8/2016 |
| EP | 3092997 | | 8/2017 |
| EP | 3251642 | | 12/2017 |
| EP | 3257488 | | 12/2017 |
| EP | 3563817 A1 | | 11/2019 |
| JP | 3213543 A | | 9/1991 |
| JP | H 03213543 | | 9/1991 |
| JP | H 04030847 | | 2/1992 |
| JP | H 06254117 | | 9/1994 |
| JP | 8071107 A | | 3/1996 |
| JP | H 08071107 | | 3/1996 |
| JP | H 08132576 | | 5/1996 |
| JP | 2000026015 | | 1/2000 |
| JP | 2000160460 | | 6/2000 |
| JP | 3086141 B2 | | 9/2000 |
| JP | 2001276120 A | | 10/2001 |
| JP | 2002035029 | | 2/2002 |
| JP | 2002178428 | | 6/2002 |
| JP | 2002238934 A | | 8/2002 |
| JP | 2002248127 | | 9/2002 |
| JP | 2003521949 | | 7/2003 |
| JP | 2004081365 | | 3/2004 |
| JP | 2004229857 | | 8/2004 |
| JP | 2004237410 | | 8/2004 |
| JP | 2004254862 | | 9/2004 |
| JP | 2004298362 | | 10/2004 |
| JP | 2005320636 | | 11/2005 |
| JP | 2006149747 | | 6/2006 |
| JP | 2006149749 | | 6/2006 |
| JP | 2006204673 | | 12/2006 |
| JP | 2007190397 | | 8/2007 |
| JP | 2008029749 | | 2/2008 |
| JP | 2008055198 | | 3/2008 |
| JP | 2008104853 | | 5/2008 |
| JP | 2008105425 | | 5/2008 |
| JP | 2008154998 | | 5/2008 |
| JP | 2008148942 | | 7/2008 |
| JP | 2008179128 | | 8/2008 |
| JP | 2008194493 | | 8/2008 |
| JP | 2008229006 | | 10/2008 |
| JP | 2008229007 | | 10/2008 |
| JP | 2008253290 | | 10/2008 |
| JP | 2008260131 | | 10/2008 |
| JP | 2014188042 | | 10/2008 |
| JP | 2008264480 | | 11/2008 |
| JP | 2008272250 | | 11/2008 |
| JP | 2008272253 | | 11/2008 |
| JP | 2008296585 | | 12/2008 |
| JP | 2009000161 | | 1/2009 |
| JP | 2009039341 | | 2/2009 |
| JP | 2009056156 | | 3/2009 |
| JP | 2009106667 | | 5/2009 |
| JP | 2009143150 A | | 7/2009 |
| JP | 2009172231 | | 8/2009 |
| JP | 2009240804 | | 10/2009 |
| JP | 2009241607 | | 10/2009 |
| JP | 2010005918 A | | 1/2010 |
| JP | 2010131833 | | 6/2010 |
| JP | 2011015707 | | 1/2011 |
| JP | 2011111165 | | 6/2011 |
| JP | 2011178124 | | 9/2011 |
| JP | 2011225000 | | 11/2011 |
| JP | 2012050882 | | 3/2012 |
| JP | 2012050883 | | 3/2012 |
| JP | 2012115358 | | 6/2012 |
| JP | 2012521498 | | 9/2012 |
| JP | 5124187 | | 11/2012 |
| JP | 5124188 | | 11/2012 |
| JP | 2013138795 | | 7/2013 |
| JP | 2014111222 | | 6/2014 |
| JP | 2014097257 | | 10/2014 |
| JP | 2015510831 | | 4/2015 |
| JP | 2015521499 | | 7/2015 |
| JP | 2015171501 A | | 10/2015 |
| JP | 2016013687 | | 1/2016 |
| JP | 2016016536 | | 2/2016 |
| JP | 5942819 | | 6/2016 |
| JP | 2016193199 | | 11/2016 |
| JP | 6149635 | | 6/2017 |
| JP | 2020054741 A | | 4/2018 |
| JP | 2020054742 A | | 4/2018 |
| JP | 2020054744 A | | 4/2018 |
| JP | 2020054745 A | | 4/2018 |
| JP | 2019081304 | | 5/2019 |
| JP | 2019166804 | | 10/2019 |
| JP | 2019181807 | | 10/2019 |
| JP | 2022117131 A | | 8/2022 |
| WO | WO 20170105997 | | 3/1996 |
| WO | WO 9925296 | | 5/1999 |
| WO | 0035398 A1 | | 6/2000 |
| WO | WO 20030059603 | | 7/2003 |
| WO | WO 20080123348 | | 10/2008 |
| WO | 2011137962 A1 | | 11/2011 |
| WO | WO 20030015681 | | 6/2013 |
| WO | WO 20140084168 | | 6/2014 |
| WO | WO 20130084977 | | 11/2014 |
| WO | WO 20160056092 | | 4/2016 |
| WO | WO 20160056093 | | 4/2016 |
| WO | WO 20160063346 | | 4/2016 |
| WO | WO 20160067387 | | 5/2016 |
| WO | WO 20160071981 | | 5/2016 |
| WO | WO 20160075974 | | 5/2016 |

(56) References Cited

FOREIGN PATENT DOCUMENTS

| WO | WO 20160098416 | 6/2016 |
| WO | WO 20160104412 | 6/2016 |
| WO | WO 20160104422 | 6/2016 |
| WO | WO 20160158499 | 10/2016 |
| WO | WO 20160158746 | 10/2016 |
| WO | WO 20160208502 | 12/2016 |
| WO | WO 20160208513 | 12/2016 |
| WO | WO 20140196669 | 6/2017 |
| WO | WO 20180061288 | 4/2018 |
| WO | WO 20180084145 | 5/2018 |
| WO | WO 2018154680 A1 | 8/2018 |
| WO | WO 2018154682 A1 | 8/2018 |
| WO | WO 2018167836 A1 | 8/2018 |
| WO | 2018156817 A4 | 11/2018 |
| WO | WO 20190046363 | 3/2019 |
| WO | WO 20190111203 | 6/2019 |
| WO | WO 2019150802 A1 | 8/2019 |
| WO | WO 20200006996 | 1/2020 |

OTHER PUBLICATIONS

American Cancer Society—What Cancer Patients Their Families and Caregivers Need to Know About COVID 19—Is Impacting Our Patient Services.
ASTM—Standard Tables of Body Measurements for Adult Females Misses Figure Type Size Range 00-20.
ASTM—Standard Tables of Body Measurements for Children Infant Size—Preemie to 24 Months.
All Office Actions, U.S. Appl. No. 15/831,448.
All Office Actions, U.S. Appl. No. 15/831,464.
All Office Actions, U.S. Appl. No. 15/832,929.
All Office Actions, U.S. Appl. No. 15/833,057.
All Office Actions, U.S. Appl. No. 15/846,745.
All Office Actions, U.S. Appl. No. 15/838,405.
All Office Actions, U.S. Appl. No. 15/839,896.
All Office Actions, U.S. Appl. No. 15/846,382.
All Office Actions, U.S. Appl. No. 15/846,341.
All Office Actions, U.S. Appl. No. 15/846,360.
All Office Actions, U.S. Appl. No. 15/846,371.
All Office Actions, U.S. Appl. No. 15/846,391.
All Office Actions, U.S. Appl. No. 15/846,409.
All Office Actions, U.S. Appl. No. 15/846,433.
All Office Actions, U.S. Appl. No. 15/846,349.
All Office Actions, U.S. Appl. No. 16/445,986.
All Office Actions, U.S. Appl. No. 16/445,838.
All Office Actions, U.S. Appl. No. 16/117,579.
All Office Actions, U.S. Appl. No. 16/115,617.
15541 PCT Search Report and Written Opinion for PCT/US2021/021315 dated Jun. 25, 2021, 14 pages.

* cited by examiner

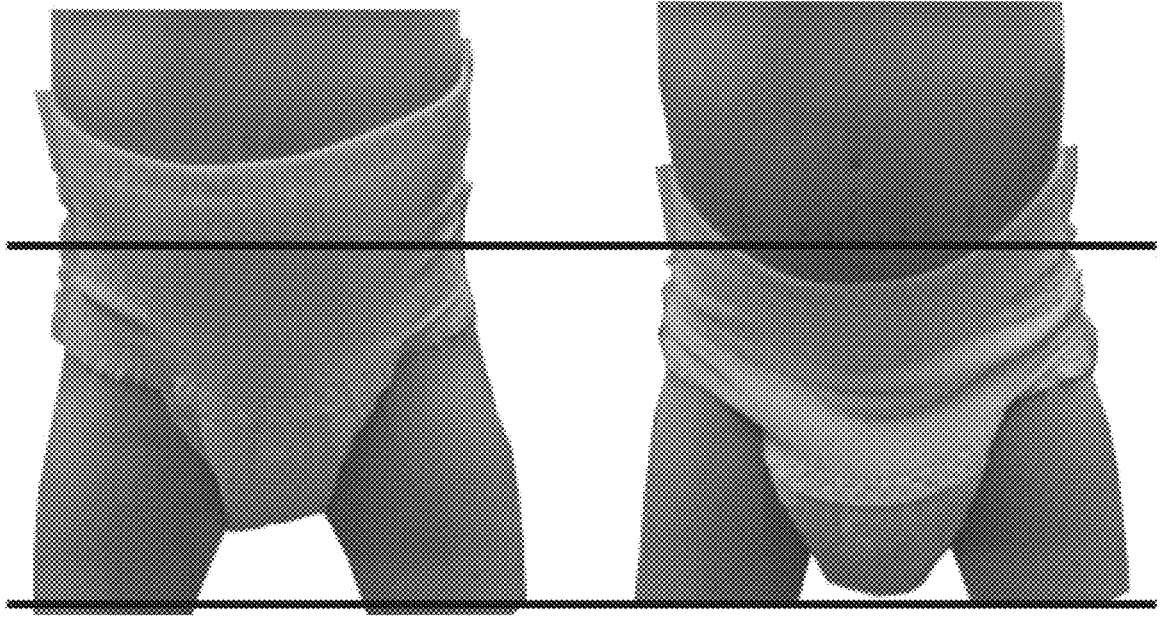
FIG. 5D    FIG. 5D´
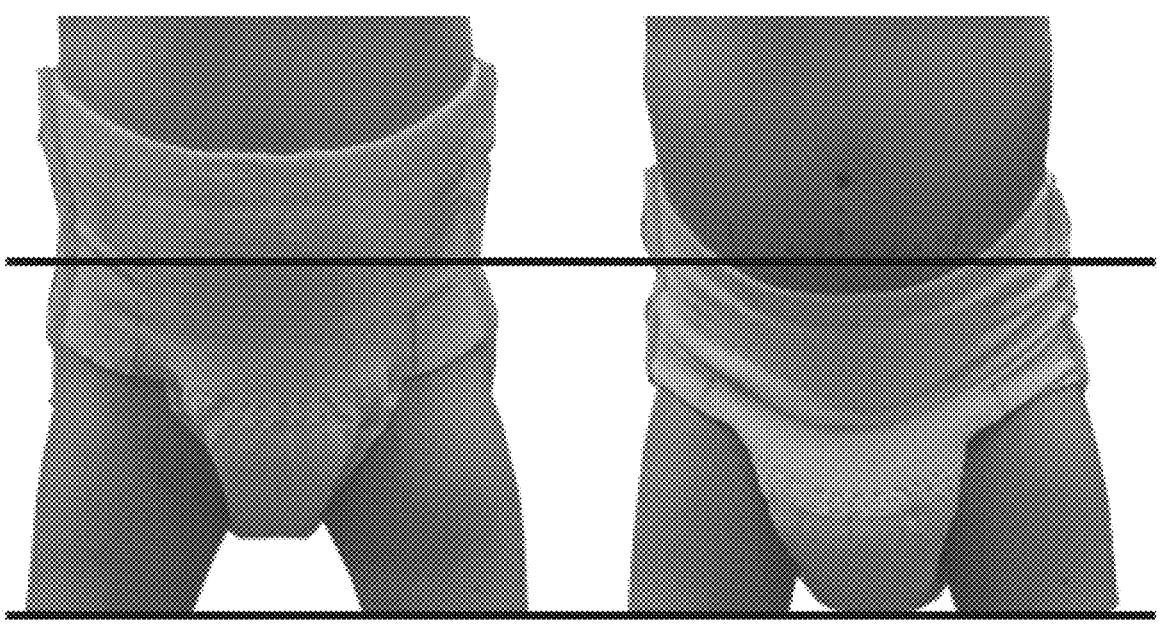
FIG. 5E    FIG. 5E´

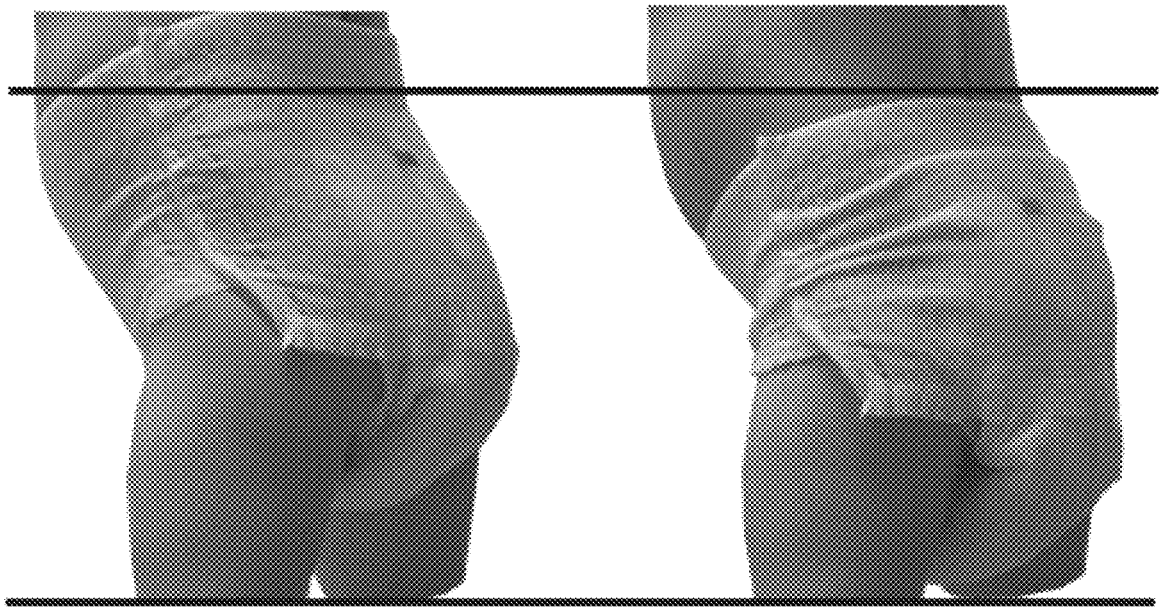
FIG. 5F          FIG. 5F´
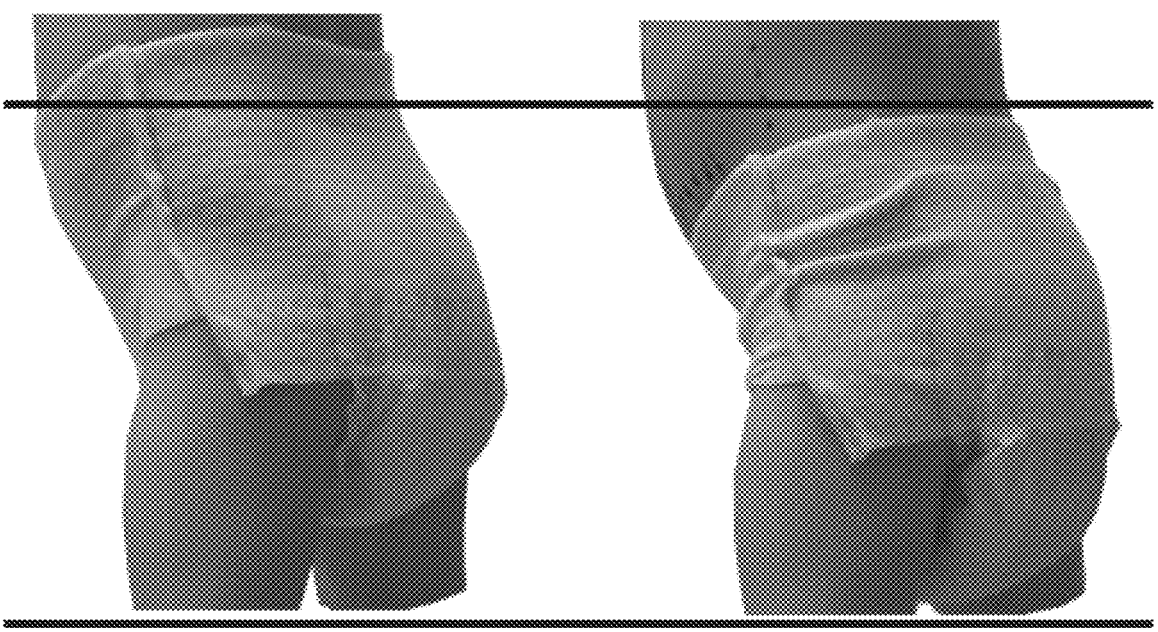
FIG. 5G          FIG. 5G´

FIG. 5J
FIG. 5J´
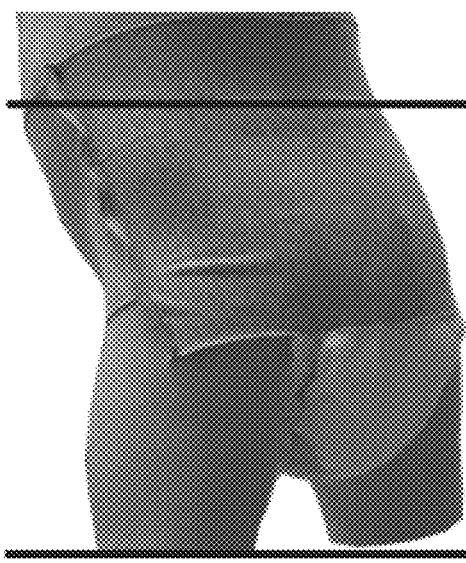
FIG. 5K
FIG. 5K´

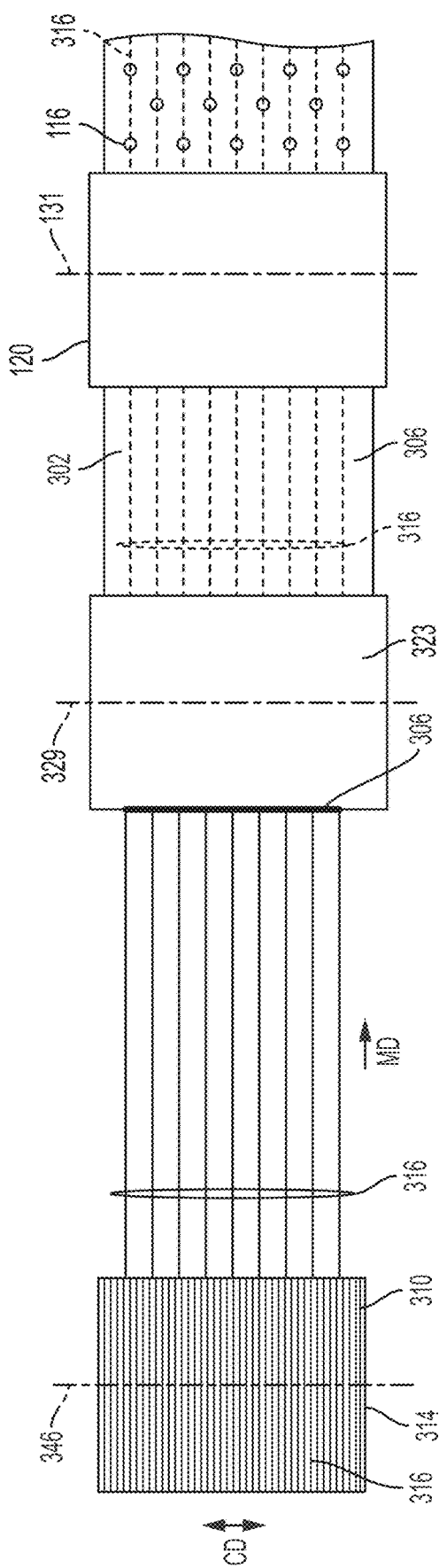

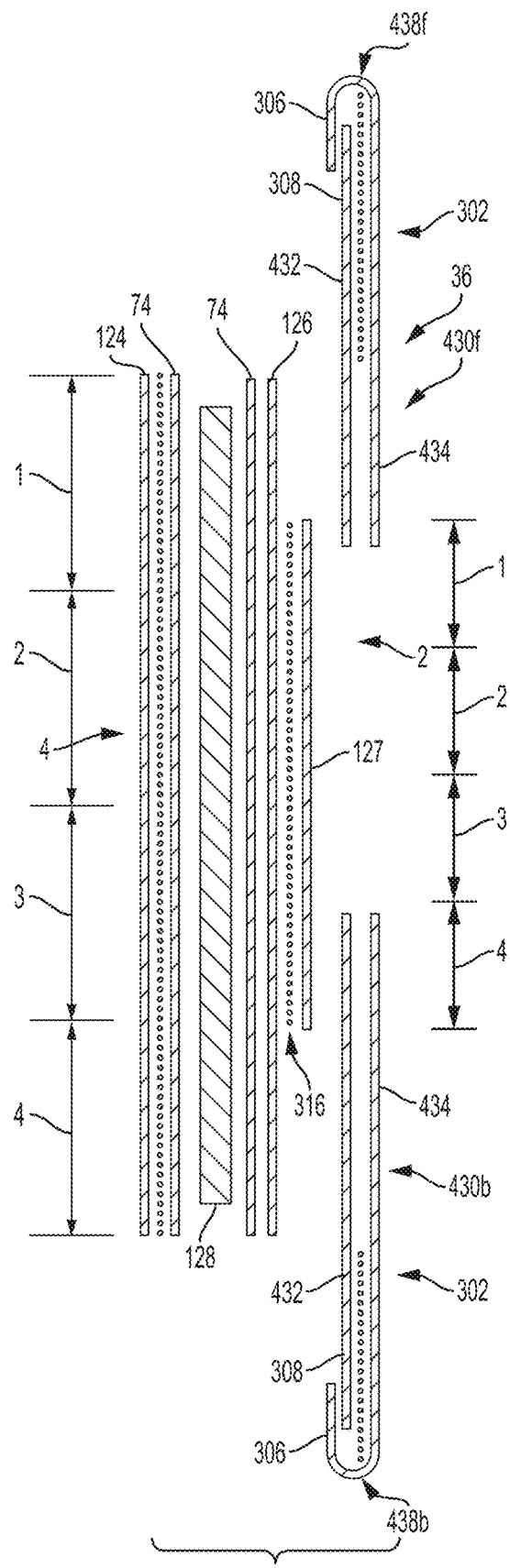
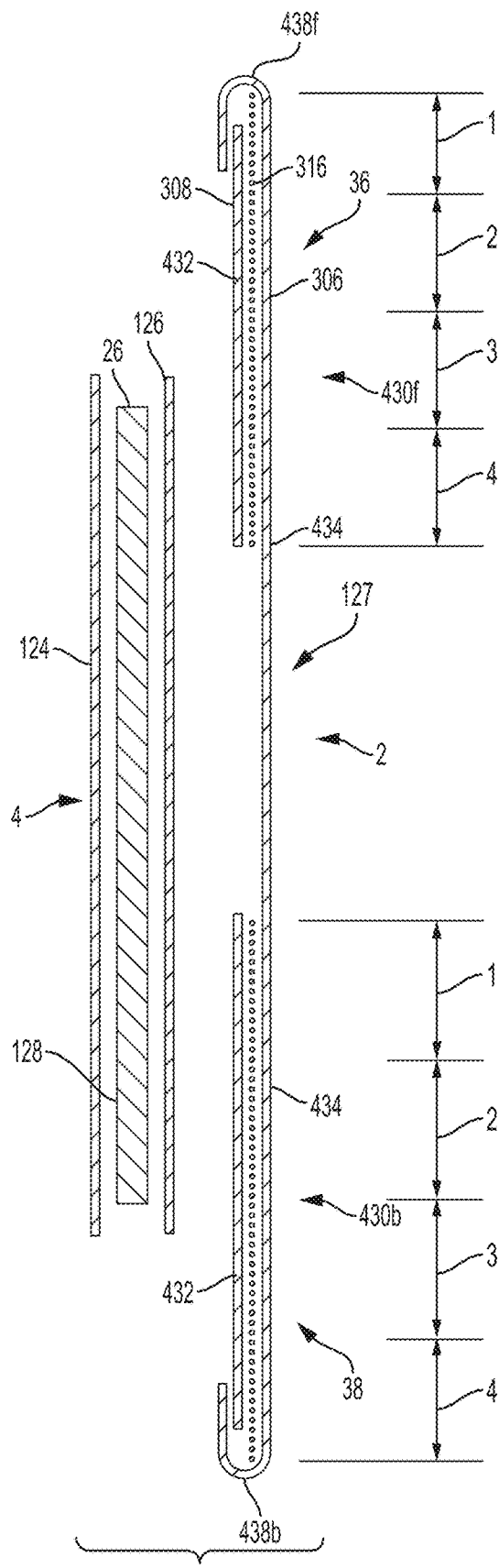
FIG. 12H
FIG. 12I

BEAMED ELASTOMERIC LAMINATE PERFORMANCE AND ZONES

CROSS REFERENCE TO RELATED APPLICATION

This application claims the benefit of U.S. Provisional Application No. 62/989,059, filed Mar. 13, 2020, which is incorporated by reference herein.

FIELD OF THE INVENTION

The present disclosure relates to absorbent articles, more particularly, to disposable absorbent articles comprising improved elastomeric laminates configured to perform in various components of the disposable absorbent articles.

BACKGROUND OF THE INVENTION

Traditional stranded elastomeric laminates as disclosed in the art are often used to make disposable pant belts. Because traditional stranded elastomeric laminates use larger elastic strands (e.g., Average-Dtex greater than 400) with larger spaces between the elastic strands (e.g., Average-Strand-Spacing greater than 4 mm) at higher pre-strains (e.g., Average-Pre-Strain greater than 200%) they have many undesirable performance parameters. Specifically, traditional laminates have higher than desired strand pressure (e.g., Pressure-Under-Strand greater than 1 psi) and modulus (e.g., Section-Modulus greater than 14 gf/mm) that result in poor sustained fit and red marking. Further, the force required to extend many belts made with traditional stranded elastomeric laminates can be much too high (e.g., Application-Force greater than 2,500 gf), making it difficult for caretakers and wearers to don the disposable pants.

To overcome many of these deficiencies, laminates utilizing closely spaced (e.g., Average-Strand-Spacing less than 4 mm), fine elastomeric strands (Average-Dtex less than 400), resulting in low strand pressure (Pressure-Under-Strand less than 1 psi) and modulus (Section-Modulus less than 10 gf/mm) may be used. While these laminates offer improvements over traditional stranded elastomeric laminates, it has been found that the modulus of zones or of the whole belt may be further improved through mechanical deformation of said zones or of the entire belt.

These new stranded elastomeric laminates comprising mechanical deformation disclosed herein provide even greater ease of application/donning without marking the wearer's skin because of the way they distribute force and these new stranded elastomeric laminates also fit as well as previously disclosed laminates, even when compared to laminates comprising closely spaced and fine elastomeric strands. This is the greatest surprise—that the new mechanically deformed stranded laminates can be easier to don, apply less pressure to the wearer's skin and still provide superior sustained fit, even when loaded with an insult.

Further, previous disclosed elastomeric laminates utilized zones. But, said zones created areas of high pressure. While the inventive laminates of the present disclosure may utilize zones, the zones of the inventive laminates have greater strain at a given stress and lower Laminate-Modulus which provide a unique set of performance factors not possible in the stranded laminates previously disclosed and utilized. And, for inventive laminates comprising multiple performance zones, the difference in performance (e.g., Laminate-Modulus and Strain-to-Modulus-Ratio) between higher Strain-to-Modulus-Ratio zones and lower Strain-to-Modulus-Ratio zones is further unique for the inventive laminates disclosed herein. The inventive laminates may also have multiple texture zones disclosed herein which may be formed in part by mechanical deformation of a first zone and lack of (or a different or a different intensity of) mechanical deformation in a second zone. Another benefit of the zones of the inventive laminates disclosed herein is that such zones help to make the disposable pant more textile garment-like and communicate comfortable fit or signal performance zones and a contoured fit. Overall, the elastomeric laminates of the present disclosure look and perform unlike any previously disclosed or marketed elastomeric laminates.

It is further disclosed herein that the inventive elastomeric laminates may alternatively or additionally comprise apertures in one or more layers or zones of the inventive elastomeric laminate. Still further, it is disclosed herein that the inventive elastomeric laminates may alternatively or additionally comprise strands having different polymer compositions. Each of these may contribute to creating zones or a whole component that exhibits the inventive properties disclosed herein.

One of several advantages to activating, aperturing, and/or using elastic strands comprising different polymer compositions is that a single beam of elastics may be used to make a laminate having multiple zones, even when a single beam is used and even when the elastics disposed on the beam have the same decitex, prestrain, and spacing.

Much of the focus of the present disclosure is directed toward disposable pants and pant belts, but please note that the new laminates of the present disclosure have many applications to disposable absorbent articles (e.g., taped diapers, pads, liners, etc.) and article components (e.g., topsheets, backsheets, cuffs, side panels, belts etc.).

Greater details of the design ambitions of the new stranded elastomeric laminates follow in the sections below.

SUMMARY OF THE INVENTION

In a first form, an elastomeric laminate of the present disclosure may comprise a plurality of elastic strands between first and second substrate layers joined by adhesive. The plurality of elastic strands may comprise an Average-Strand-Spacing from about 0.25 mm to about 4 mm and an Average-Dtex from about 10 to about 400. A first section of the elastomeric laminate may comprise the plurality of elastics and a mechanically deformed portion forming ridges and valleys, where the ridges and valleys run substantially perpendicular to the plurality of elastics. The first section of the elastomeric laminate may have a Laminate-Modulus from about 3 gf/mm to about 12 gf/mm, a Strain of greater than 110% at a Stress of 9.1 gf/mm, and a Strain-to-Modulus-Ratio greater than about 30 and less than about 80.

The elastomeric laminate may further comprise a second section that doesn't comprise ridges and valleys and the second section may have a greater Laminate-Modulus than the first section.

The second section may comprise the plurality of elastics.
The first section of the elastomeric laminate may comprise a plurality of apertures forming an apertured portion.

The elastomeric laminate may form at least a portion of an absorbent article component where the absorbent article component selected from an ear, a side panel, a belt, a topsheet, a backsheet, a cuff, and combinations thereof.

The first section of the elastomeric laminate may have a Laminate-Modulus from about 3 to about 8 gf/mm, and the second section, when present, of the elastomeric laminate may have a Laminate-Modulus from about 4 to about 10 gf/mm.

The first section of the elastomeric laminate may have a Laminate-Modulus from about 3 gf/mm to about 10 gf/mm, a Strain of greater than 125% at a Stress of 9.1 gf/mm, and a Strain-to-Modulus-Ratio greater than about 30 and less than about 65.

The first section of the elastomeric laminate may form at least a portion of a waist region.

In second form, a disposable absorbent pant article of the present disclosure may comprise a chassis comprising a topsheet, a backsheet and an absorbent core disposed between the topsheet and the backsheet. A first plurality of elastic strands may be disposed in a front waist region, and a second plurality of elastic strands may be disposed in a back waist region. The front and back waist regions may be joined together at laterally opposed side seams to form a waist and leg openings. The front waist region may be a region between a) a proximal most front axis extending parallel to the lateral axis and passing through proximal most points of the laterally opposed side seams; and b) a distal most front axis extending parallel to the lateral axis and passing through distal most points of the laterally opposed side seams. The back waist region may be a region between a) a proximal most back axis extending parallel to the lateral axis and passing through proximal most points of the laterally opposed side seams; and b) a distal most back axis extending parallel to the lateral axis and passing through distal most points of the laterally opposed side seams. The front waist region may comprise a front component region disposed between and including a front distal most elastic strand of the front waist region and a proximal most elastic strand of the front waist region. The front component region may be defined by a front distal component region line extending parallel to the lateral axis and passing through a distal most point of the front distal most elastic strand and a front proximal component region line extending parallel to the lateral axis and passing through a proximal most point of the front proximal most elastic strand. The front component region may then divided into 4 equal component sections, defined by first, second, and third component section lines, each disposed parallel to the lateral axis and disposed at 25%, 50% and 75% of the distance between the front distal component region line and front proximal component region line. The front component region may comprise a first component section, Front Section 1, comprising the front distal most elastic strand, a fourth component section, Front Section 4, comprising the front proximal most elastic strand, a second component section, Front Section 2, adjacent to Front Section 1, and a third component section, Front Section 3, disposed between Front Sections 2 and 4. The back waist region may comprise a back component region disposed between and including a back distal most elastic strand of the back waist region and a proximal most elastic strand of the back waist region. The back component region may be defined by a back distal component region line extending parallel to the lateral axis and passing through a distal most point of the back distal most elastic strand and a back proximal component region line extending parallel to the lateral axis and passing through a proximal most point of the back proximal most elastic strand. The back component region may then divided into 4 equal component sections, defined by first, second, and third component section lines, each disposed parallel to the lateral axis and disposed at 25%, 50% and 75% of the distance between the back distal component region line and back proximal component region line. The back component region may comprise a first component section, Back Section 1, comprising the back distal most elastic strand, a fourth component section, Back Section 4, comprising the back proximal most elastic strand, a second component section, Back Section 2, adjacent to Back Section 1, and a third component section, Back Section 3, disposed between Back Sections 2 and 4. At least one of Front Sections 1-4 may comprise the first plurality of elastics and at least one of a plurality of apertures and a mechanically deformed portion forming ridges and valleys, where the at least one of Front Sections 1-4 may have a Laminate-Modulus from about 3 gf/mm to about 12 gf/mm, a Strain of greater than 110% at a Stress of 9.1 gf/mm, and a Strain-to-Modulus-Ratio greater than about 30 and less than about 80. The disposable absorbent pant article may have an Application-Stress of from about 7.5 gf/mm to about 14 gf/mm, and a Sustained-Fit-Load-Stress greater than 30% of the Application-Stress, and a Sustained-Fit-Unload-Stress greater than 25% of the Application-Stress.

At least one of Front Sections 1-4 may comprise mechanically deformed portions forming ridges and valleys, and may comprise an inner belt nonwoven and an outer belt nonwoven, as well as the first plurality of elastics. Further, at least one of Back Sections 1-4 may comprise mechanically deformed portions forming ridges and valleys, and may comprise an inner belt nonwoven and an outer belt nonwoven, as well as the second plurality of elastics.

At least two of Front Sections 1-4 may comprise mechanically deformed portions forming ridges and valleys, and at least two of Back Sections 1-4 may comprise mechanically deformed portions forming ridges and valleys.

Each of Front Sections 1-4 may comprise mechanically deformed portions forming ridges and valleys, and each of Back Sections 1-4 may comprise mechanically deformed portions forming ridges and valleys.

The disposable absorbent pant article may have a Leg-Hoop-Max-Strain of greater than 120% at a force of less than 650 gf.

At least one of Front Sections 1-4 may comprise a plurality of apertures forming an apertured portion and the apertured portion of the front component region may be disposed through a garment-facing belt nonwoven, but not a wearer-facing belt nonwoven.

One or both of Back Sections 1, 3, and 4 may have a lower Laminate-Modulus than one or both of Back Section 2.

One or both of Front Sections 1 and 2 may have a lower Laminate-Modulus than one or both of Front Sections 3 and 4.

The absorbent article may be divided into three article sections, Section L, Section M, and Section R, where the article sections are defined by a left article section line extending parallel to the longitudinal axis and passing through a left laterally distal most point of a left side edge of the chassis and by a right article section line extending parallel to the longitudinal axis and passing through a right laterally distal most point of a right side edge, which is laterally opposed from the left side edge of the chassis, wherein any portion of the article to one lateral side or the other of the Section M defines Section L and the laterally opposed Section R, and wherein Front Sections L and R comprise mechanically deformed portion forming ridges and valleys and Section M is substantially free from ridges and valleys.

In a third form, a disposable absorbent pant article of the present disclosure may comprise a chassis comprising a topsheet, a backsheet and an absorbent core disposed between the topsheet and the backsheet. A first plurality of elastic strands may be disposed in a front waist region, and the first plurality of elastic strands may comprise a first polymer composition. A second plurality of elastic strands may be disposed in the front waist region, and the second plurality of elastic strands may comprise a second polymer composition. Each of the first and second pluralities of elastic strands may have an Average-Strand-Spacing from about 0.25 mm to about 4 mm. Each of the first and second pluralities of elastic strands may have an Average-Dtex from about 10 to about 400. The first and second polymer compositions may be different. The front and back waist regions may be joined together at laterally opposed side seams to form a waist and leg openings. The front waist region may be defined as a region between a) a proximal most front axis extending parallel to the lateral axis and passing through proximal most points of the laterally opposed side seams; and b) a distal most front axis extending parallel to the lateral axis and passing through distal most points of the laterally opposed side seams. The front waist region may comprise a front component region disposed between and including a front distal most elastic strand of the front waist region and a proximal most elastic strand of the front waist region. The front component region may be defined by a front distal component region line extending parallel to the lateral axis and passing through a distal most point of the front distal most elastic strand and a front proximal component region line extending parallel to the lateral axis and passing through a proximal most point of the front proximal most elastic strand. The front component region may then divided into 4 equal component sections, defined by first, second, and third component section lines, each disposed parallel to the lateral axis and disposed at 25%, 50% and 75% of the distance between the front distal component region line and front proximal component region line. The front component region may comprise a first component section, Front Section 1, comprising the front distal most elastic strand, a fourth component section, Front Section 4, comprising the front proximal most elastic strand, a second component section, Front Section 2, adjacent to Front Section 1, and a third component section, Front Section 3, disposed between Front Sections 2 and 4. At least one of Front Sections 1 and 4 may comprise the first plurality of elastics, at least one of Front Sections 2 and 3 may comprise the second plurality of elastics, and at least one of Front Sections 1 and 4 may have a lower Laminate-Modulus than the at least one of Front Sections 2 and 3.

Front Sections 1 and 4 may have a first Laminate-Modulus and Front Sections 2 and 3 may have a second Laminate-Modulus where the second Laminate-Modulus in one or both of Sections 2 and 3 is higher than the first Laminate-Modulus in one or both of Sections 1 and 4.

BRIEF DESCRIPTION OF THE DRAWINGS

FIG. 5D is a front view illustrating the initial fit of a comparative product comprising beamed laminate belts. The Product in FIG. 5D is further detailed in Table B.

FIG. 5D' is a front view illustrating the final fit of the comparative product of FIG. 5D. The product in FIG. 5D' is further detailed in Table B.

FIG. 5E is a front view of the initial fit of an inventive product, the inventive product being the same as FIG. 5D, except that the belts have been MD Activated. The product in FIG. 5E is further detailed in Table B.

FIG. 5E' is a front view of the final fit of the inventive product of FIG. 5E. The product in FIG. 5E' is further detailed in Table B.

FIG. 5F is a perspective side view illustrating the initial fit of the comparative product of FIG. 5D. The product in FIG. 5F is further detailed in Table B.

FIG. 5F' is a perspective side view illustrating the final fit of the comparative product of FIG. 5D. The product in FIG. 5F' is further detailed in Table B.

FIG. 5G is a perspective side view of the initial fit of the inventive product of FIG. 5E. The product in FIG. 5G is further detailed in Table B.

FIG. 5G' is a perspective side view of the final fit of the inventive product of FIG. 5E. The product in FIG. 5G' is further detailed in Table B.

FIG. 5H' is a front view illustrating the final fit of the inventive product of FIG. 5E.

FIG. 5I' is a front view of the final fit of the comparative product of FIG. 5I

FIG. 5J is a perspective side view of the initial fit of the inventive product of FIG. 5H.

FIG. 5J' is a perspective side view illustrating the final fit of the inventive product of FIG. 5H.

FIG. 5K is a perspective side view illustrating the initial fit of the comparative product of FIG. 5I.

FIG. 5K' is a perspective side view of the final fit of the comparative product of FIG. 5I.

FIG. 9G is a top view of the converting apparatus of FIG. 9F taken along line 9G-9G.

FIG. 12H is a cross-section view of an alternate embodiment of the pant of FIG. 12E taken along the longitudinal axis 42, showing longitudinally opposing discrete belts, wherein elastics 316 are oriented parallel to the lateral axis 44 between the core wrap 74 and the topsheet 124 and oriented parallel to the lateral axis 44 between the backsheet film 126 and the backsheet nonwoven 127.

FIG. 12I is a cross-section view of an alternate embodiment of the belt pant of FIG. 12E taken along the longitudinal axis 42, showing longitudinally opposing discrete inner belt layers 432 and a common outer belt layer 434, and showing elastic strands 316 extending continuously across the core.

DETAILED DESCRIPTION

Introduction

Figure 1A:
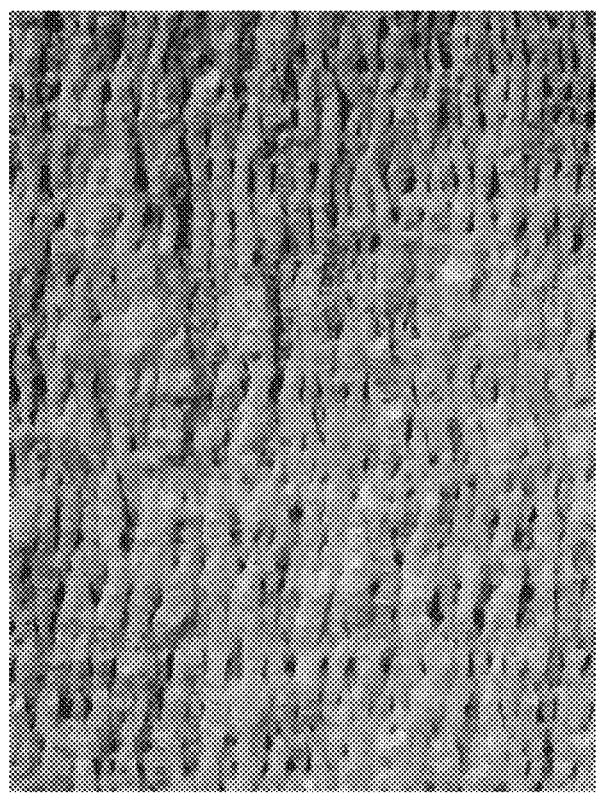
FIG. 1A is a top view illustrating a comparative, non-inventive laminate.
Figure 1B:
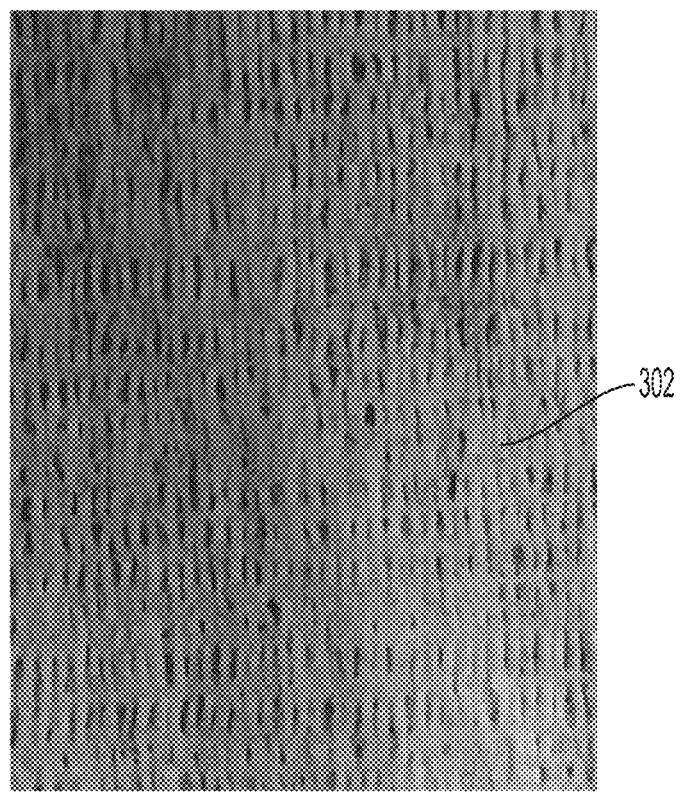
FIG. 1B is a top view illustrating an inventive laminate of the present disclosure that has been deformed via MD activation.
Figure 1C:
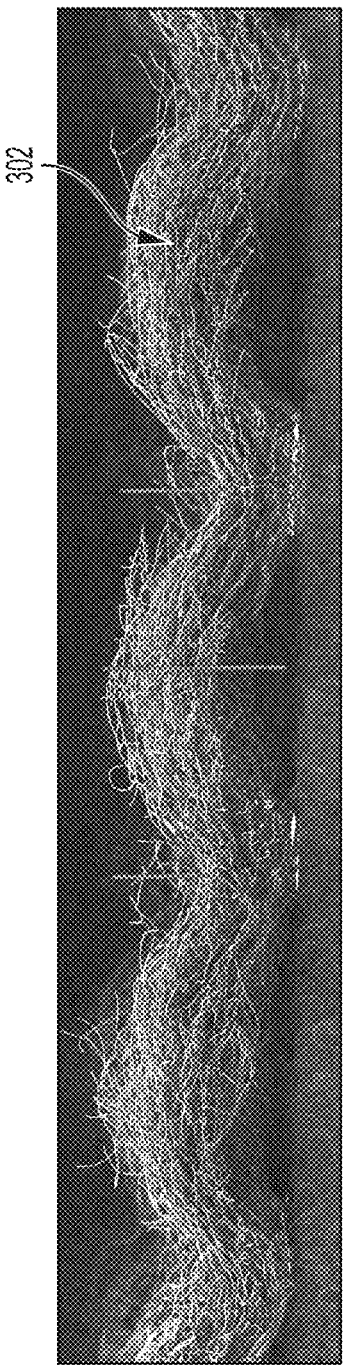
FIG. 1C is a side view illustrating an inventive laminate of the present disclosure that has been deformed via MD activation.
Figure 1D:
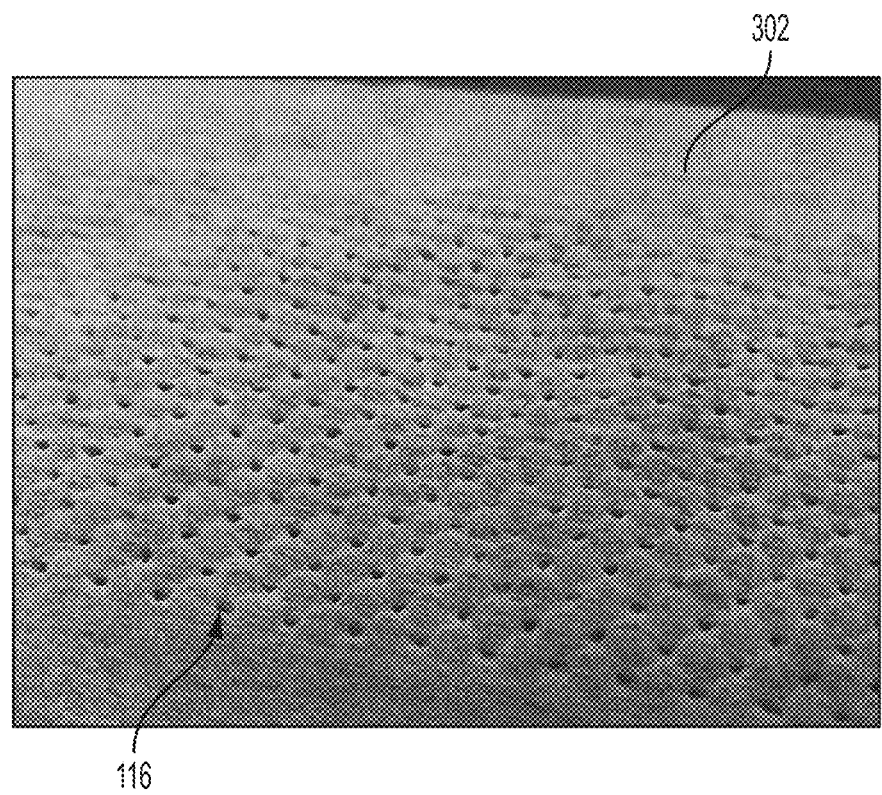
FIG. 1D is a perspective top view illustrating an inventive laminate of the present disclosure that has been deformed via aperturing.
Figure 1E:
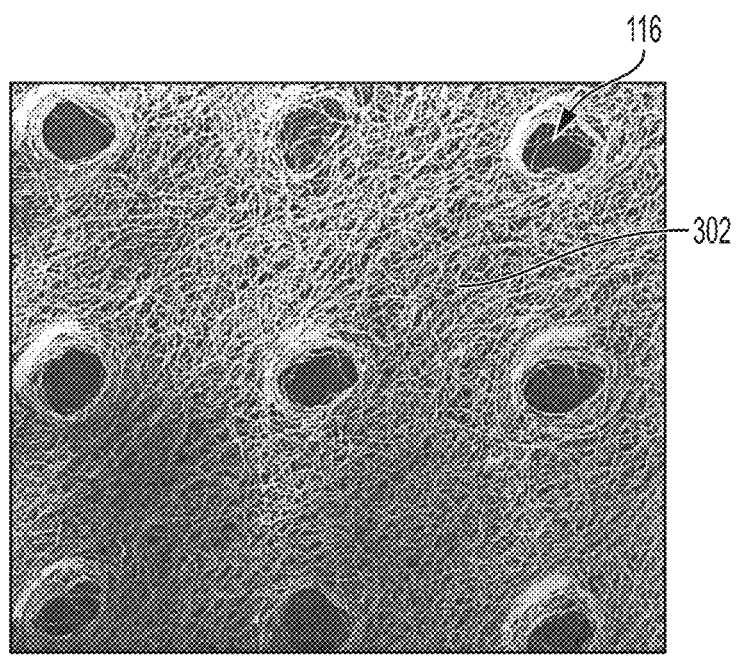
FIG. 1E is a top view illustrating an inventive laminate of the present disclosure that has been deformed via aperturing.

The present disclosure details improved stranded elastomeric laminates (also referred to as "beamed laminates" comprising "beamed elastics" or "beamed elastomeric laminates") comprising a greater number of elastic strands having a greater fineness (i.e., lower decitex) and a closer spacing than has been previously disclosed or practiced in disposable absorbent articles. These improved stranded elastomeric laminates can be used as disposable absorbent article (e.g., disposable taped diapers, pants, pads, liners, etc.) components (e.g., topsheets, backsheets, belts, ears, side panels, cuffs, etc.) for improved fit and gasketing at the waist, legs, crotch, and sides of the wearer to provide the greatest level of extensibility, ease of application, the most comfortable wearing conditions, improved leakage protection and a better sustained fit. Further, the stranded elastomeric laminates of the present disclosure may also comprise one or more zones (including each of the zones) that have been mechanically deformed by MD activation and/or aperturing; and may further or alternatively comprise elastomeric strands comprising different polymer compositions. One or a combination of these features greatly improve laminate stretch (even versus previously disclosed beamed laminates) without compromising fit (which is quite counterintuitive and unexpected) and said deformation can also enable laminates comprising different zones (both visually different and that perform differently).

Definitions

The following term explanations may be useful in understanding the present disclosure:

"Disposable," in reference to absorbent articles, means that the absorbent articles, are generally not intended to be laundered or otherwise restored or reused as absorbent articles (i.e., they are intended to be discarded after a single use and, preferably, to be recycled, composted or otherwise discarded in an environmentally compatible manner). Disposable absorbent articles often comprise adhesive between the layers and/or elements to hold the article together (e.g., ear panels, side panels, and belts are joined to the chassis via adhesive and the layers of the ear panels, side panels, belts, and chassis are joined together using adhesive). Alternatively, heat and/or pressure bonding are used with the adhesive or in place of the adhesive. In such instances portions of the material layers may become partially melted and pressed together such that once cooled they are physically bonded together. Nonwovens (including, for example, polypropylene, polyethylene, etc.) adhesives (including, for example, styrenic block copolymers (e.g., SIS, SBS)), and absorbent gelling material (AGM 26—see FIGS. 12E-G) make up more than 50%, more than 75%, and often more than 90% of the disposable absorbent article weight. And, a core comprising the AGM 26 is often held within the chassis in a manner that would encapsulate and contain the AGM 26 under normal conditions. Such disposable absorbent articles typically have an absorbent capacity of greater than about 100 mL of fluid and can have capacities of up to about 500 mL of fluid or more. Stitching (including the use of thread) and/or woven materials are typically not used to make a disposable absorbent article. If stitching or woven materials are used, they make up an extremely small percentage of the disposable absorbent article. Some landing zones of disposable absorbent articles for fasteners can comprise a woven material, but no other part of a disposable absorbent article typically comprises woven materials.

"Absorbent article" refers to devices, which absorb and contain body exudates and, more specifically, refers to devices, which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, feminine pads, absorbent inserts, absorbent pad and panty (disposable and semi-durable) systems and the like.

"Proximal" and "Distal" refer respectively to the location of an element relatively near to or far from the longitudinal or lateral centerline of a structure (e.g., the proximal edge of a longitudinally extending element is located nearer to the longitudinal axis than the distal edge of the same element is located relative to the same longitudinal axis).

"Wearer-facing" and "garment-facing" refer respectively to the relative location of an element or a surface of an element or group of elements. "Wearer-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal."

"Lateral" refers to a direction running from a longitudinally extending side edge to an opposing longitudinally extending side edge of the article and generally at a right angle to the longitudinal direction. Directions within 45 degrees of the lateral direction are considered to be "lateral."

"Disposed" refers to an element being located in a particular place or position.

"Joined" encompasses configurations whereby an element is directly secured to another element by affixing the element directly to the other element, and configurations whereby an element is indirectly secured to another element by affixing the element to intermediate member(s), which, in turn are affixed to the other element.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable."

"Elastic," "elastomer," or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force. Elastomeric materials may include elastomeric films, scrims, nonwovens, ribbons, strands and other sheet-like structures.

"Pre-strain" refers to the strain imposed on an elastic or elastomeric material prior to combining it with another element of the elastomeric laminate or the absorbent article. Pre-strain is determined by the following equation Pre-strain=((extended length of the elastic-relaxed length of the elastic)/relaxed length of the elastic)*100.

"Decitex" also known as Dtex is a measurement used in the textile industry for measuring yarns or filaments. 1 Decitex=1 gram per 10,000 meters. In other words, if 10,000 linear meters of a relaxed yarn or filament weights 500 grams that yarn or filament would have a decitex of 500.

"Substrate" is used herein to describe a material which is primarily two-dimensional (i.e., in an XY plane) and whose thickness (in a Z direction) is relatively small (i.e. 1/10 or less) in comparison to its length (in an X direction) and width (in a Y direction). Non-limiting examples of substrates include a web, layer or layers of fibrous materials, nonwovens, films and foils such as polymeric films or metallic foils. These materials may be used alone or may comprise two or more layers laminated together. As such, a web is a substrate.

"Nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

"Machine direction" (MD) is used herein to refer to the direction of material flow through a process. In addition, relative placement and movement of material can be described as flowing in the machine direction through a process from upstream in the process to downstream in the process.

"Cross direction" (CD) is used herein to refer to a direction that is generally perpendicular to the machine direction.

"Taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1.

"Pant" (also referred to as "training pant", "pre-closed diaper", "diaper pant", "pant diaper", "panty", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be pre-formed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be pre-formed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897,545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

"Side Seam" is the area connecting the front waist region to the back waist region to form the waist and leg openings. Side seams may be formed as permanent seams via thermal, pressure, heat or ultrasonic bonding. Side seams may also be formed via fastening elements to create a refastenable side seam. In such cases the length of the side seam is determined by the length of the fastener or fasteners. Side seams need to have sufficient strength as to not open during use but to be easily opened for removal.

"Closed-form" means opposing waist regions are joined, as packaged, either permanently or refastenably to form a continuous waist opening and leg openings.

"Open-form" means opposing waist regions are not initially joined to form a continuous waist opening and leg openings but comprise a closure means such as a fastening system to join the waist regions to form the waist and leg openings before or during application to a wearer of the article.

"Dtex-to-Spacing-Ratio" is determined by dividing the elastic decitex by the elastic spacing of the plurality of elastics being examined. Elastomeric laminates of the present disclosure may have Dtex-to-Spacing-Ratios of from about 65:1 to about 300:1, or from about 80:1 to about 200:1.

"Dtex-to-Nonwoven-Basis-Weight-Ratio" is determined by dividing the elastic decitex by the nonwoven basis weight of the one or more nonwoven substrates of the elastomeric laminate disposed on one side (garment facing side or wearer-facing side) of the elastic strand, i.e. the inner or outer elastomeric laminate substrate layers. Elastomeric laminates of the present disclosure may have Dtex-to-Nonwoven-Basis-Weight-Ratios of from about 1.5 to about 15, from about 3 to about 12, or from about 4 to about 10.

"Application-Force" is the force that a wearer of caretaker might encounter while donning the absorbent article. The Application-Force is derived from a two cycle Hip-Hoop-Test.

"Sustained-Fit-Load-Force" is the force that an article applies to the wearer when the wearer's waist extends for example during respiration or during wearer movement like when a wearer goes from a standing position to a sitting position or from a prone position to a sitting position. The Sustained-Fit-Load-Force is derived from a two cycle Hip-Hoop-Test.

"Sustained-Fit-Unload-Force" is the force that an article applies to the wearer when the wearer's waist contracts for example during respiration or during wearer movement like when a wearer goes from a sitting position to a standing position or from a sitting position to a prone position. The Sustained-Fit-Unload-Force is derived from a two cycle Hip-Hoop-Test.

"Mechanical Deformation" occurs when a substrate or a laminate is MD activated or apertured.

"Ring rolling" occurs when the elastomeric laminate is subjected to incremental straining. The incremental strain or elongation is applied to a specified region of the elastomeric laminate wherein the nonwoven fibers of the elastomeric laminate in the regions of deformation are physically altered. The fibers are strained until fiber elongation or permanent deformation of the fiber occurs. The amount of strain necessary to cause fiber elongation or permanent deformation will depend upon many properties including the material composition, denier of the fiber, yarn count, depth of engagement of teeth, footprint of deformation and tension on the web during the deformation process.

Other definitions may be presented herein.

Elastomeric Laminate Formation

This section provides some details related to the process of making stranded elastomeric laminates of the present disclosure. Referring generally to FIGS. 9A-J, a plurality of elastic strands 316 (from about 10 strands to about 1500 strands having a decitex from about 10 to about 400) unwind about a first axis of rotation 346 from a first beam 314 (which is a first metering device 310) in the machine direction MD and transfer the plurality of elastic strands 316 from the first beam 314 (e.g., a warp beam) to a second metering device 312 (which includes a first roller 323 having a second axis of rotation 329 and a second roller 331 having a third axis of rotation 334, which form a nip 336). The plurality of elastic strands 316 may be stretched along the machine direction MD between the first metering device 310 and the second metering device 312 to prestrain the plurality of elastics 316 (from about 50% to about 300%). The stretched elastic strands 316 may be joined via an adhesive 351 from an adhesive applicator 349 (or the plurality of elastics 316 may be joined via other suitable means, such as ultrasonically) with a first substrate layer 306 and a second substrate layer 308 at the nip formed by the second metering device 312 to produce an elastomeric laminate 302, such that each of the strands are spaced (in the CD) in the elastomeric laminate from about 0.25 mm to about 4 mm. It is this process that forms the elastomeric laminate 302 of the present disclosure and that may be further incorporated into the various absorbent article components such as the belts, ear panels, side panels, transverse barriers, topsheets, backsheets, cuffs, waistbands, waistcaps, and/or chassis to offer the benefits described in this patent application. Further details of the process of creating beamed elastomeric laminate(s) for use in disposable absorbent articles are disclosed in U.S. Publication No. 62/436,589, titled "Methods and Apparatuses for Making Elastomeric Laminates with Elastic Strands Unwound from Beam," first-named inventor being Schneider, filed on Dec. 20, 2016. The elastomeric laminate 302 may be produced as part of the absorbent article manufacturing line, or may be produced offline, and unwound as an elastomeric laminate that is fed into the absorbent article manufacturing line. The disclosure of this section provides details related to forming the base or initial elastomeric laminate 302. Details for deforming this elastomeric laminate 302 to create the inventive laminates of the present disclosure are provided below.

Mechanical Deformation of the Elastomeric Laminate

Elastomeric laminates 302 of the present disclosure may be mechanically deformed via MD activation and/or aperturing in order to achieve improved performance (e.g., ease of donning, less red marking, increased breathability) and improved garment-like aesthetics (smoother textures and assorted textures).

MD Activation

As shown in FIGS. 1B, 1C, 2A, 2D, 9A-E, 9H, 9I, 12A-F, 12K, 12L, 12S-V, 13, and 14, the fibers in the elastomeric laminate 302 of the present disclosure may be subjected to incremental strains via MD activation. The incremental strains or elongation may be applied to a portion of or the entire elastomeric laminate 302. A sufficient strain may be applied so that the fibers of one or both of the substrate layers disposed in one direction will be strained until fiber elongation or permanent deformation of the fiber occurs, such that the portions of the substrate layers 306 and 308 making up the ridges 102 and valleys 104 remain thicker than the stretched out middle transition portions 139, which is a lower basis weight (versus the ridges and valleys) due to being stretched by the deformation process—see FIG. 2A. The amount of strain necessary to cause fiber elongation or permanent deformation will depend upon many properties including the material composition of the fiber, denier of the fiber, bond pattern of the substrate, yarn count, depth of engagement of teeth, pitch of teeth, footprint of deformation, tension on the web during the deformation step and processing speed. Generally, the fiber elongation and/or deformation will primarily occur in one direction. In cases where the fibers disposed orthogonal or perpendicular to the direction in which the fiber elongation or deformation occurs may remain substantially physically unaltered. Substantially unaltered physical properties of the fibers means that the fibers will have the same mechanical strength, diameter and elongation to break. In cases where the fibers disposed at an angle to or parallel to the direction in which the fiber elongation or deformation occurs the fibers may become oriented in the direction of fiber elongation/deformation. However, in limited cases, a small number of these fibers may be torn or elongated as long as the appearance, strength, and usefulness of the elastomeric laminate is not substantially changed.

The fibers in the orthogonal direction to the fibers being elongated or deformed will typically be redistributed. Redistributed means that the fibers are bunched, gathered, or moved to a new location within the substrate layer due to the fibers sliding over and passed each other. The fibers will typically have substantially unaltered physical properties resulting from the redistribution.

Figure 9A:
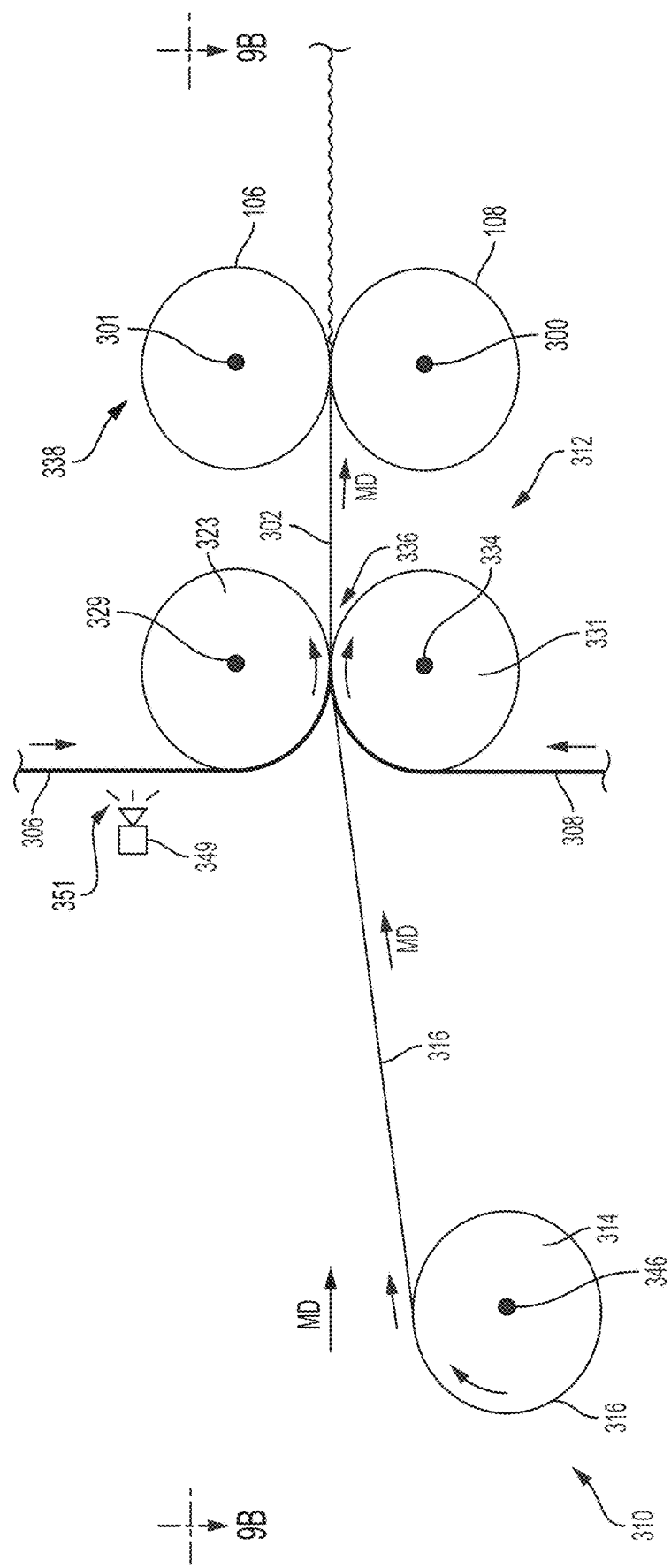
FIG. 9A is a schematic side view of a converting apparatus adapted to manufacture an elastomeric laminate including equipment for deforming the elastomeric laminate via MD activation.
Figure 9B:
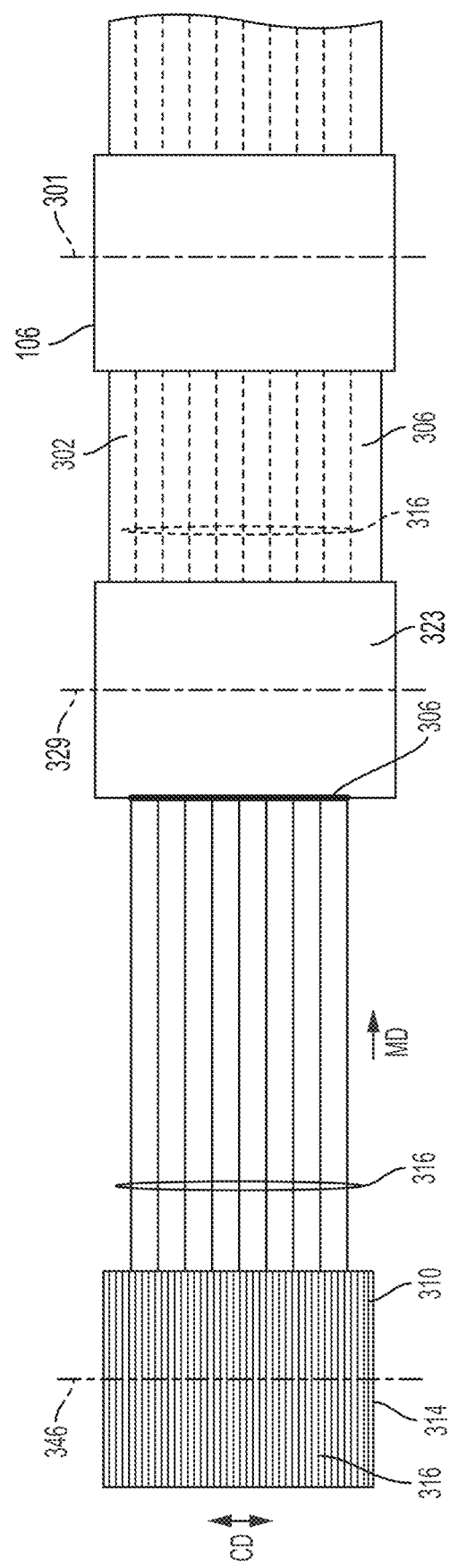
FIG. 9B is a top view of the converting apparatus of FIG. 9A taken along line 9B-9B.
Figure 9C:
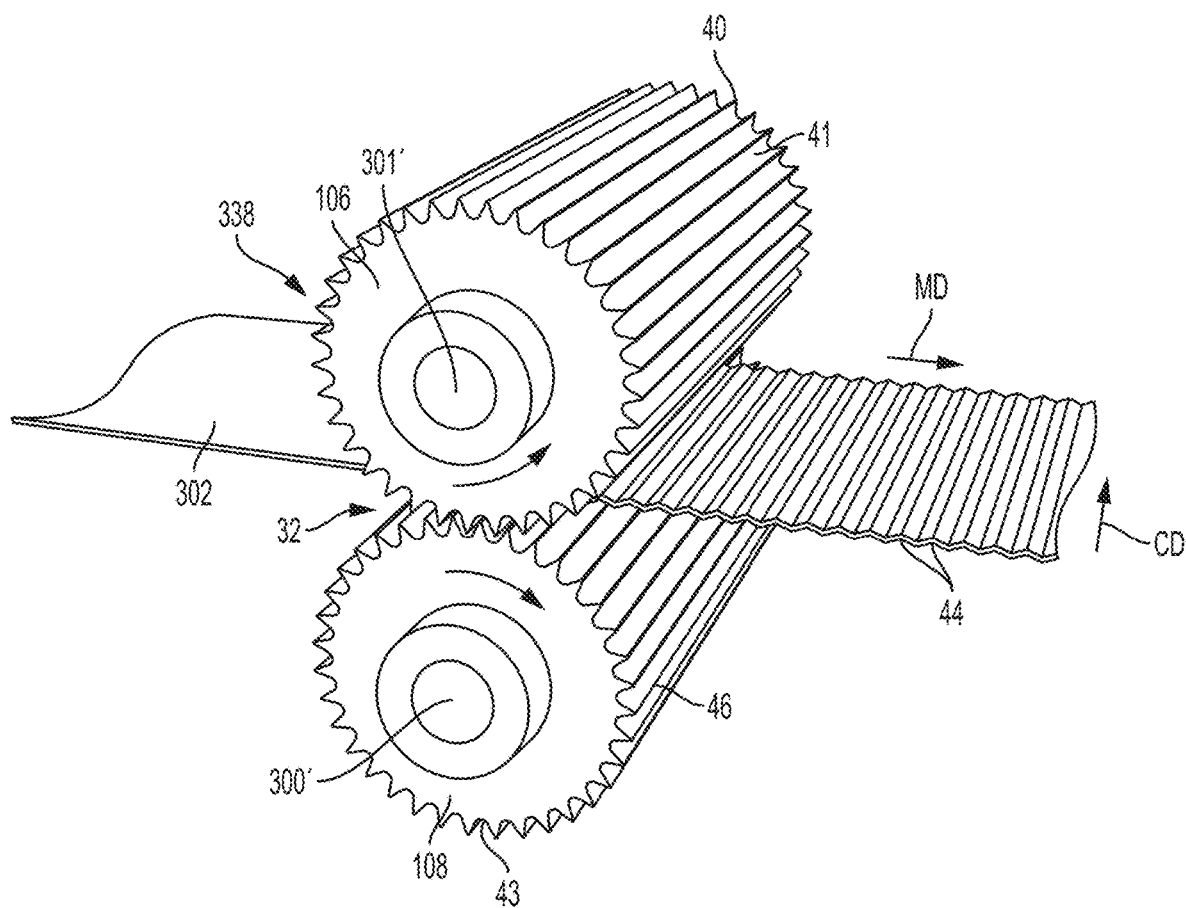
FIG. 9C is a perspective side view of a converting apparatus adapted to deform an elastomeric laminate via MD activating the elastomeric laminate.

In order to activate elastomeric laminates of the present disclosure, they may be trapped between two engaging patterned rolls that are driven in a rotating motion—see FIGS. 9A-9D. As shown in FIGS. 9C and D, the rolls have corresponding teeth 40, 46 and groves 41, 43 that create an incremental unidirectional strain upon any material that passes between them. While the teeth and grooves of FIGS. 9C and D are straight and run along the cross-machine direction (CD), the intermeshing teeth and grooves may alternatively be curved or arcuate, or may be angled relative to the CD and machine directions (MD), such alternative configurations translating said shape to the substrate run through said alternative rolls—such may also be true for plates—such as the ones illustrated by FIG. 9E.

Depth of engagement is typically from about 0.010 to 0.150 inches or from about 0.020 to about 0.100 inches. The pitch, distance between teeth, is typically from about 0.040 to about 0.300 inches or from about 0.060 to about 0.200 inches, or from about 0.080 to about 0.100.

The resulting elastomeric laminate 302 appearance is influenced by the composition of the nonwoven layers as well as the decitex, spacing, prestrain, and relative angle of the elastic strands disposed between the nonwoven layers. The bond pattern in the substrate, e.g., nonwoven layer, as well as the relative spacing, number, and size of the protruding teeth or pattern, along with the depth of the protrusion, i.e., engagement, tension on the elastomeric web and speed of the rotating rolls are also influential with regard to the final appearance of the elastomeric laminate.

Elastomeric laminates 302 of the present disclosure may be achieved by use of mating plates (see FIG. 9E) or rolls (see FIGS. 9C and D). Referring to FIG. 9E, there is shown an apparatus 110 used to form the elastomeric laminate. Apparatus 110 includes the intermeshing plates 112 and 114. Plates 112 and 114 include a plurality of intermeshing teeth and grooves 40', 41', 43', and 46'. Plates 112 and 114 are brought together under pressure in a non-interfering, intermeshing manner to form the elastomeric laminate of the present disclosure. That is, teeth and grooves 40' with 43' and 46' with 41' are caused to intermesh but preferably do not contact each other during the elongation deformation process. Plate 114 illustrates that zones 558 free from teeth or grooves may be present to leave the elastomeric laminate 302 undeformed in said zones 558. Like zones free from teeth or grooves may be also be part of an intermeshing roll design.

Figure 9D:
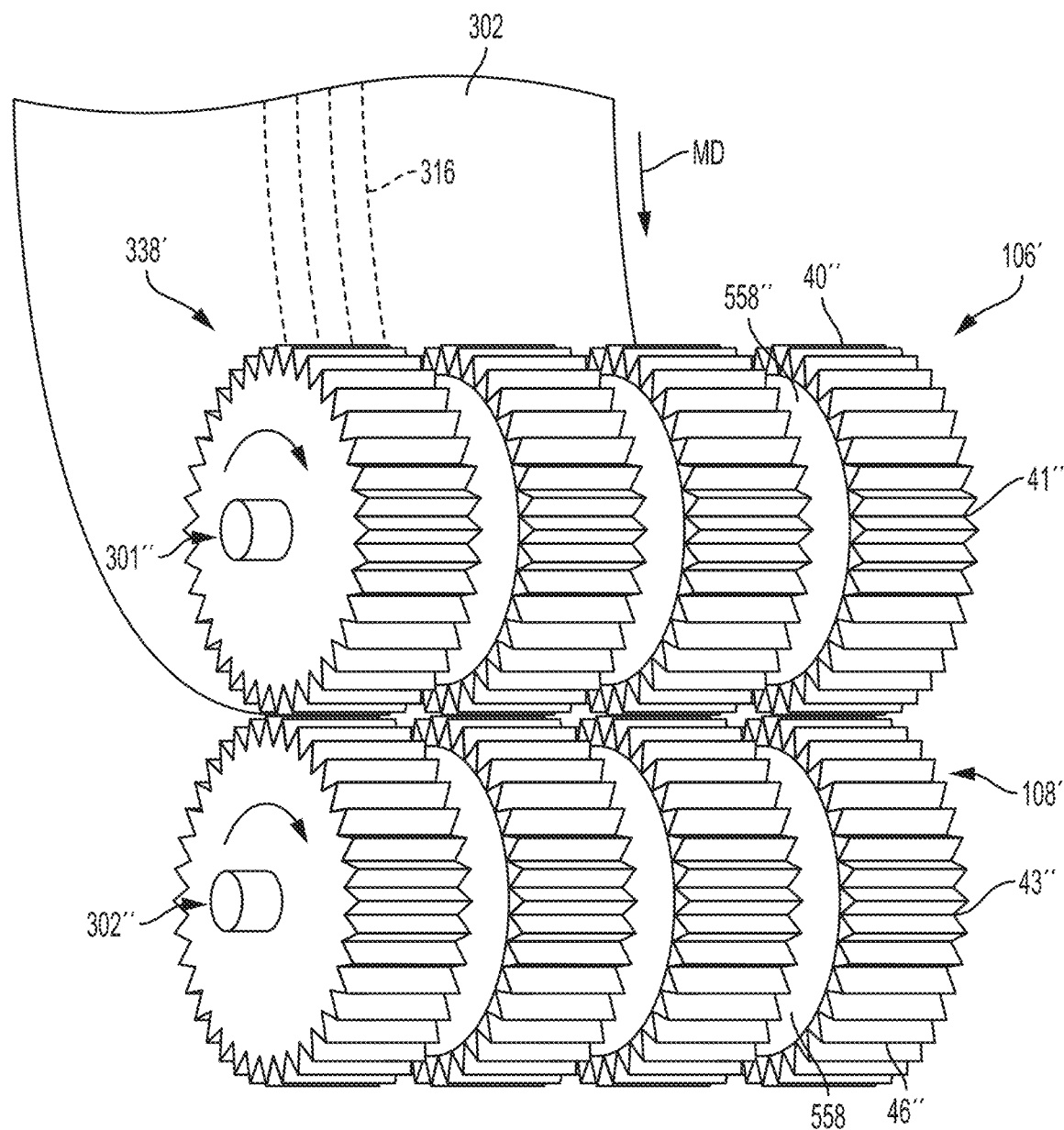
FIG. 9D is a perspective front view of a converting apparatus adapted to deform an elastomeric laminate via MD activating the elastomeric laminate.
Figure 9E:
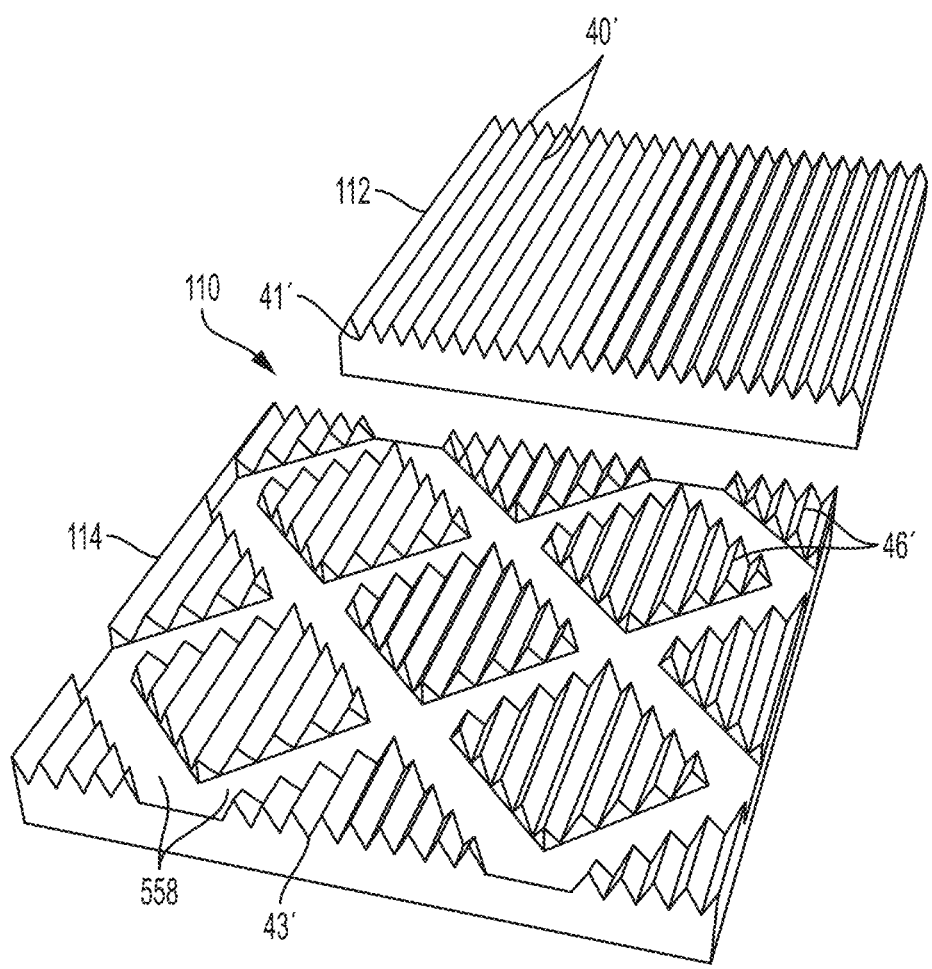
FIG. 9E is a perspective side view of a converting apparatus adapted to deform an elastomeric laminate.
Figure 9F:
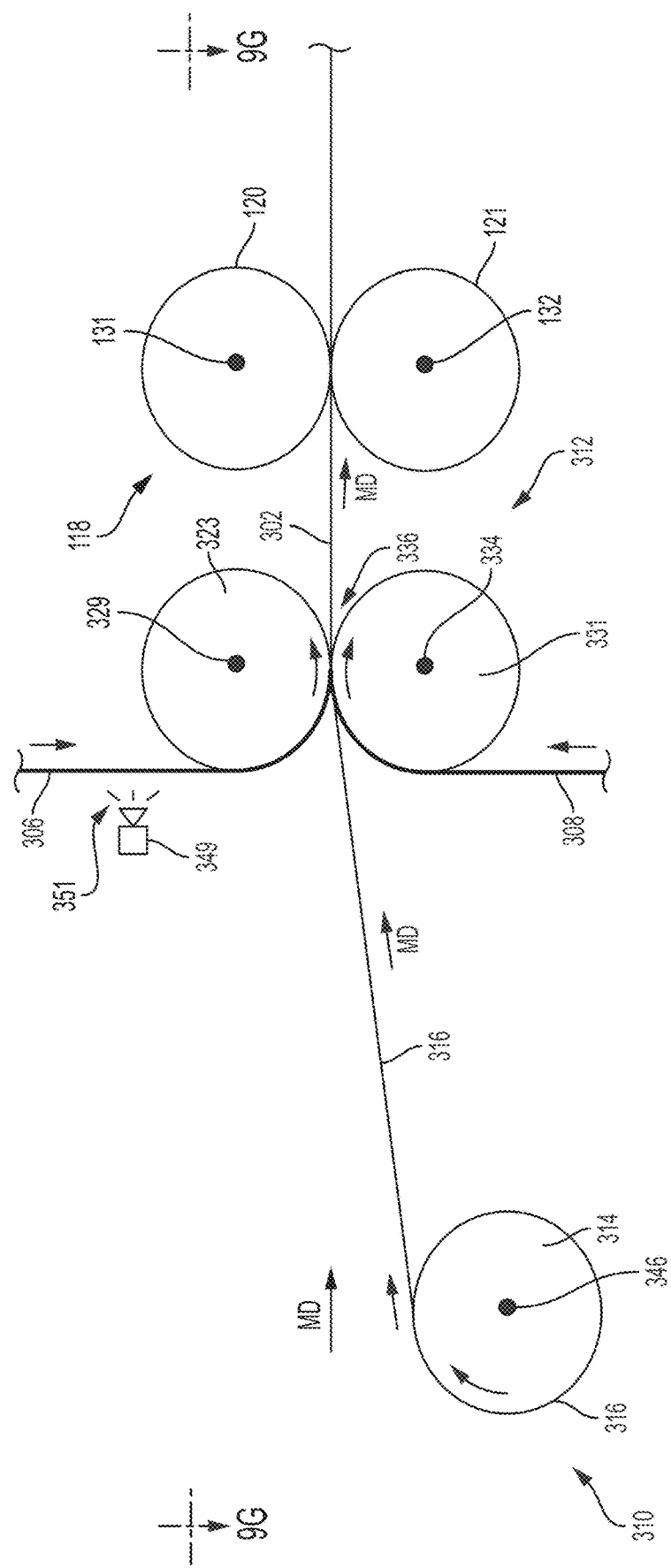
FIG. 9F is a schematic side view of a converting apparatus adapted to manufacture an elastomeric laminate including equipment for deforming the elastomeric laminate via aperturing.
Figure 9H:
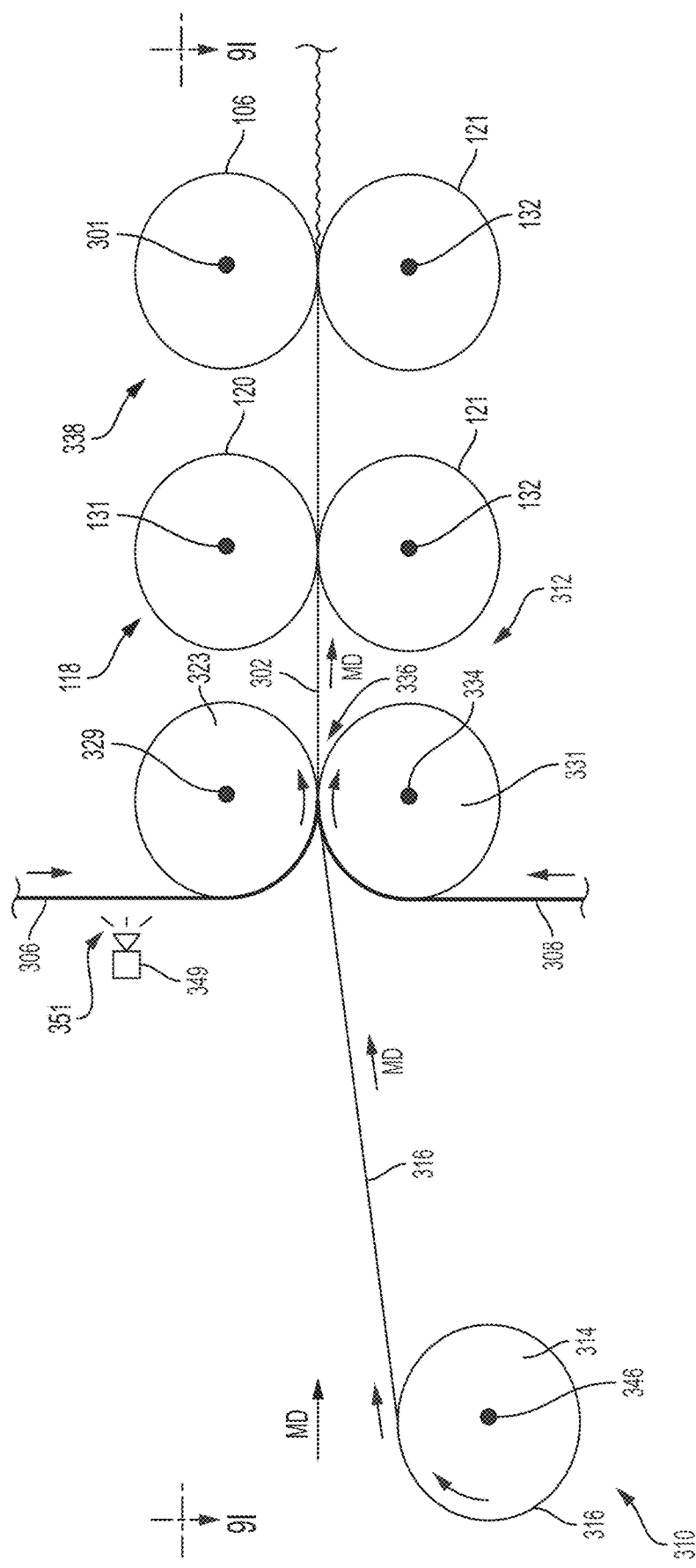
FIG. 9H is a schematic side view of a converting apparatus adapted to manufacture an elastomeric laminate including equipment for deforming the elastomeric laminate via aperturing and MD activation.
Figure 9I:
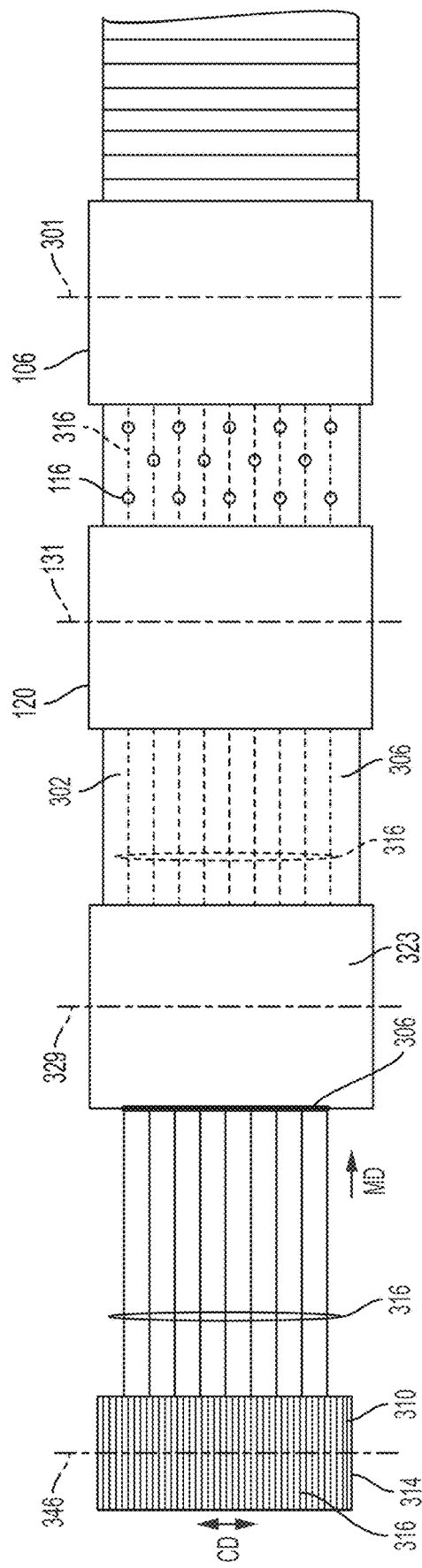
FIG. 9I is a top view of the converting apparatus of FIG. 9H taken along line 9I-9I.

Referring now to FIG. 9D, there is shown an alternative apparatus generally indicated as 338' for forming the elastomeric laminate 302 in accordance with the teachings of the present disclosure. Apparatus 338' includes a pair of rolls 106' and 108'. Rolls 106' and 108' each have a plurality of teeth and grooves 40", 41", 43", and 46" extending about the circumference of rolls 106' and 108'. As the laminate 302 passes between rolls 106' and 108', grooved regions 558" will leave portions of the elastomeric laminate undeformed, while the portions of the elastomeric laminate passing between the teeth and grooves will be incrementally strained, in this case in the machine direction. The amount of incremental straining in these portions of the formed elastomeric laminate is controlled by the degree of intermeshing between the teeth and grooves 40' with 43' and 46' with 41'. The degree of intermeshing can be accurately controlled by fixing the distance between roll centers, 301" and 302", such that the desired degree of incremental stretching is achieved.

FIG. 9C is an enlarged perspective illustration of a mechanical deformation arrangement 338 employing opposed pressure applicators having three-dimensional surfaces which at least to a degree are complimentary to one another. The mechanical deformation arrangement 338 shown in FIG. 9C comprises incremental stretching rollers 106 and 108. The elastomeric laminate 302 passes through the nip 105 formed by incremental stretching rollers 106 and 108 as the incremental stretching rollers rotate in the direction indicated by the arrows associated therewith. Uppermost incremental stretching roller 106 comprises a plurality of teeth 40 and corresponding grooves 41 which extend about the entire circumference of roller 106. Lowermost incremental stretching roller 108 comprises a plurality of teeth 46 and corresponding grooves 43 which extend about the entire circumference of roller 108. The teeth 40 on roller 106 intermesh with or engage the grooves 43 on roller 108, while the teeth 46 on roller 108 intermesh with or engage the grooves 41 on roller 106.

The teeth 40 and 46 on rollers 106 and 108, respectively, extend in a direction substantially perpendicular to the first direction of the elastomeric laminate or in a direction substantially parallel to the width of the elastomeric laminate. That is, teeth 40 and 46 extend in a direction parallel to the cross-machine or CD direction of the elastomeric laminate. The incremental stretching rollers 106 and 108 incrementally stretch the elastomeric laminate in a direction generally perpendicular to the CD direction, i.e., in a direction parallel to the first direction, thereby deforming a portion of the elastomeric laminate such that it remains in its deformed condition after passing through the incremental stretching rollers 106 and 108 and the tension on the elastomeric laminate is released. By elongating the elastomeric laminate, the nonwovens forming a portion of the elastomeric laminate are substantially deformed and as such do not return to their pre-deformation form.

After being deformed by passing through the incremental stretching rollers 106 and 108, the deformed elastomeric laminate includes a plurality of ridges 102 and valleys 104. The ridges and valleys extend in a substantially linear direction parallel to one another across the entire width of the elastomeric laminate. The ridges 102 and valleys 104 are shown to be extending in a direction substantially parallel to the CD or cross-machine direction. As seen in FIG. 9C, each ridge and valley extends across the elastomeric laminate from one edge to the other edge of the laminate. This embodiment establishes the ridges and valleys across the entire width of the web thereby providing uniformity of texture and extensibility across the elastomeric laminate. If the ridges and valleys do not extend entirely across the elastomeric laminate, the portion of the elastomeric laminate that is free of ridges and valleys will have a different level of extensibility which is less than the portions of the elastomeric laminate comprising the ridges and valleys and the portion free of the ridges and valleys will also have a higher Laminate-Modulus than the portion comprising the ridges and valleys.

The incremental stretching rollers 106 and 108 may include any number of teeth and grooves to provide the desired deformation of the elastomeric laminate. In addition, the teeth and grooves may be nonlinear, such as for example, curved, sinusoidal, zig-zag, etc. The size and amount of engagement of the teeth and grooves on the incremental stretching rollers 106 and 108 may be of any desired dimension. In addition, the teeth and grooves may extend in a direction other than perpendicular to the travel direction of the elastomeric laminate. For example, the teeth and grooves may extend at an angle to the CD direction, but it may be desirable that the angle does not become parallel to the MD or machine direction, or it may be desirable that the angle does not come within 10 degrees of parallel to the MD, or it may be desirable that the angle does not come within 25 degrees of parallel to the MD, or it may be desirable that the angle comes no closer than within 45 degrees of parallel to the MD.

It may be desirable to first CD activate (as a first process step) the laminate 302, such that the ridges and valleys run along the MD; then to MD activate (as the second process step) the laminate 302, such that the ridges and valleys run along the CD.

It may be desirable to first CD activate (as a first process step) an over-bonded (see, for example, U.S. Pat. No. 5,628,097) laminate 302, such that the ridges and valleys run along the MD and such that the CD activation breaks open the over-bonded sites to form apertures; then to MD activate (as the second process step) the laminate 302, such that the ridges and valleys run along the CD.

Aperturing

As shown in FIGS. 1D, 1E, 2B-D, 9F, G-J, and FIGS. 12 M-R, 12U, and 12V, another form of deforming the elastomeric laminate is via aperturing. Aperturing may be done in combination with MD activation (see FIGS. 9H and I, and 12U and V) or as an alternative to MD activation. As will be described in more detail below, certain combinations of aperturing and MD activation may be desirable. When combining MD activation and aperturing on the same web, it may be desirable to first MD activate the web and then to aperture the web to avoid further propogating or distorting the apertures. However, it may be desirable to first aperture the web then to MD activate the web to create or open the apertures. Further, the substrates forming the laminate may comprise bond sites that when MD activate fracture to form apertures.

Figure 9J:
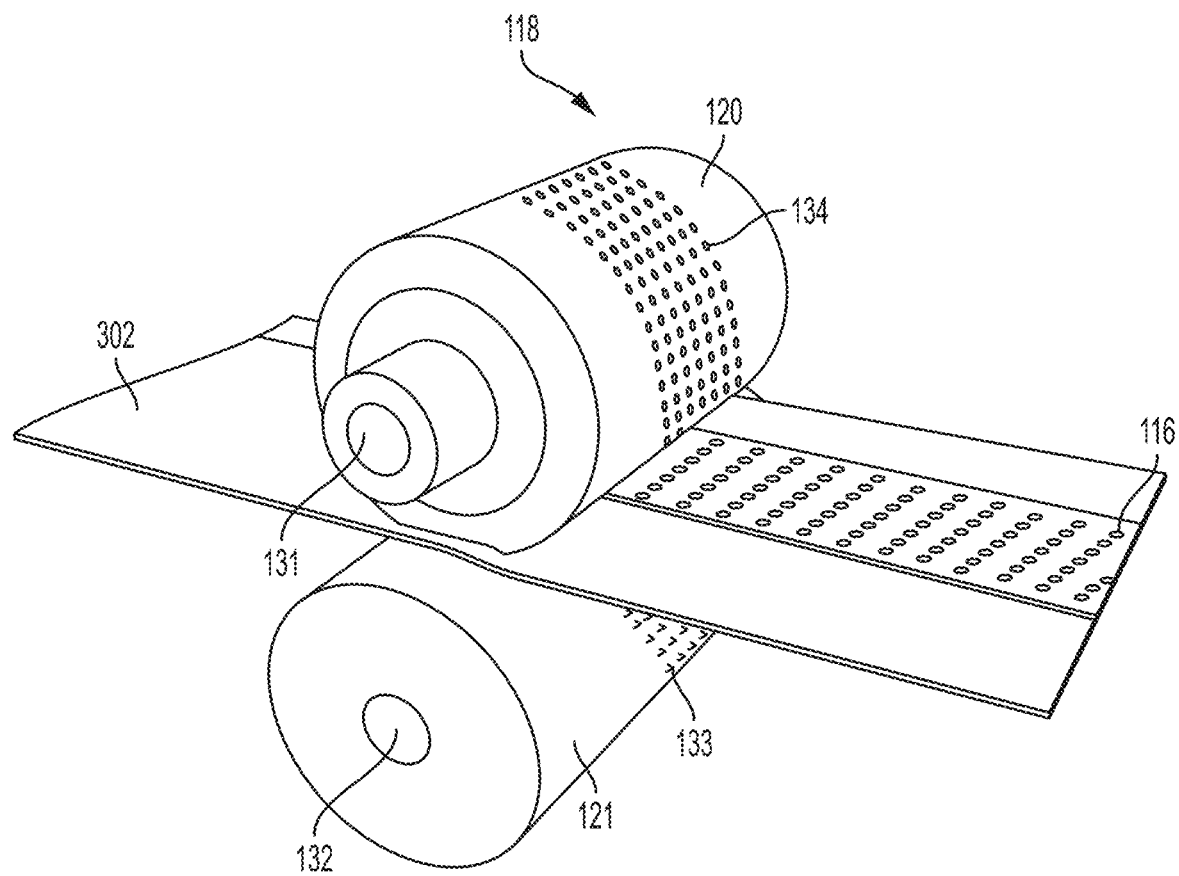
FIG. 9J is a perspective side view of a converting apparatus adapted to deform an elastomeric laminate via aperturing.
Figure 10:
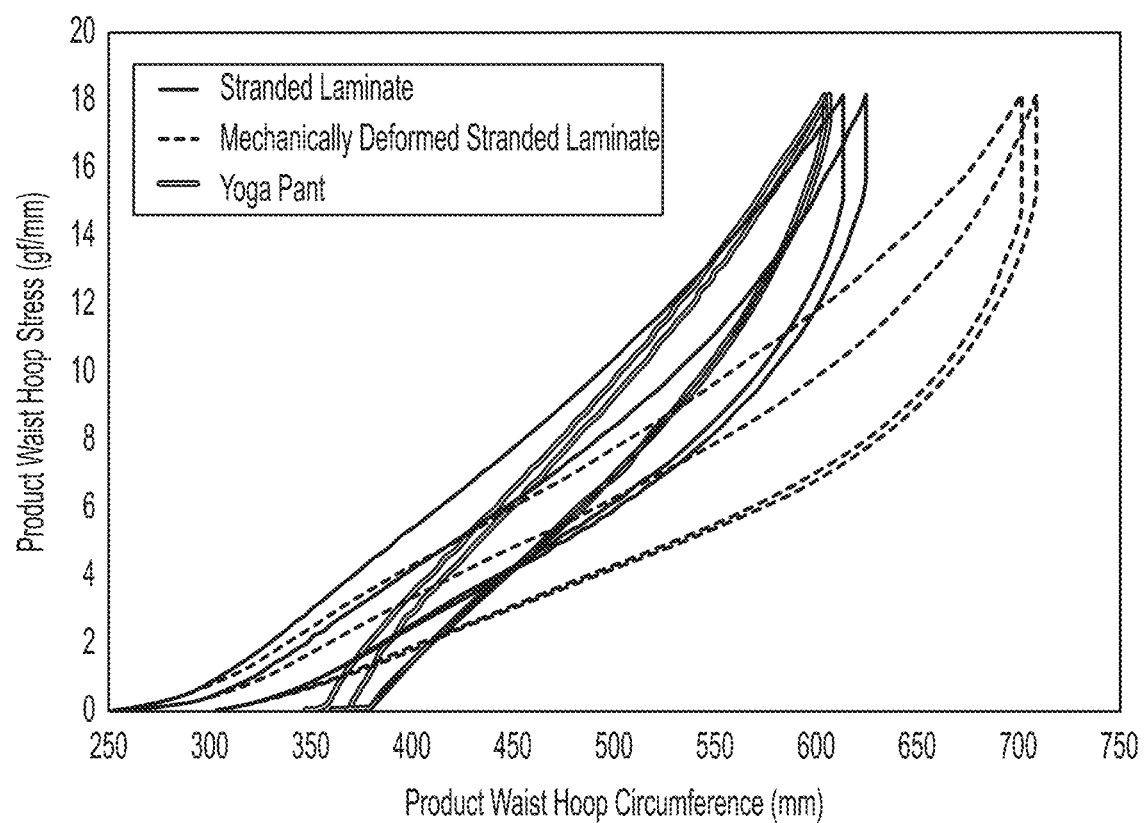
FIG. 10 shows the Waist-Hoop-Stress versus Waist-Hoop-Circumference curves of: a beamed laminate consistent with the belt of FIG. 5D, that same beamed laminate after MD activation consistent with FIG. 5E, and a comparative yoga pant consistent with FIG. 5I, as generated in the Hip-Hoop-Test.

FIG. 9J illustrates aperturing an elastomeric laminate of the present disclosure by trapping an elastomeric laminate 302 between two engaging patterned rolls 120 and 121 that are driven in a rotating motion. The rolls 120 and 121 may have corresponding holes 134 and teeth 133, where the teeth 133 pierce the elastomeric laminate 302, or one of the substrate layers 306, 308 making up the elastomeric laminate 302, and interface with the holes 134 to create apertures 116, such as the ones illustrated in FIG. 1E. The apertures 116 may be generally circular, oval, triangular, may be slits, arcs, or combinations thereof.

Aperturing of the elastomeric laminate or one or more of the substrate layers making up the elastomeric laminate can increase the extensibility and/or lower the Laminate-Modulus of the elastomeric laminate, as well as increasing the breathability of the substrate layer and/or the overall laminate. Typically, the higher the percentage of surface area of the elastomeric laminate occupied by the apertures, the higher the extensibility and the lower the Laminate-Modulus. One or more of the elastomeric laminate substrate layers 306, 308 may comprise apertures 116 wherein the elastic strands 316 are present in the aperture area—see FIG. 2B. The apertures 116 may go through one or all of the substrate layers of an absorbent article component, such that the apertures are aligned or such that the apertures 116 of the substrate layers (e.g., 306, 308) are not aligned. When not aligned, the substrate layers (e.g., 306, 308) may have color contrast so that the apertures are more noticeable. Alternatively, the elastomeric laminate 302 may comprise a first laminate substrate 306 and a second laminate substrate 308 adhesively bonded (such as via spiral, slot, spray, a discrete pattern (in the CD and/or the MD), or combinations thereof) together with the elastic strands disposed between the first and second laminate substrates, the apertures may extend through both of the laminate substrates and through the elastic strands 316 severing some or all of the strands in the aperture area—see FIG. 2C, where the elastic element 316 snapped back and clear from the apertures 116 to the glue block 141 end edges 135. The mechanical transformation that forms the apertures may be carried out on one or both of the substrate layers prior to combining them to form the elastomeric laminate. Alternatively, the mechanical transformation forming the apertures may be carried out after the laminate is formed.

Figure 12A:
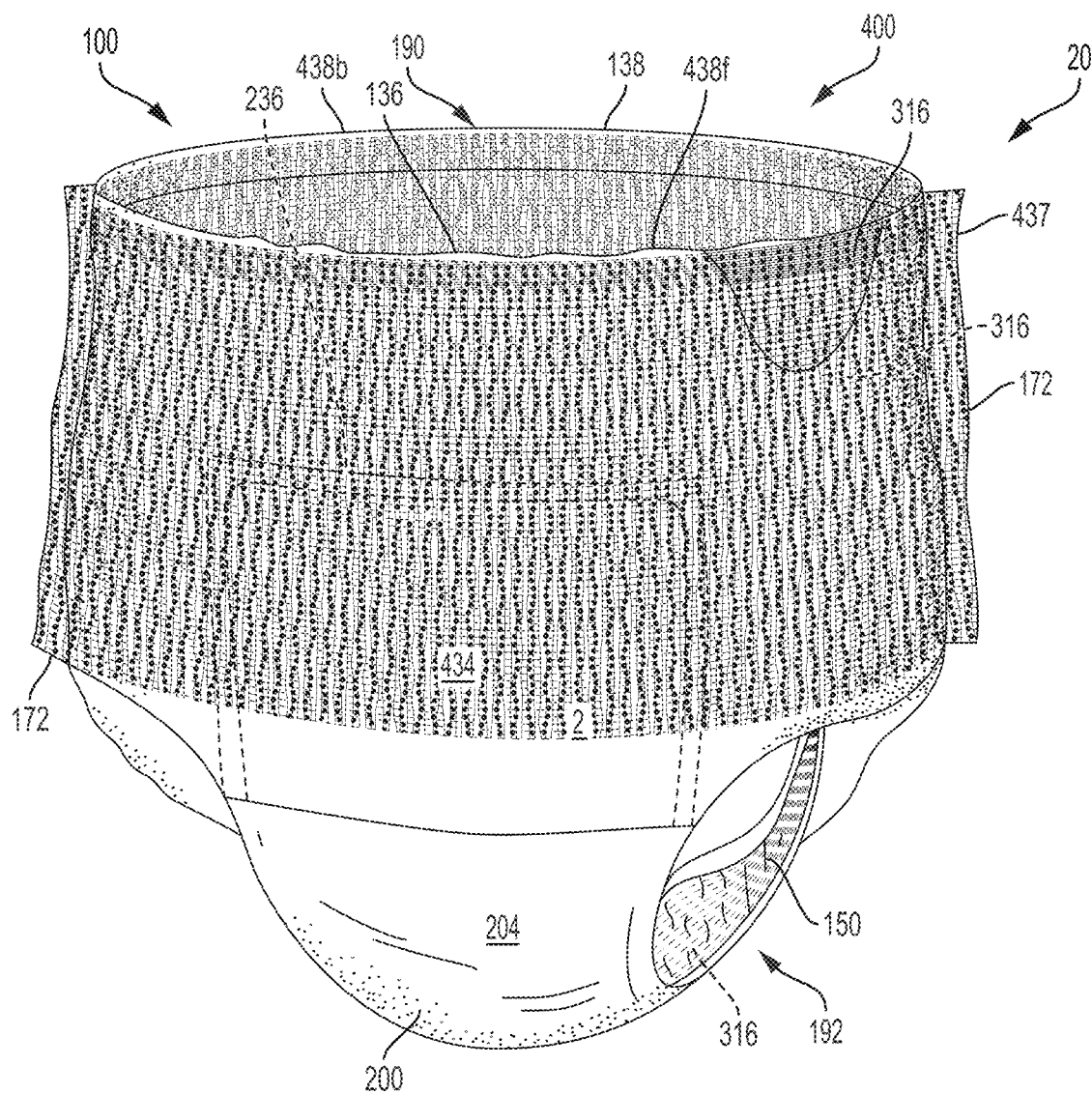
FIG. 12A is a perspective front view of a pant comprising discrete front and back belts that have been deformed via MD activation.
Figure 12B:
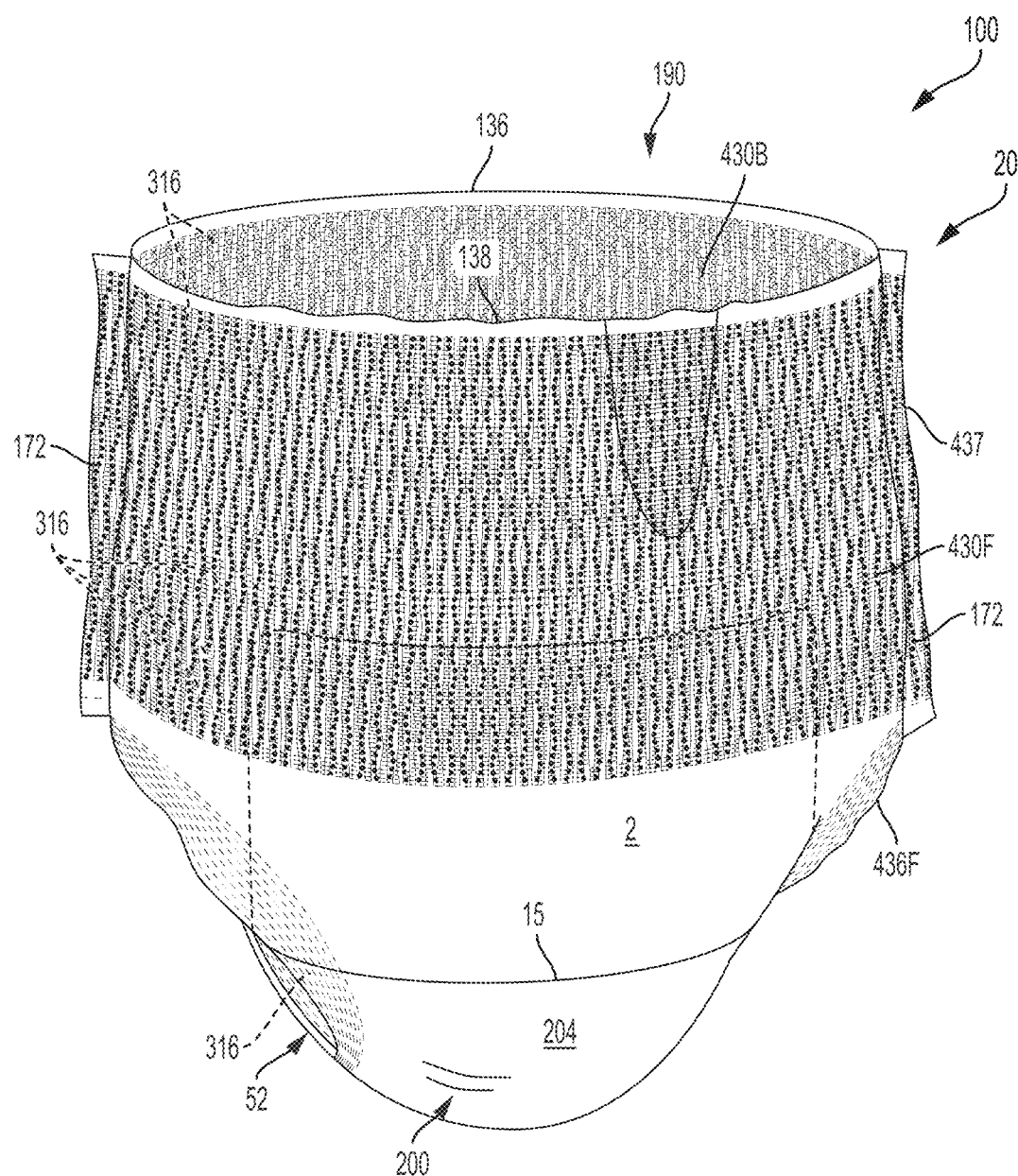
FIG. 12B is a perspective back view of the pant of FIG. 12A.

The surface area of the elastomeric laminate 302, when stretched out and laid flat, occupied by the apertures themselves may be from about 2% to about 25%, or from about 5% to about 20%, or from about 10% to about 15%. In general, the higher the surface area percentage occupied by the apertures the greater the extensibility and the lower the modulus. The apertures 116 can be formed via needle punching, hot air welding/aperturing, thermal bonding/aperturing, ultrasonic bonding/aperturing, pressure welding/aperturing, stretch aperturing, substrate bonds or slits that open to form apertures when activated (see, for example, U.S. Pat. No. 6,830,800 and U.S. Pat. App. No. 2003/0021951). The apertures 116 may be distributed uniformly across the surface of the elastomeric laminate or may be selectively disposed in one or more of Sections 1, 2, 3, and 4 (See FIGS. 12O and 12P where apertures are selectively in Sections 1 and 4, but are not in Sections 2 and 3). As shown in FIGS. 12Q and R, the apertures 116 may be selectively disposed in one or more of sections L, M or R. In certain embodiments the aperturing may only be present in Sections 3 and 4 of Section M (see FIG. 12U)—in such embodiments the apertures allow the elastomeric laminate to relax partially thereby allowing the chassis to be less contracted in the overlap region than it might have been if the apertures were not present in the elastomeric laminate. Further, the apertures 116 may be present in areas of the elastomeric laminate 302 not overlapping the chassis to not only provide an incremental increase in extensibility, a reduction in Laminate-Modulus, but to improve breathability perception and functionally (see, for example, FIGS. 12Q and 12R).

Deformation Zones

Figure 2A:
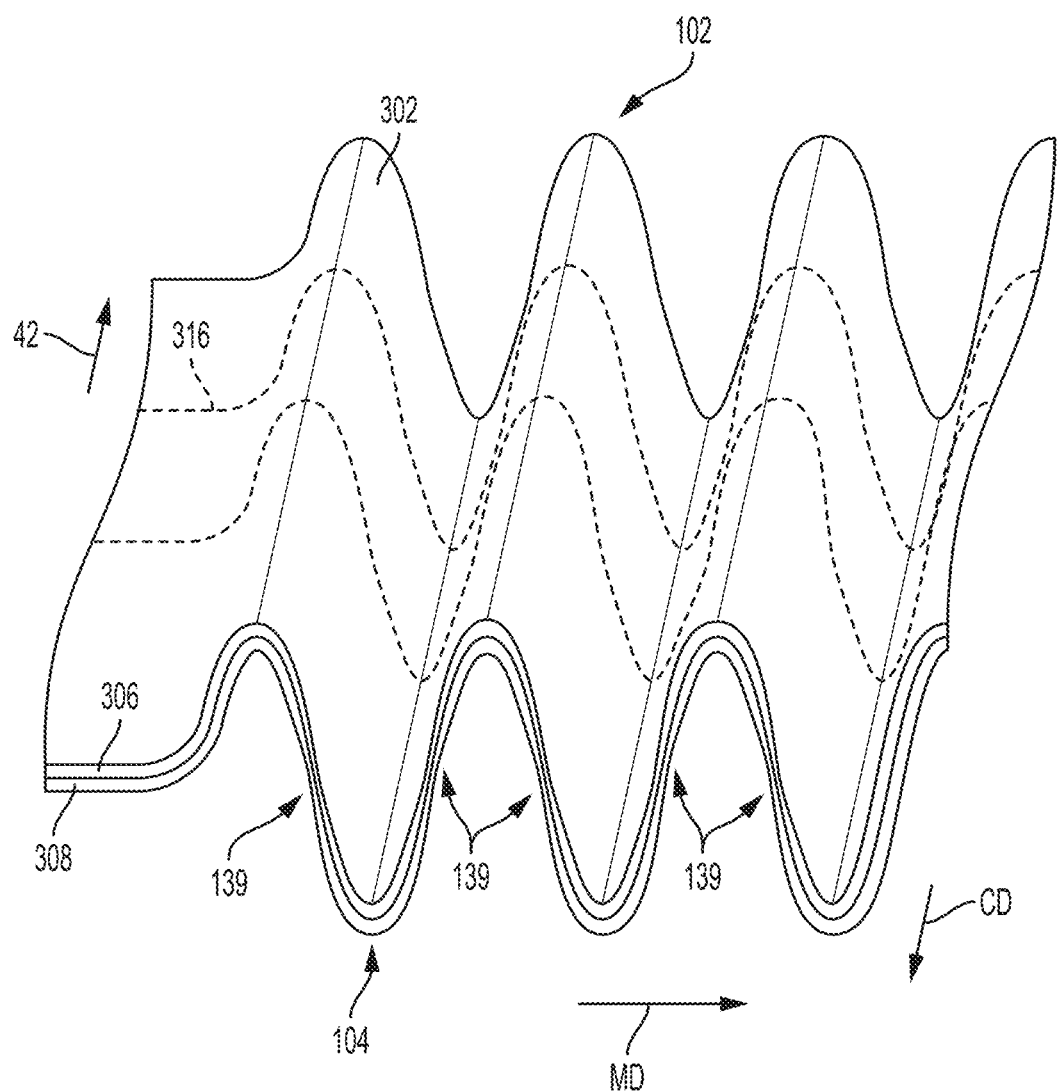
FIG. 2A is a perspective side view illustrating an inventive laminate of the present disclosure that has been deformed via MD activation.
Figure 2B:
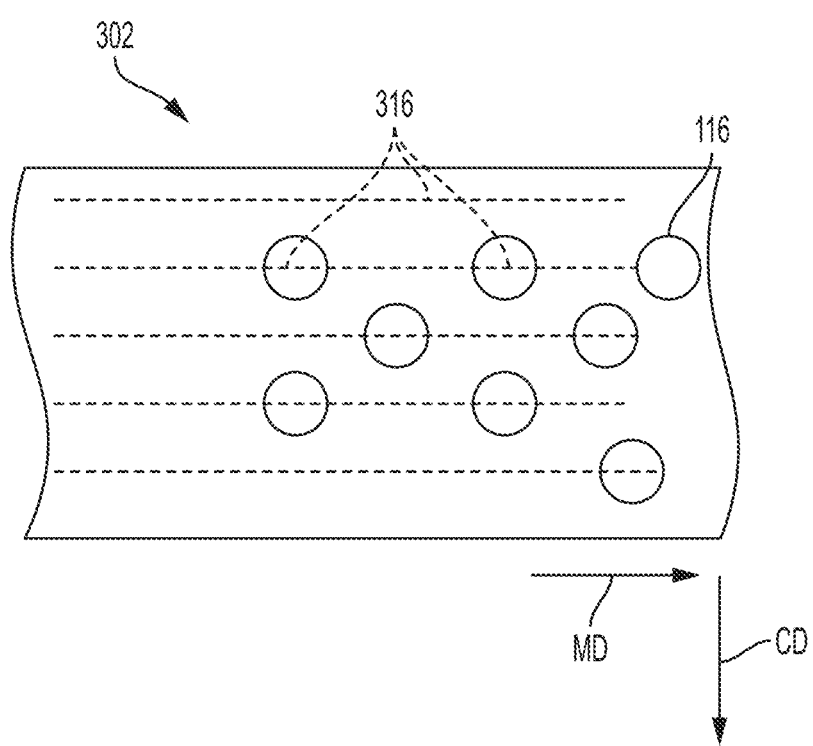
FIG. 2B is a top view illustrating an inventive laminate of the present disclosure that has been deformed via aperturing.
Figure 2C:
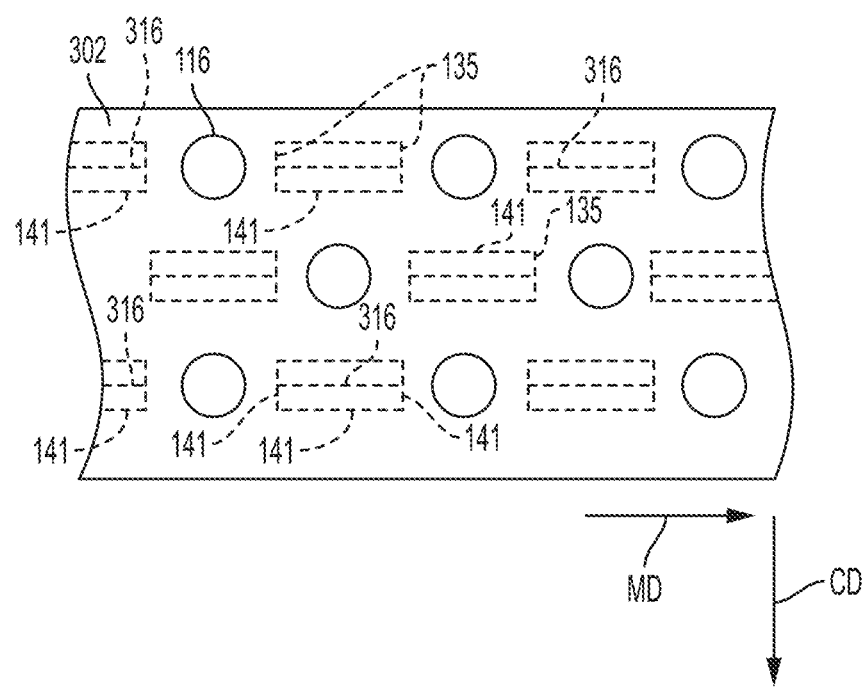
FIG. 2C is a top view illustrating an inventive laminate of the present disclosure that has been deformed via aperturing.
Figure 2D:
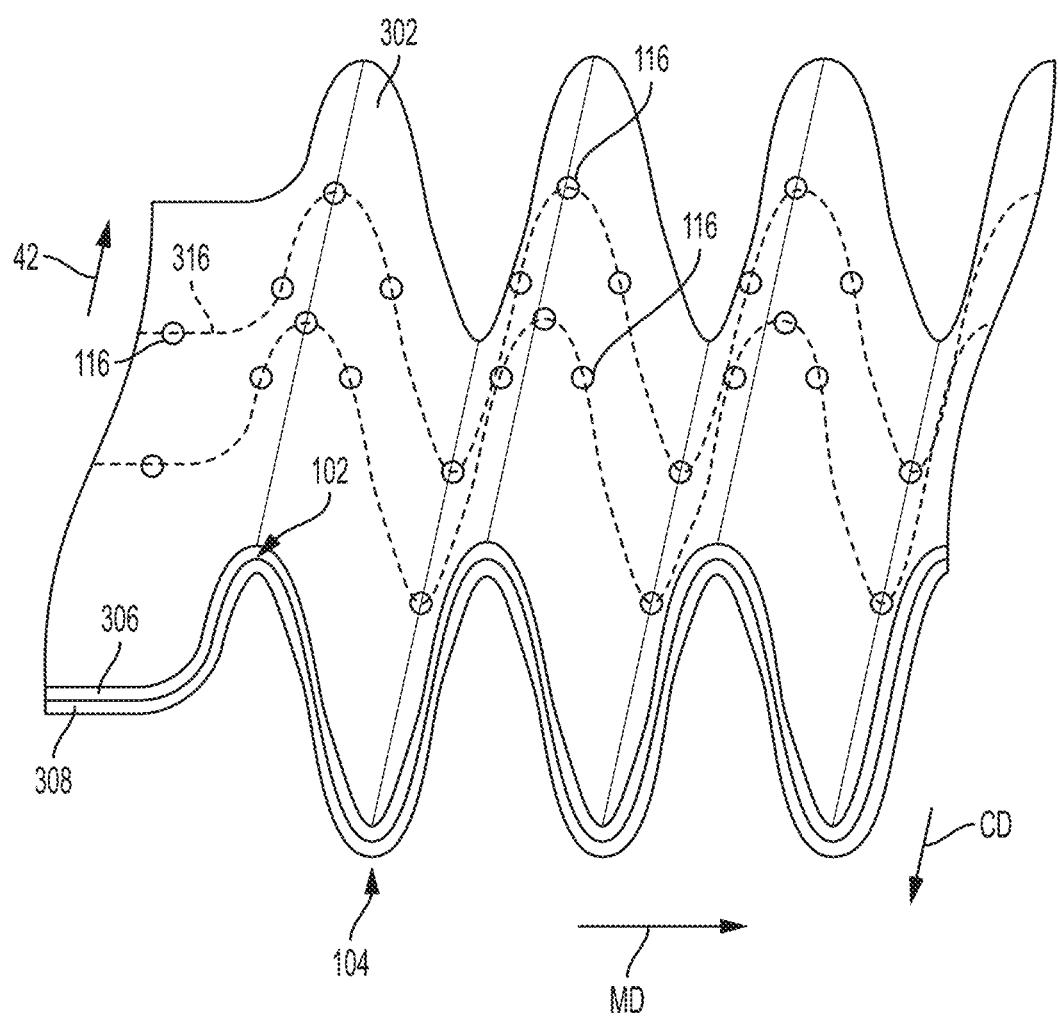
FIG. 2D is a perspective side view illustrating an inventive laminate of the present disclosure that has been deformed via aperturing and MD activation.

As shown in FIGS. 12A-F, 12K-V, 13, and 14, an article component (e.g., a belt, a side panel, and ear panel, etc.) may comprise a plurality of the same or different mechanical deformation zones that may be of similar shape, scale, disposition, and/or pattern in various sections (e.g., Sections 1, 2, 3, 4, L, R, or M). As shown in FIG. 2A, the mechanical deformation zones may be formed in an elastomeric laminate 302 by MD activation to create a pattern of generally longitudinally oriented alternating ridges 102 and valleys 104. An elastomeric laminate 302 like the one illustrated in FIG. 2A may be used as a belt 430 and oriented so that the machine direction of the laminate is parallel with a transverse axis of an absorbent article comprising the belt 430. As shown in FIG. 2B, the mechanical deformation zones may be formed in an elastomeric laminate 302 by aperturing to create a pattern of apertures 116.

Figure 12C:
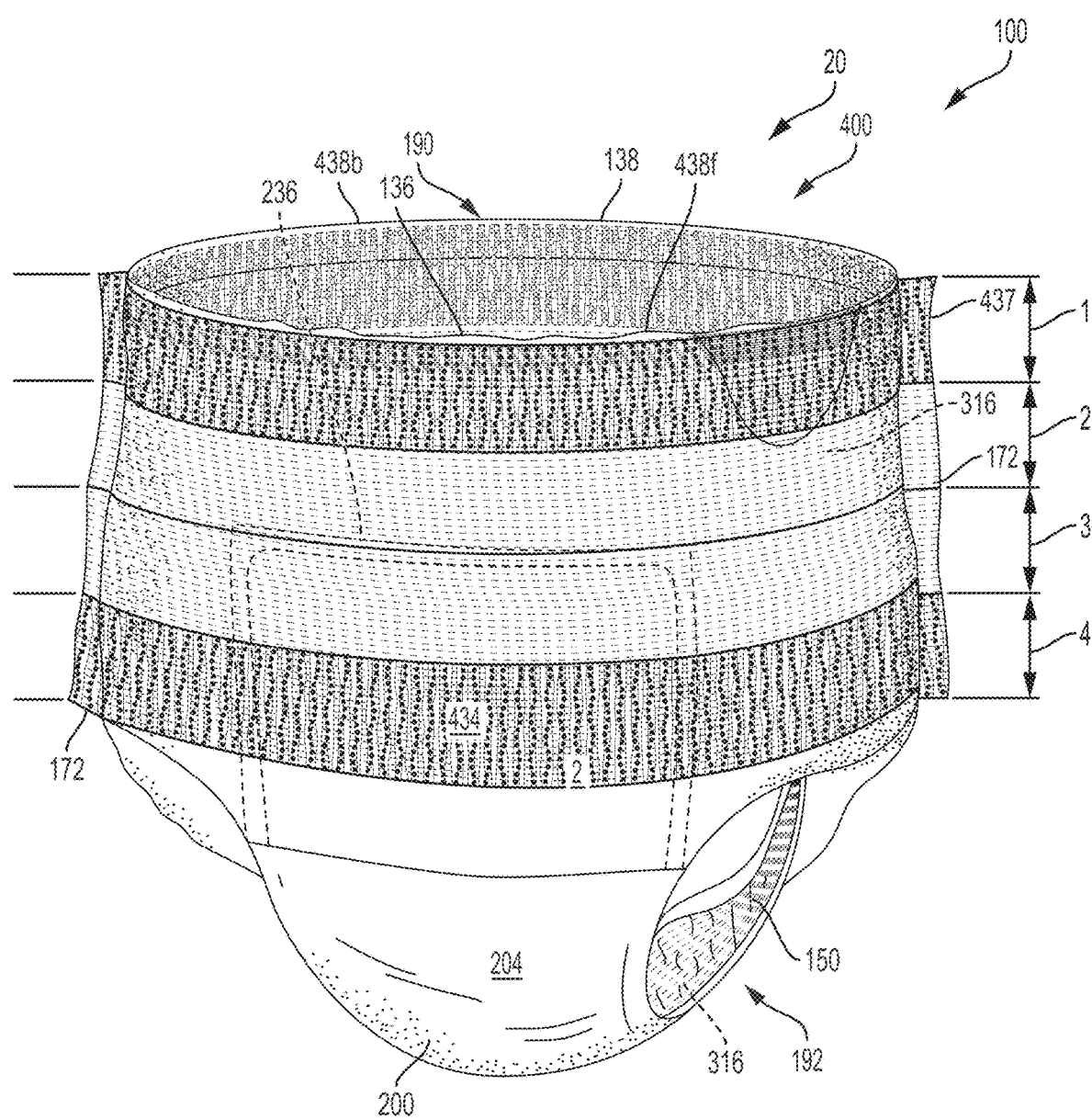
FIG. 12C is a perspective front view of a pant comprising discrete front and back belts comprising Sections 1 and 4 that have been deformed via MD activation.
Figure 12D:
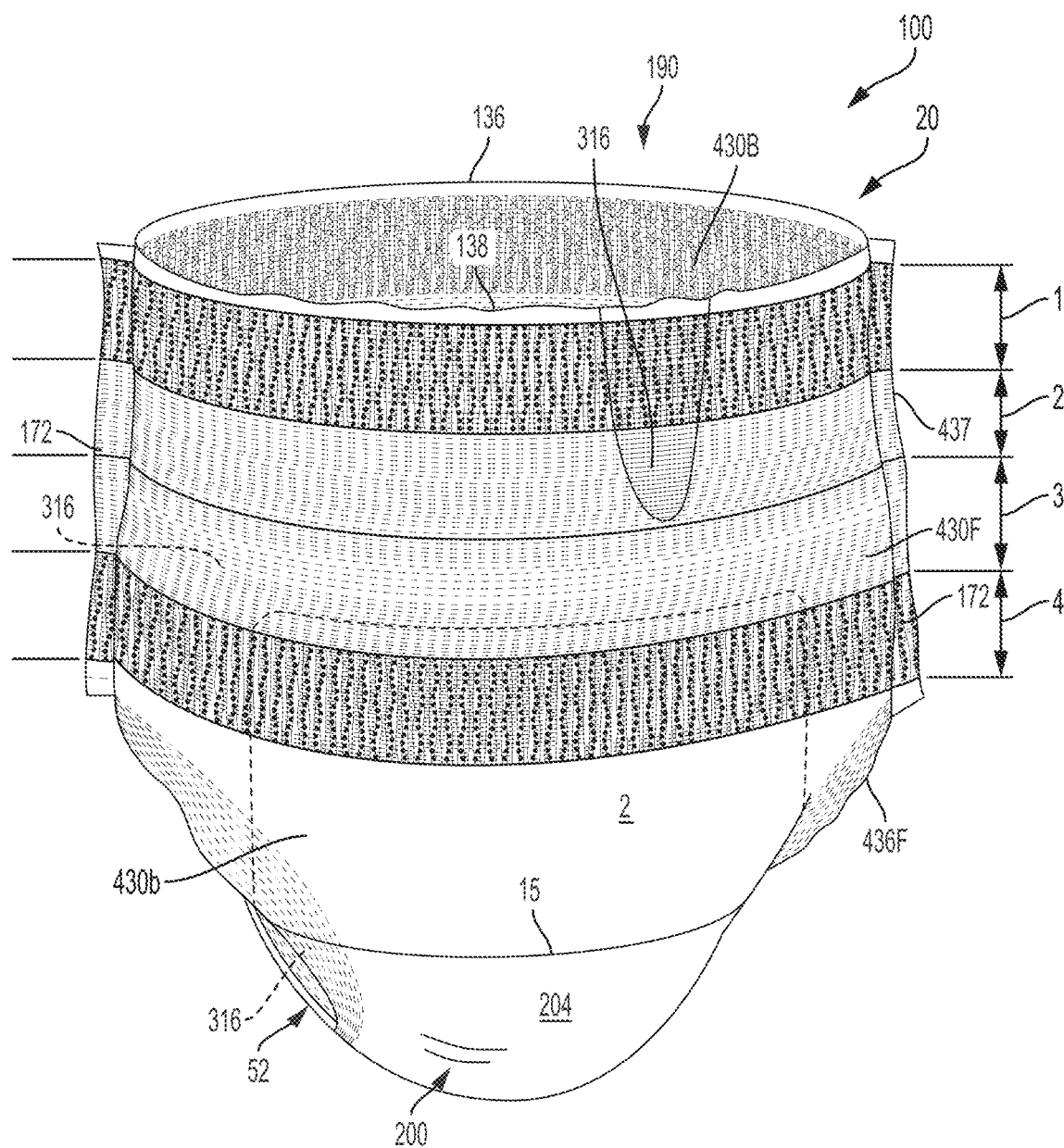
FIG. 12D is a perspective back view of the pant of FIG. 12C, illustrating that Sections 1 and 4 of the back belt have been deformed via MD activation.

As shown in FIGS. 12C, D, F, K, L, O-T, the elastomeric laminate 302 may also include undeformed (unaltered) zones, i.e., zones that have not been mechanically deformed—see particularly Sections 2 and 3 in FIG. 12C. Or, instead of undeformed zones, the contrasting sections may have different mechanical deformation arrangements accomplished by a different tooth height, tooth spacing, tooth pitch, undeformed surface area, tooth shape of the plate or roll. For example, Sections 1 and 4 may be mechanically deformed by intermeshing rolls having a first tooth configuration and Sections 2 and 3 may be mechanically deformed by intermeshing rolls (or plates) having a second tooth configuration (e.g., a different tooth height, tooth spacing, tooth pitch, undeformed surface area, tooth shape). A mechanical deformation process similar to the one shown in FIG. 9D could be used to create such a mechanical deformation arrangement. Another way to accomplish contrasting sections is to use one deformation type over the whole substrate and use a second deformation type over certain sections—see FIG. 12V where Sections L, M, and R are apertured, but only Sections L and R are MD-activated. Still, another way to accomplish contrasting sections is to use one deformation type in some sections, but a second deformation type in other sections—see FIG. 12U where Section M is apertured, but not MD-activated, and Sections L and R are MD-activated, but not apertured.

Each of the sections of the elastomeric laminate 302 may comprise a mechanical deformation arrangement to form the same or similar texture zone (i.e., the same or substantially the same presentation of texture due to pattern of deformation, degree of deformation, etc. Alternatively, the mechanical deformation arrangement in one or more Sections 1, 2, 3, 4, L, M, and R may be different from the mechanical deformation arrangement in another Section to form different texture or performance zones. Different texture or performance zones may be formed by adjusting the depth of engagement of the mechanical tooling, spacing of elements on the mechanical tooling, as well as nonwoven type, bond pattern, web tension, strain rate of the laminate during the deformation process, etc. It should also be noted that the texture and/or mechanical deformation arrangement may be mirrored across one or both of the longitudinal and/or lateral centerlines to create a balanced more holistic textural appearance.

The garment-facing surface 2 of a substrate in the area where a wearer-facing surface 4 of the article component is joined to the chassis, often by spiral or slot-coated adhesive, may have a discernable textural difference even when it comprises the same mechanical deformation arrangement and the same elastic profile as adjacent areas of the article component because the adhesive joining the article component to the chassis may partially deaden the impact of elastics 316 in that area; further, the elastic strands may be severed in said area so that they do not run continuously across the chassis 200.

As shown in FIGS. 12A, B, E, M, and N, the elastomeric laminate 302 may comprise a transversely (from side seam to side seam) and a longitudinally (from the most distal component elastic to the most distal component elastic) continuous mechanical deformation arrangement. FIGS. 12C, D, F, O, and P illustrate a transversely continuous mechanical deformation arrangement, that is interrupted (i.e., non-continuous) longitudinally. FIGS. 12K, L, Q, and R illustrate a longitudinally continuous mechanical deformation arrangement, that is interrupted (i.e., non-continuous) transversely.

Extend/Cooperate

As shown in FIGS. 12C and D, the deformation from one section may "extend into" another section or "cooperate" with deformation in various sections to form a larger composite zone. For instance, an end edge of a deformation zone in a section may substantially align with an end edge of the deformation zone in an adjacent section such that the deformation zone is, or appears to be, continuous through multiple sections or such that a larger composite zone is formed (e.g., an arc, serpentine curves, etc.). For example, a deformation zone in Section 2 may have an end edge 151 that is substantially aligned with an end edge 152 of a deformation zone in Section 3—see FIG. 12S. In this way, a deformation zone may extend or appear to extend through Sections 1, 2, 3, 4 and/or L, R, and M. Furthermore, as shown in FIG. 12T, an end edge of a deformation zone in a section disposed in a first waist region may substantially align with an end edge of a deformation zone in an adjacent section disposed in a second waist region such that the deformation zone is, or appears to be, continuous from a first waist region to a second waist region such that a larger composite zone is formed—see end edges 143/144 of texture zones in Section 1 of front belt 430f and Section 1 of 430b and see end edges 145/146 of texture zones in Section 4 of front belt 430f and Section 4 of 430b.

Figure 12E:
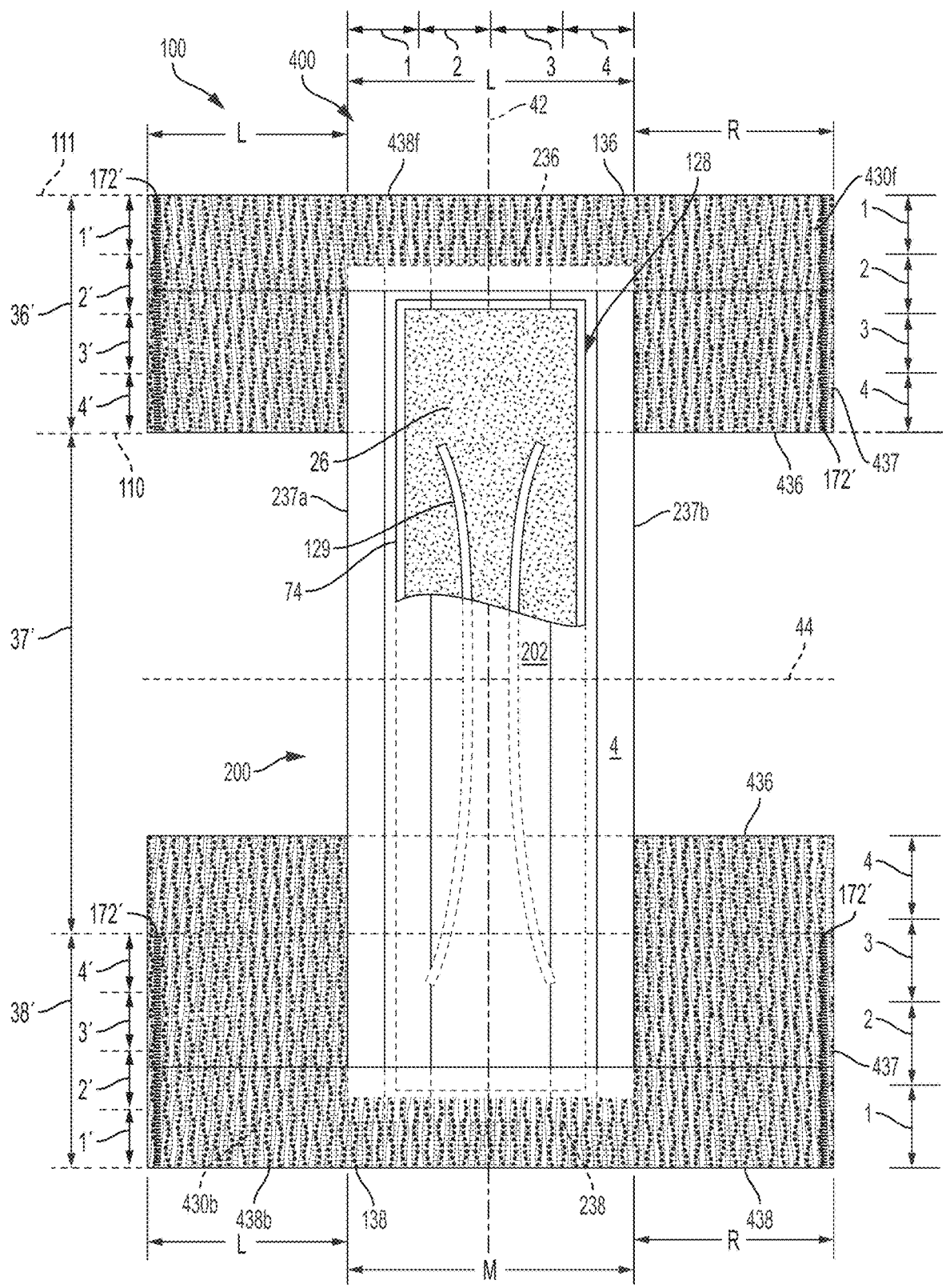
FIG. 12E is a plan view of the pant of FIG. 12A, prior to joining side edges of the belt to form the waist and leg openings.
Figure 12F:
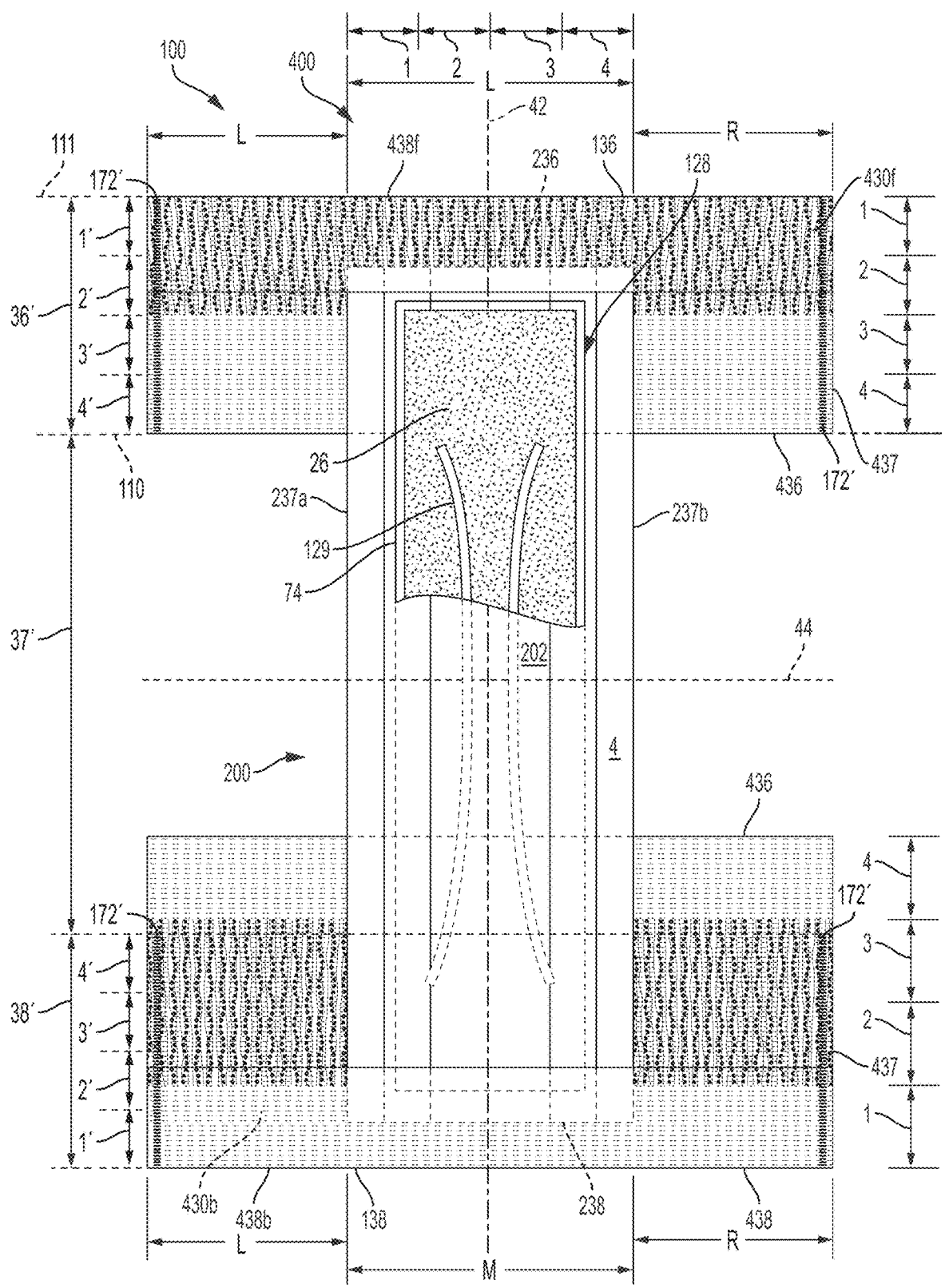
FIG. 12F is a plan view of the pant of FIG. 12A, prior to joining side edges of the belt to form the waist and leg openings, illustrating that Sections 1 and 2 of the front belt have been deformed via MD activation and illustrating that Sections 2 and 3 of the back belt have been deformed via MD activation.
Figure 12G:
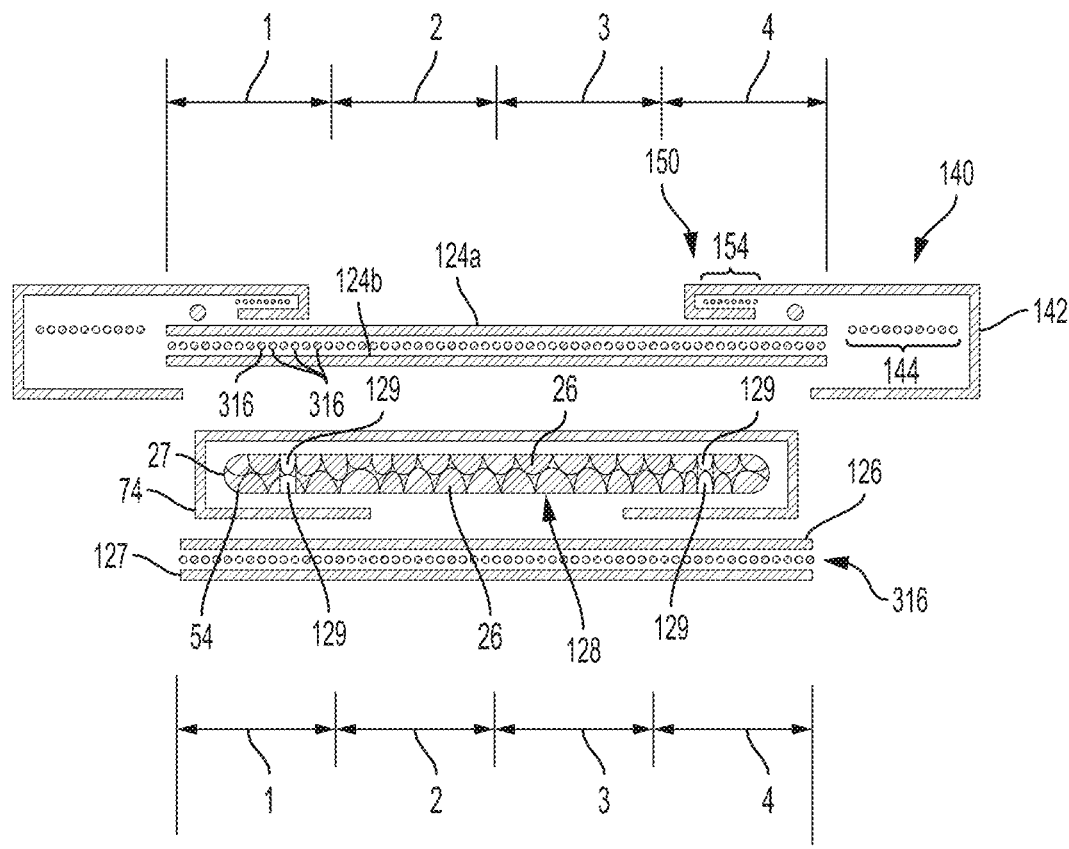
FIG. 12G is a cross-section view of the pant of FIG. 12E taken along the transverse axis 44, illustrating the elasticized topsheet (showing elastics 316 oriented parallel to the longitudinal axis 42) and the elasticized backsheet (showing elastics 316 oriented parallel to the longitudinal axis 42).
Figure 12J:
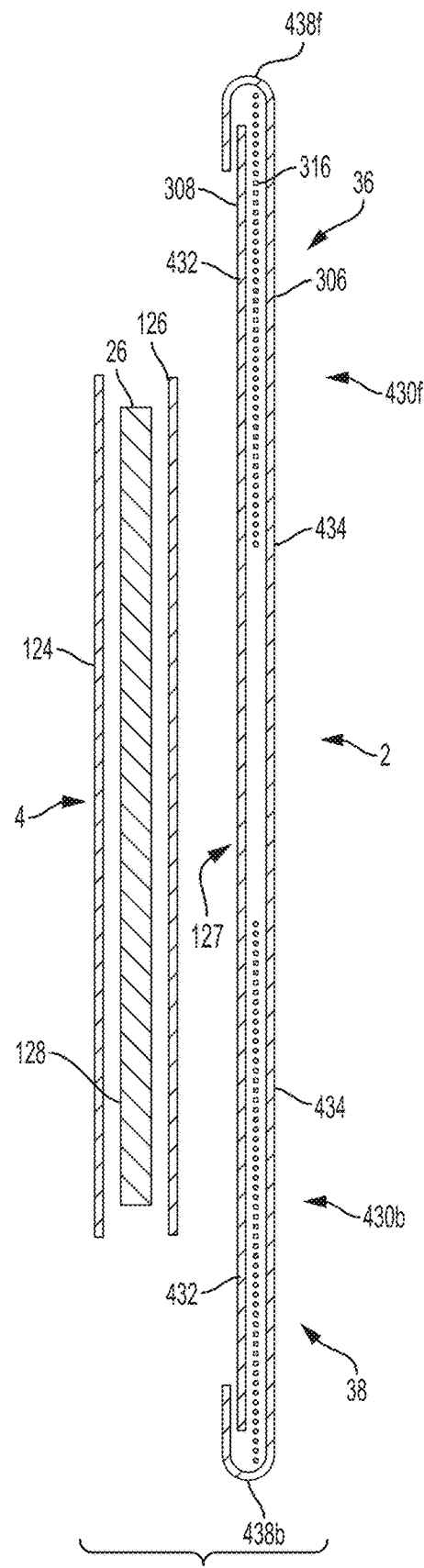
FIG. 12J is a cross-section view of an alternate embodiment of the belt pant of FIG. 12E taken along the longitudinal axis 42, showing a common inner belt layer 432 and common outer belt layer 434.
Figure 12K:
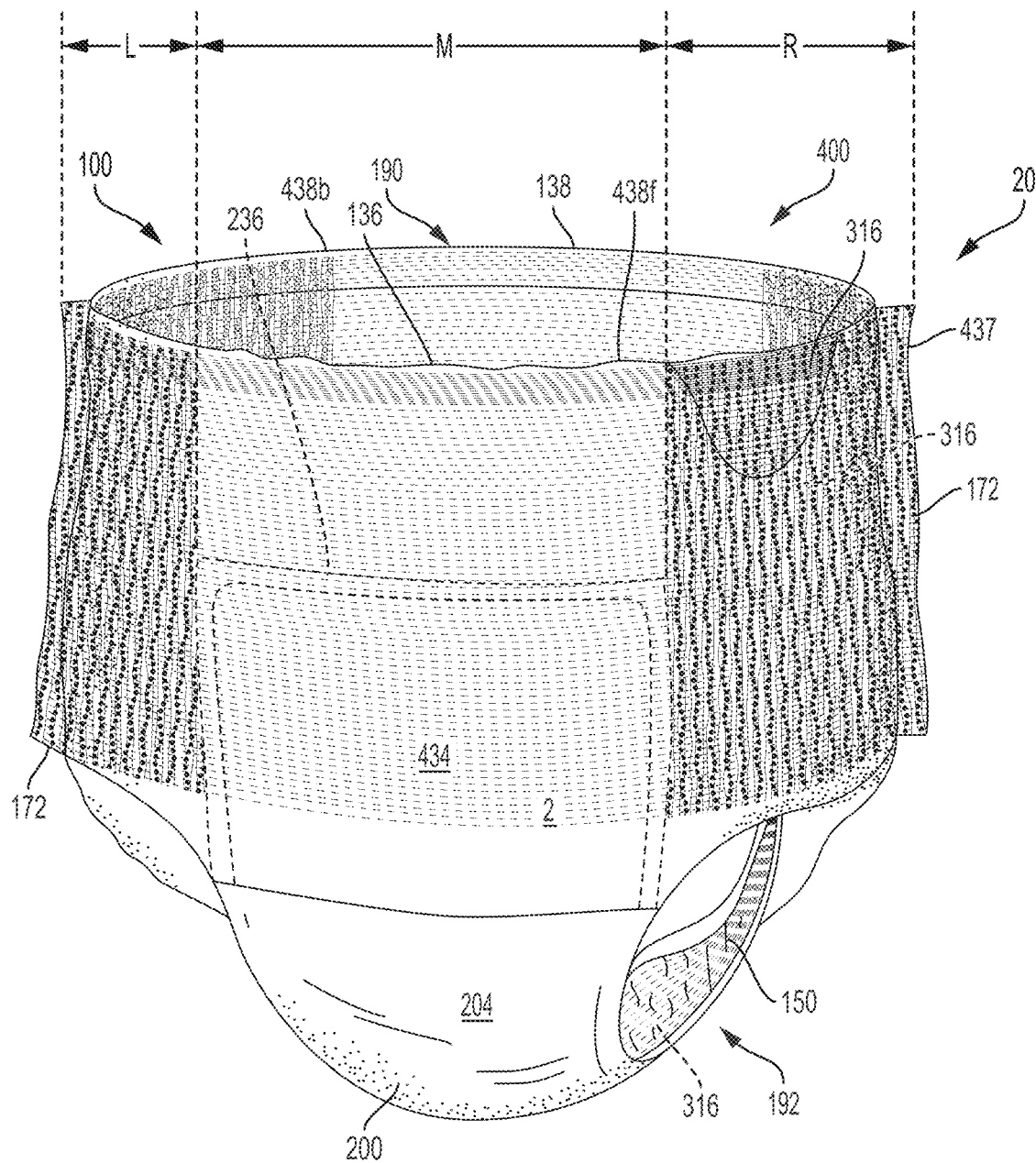
FIG. 12K is a perspective front view of a pant comprising discrete front and back belts comprising Sections L and R that have been deformed via MD activation.
Figure 12L:
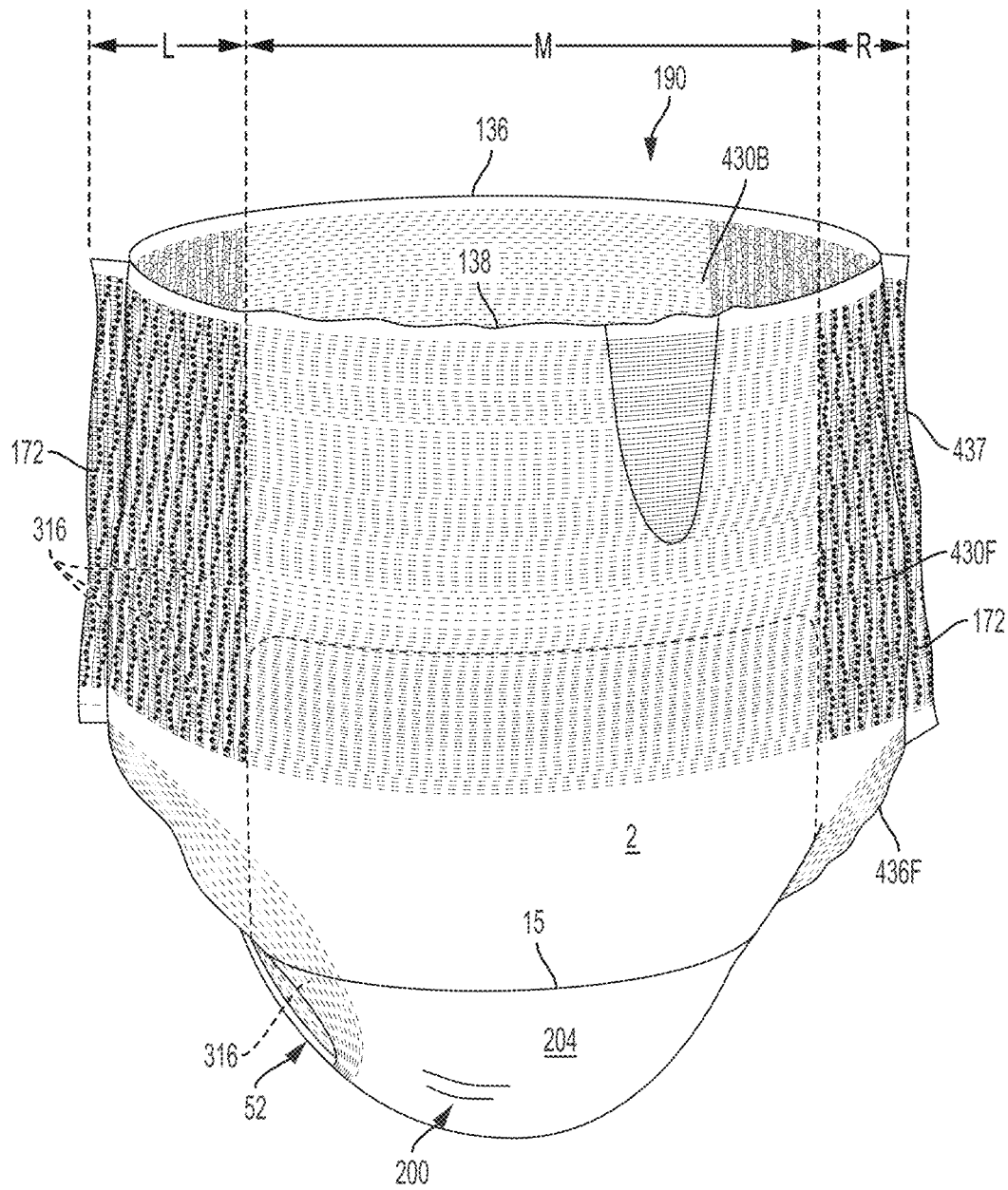
FIG. 12L is a perspective back view of the pant of FIG. 12K, illustrating that Sections L and R of the back belt have been deformed via MD activation.
Figure 12M:
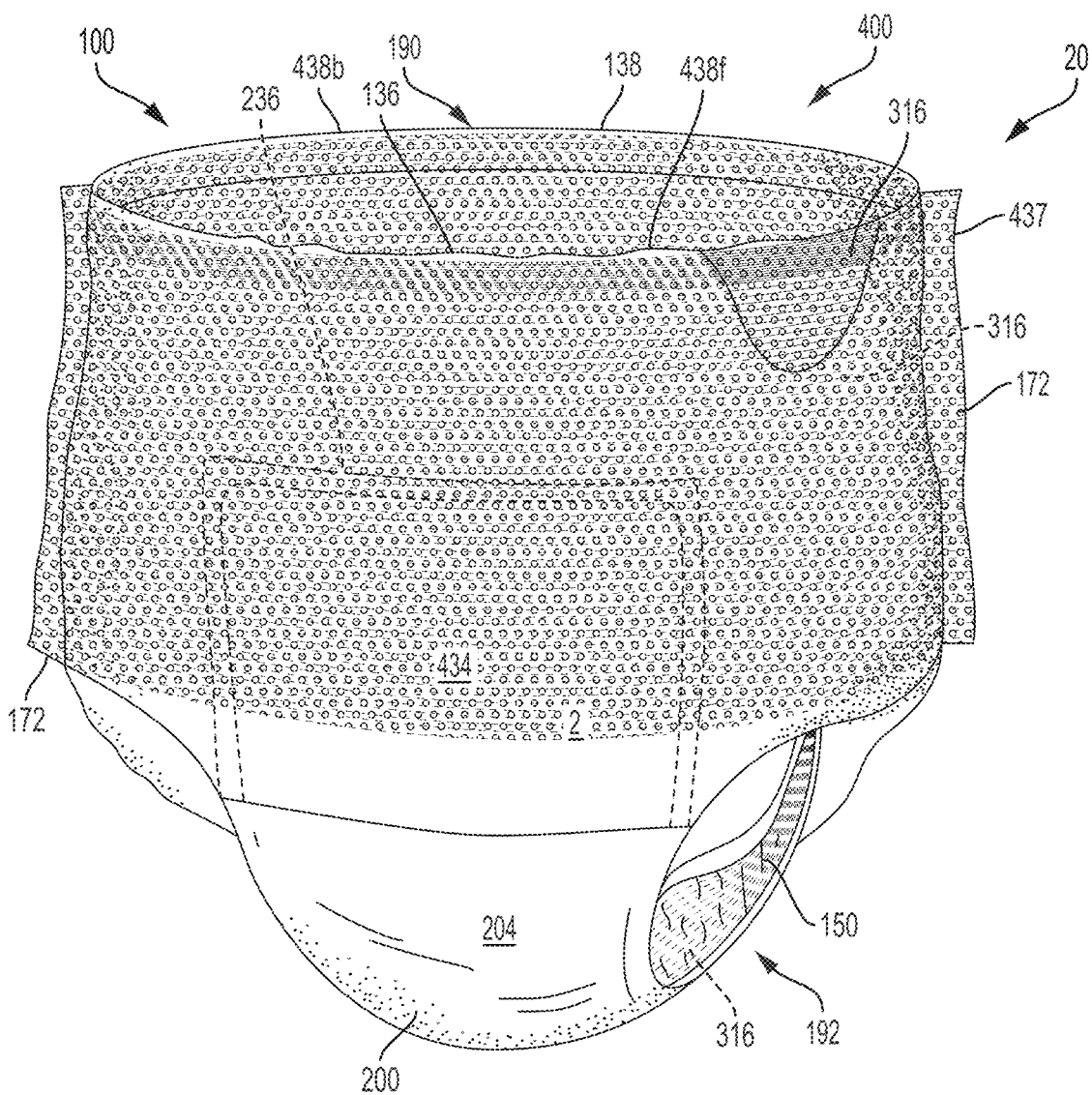
FIG. 12M is a perspective front view of a pant comprising discrete front and back belts that have been deformed via aperturing.
Figure 12N:
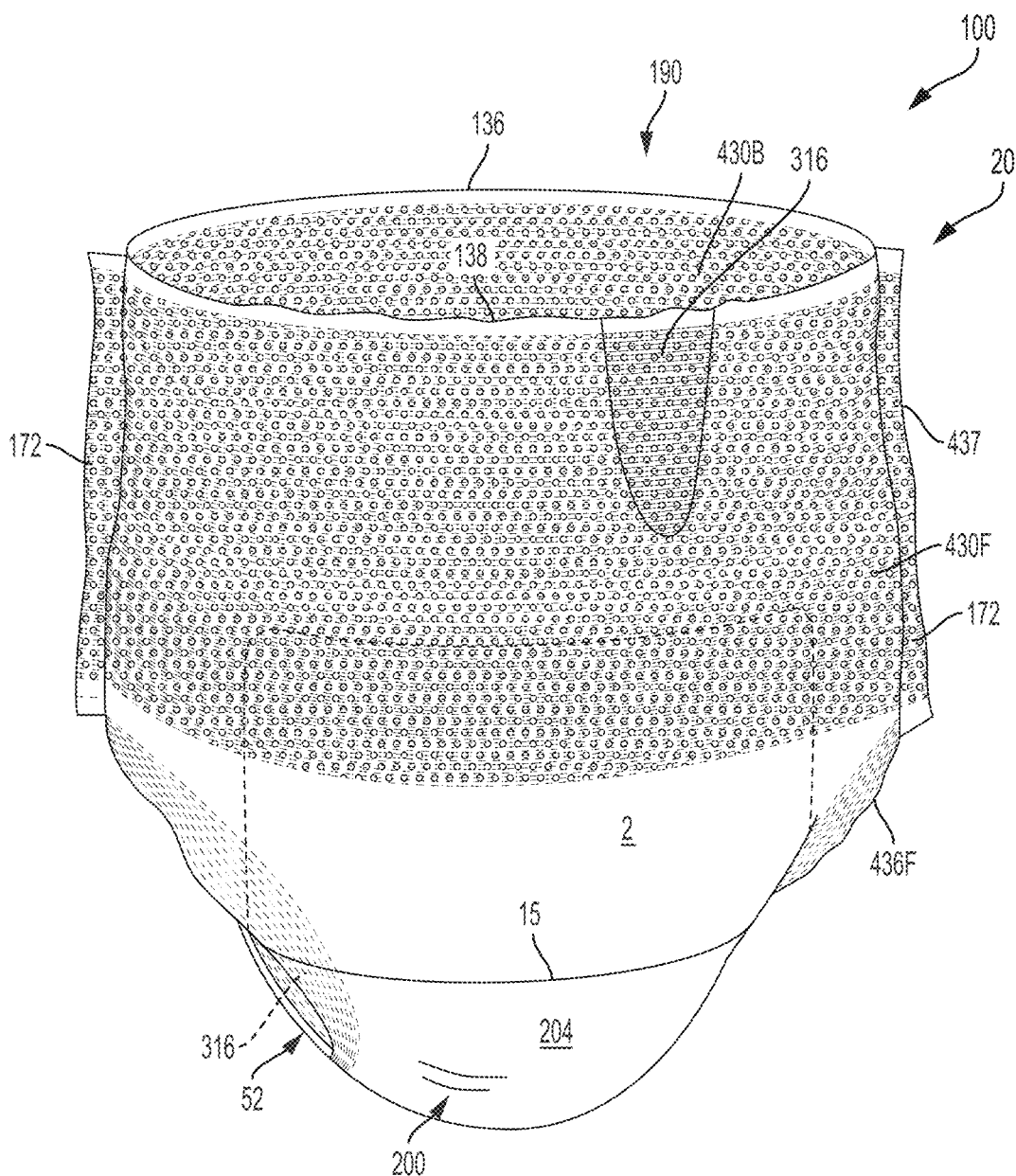
FIG. 12N is a perspective back view of the pant of FIG. 12M.
Figure 12O:
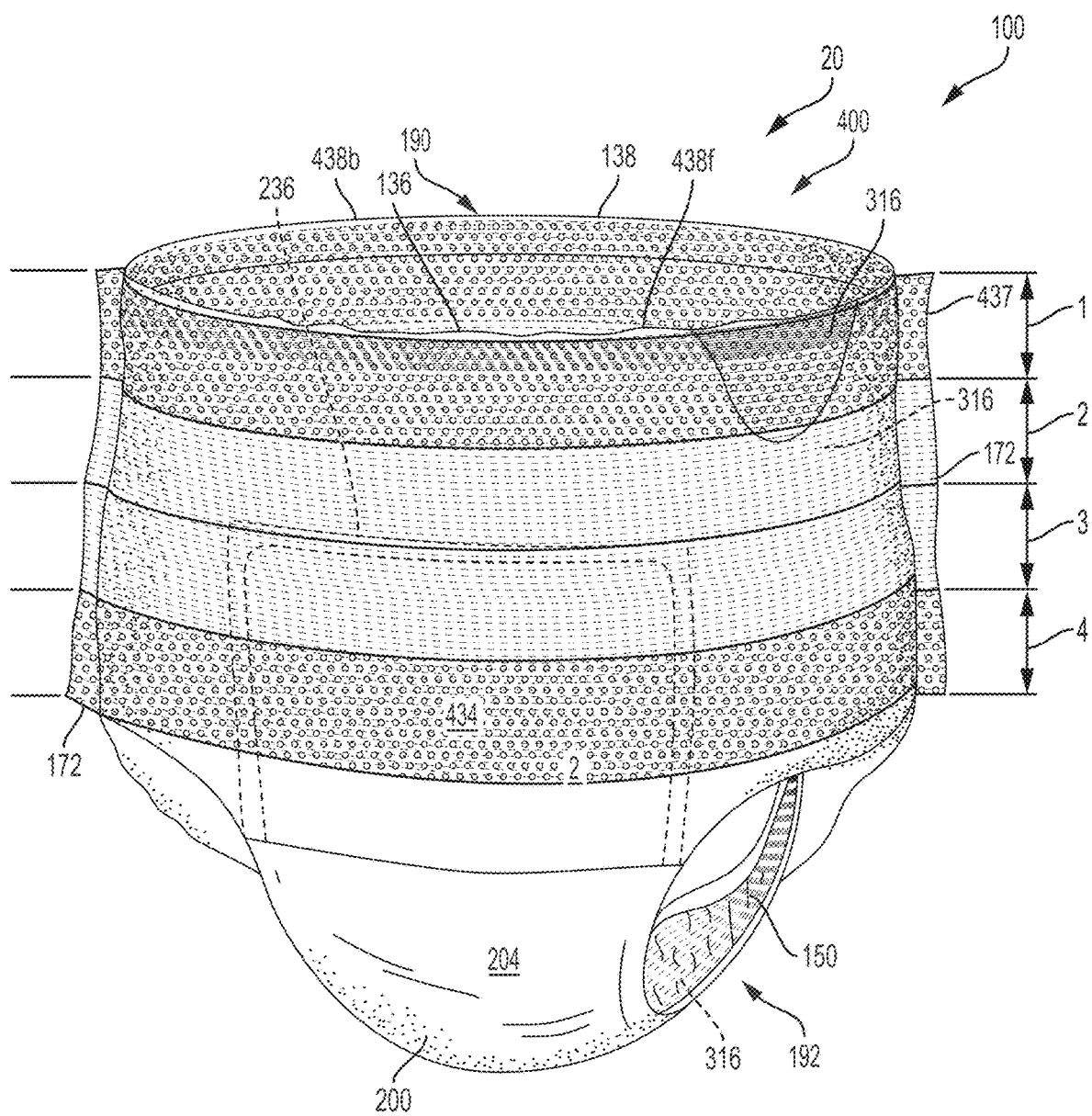
FIG. 12O is a perspective front view of a pant comprising discrete front and back belts comprising Sections 1 and 4 that have been deformed via aperturing.
Figure 12P:
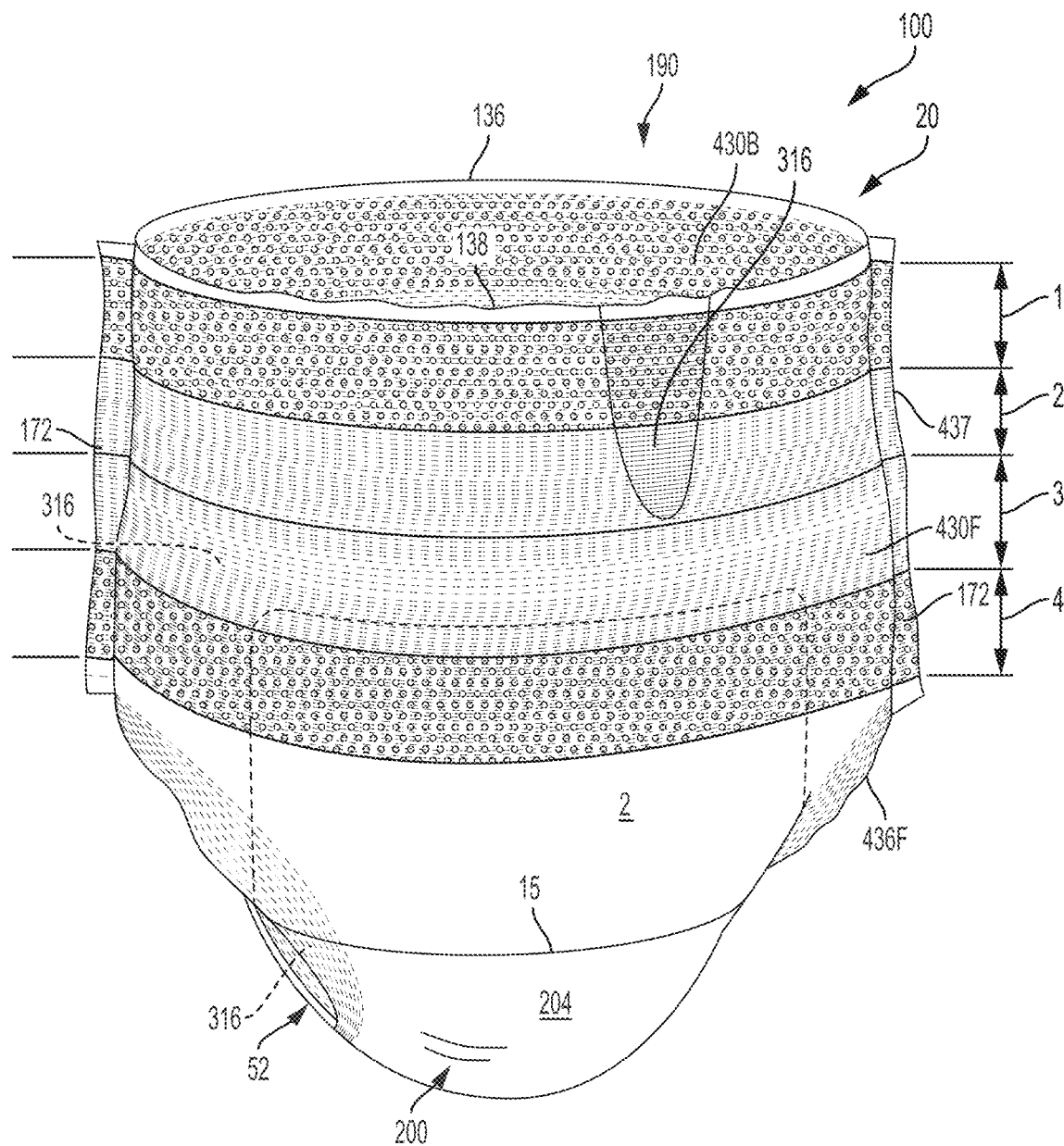
FIG. 12P is a perspective back view of the pant of FIG. 12O, illustrating that Sections 1 and 4 of the back belt have been deformed via aperturing.
Figure 12Q:
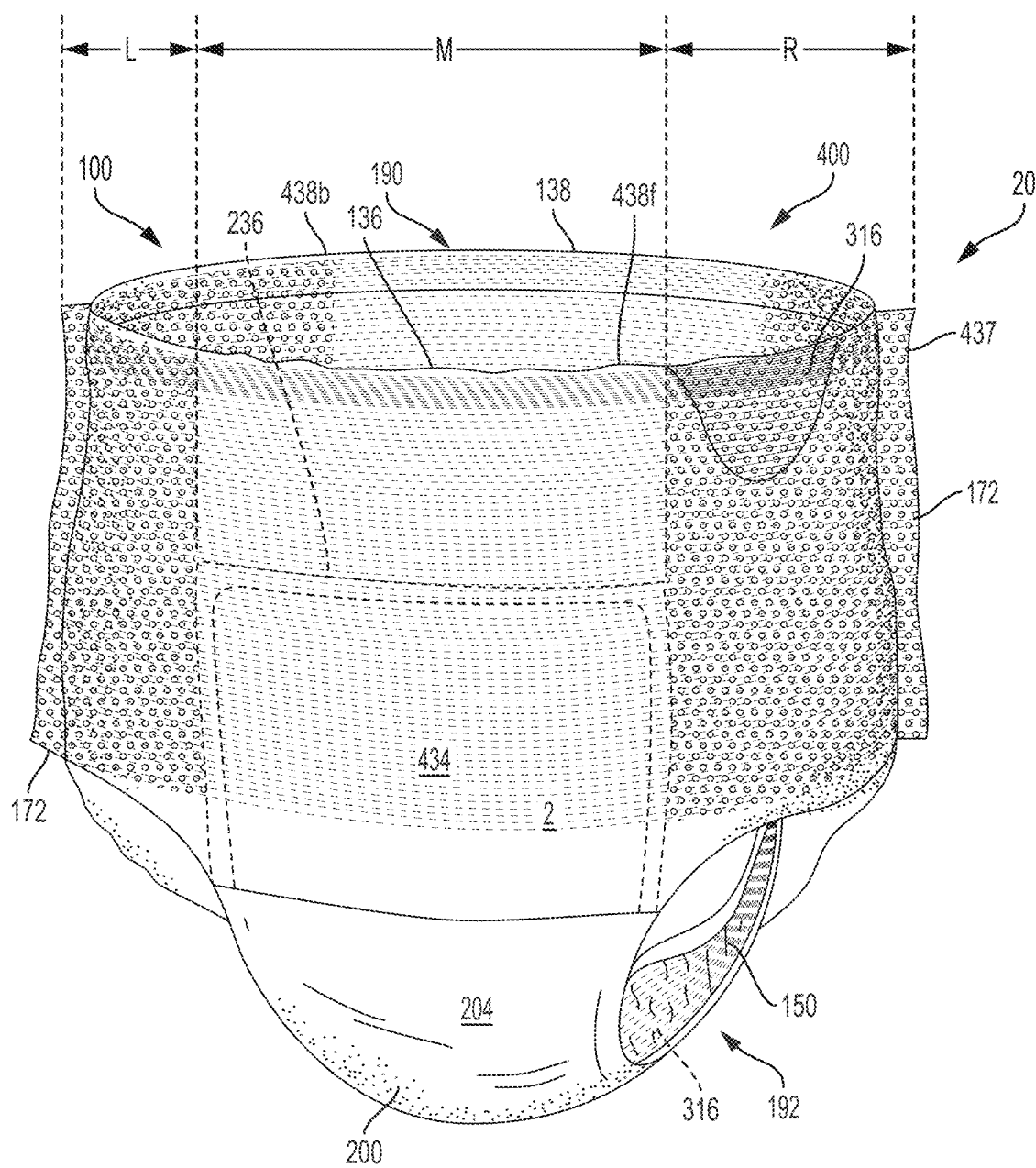
FIG. 12Q is a perspective front view of a pant comprising discrete front and back belts comprising Sections L and R that have been deformed via aperturing.
Figure 12R:
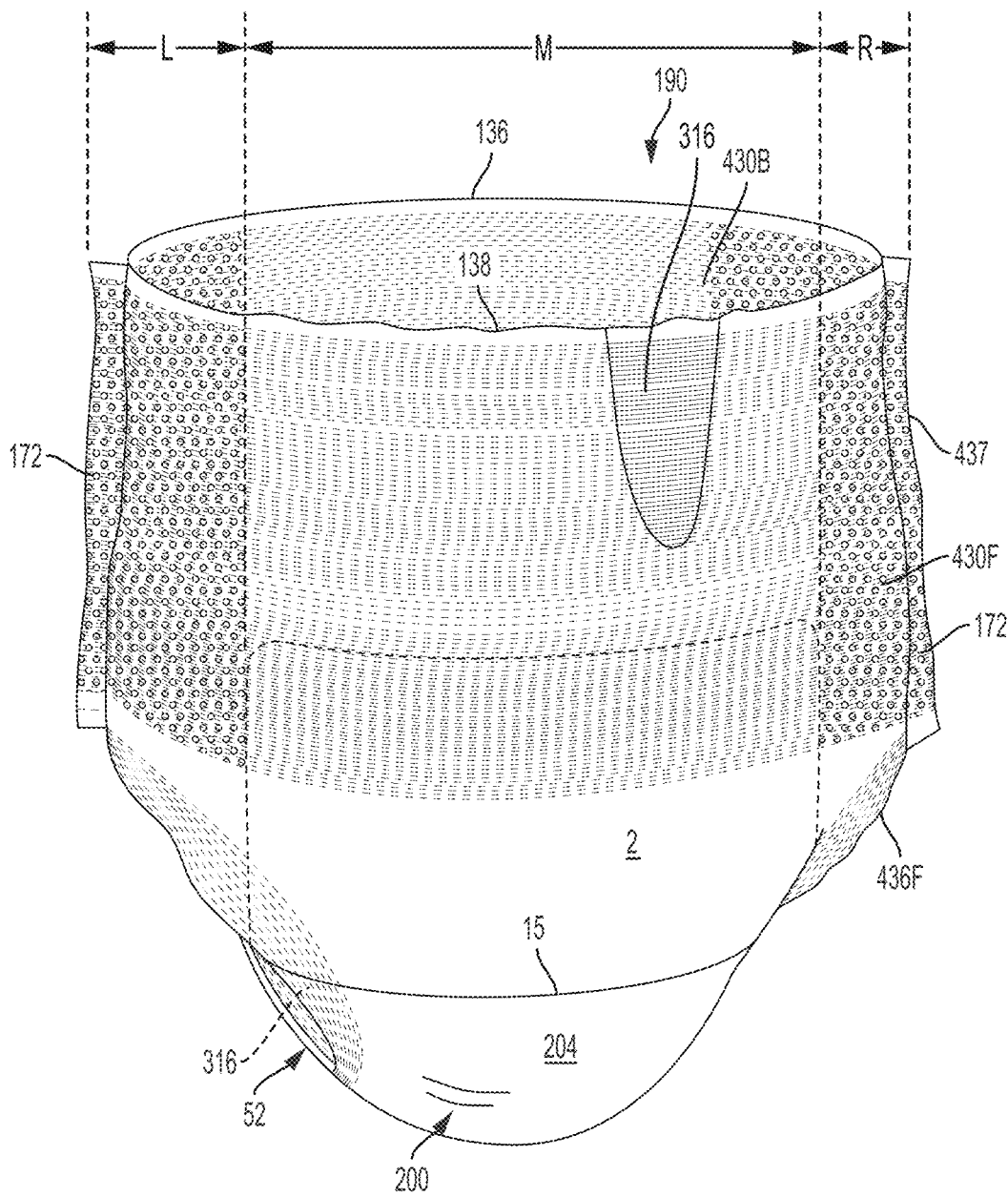
FIG. 12R is a perspective back view of the pant of FIG. 12Q, illustrating that Sections L and R of the back belt have been deformed via aperturing.
Figure 12S:
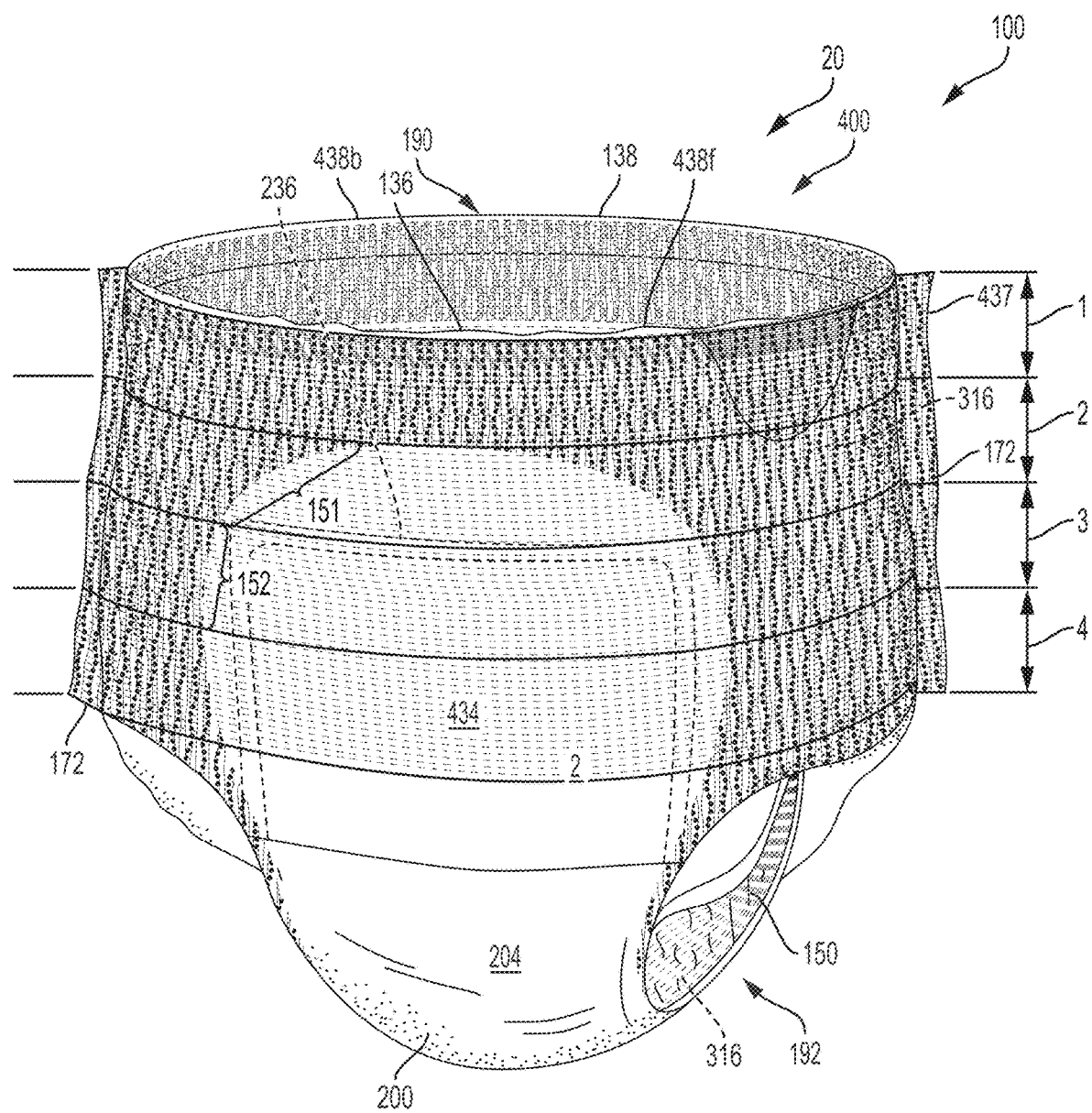
FIG. 12S is a perspective front view of a disposable absorbent pull-on pant comprising two distinct texture zones.
Figure 12T:
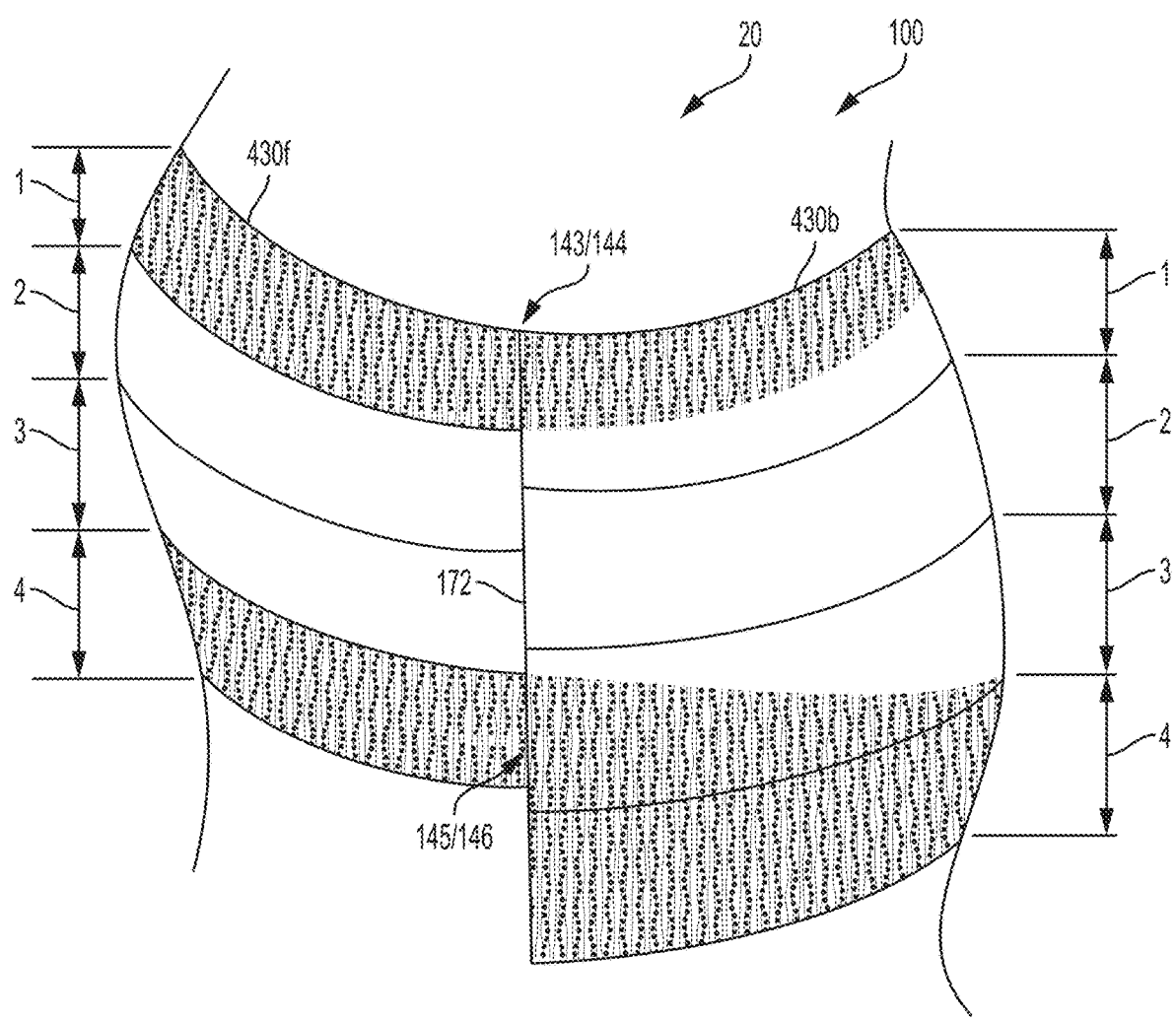
FIG. 12T is a side view of the pant of FIG. 12C.
Figure 12U:
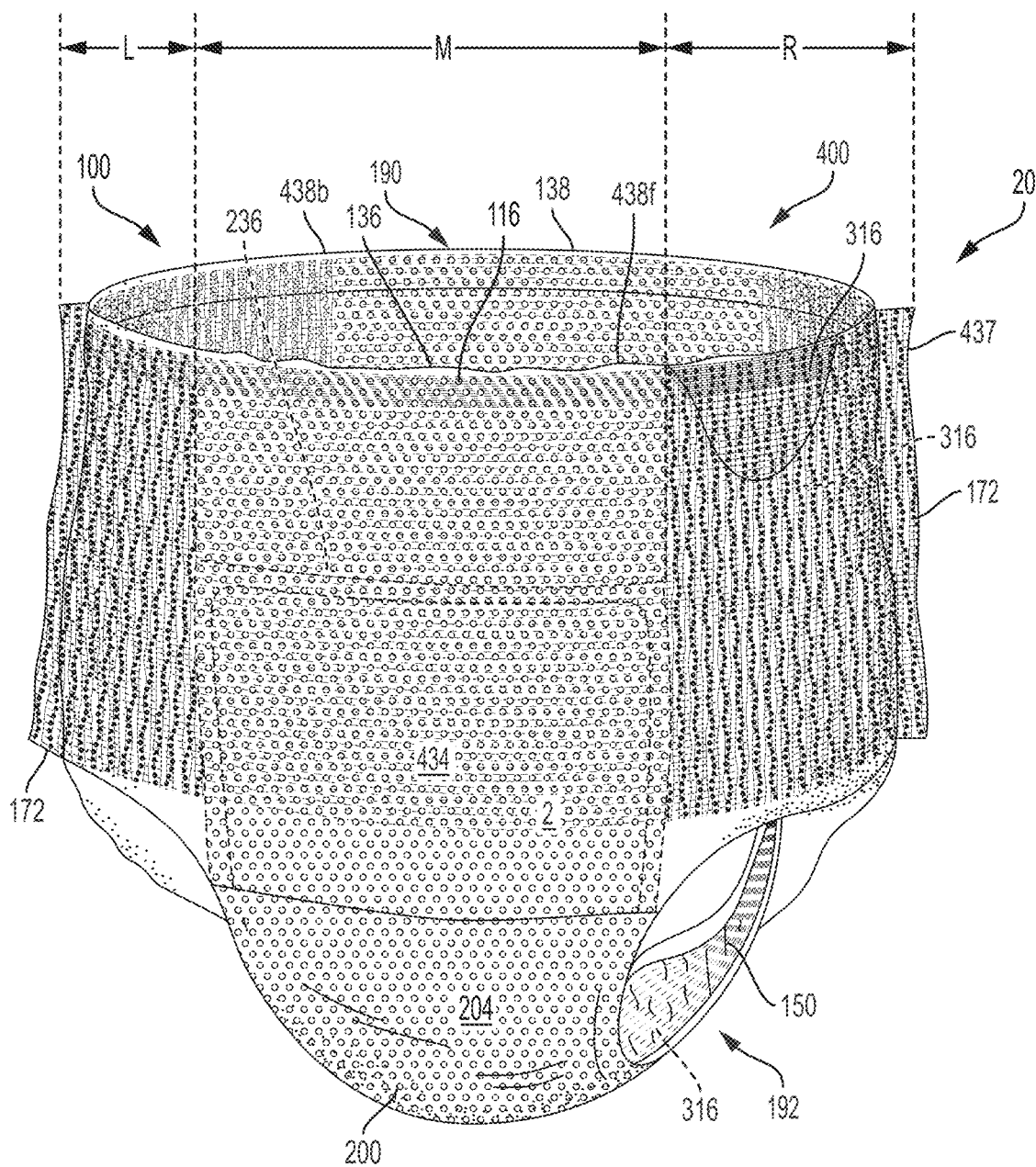
FIG. 12U is a perspective front view of a pant comprising discrete front and back belts comprising Sections L and R that have been deformed via MD activation and Section M that has been deformed via aperturing.

As shown in FIG. 12U, it may be desirable to MD activate Sections L and R of the front and back belts, but not Sections M of the front and back belts—Sections M of the front and back belts may be apertured, where Sections L and R of the front and back belts are not. FIG. 12U also illustrates that the chassis 200 (particularly the outer cover nonwoven or the backsheet nonwoven (see substrate layer 127 on FIGS. 12H-J—but not the backsheet film 126) may be apertured as well.

Figure 12V:
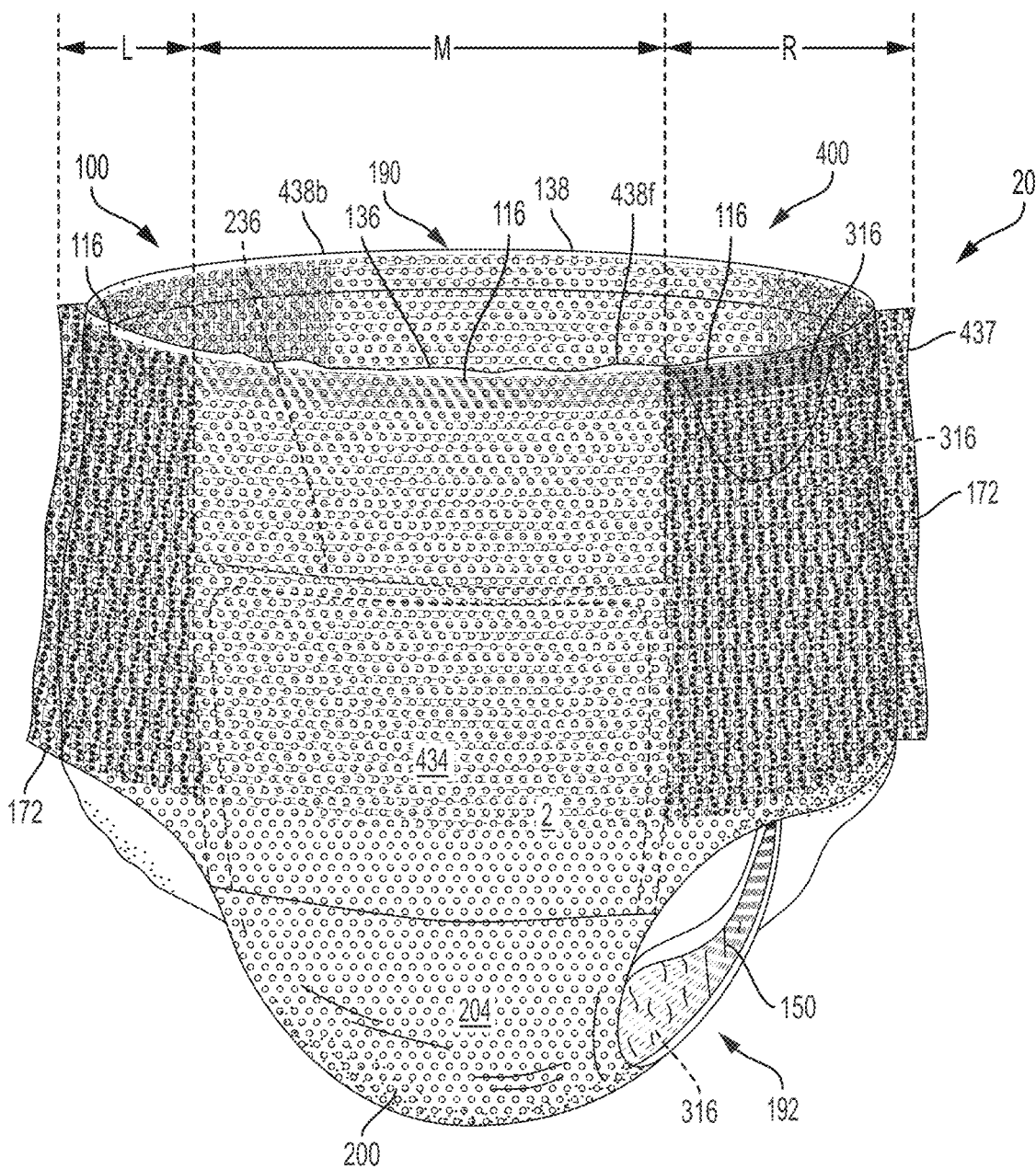
FIG. 12V is a perspective front view of a pant comprising discrete front and back belts comprising Sections L and R that have been deformed via MD activation and Sections L, M, and R that has been deformed via aperturing.

As shown in FIG. 12V, it may be desirable to MD activate Sections L and R of the front and back belts, but not Sections M of the front and back belts—and, in combination with this, Sections L, M, and R of the front and back belts may be apertured.

Textures

Beyond the improved performance of elastomeric laminates that have been mechanically deformed, these laminates may comprise desirable textures. The textures of the inventive elastomeric laminates are in contrast to traditional stranded elastomeric laminates, and even in contrast to previously disclosed beamed elastomeric laminates—See FIG. 1A (traditional beamed substrate) and 1B (MD-activated beamed substrate).

Absorbent articles comprising traditional stranded elastomeric laminates, i.e., those having elastics with a decitex above 400, elastic spacing greater than 4 mm and elastic pre-strain above 200% have a texture comprising large, random rugosities that are present on the wearer-facing surface as well as the garment facing surface. The texture formed by such large, random, rugosities does not provide the appearance of a textile garment and the size and harshness can adversely impact the skin of the wearer leaving marks and indentations.

Absorbent articles comprising beamed elastics and elastomeric laminates formed from beamed elastic, especially beamed elastomeric laminates that have been MD activated and/or apertured have much more intentional, well-defined and deliberate textures enabled by the beamed elastics incorporated into the elastomeric laminate. These intentional, well-defined and deliberate textures and zones of texture can be used to communicate the intended use of the article, the function of the article, as well as the intended wearer. The intentional, well-defined and deliberate textures and zones of texture enabled by beamed elastic based laminates are consistent with textile garments that typically have such identifiable textural patterns as well as patterns to communicate function. For example, it is easy to differentiate between leggings meant for lounging and leggings meant for high activity endeavors like aerobics, running or sports because of the visual nature of the design and in particular the textures and/or zones of texture.

The intentional, well-defined and deliberate textures and textural zones enabled by beamed elastic laminates also can impact distribution of forces in the belt as well as sustained fit by providing structural features, for example vertically oriented gathers, enabled by the textures themselves, glue patterns, and/or substrate deformation resulting from MD activation and/or aperturing that increase bucking resistance and prevent rollover, sagging, collapse and slippage of the elastomeric laminate in use.

It may be desirable that the side panels are textured (e.g., MD activated to comprise ridges and valleys), but that the chassis does not comprise ridges and valleys. This may be especially desirable where the side panels or ear panels are discrete (see FIGS. 13 and 14), such that the materials used to make the side or ear panels are separate from the outer cover nonwoven, which may not be MD activated—and thus being free from ridges and valleys. Particularly, Front Sections L and R may comprise a mechanically deformed portion forming ridges and valleys and Section M may be substantially free (or completely free) from ridges and valleys, such that less than 30%, or less than 20%, or less than 10% of the surface area of Section M comprises ridges and valleys. Such an embodiment may be desirable on a continuous belt, but the MD activation would need to be intermittent and registered so that the chassis is placed between the MD activated portions of the belt.

It may be desirable that the side panels are apertured, but that the chassis does not comprise apertures. This may be especially desirable where the side or ear panels are discrete (see FIGS. 13 and 14), such that the materials used to make the side or ear panels are separate from the outer cover nonwoven, which may not be apertured—and thus being free from apertures. Particularly, Front Sections L and R may comprise apertures and Section M may be substantially free (or completely free) from apertures, such that less than 30%, or less than 20%, or less than 10% of the surface area of Section M comprises apertures. Such an embodiment may be desirable on a continuous belt, but the aperturing would need to be intermittent and registered so that the chassis is placed between the apertured portions of the belt.

Chemistry and Structure of Elastomeric Strands of the Present Disclosure

Beamed elastics (e.g., 316) may be formed from Spandex fibers. One type of Spandex fiber is "PolyUrethane Urea" elastomer or the "high hard segment level PolyUrethane" elastomer, which may be formed into fibers using a solution (solvent) spinning process (as opposed to being processable in the molten state.) The Urea linkages in PolyUrethane Urea provides strong mutual chemical interactions crucial for providing "anchoring" that enables good stress relaxation performance at temperatures near body temperature on timescales corresponding to diaper wear, including overnight. This type of anchoring enables better Force-Relaxation-Over-Time (i.e., little force decay with time when held in stretched condition at body temperature) over many thermoplastic polyurethane (PolyUrethane with hard segment melting below 200 deg. C.) or thermoplastic Styrenic block copolymers.

The Urea linkage present in Spandex requires it to be made by spinning process. Spandex can't be melted/remelted or extruded like Styrenic block copolymers. Spandex pre-polymer is combined with solvent and additives, and the solution is spun to make solid spandex fiber. Multiple fibers are then formed together to make one spandex strand. The Spandex strands may have surface finish to avoid blocking and wound onto spools. The one spandex fiber may have a decitex of about 15, so a 500 decitex strand may have nominally 33 fibers wound together to make one strand. Depending on the decitex we use for beam approach, we may have 40 fibers (or filaments 317), 30 fibers, 20 fibers, 15 fibers, 8 fibers, 5 fibers, 3 fibers or even as low as 2 fibers. Spandex fiber can be mono-component or bi-component (as disclosed in WO201045637A2).

Further related to the chemistry of beamed elastics, it may be desirable to coat the beamed elastics with an oil, such as a silicone oil or mineral oil, including about 10%, about 7%, about 5%, about 3%, or about 1% silicone oil or mineral oil. Treating the beamed elastics with oil helps to prevent blocking (cross-linking) when the strands are wound to a spool or a beam and it also lowers the COF for the strand in textile machinery (for weaving, knitting and warping processes).

Commercially available Spandex strands may also be known as Lycra, Creora, Roica, or Dorlastan. Spandex is often referred as Elastan fiber or Polyurethane fiber.

LYCRA HYFIT strands, a product of Invista, Wichita, Kans., are a suitable for making the strands that make up the plurality of elastics 316 that make up the elastomeric laminate 302. Some strands, for example, the aforementioned LYCRA HYFIT, may comprise a number of individual fibers wound together to form the strand. With regard to elastic strands formed of a number of individual fibers it has been discovered that the individual fibers can move relative to each other changing the cross-sectional shape of the strand as well as becoming unraveled which can lead to poor control of the strands as well as poor bonding/adhering/joining of the elastic strands to one or both of the first substrate layer 306 and second substrate layer 308 of the elastomeric laminate 302. In order to minimize the negatives with regard to strands comprising a plurality of fibers it would be advantageous to minimize the number of fibers in a given strand. It would therefore be desirable to have less than about 40 fibers per strand, less than about 30 fibers per strand, less than about 20 fibers per strand, less than about 10 fibers per strand, less than about 5 fibers per strand and 1 fiber forming the strand. In the case of a single fiber forming the strand which can deliver comparable performance to the multi-fiber strands of the prior art it would be desirable for the fiber to have a fiber decitex from about 22 to about 300 and a fiber diameter from about 50 micrometers to about 185 micrometers.

Elastomeric Strands Having Different Polymer Compositions

While multiple warp beams may be used to create different performance and different texture zones via beams comprising a different number of elastics, and/or elastics having different decitex, and/or the elastics of the two beams may be disposed at different spacing, and/or the separate beams may deliver elastics having different pre-strain, and/or the different beams may deliver elastics having different orientations in the product, e.g. liner, arcuate, angled, etc.; a single beam may alternatively be used to accomplish some of the same performance zone and texture zone differences.

A single warp beam may be used to create different performance and different texture zone via winding the warp beam with elastic strands having different polymer compositions. The advantage to this is that a single beam may comprise elastic strands that are the same decitex, same prestrain, same spacing; the only difference being that the strands are made from two, three, four, etc. different polymer compositions. This is an advantage because the beam would run out of elastics at the same time, which may not be true for two separate beams wound with elastic strands of different decitex or strains.

For instance, a single beam may be wound with a first plurality of strands comprising polymer composition A, and the beam may also be wound with a second plurality of strands comprising polymer composition B. Polymer composition A may be selected from rubber block polymers including polyesters such as polyethylene adipate, polypropylene adipate, and polybutylene adipate, poly-1,5-pentanediol, 1,6-hexanediol, or 1,10-decanediol or polyethers such as poly ethylene glycol, polypropylene glycol, polytetramethylene glycol and the like; and from rigid blocks including diphenylmethane 4,4'-diisocyanate (MDI), toluene-2,4-diisocyanate (TDI), hexamethylene diisocyanate (HDI), methylene dicyclohexyl diisocyanate (hydrogenated MDI (HMDI)) or isophorone diisocyanate (IPDI); and from optional coupling agents for the rigid block including diamines (Hydrazine and ethylene diamine, etc.) or diols (butane diol, 1,5-pentanediol, 1,6-hexanediol, etc.). Polymer composition B may be selected from rubber block polymers including polyesters such as polyethylene adipate, polypropylene adipate, and polybutylene adipate, poly-1,5-pentanediol, 1,6-hexanediol, or 1,10-decanediol or polyethers such as poly ethylene glycol, polypropylene glycol, polytetramethylene glycol and the like; and from rigid blocks including diphenylmethane 4,4'-diisocyanate (MDI), toluene-2,4-diisocyanate (TDI), hexamethylene diisocyanate (HDI), methylene dicyclohexyl diisocyanate (hydrogenated MDI (HMDI)) or isophorone diisocyanate (IPDI); and from optional coupling agents for the rigid block including diamines (Hydrazine and ethylene diamine, etc.) or diols (butane diol, 1,5-pentanediol, 1,6-hexanediol, etc.), but polymer composition B may be a different combination of rubber and rigid blocks and/or different optional coupling agents than polymer composition A.

Further, the beam may also comprise a third plurality of strands comprising polymer composition C, which may be selected from rubber block polymers including polyesters such as polyethylene adipate, polypropylene adipate, and polybutylene adipate, poly-1,5-pentanediol, 1,6-hexanediol, or 1,10-decanediol or polyethers such as poly ethylene glycol, polypropylene glycol, polytetramethylene glycol and the like; and from rigid blocks including diphenylmethane 4,4'-diisocyanate (MDI), toluene-2,4-diisocyanate (TDI), hexamethylene diisocyanate (HDI), methylene dicyclohexyl diisocyanate (hydrogenated MDI (HMDI)) or isophorone diisocyanate (IPDI); and from optional coupling agents for the rigid block including diamines (Hydrazine and ethylene diamine, etc.) or diols (butane diol, 1,5-pentanediol, 1,6-hexanediol, etc.), but polymer composition C may be a different combination of rubber and rigid blocks and/or different optional coupling agents than polymer compositions A and/or B.

For instance, a single beam may be wound with a first plurality of strands comprising polymer composition A, the beam may also be wound with a second plurality of strands comprising polymer composition B. This arrangement may be useful for creating the same effect as the embodiment illustrated in FIG. 12C, where Sections 1 and 4 may comprise the first plurality of elastics comprising polymer composition A and wherein Sections 2 and 3 may comprise the second plurality of elastics comprising polymer composition B—using polymer compositions A and B may be used as an alternative to mechanical deformation or may be used in combination with mechanical deformation to enhance the effect. Even if polymer compositions A and B are close in performance, the number of elastics in each section, may have an additive effect, turning the slight performance difference into a material performance and/or texture difference—this is especially true when beamed elastics are used because each of Sections 1-4 may comprise over a hundered fine elastic elements 316. Thus, an embodiment like FIG. 12C may have a higher Laminate-Modulus in Sections 2 and 3, and a lower Laminate-Modulus in Sections 1 and 4 or vice versa.

A single beam may be wound with a first plurality of strands comprising polymer composition A, the beam may also be wound with a second plurality of strands comprising polymer composition B, and the beam may also be wound with a third plurality of strands comprising polymer composition C, wherein each of polymer compositions A, B, and C are different polymer compositions, each having a different modulus, and each being the same decitex and wound on the beam at the same spacing and the same strain.

Elastomeric Laminates of the Present Disclosure

An "elastomeric laminate 302" of the present disclosure may comprise a plurality of elastics 316 between a first substrate 306 and a second substrate layer 308, where the plurality of elastics 316 (often referred to as a "first plurality of elastics," a "second plurality of elastics," etc.) has an Average-Strand-Spacing from about 0.25 mm to about 4 mm, an Average-Dtex from about 10 to about 400, a Pressure-Under-Strand from about 0.1 to about 1 psi, the elastomeric laminate being mechanically deformed. Said elastomeric laminate may also comprise a first plurality of elastics having a different polymer composition than a second plurality of elastics.

Further, an "elastomeric laminate 302" of the present disclosure may comprise a plurality of elastics 316 between a first substrate 306 and a second substrate layer 308, where the plurality of elastics 316 (often referred to as a "first plurality of elastics," a "second plurality of elastics," etc.) has an Average-Strand-Spacing from about 0.25 mm to about 4 mm, an Average-Dtex from about 10 to about 400, a Pressure-Under-Strand from about 0.1 to about 1 psi, and the elastomeric laminate comprising a first plurality of elastics having a different polymer composition than a second plurality of elastics. Said elastomeric laminate may also be mechanically deformed.

Said elastomeric laminate 302 may be used to form various article components or at least a portion of various absorbent article components, e.g. a belt, side panel, waistband or leg cuff. Further, the elastomeric laminate 302 may be used to form regions of the article or at least a portion of an article region, e.g., front waist region, crotch region or back waist region. When the elastomeric laminate 302 forms at least a portion of at least one of the group consisting of a belt, a chassis, a side panel, a topsheet, a backsheet, and an ear panel, and combinations thereof, the plurality of elastics 316 of the elastomeric laminate 302 may comprise from about 40 to about 1000 elastic strands. And, when the elastomeric laminate 302 forms at least a portion of at least one of the group consisting of a waistband, a waistcap, an inner leg cuff, an outer leg cuff, and combinations thereof, the first plurality of elastics 316 of the elastomeric laminate 302 may comprise from about 10 to about 400 elastic strands. Ultimately, "plurality of elastics" is a term of context, where certain properties (e.g., Average-Dtex, Average-Strand-Spacing, Pressure-Under-Strand, etc.), arrangements, attributes, characteristics, disposition, etc. of the elastics are referenced to define what a certain "plurality of elastics" is.

Further, the elastomeric laminate 302 may form at least a portion of one or more of the group of article components including a belt 430, a side panel 330, chassis 200, a topsheet 124, backsheet 125, and an ear panel 530, the elastomeric laminate 302 may comprise a plurality of elastics 316 having from about 40 to about 1000 elastic strands with an Average-Strand-Spacing from about 0.25 mm to about 4 mm, Average-Dtex from about 10 to about 400, an Average-Pre-Strain from about 50% to about 300%; and a first substrate 306 and a second substrate 308 each having a basis weight from about 6 grams per square meter to about 45 grams per square meter.

When the elastomeric laminate 302 may form at least a portion of one or more of the group of article components including a waistband 122, waistcap 123, inner leg cuff 150, outer leg cuff 140 and a transverse barrier 16, and may comprise a plurality of elastics 316 having from about 10 to about 400 elastic strands with an Average-Strand-Spacing from about 0.25 mm to about 4 mm, Average-Dtex from about 10 to about 400, an Average-Pre-Strain from about 50% to about 300% and a first substrate 306 and/or second substrate 308 each having a basis weight from about 6 grams per square meter to about 45 grams per square meter.

Any one of the belt 430, side panel 330, ear panel 530, chassis 200, topsheet 124, backsheet 125, waistband 122, waistcap 123, inner leg cuff 150, outer leg cuff 140 or transverse barrier may: comprise an elastomeric laminate 302 comprising a plurality of elastics 316 having Pressure-Under-Strand from about 0.1 psi to about 1 psi, or from about 0.2 psi to about 0.8 psi; comprise an elastomeric laminate comprising a Percent-Contact-Area of greater than about 13% at 100 um and/or greater than about 27% at 200 um and/or greater than about 39% at 300 um and/or a 2%-98%-Height-Value of <1.6 mm; comprise an elastomeric laminate comprising a Percent-Contact-Area of greater than about 13% at 100 um and/or greater than about 27% at 200 um and/or greater than about 36% at 300 um and/or a 2%-98%-Height-Value of <2.2 mm; comprise an elastomeric laminate comprising a Rugosity-Frequency of from about 0.2 mm$^{-1}$ to about 1 mm$^{-1}$ and a Rugosity-Wavelength of from about 0.5 mm to about 5 mm.

Beyond the beamed elastic strands 316 that may be used in each of the absorbent article components, other elastic components such as elastic nonwovens, elastomeric films, elastomeric foams, elastomeric scrims, and elastomeric ribbons, or combinations thereof, may be used in combination with the beamed elastics 316.

Absorbent Articles of the Present Disclosure

Products comprising elastomeric laminates of the present disclosure may comprise absorbent articles 100 of differing structure and/or form that are generally designed and configured to manage bodily exudates such as urine, menses, and/or feces, such as disposable taped and pants, including baby and adult disposable absorbent articles.

As shown in the figures, the absorbent articles 100 of the present disclosure may comprise a chassis 200 comprising a topsheet 124, a backsheet 125, and an absorbent core 128 disposed at least partially between the topsheet 124 and the backsheet 125. The chassis 200 may further comprise an inner leg cuff 150 and an outer leg cuff 140 (the cuffs generally referred to as 52).

Figure 18A:
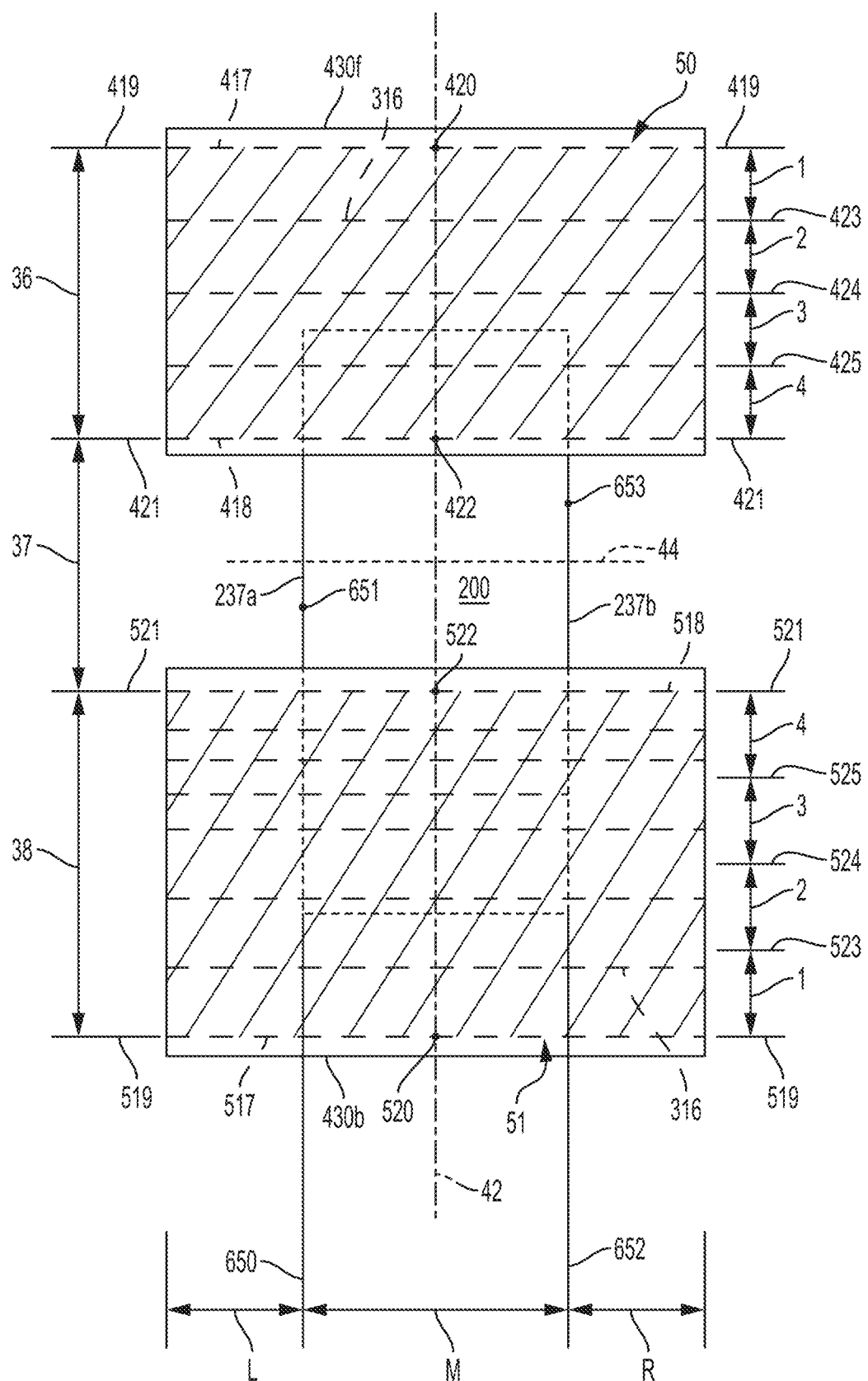
FIG. 18A is a plan view of a pant, prior to joining side edges of the belt to form the waist and leg openings, illustrating front and back component regions 50 and 51.

One end portion of an absorbent article 100 may be configured as a front waist region 36 and the longitudinally opposing end portion may be configured as a back waist region 38. An intermediate portion of the absorbent article 100 extending longitudinally between the front waist region 36 and the back waist region 38 may be configured as a crotch region 37. The length of each of the front waist region 36, the back waist region 38 and the crotch region 37 may be about ⅓ of the length of the absorbent article 100, for example (see, for example, FIG. 14). Alternatively, the length of each of the front waist region 36, the back waist region 38, and the crotch region 37 may have other dimensions (e.g., defined by the longitudinal dimension of the belt immediately adjacent the side seam or the longitudinal dimension of the ear panel/side panel immediately adjacent the center chassis—see, for example, FIGS. 12E and 13; or in the case where an article has a continuous component such as the pant in FIG. 18C, the side seam 172 (or where the side seam will be or was 172') may define the boundaries between the front and back waist regions and the crotch region (see the alternative component sections 1'-4' and alternative front and back waist regions 36' and 38' and crotch region 37' in FIGS. 12E and 12F, where the back belt is longitudinally longer than the front belt).

When the side seams are used to define the front and back waist regions and crotch region, such may be described as follows:

"The front waist region 36 is a region between a) a proximal most front axis 410 extending parallel to the lateral axis 44 and passing through proximal most points of the laterally opposed front side seams 172 or 172'; and b) a distal most front axis 411 extending parallel to the lateral axis and passing through distal most points of the laterally opposed front side seams 172 or 172'; and the back waist region 38 is a region between a) a proximal most back axis 510 extending parallel to the lateral axis 44 and passing through proximal most points of the laterally opposed back side seams 172 or 172'; and b) a distal most back axis 511 extending parallel to the lateral axis and passing through distal most distal points of the laterally opposed back side seams 172 or 172'."

The absorbent article 100 may have a laterally extending front waist end edge 136 in the front waist region 36 and a longitudinally opposing and laterally extending back waist end edge 138 in the back waist region 38.

The chassis 200 of the absorbent article 100 may comprise a first longitudinally extending side edge 237a and a laterally opposing and second longitudinally extending side edge 237b. Both of the side edges 237 may extend longitudinally between the front waist end edge 136 and the back waist end edge 138. The chassis 200 may form a portion of the laterally extending front waist end edge 136 in the front waist region 36 and a portion of the longitudinally opposing and laterally extending back waist end edge 138 in the back waist region 38. Furthermore, the chassis 200 may comprise a chassis interior surface 202 (forming at least a portion of the wearer-facing surface 4), a chassis exterior surface 204 (forming at least a portion of the garment-facing surface 2), a longitudinal axis 42, and a lateral axis 44. The longitudinal axis 42 may extend through a midpoint of the front waist end edge 136 and through a midpoint of the back waist end edge 138, while the lateral axis 44 may extend through a midpoint of the first side edge 237a and through a midpoint of the second side edge 237b.

Referring to FIG. 12E, often true for belted absorbent articles, the chassis 200 may have a length measured along the longitudinal axis 42 that is less than the length of the absorbent article 100. Both of the side edges 237 of the chassis 200 may not extend longitudinally to one or both of the front waist end edge 136 and the back waist end edge 138. The chassis 200 may not form a portion of one or both of the laterally extending front waist end edge 136 in the front waist region 36 and the longitudinally opposing and laterally extending back waist end edge 138 in the back waist region 38.

Referring to FIG. 12G, the chassis 200 may comprise elastics 316 oriented parallel to the longitudinal axis 42 between the backsheet nonwoven 127 and backsheet film 126. Alternatively, the chassis 200 may have elastics 316 oriented parallel to the longitudinal axis 42 between the core wrap 74 and the backsheet 125. Still further, in FIG. 12H the chassis 200 comprises elastics 316 oriented parallel with the lateral axis 44 between the backsheet film 126 and the backsheet nonwoven 127. FIG. 12G also shows elastics 316 oriented parallel with the longitudinal axis 42 between a first topsheet layer 124a and a second topsheet layer 124b. Still further, FIG. 12H shows elastics 316 oriented parallel with the lateral axis 44 between the topsheet 124 and the core wrap 74.

A portion or the entirety of the absorbent article 100 may be made to be laterally elastically extensible. The extensibility of the absorbent article 100 may be desirable in order to allow the absorbent article 100 to conform to a body of a wearer during movement by the wearer. The extensibility may also be desirable, for example, in order to allow the caregiver to extend the front waist region 36, the back waist region 38, the crotch region 37, and/or the chassis 200 to provide additional body coverage for wearers of differing size, i.e., to tailor the fit of the absorbent article 100 to the individual wearer and to aide in ease of application. Such extension may provide the absorbent article 100 with a generally hourglass shape, so long as the crotch region 37 is extended to a relatively lesser degree than the waist regions 36 and/or 38. This extension may also impart a tailored appearance to the absorbent article 100 during use.

Figure 13:
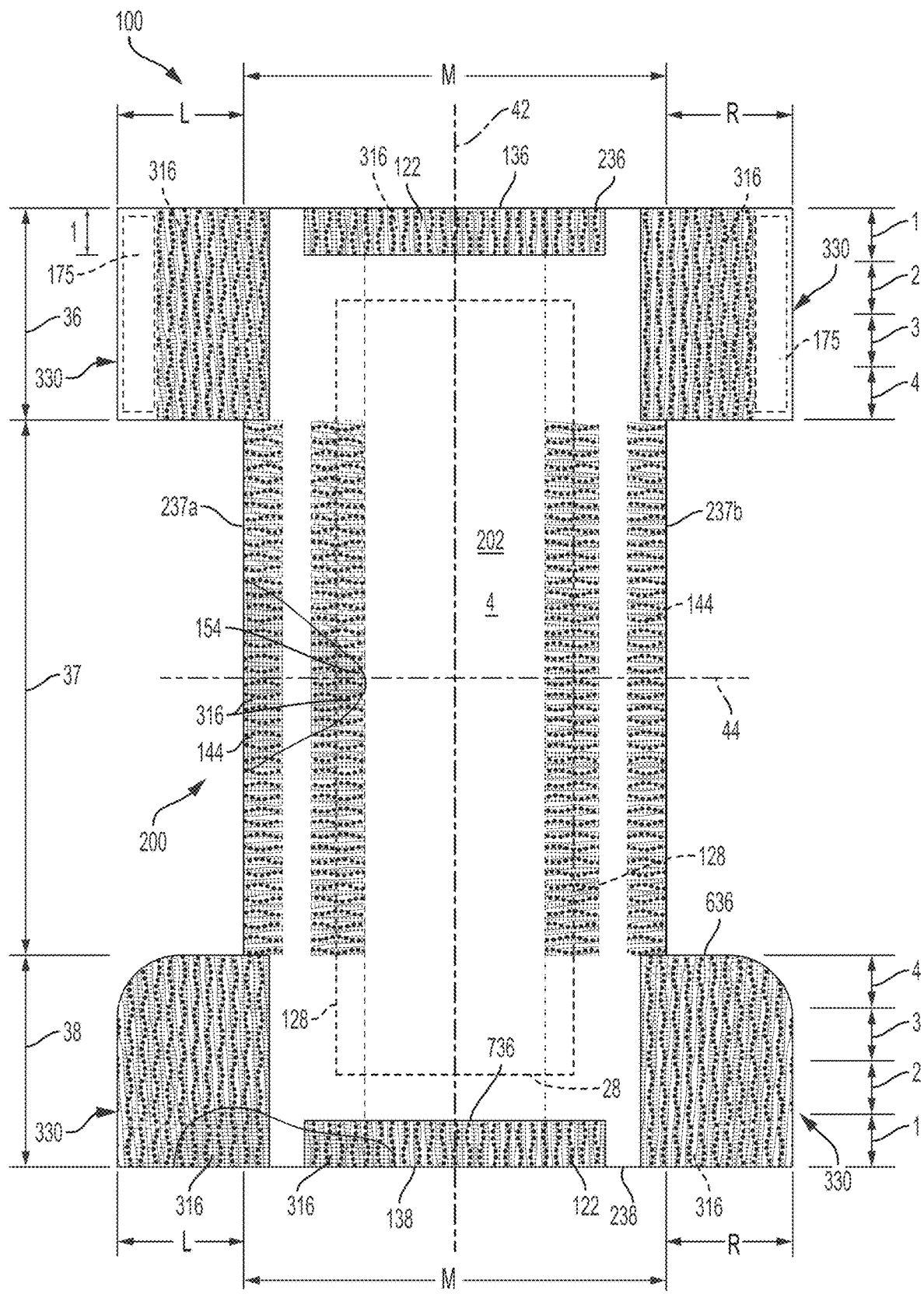
FIG. 13 is a plan view of a pant prior to joining the side panels to form the waist and leg openings. The side panels, waistband, inner leg cuff, and outer leg cuff have been MD activated.
Figure 14:
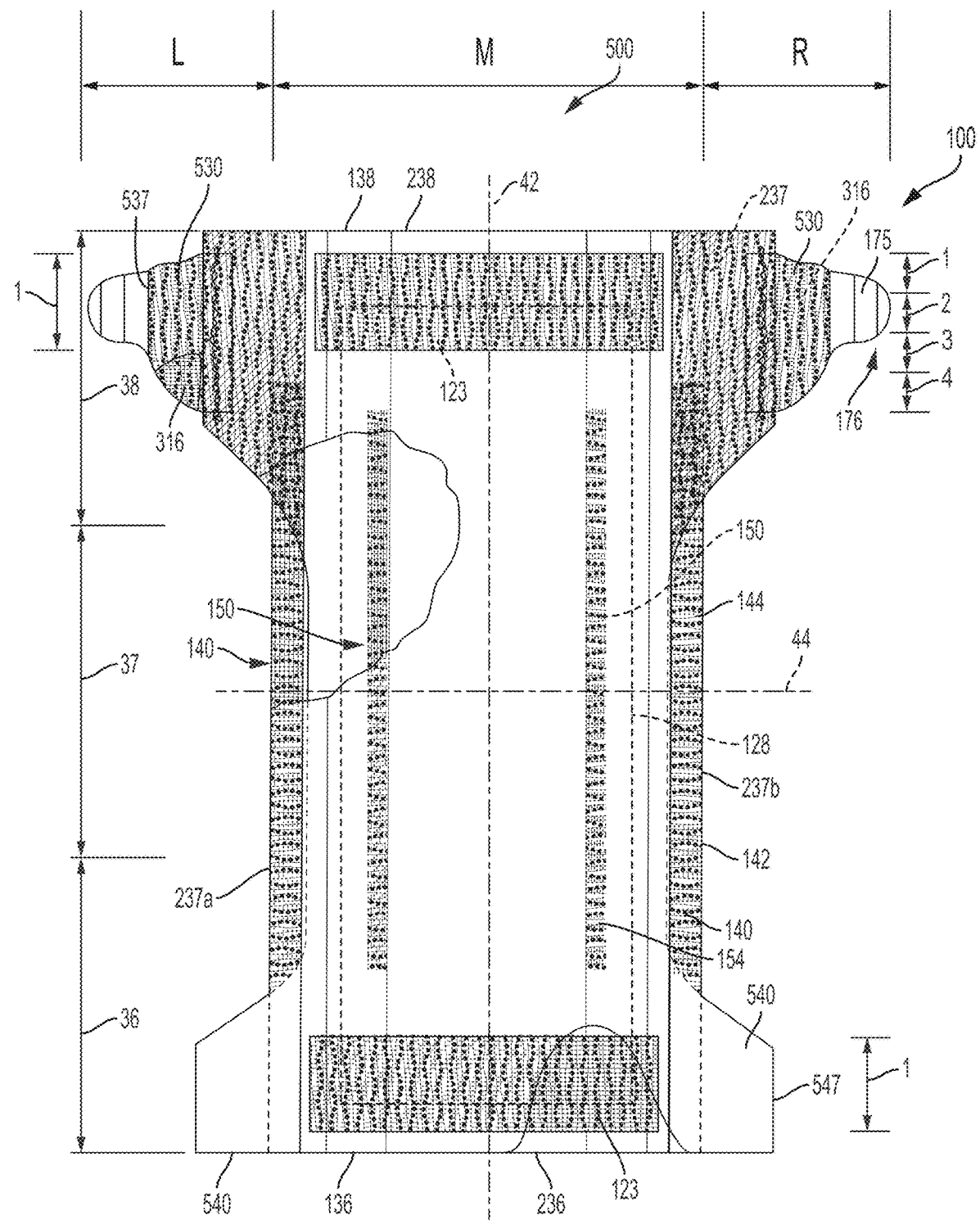
FIG. 14 is a plan view of a taped diaper comprising a pair of shaped discrete elastomeric ear panels 530 and a pair of non-elastomeric ear panels 540. The ear panels waistcap, inner leg cuff, and outer leg cuff have been MD activated.
Figure 15:
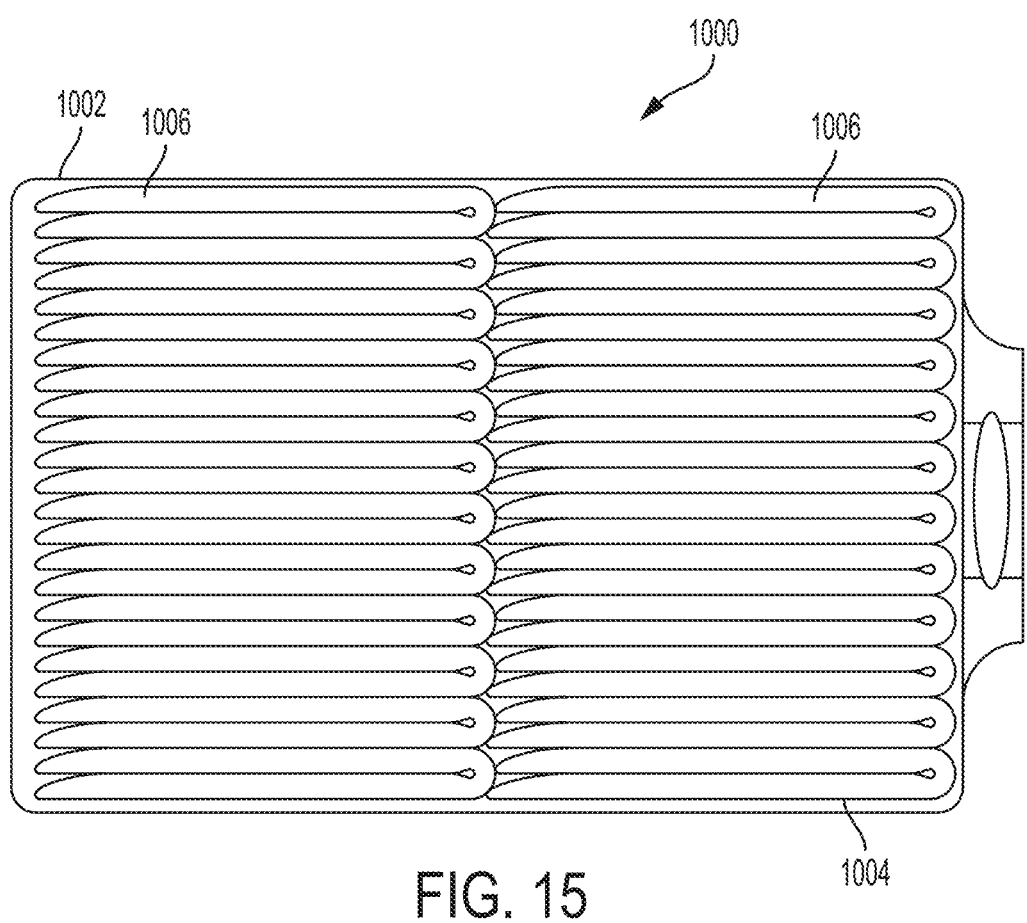
FIG. 15 illustrates packaged disposable absorbent articles comprising inventive laminates of the present disclosure.

The chassis 200 may be substantially rectangular and may have discrete side panels 330 (FIG. 13), extensible ear panels 530 (FIG. 14) and/or non-extensible ear panels 540 (FIG. 14) joined to the chassis 200 at or adjacent the chassis side edges 237 in one or both of the front waist region 36 and back waist region 38. Portions of one or more of the chassis side edges 237, the chassis front end edge 236 and the chassis back end edge 238 may be arcuate or curved either convexly or concavely. The chassis 200 may comprise integral side panels 330, integral extensible ear panels, integral belts 430 or integral non-extensible ear panels 540 formed by one or more of the outer cover nonwoven, backsheet film, outer leg cuff material, topsheet or core wrap 74 disposed in one or both of the front and back waist regions (FIG. 14). Alternatively, the chassis 200 may comprise discrete side panels 330 (see FIG. 13), discrete extensible ear panels 530 (see FIG. 14), or discrete belts 430 or belt layers (FIGS. 12H; and 12I (inner belt layers 432)). The chassis may be shaped or non-rectangular, in one waist region and substantially rectangular in the opposing waist region. Alternatively, the chassis may be substantially rectangular in one or both of the waist regions and non-rectangular in the crotch region.

Absorbent articles of the present disclosure may comprise a plurality of laterally extending elastic elements wherein the elastic elements are present in a first waist region, the crotch region and in the opposing second waist region.

Closed-Form Pant Article

Closed-form, pant-style, absorbent articles are generally disclosed in FIGS. 5D-K', 12A-D, 12K-V and are designed to be packaged in closed-form having a waist opening 190 and two leg openings 192, and designed to be donned onto the wearer like a pair of durable underwear. The pant may comprise discrete elastomeric side panels 330 (FIG. 13) and/or discrete belts 430 (FIGS. 12A-F, 12H, 12I (inner belts), 12K-12V and 18A) in one or both of the front waist region 36 and back waist region 38. Alternatively, the side panels 330 and/or belts 430 may be formed integrally with other elements of the article such as the chassis 200.

When the absorbent article comprises front and back belts 430, the sides of front and back belts 430 on one side of the article may be joined permanently or refastenably to each other and the front and back side panels on the opposing side of the article may be joined permanently or refastenably to each other to create a waist opening 190 and a pair of leg openings 192. The belts 430 provide an elastically extensible feature that provides a more comfortable and contouring fit by initially conformably fitting the article 100 to the wearer and sustaining this fit throughout the time of wear well past when the pant has been loaded with exudates since the elastomeric side panels allow the sides of the pant to expand and contract. Further, the elastomeric belts 430 provide ease of application and develop and maintain wearing forces and tensions to maintain the article 100 on the wearer and enhance the fit, especially when beamed elastomeric laminates are used to form the belts 430. The elastomeric side panels enable ease of application allowing the pant to be pulled conformably over the hips of the wearer and positioned at the waist where the belts 430 conform to the body and provide tension sufficient to maintain the articles position on the wearer. The tension created by the side panels is transmitted from the elastic belts 430 along the waist opening 190 and along at least a portion of the leg opening 192. Typically, particularly regarding discrete side panels 330, the chassis 200 is disposed between the side panels 330 and extends to form a portion of the waist edge 136 and/or 138 of the pant comprising side panels 330. In other words, a portion of the waist edge 136 and/or 138 in one or both of the front waist region 36 and back waist region 38 may be formed in part by the side panels 330 and in part by the chassis 200.

The pant comprising side panels 330 (or belts 430) may also comprise a pair of laterally opposing refastenable seams. The refastenable side seam may be formed by refastenably joining an interior surface of a portion of the article, e.g., a side panel 330, to an exterior surface of another portion of the article 100, e.g., a longitudinally opposing side panel 330 or the chassis 200 to form the refastenable side seam. FIG. 13 illustrates a front side panel 330 comprising a fastener 175 comprising hooks facing away from a wearer (the fastener 175 disposed on an exterior surface of the front side panel 3300 that refastenably attaches to a mating fastener 178 (loops or a suitable nonwoven in FIG. 13), the mating fastener 178 being disposed on an interior surface of the back side panel 330b.

The pant comprising belts 430 may also comprise a first permanent side seam 172 and a laterally opposing second permanent side seam 172. The permanent side seam 172 may be formed by joining an interior surface of a portion of the article 100, e.g. belt 430, to an exterior surface of another portion of the article 100, e.g. a longitudinally opposing belt 430 or the chassis 200 to form the permanent side seam 172. Alternatively, the permanent side seam 172 may be formed by joining an interior surface of a portion of the article 100, e.g. a belt 430, to an interior surface of another portion of the article 100, e.g. a longitudinally opposing belt 430 to form the permanent side seam 172. Any pants comprising side panels 330 configurations described above may comprise a waistband 122 wherein at least a portion of the waistband 122 (as illustrated in FIG. 13) is disposed at or immediately adjacent the waist edge 136 and/or 138 and overlaps a portion of the center chassis 200. The waistband 122 may extend laterally to overlap portions of the inner leg cuffs 150 and/or portions of the elastomeric side panels 330. The waistband 122 may be disposed on the interior surface 202 of the chassis 200 or alternatively between the topsheet 124 and the backsheet 125.

Particularly regarding belts 430, as illustrated in FIGS. 12I and J, the inner belt layer 432 and/or the outer belt layer 434 of the first and second elastomeric belts 430 may be formed by a common belt layer. When the first and second elastomeric belts 430 have a common belt layer, the common belt layer may extend from a first waist edge in a first waist region to a longitudinally opposing second waist edge in a second waist region, i.e. front waist edge 136 to back waist edge 138.

Also, particularly regarding belted pants 400, as illustrated in FIGS. 12E, the belt pant 400 may have a first elastomeric belt 430 disposed in a first waist region having a first longitudinal length and a second elastomeric belt 430 disposed in a second waist region having a second longitudinal length wherein the longitudinal length of the first belt is greater than the longitudinal length of the second belt along the side edge of the belt at or adjacent the side seam. This length difference helps provide buttock coverage in the back of the pant providing a more underwear-like appearance. And, while this advantage is disclosed for belted pants 400, there is also an advantage in having longitudinally longer side panels 330 in the back waist region 38.

Open-Form Taped Article

Open-form, taped-style, absorbent articles are generally disclosed in FIG. 14. The taped diaper 500, open-form article, may comprise elastomeric ear panels 530 in one or both of the front waist region 36 and back waist region 38. The elastomeric ear panels 530 may be unitary structurally with other elements of the article 100 or as a separate element joined to another element of the article 100. The elastomeric ear panels 530 provide an elastically extensible feature that provides a more comfortable and contouring fit by initially conformably fitting the article 100 to the wearer and sustaining this fit throughout the time of wear well past when the taped diaper 500 has been loaded with exudates since the elastomeric ear panels 530 allows the diaper to expand and contract to fit the wearer. Further, the elastomeric ear panels 530 develop and maintain wearing forces (tensions) and enhance the tensions developed and maintained by the fastening system 179 (including the fasteners 175 (e.g., hooks) that may be releasably engaged with a mating fasteners 178 (e.g., loops)), to maintain the article 100 on the wearer and enhance the fit. The elastomeric ear panels 530 especially assist in maintaining the primary line of tension formed by the fastening system 179 allowing the diaper to conformably fit over the hips of the wearer where there is dynamic motion, and initially pre-tensioning the waist opening 190 and leg opening 192 since the diaperer typically stretches the elastomeric ear panels 530 when applying the taped diaper 500 on the wearer so that when the elastomeric ear panels 530 contract, tension is transmitted from the elastomeric ear panels 530 along the waist opening 190 and along at least a portion of the leg opening 192. While the open-form article of the present disclosure may have the elastomeric ear panels 530 disposed in the back waist region 38, alternatively, the taped diaper 500 may be provided with elastomeric ear panels 530 disposed in the front waist region 36 or in both the front waist region 36 and the back waist region 38. The open-form article may also have elastomeric ear panels 530 disposed in a first waist region and elastomeric ear panels 530 or non-elastomeric ear panels 540 disposed in a second waist region.

Alternatively, the open-form, taped-style, absorbent articles may comprise an elastomeric belt 430 disposed in one of the waist regions. The elastomeric belt 430 may be joined and/or positioned in a particular place or position and may be unitary structurally with other elements of the article 100 or as a separate element joined to another element of the article 100. A belted taped diaper the elastomeric belt 430 may be disposed in the back waist region 38. The elastomeric belt 430 may have fasteners disposed at or adjacent the laterally opposing ends of the belt. Fasteners 175 may be disposed on the interior surface of the belt 430 to engage with a discrete mating fastening component 178 or with the exterior surface 204 of the article (like the backsheet nonwoven 127) to fasten the article on the wearer.

Outer Cover Material

The backsheet 125 may comprise a backsheet film 126 and backsheet nonwoven 127. The backsheet nonwoven 127 may also be referred to as the outer cover material. The outer cover material forms at least a portion of the garment-facing surface of the absorbent article 100 and effectively "covers" the backsheet film 126 so that the film is not present on the garment-facing surface. The outer cover material may comprise a bond pattern, apertures, textures and/or three-dimensional features. The texture, aperture pattern, etc. of the backsheet may be formed in a way to complement or correspond to the mechanical deformation arrangements of the side panels, ear panels or belt portions of the article.

Absorbent Core

As used herein, the term "absorbent core" 128 refers to the component of the absorbent article 100 having the most absorbent capacity and that comprises an absorbent material. Referring to FIGS. 12H-J in some instances, absorbent material (e.g., 26) may be positioned within a core bag or a core wrap 74. The absorbent material may be profiled or not profiled, depending on the specific absorbent article. The absorbent core 128 may comprise, consist essentially of, or consist of, a core wrap, absorbent material, and glue enclosed within the core wrap. The absorbent material may comprise synthetic fibers, cellulosic fibers, superabsorbent polymers, foams or combinations thereof. In some instances, the absorbent material may comprise at least 80%, at least 85%, at least 90%, at least 95%, at least 99%, or up to 100% superabsorbent polymers, by weight of the absorbent material. In such instances, the absorbent material may free of air felt, or at least mostly free of air felt—in such cases the AGM 26 may be held in place by an adhesive 54, such as a thermoplastic adhesive. And, for swim diapers, the article may be free of superabsorbent polymers. The absorbent core periphery, which may be the periphery of the core wrap, may define any suitable shape, such as rectangular, "T," "Y," "hour-glass," or "dog-bone" shaped, for example. An absorbent core periphery having a generally "dog bone" or "hour-glass" shape may taper along its width towards the crotch region 37 of the absorbent article 100.

Referring to FIGS. 12E-G, the absorbent core 128 may have areas having little or no absorbent material, where a wearer-facing surface of the core bag 74 may be joined to a garment-facing surface of the core bag 74. These areas having little or no absorbent material may be referred to as "channels" 129. These channels can embody any suitable shapes and any suitable number of channels may be provided. In other instances, the absorbent core may be embossed to create the impression of channels. The absorbent core in FIGS. 12E-G is merely an example absorbent core. Many other absorbent cores with or without channels are also within the scope of the present disclosure.

As used herein, a loaded absorbent core is one holding (or capable of holding) a load of at least 50, 100, or 200 milliliters (mls) for diapers, pants, and adult incontinence articles. The disposable absorbent articles of the present disclosure comprising an absorbent core are designed to fit the wearer with an empty absorbent core (i.e., one that is not loaded), as well as being capable of fitting the wear for an appreciable time (2 or more hours) even when the core is loaded.

Acquisition Materials

One or more acquisition materials (e.g., AGM 26) may be present at least partially intermediate the topsheet 124 and the absorbent core 128. The acquisition materials are typically hydrophilic materials that provide significant wicking of bodily exudates. These materials may dewater the topsheet 124 and quickly move bodily exudates into the absorbent core 128. The acquisition materials 130 may comprise one or more nonwoven materials, foams, cellulosic materials, cross-linked cellulosic materials, air laid cellulosic nonwoven materials, spunlace materials, or combinations thereof, for example. In some instances, portions of the acquisition materials may extend through portions of the topsheet 124, portions of the topsheet 124 may extend through portions of the acquisition materials, and/or the topsheet 124 may be nested with the acquisition materials. Typically, an acquisition material or layer may have a width and length that are smaller than the width and length of the topsheet 124. The acquisition material may be a secondary topsheet in the feminine pad context. The acquisition material may have one or more channels as described in the absorbent core 128 section (including the embossed version). The channels in the acquisition material may align or not align with channels in the absorbent core 128. In an example, a first acquisition material may comprise a nonwoven material and as second acquisition material may comprise a cross-linked cellulosic material.

Topsheets

The absorbent articles 100 of the present disclosure may comprise a topsheet 124. The topsheet 124 is the part of the absorbent article 100 that is in contact with the wearer's skin. The topsheet 124 may be joined to portions of the backsheet 125, the absorbent core 128, the leg cuffs 52, and/or any other layers as is known to those of ordinary skill in the art. The topsheet 124 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured, may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet. The topsheet may comprise a bond pattern, apertures, and/or three-dimensional features.

Backsheets

The absorbent article 100 of the present disclosure may comprise a backsheet 125. The backsheet 125 is generally that portion of the absorbent article 100 positioned proximate to the garment-facing surface of the absorbent core 128. The backsheet 125 may be joined to portions of the topsheet 124, the backsheet nonwoven 127, the absorbent core 128, and/or any other layers of the absorbent article by any attachment methods known to those of skill in the art. The backsheet film 126 prevents, or at least inhibits, the bodily exudates absorbed and contained in the absorbent core 128 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet. The backsheet may comprise a bond pattern, apertures, and/or three-dimensional features.

Leg Cuffs

The absorbent articles 100 of the present disclosure may comprise leg cuffs 52, which include inner leg cuffs 150 and outer leg cuffs 140. The inner leg cuffs 150 may be positioned laterally inboard of outer leg cuffs 140. Each of the leg cuffs 52 may be formed by a piece of material which is bonded to the absorbent article 100 so it can extend upwards from a wearer-facing surface of the absorbent article 100 and provide improved containment of body exudates approximately at the junction of the torso and legs of the wearer. The inner leg cuffs 150 are delimited by an edge joined directly or indirectly to (or formed by) the topsheet and/or the backsheet and a free terminal edge, which is intended to contact and form a seal with the wearer's skin. The inner leg cuffs 150 may extend longitudinally at least partially (or fully) between the front end edge 136 and the back end edge 138 of the absorbent article 100 on opposite sides of the chassis and may be at least present in the crotch region 37. The inner leg cuffs 150 may each comprise one or more elastics 316 (e.g., elastic strands or strips) near or at the free terminal edge. These elastics 316 cause the inner leg cuffs 150 to help form a seal around the legs and torso of a wearer. The outer leg cuffs 140 extend at least partially between the front end edge 136 and the back end edge 138. The outer leg cuffs 140 essentially cause portions of the absorbent article 100 proximate to the chassis side edges 237a and 237b to help form a seal around the legs of the wearer. The outer leg cuffs 140 may extend at least within the crotch region 37.

Waistbands/Waistcaps

The absorbent articles 100 of the present disclosure may comprise one or more elastic waistbands 122. The elastic waistbands 122 may be positioned on the garment-facing surface or the wearer-facing surface, or may be formed therebetween. As an example, a first elastic waistband 122 may be present in the front waist region 36 near the front waist edge 136 and a second elastic waistband 122 may be present in the back waist region 38 near the back waist edge 138. The elastic waistbands 122 may aid in sealing the absorbent article 100 around a waist of a wearer and at least inhibiting bodily exudates from escaping the absorbent article 100 through the waist opening circumference. In some instances, an elastic waistband may fully surround the waist opening 190 of the absorbent article 100. A waist cap 123 may be formed by an extension of the waistband 122 and may remain unattached to the underlying structure in the central portion of the waist cap 123 to allow bodily exudates that flow along the topsheet 124 to be trapped between the topsheet 124 and the underside of the waist cap 123. In other words, the waist cap 123 may be joined to the underlying structure, e.g., center chassis 200 of the absorbent article 100 along the longitudinally distal edge of the waist cap 123 and/or along the laterally opposing side edges of the waist cap 123.

Belts

Beyond what was disclosed about belts in the Open-Form Taped Article and Closed-Form Pant Article Sections above, the front and back belts 430*f* and 430*b* may comprise front and back inner belt layers 432 and front and back outer belt layers 434 having an elastomeric material (e.g., strands 316 or a film (which may be apertured)) disposed at least partially therebetween. The elastic strands 316 or the film may be relaxed (including being cut) to reduce elastic strain over the absorbent core 128 or, may alternatively, run continuously across the absorbent core 128. The elastics strands 316 may have uniform or variable spacing therebetween in any portion of the belts. The elastic strands 316 may also be pre-strained the same amount or different amounts. The front and/or back belts 430*f* and 430*b* may have one or more elastic element free zones where the chassis 200 overlaps the belts 430*f* and 430*b*. In other instances, at least some of the elastic strands 316 may extend continuously across the chassis 200. The inner and/or outer belt layer may comprise a bond pattern, apertures, and/or three-dimensional features.

The front and back inner belt layers 432 and the front and back outer belt layers 434 may be joined using adhesives, heat bonds, pressure bonds, ultrasonic, or thermoplastic bonds. Various suitable belt layer configurations can be found in U.S. Pat. Appl. Pub. No. 2013/0211363.

Front and back belt end edges 438*f* and 438*b* may extend longitudinally beyond the front and back chassis end edges 236 and 238 or they may be co-terminus. The front and back belt side edges 437 may extend laterally beyond the chassis side edges 237*a* and 237*b*. The front and back belts 430*f* and 430*b* may be continuous (i.e., having at least one layer that is continuous (see 434 in FIGS. 12I and 12J) from belt end edge 438*f* to the opposite belt end edge 438*b*). Alternatively, the front and back belts 430*f* and 430*b* may be discontinuous from belt end edge 438*f* to the opposite belt end edge 438*b* (see 432 and 434 in FIG. 12H), such that they are discrete.

As disclosed in U.S. Pat. No. 7,901,393, the longitudinal length (along the central longitudinal axis 42) of the back belt 430*b* may be greater than the longitudinal length of the front belt 430*f*, and this may be particularly useful for increased buttocks coverage when the back belt 430*b* has a greater longitudinal length versus the front belt 430*f* adjacent to or immediately adjacent to the side seams 172. Alternatively, the bottom corners of the longer back belt may be trimmed in diagonal lines or curves.

The front and back belts 430*f* and 430*b* may include slits, holes, and/or perforations providing increased breathability, softness, and a garment-like texture. Underwear-like appearance can be enhanced by substantially aligning the waist and leg edges at the side seams 172.

Component Sections of the Present Disclosure

Components of absorbent articles comprising elastomeric laminates 302 may be sectioned to enable measurement and detailed characterization of the structure. Waistband 122 (see FIG. 13), waistcap 123 (see FIG. 14), inner leg cuff 150, outer leg cuff 140, and transverse barrier 165 all comprise 1 section. With regard to the waistband 122, waistcap 123, inner leg cuff 150, outer leg cuff 140 and transverse barrier 165 the section is defined as the region disposed between and including the distal most elastic and the proximal most elastic.

Other components such as the chassis 200, topsheet 124 (see FIGS. 12G and H), backsheet 125 (see FIGS. 12G and H), side panel 330 (see FIG. 13), ear panel 530 (FIG. 14), and belt panel (e.g., front and back belts) 430 (see FIGS. 12C-F, 12I, 12O and P, 12S and T) all comprise multiple sections as described herein. With regard to the side panel 330, ear panel 530 and belt panel 430 the portion of the component to be sectioned is defined as the region disposed between and including the distal most elastic of the elastomeric laminate 302 and the proximal most elastic of the elastomeric laminate 302 forming the component—except in cases where only a portion of the component is defined to be sectioned, then it is the region disposed between and including the distal most elastic of the defined portion of the elastomeric laminate 302 and the proximal most elastic of the defined portion elastomeric laminate 302 (see alternative back waist region 38' in FIGS. 12E and 12F, which is a portion of the back belt component). The region is defined by a first line extending parallel to the lateral axis 44 (of the article that the component is part of) and passing through the distal most point of the distal most elastic and a second line extending parallel to the lateral axis and passing through the proximal most point of the proximal most elastic. For each of these elements, the region is then divided into 4 equal sections, defined by three lines disposed parallel to the lateral axis 44 and disposed at 25%, 50% and 75% of the distance between the first line and second line. The region comprises a first section, "1" or "Section 1," which includes the distal most elastic; a fourth section, "4" or "Section 4," which includes the proximal most elastic; a second section, "2" or "Section 2," disposed adjacent to Section 1; and a third section, "3" or "Section 3," disposed between the Sections 2 and 4. In the claims, any one of Sections 1-4 may be generally referred to as "a first section;" and any two of Sections 1-4 may be generally referred to as "first and second sections," etc. Such is also the case for Sections L, M, and R.

For example, a front waist region 36 comprising a front belt 430*f* may be sectioned as follows (see FIGS. 18A-C):

"Wherein the front waist region 36 comprises a front component region 50 disposed between and including a front distal most elastic strand 417 of the front waist region 36 and a proximal most elastic strand 418 of the front waist region 36;

wherein the front component region 50 is defined by a front distal component region line 419 extending parallel to the lateral axis 44 and passing through a distal most point 420 of the front distal most elastic strand 417 and a front proximal component region line 421 extending parallel to the lateral axis 44 and passing through a proximal most point 422 of the front proximal most elastic strand 418;

wherein the front component region 50 is then divided into 4 equal component sections, defined by first, second, and third component section lines 423, 424, and 425, each disposed parallel to the lateral axis 44 and disposed at 25%, 50% and 75% of the distance between the front distal component region line 419 and front proximal component region line 421;

wherein the front component region 50 comprises a first component section, Front Section 1, comprising the front distal most elastic strand 417, a fourth component section, Front Section 4, comprising the front proximal most elastic strand 418, a second component section, Front Section 2, adjacent to Front Section 1, and a third component section, Front Section 3, disposed between Front Sections 2 and 4." For example, a back waist region 38 comprising a back belt 430f may be sectioned as follows (see FIGS. 18A-C):

"Wherein the back waist region 38 comprises a back component region 51 disposed between and including a back distal most elastic strand 517 of the back waist region 38 and a proximal most elastic strand 518 of the front waist region 38;

wherein the back component region 51 is defined by a back distal component region line 519 extending parallel to the lateral axis 44 and passing through a distal most point 520 of the back distal most elastic strand 517 and a back proximal component region line 521 extending parallel to the lateral axis 44 and passing through a proximal most point 522 of the back proximal most elastic strand 518;

wherein the back component region 51 is then divided into 4 equal component sections, defined by first, second, and third component section lines 523, 524, and 525, each disposed parallel to the lateral axis 44 and disposed at 25%, 50% and 75% of the distance between the back distal component region line 519 and back proximal component region line 521;

wherein the back component region 51 comprises a first component section, Back Section 1, comprising the back distal most elastic strand 517, a fourth component section, Back Section 4, comprising the back proximal most elastic strand 518, a second component section, Back Section 2, adjacent to Back Section 1, and a third component section, Back Section 3, disposed between Front Sections 2 and 4."

Figure 18B:
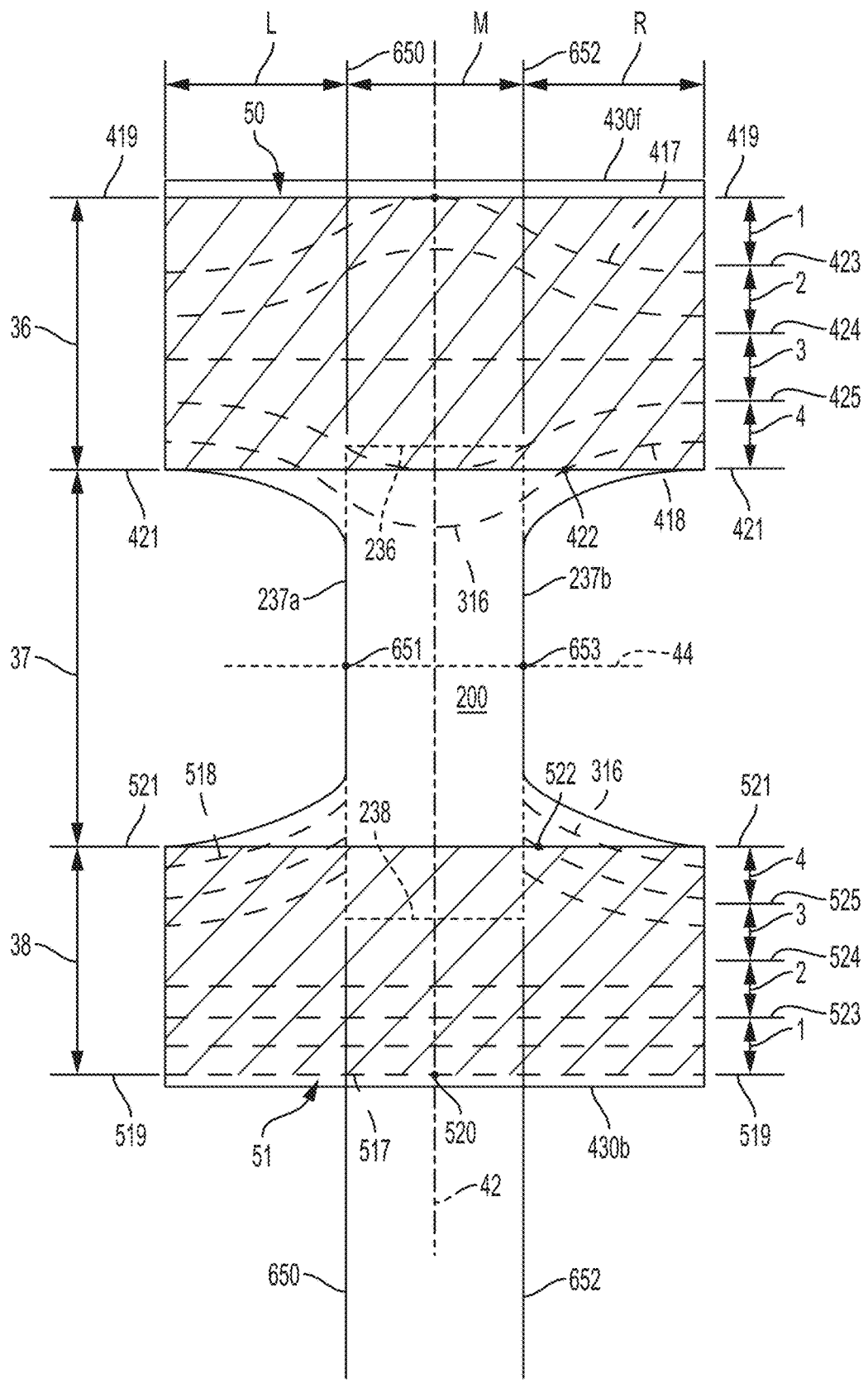
FIG. 18B is a plan view of a pant, prior to joining side edges of the belt to form the waist and leg openings, illustrating front and back component regions 50 and 51.
Figure 18C:
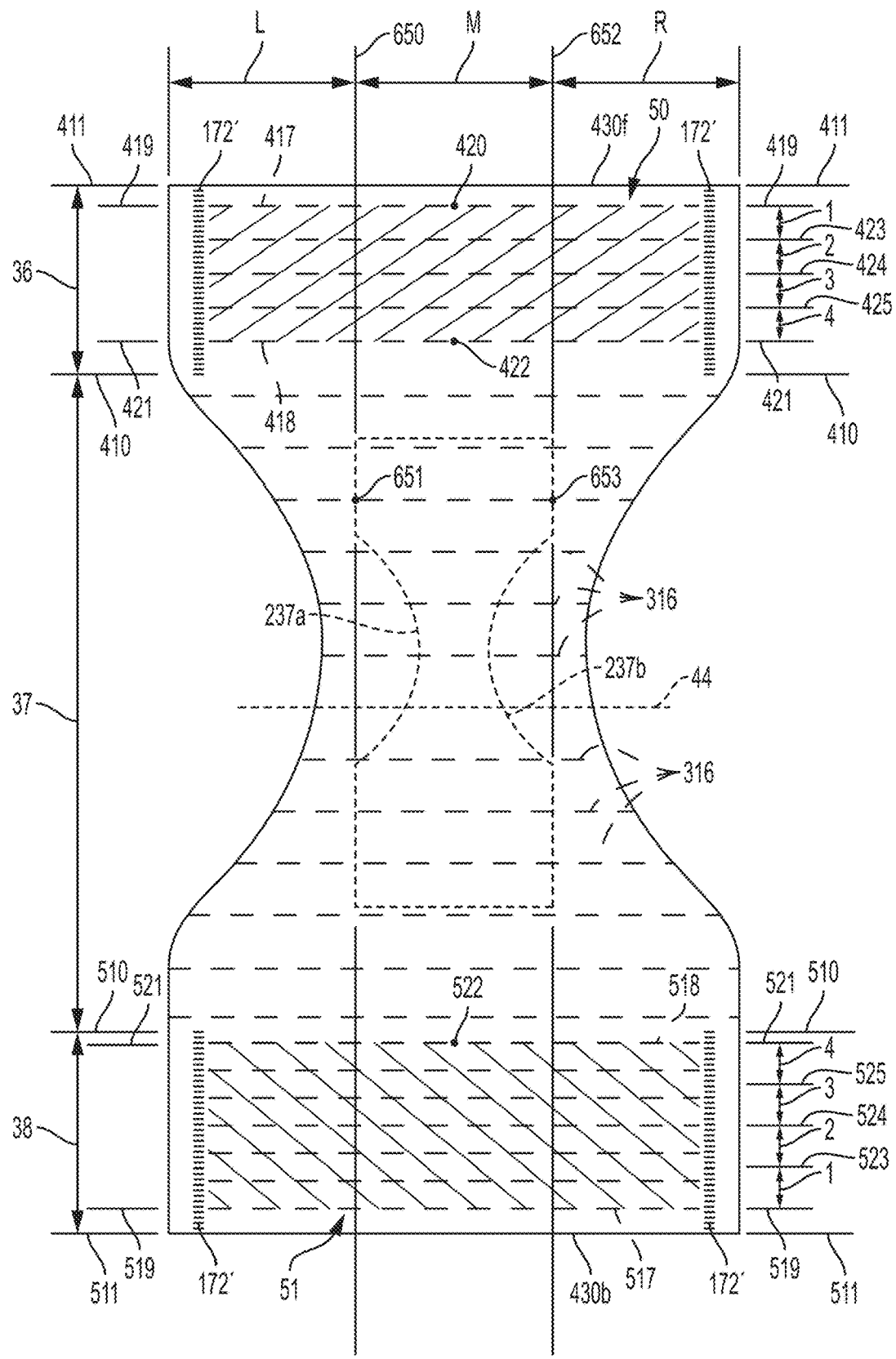
FIG. 18C is a plan view of a pant, prior to joining side edges of the belt to form the waist and leg openings, illustrating front and back component regions 50 and 51.

For embodiments wherein the laterally extending elastic disposed in one or both waist regions comprises and arcuate portion extending longitudinally inward of the proximal most point of the side seam, the proximal most point of the of the proximal most elastic is the point at which the elastic intersects a line extending laterally from the proximal most point of a first side seam to the proximal most point of the laterally opposing side seam as shown in FIG. 18B.

With regard to the chassis 200, topsheet 124 (see FIG. 12G), and backsheet 125 (see FIG. 12G) wherein the elastics 316 of the elastomeric laminate 302 extend in a substantially longitudinal orientation, the portion of the component to be sectioned is defined as the region disposed between and including the distal most elastic of the elastomeric laminate 302 on a first side of the longitudinal axis 42 and the distal most elastic of the elastomeric laminate 302 on a second side of the longitudinal axis 42. The region is defined by a first line extending parallel to the longitudinal axis 42 and passing through the distal most point of the distal most elastic on a first side of the longitudinal axis 42 and a second line extending parallel to the longitudinal axis 42 and passing through the distal most point of the distal most elastic on a second side of the longitudinal axis 42. For each of these elements, the region is then divided into 4 equal sections, defined by three lines disposed parallel to the longitudinal axis 42 and disposed at 25%, 50% and 75% of the distance between the first line and second line. The region comprises a first section, "1" or "Section 1," which includes the distal most elastic on the first side of the longitudinal axis; a fourth section, "4" or "Section 4," which includes the distal most elastic on the second side of the longitudinal axis; a second section, "2" or "Section 2," disposed adjacent to Section 1; and a third section, "3" or "Section 3," disposed between Sections 2 and 4.

With regard to the chassis 200, topsheet 124, and backsheet 125 (see FIG. 12H) wherein the elastics 316 of the elastomeric laminate 302 extend in a substantially lateral orientation, the portion of the component to be sectioned is defined as the region disposed between and including the distal most elastic of the elastomeric laminate 302 on a first side of the lateral axis 44 and the distal most elastic of the elastomeric laminate 302 on a second side of the lateral axis 44. The region is defined by a first line extending parallel to the lateral axis 44 and passing through the distal most point of the distal most elastic on a first side of the lateral axis 44 and a second line extending parallel to the lateral axis 44 and passing through the distal most point of the distal most elastic on a second side of the lateral axis 44. For each of these elements, the region is then divided into 4 equal sections, defined by three lines disposed parallel to the lateral axis 44 and disposed at 25%, 50% and 75% of the distance between the first line and second line. The region comprises a first section, "1" or "Section 1," which includes the distal most elastic on the first side of the lateral axis; a fourth section, "4" or "Section 4," which includes the distal most elastic on the second side of the lateral axis; a second section, "2" or "Section 2," disposed adjacent to Section 1; and a third section, "3" or "Section 3," disposed between Sections 2 and 4.

Absorbent Article Sections of the Present Disclosure

Beyond the absorbent article "component sections" described above, the absorbent article itself may be divided into "article sections"—see FIGS. 12E, F, K, L, Q, R, U, and V, 13, 14, and 18A-C. Article sections may be used to enable characterization of the structure of article components that overlap the chassis and that extend laterally beyond the chassis. Particularly, a middle section "M" or "Section M" of the article region is defined by a left article region line 650 extending parallel to the longitudinal axis 42 and passing through a left laterally distal most point 651 of a left side edge 237a of the chassis 200 and by a right article region line 652 extending parallel to the longitudinal axis 42 and passing through a right laterally distal most point 653 of a right side edge 237b (laterally opposed from the left side edge 237a) of the chassis 200. Everything to one lateral side or the other of the M article section are the left article section "L" or "Section L" and laterally opposed right article section "R" or "Section R." Sections L and R can be more particularly referred to by referencing whether Sections L, R, or M are in the front, back, or crotch regions 33, 38, and 37, and, as appropriate, which article section it overlaps with. For instance, with regard to a belt 430, it may be referred to as having a Section 1 (adjacent a waist opening 190) in Section L of the front waist region 36. As another example, a portion of the belt 430 may be referenced that is longitudinally beyond the chassis 200 in the Section M in the back waist region 38.

Performance of Elastomeric Laminates and Articles of the Present Disclosure

General

Part or all of the absorbent article 100 can be mechanically deformed by being MD activated and/or apertured, thereby becoming extensible to a degree greater than the inherent extensibility of the material or materials from which the article is made (e.g., the backsheet nonwoven, the inner liner, belts, side panel, elastomeric laminates, or combinations thereof). Advantageously, the elastic-like behavior of the elastomeric laminate can be modified by mechanically deforming a portion or all of the laminate as described below. The additional extensibility may be desirable in order to allow the absorbent article 100 to extend to be donned on the body of a wearer and to adjust to body dimensional changes during movement by the wearer. The additional extensibility may also be desirable, for example, to allow the user of a pull-on diaper 20 (including absorbent article 100) having a particular size before extension to extend the front and/or back waist regions 36 and 38 to enable the pull-on diaper to be pulled over the hips of the wearer and then to contract to encircle the waist of an individual wearer whose waist circumference is typically smaller than the circumference as measured at the hips of the wearer. Such extension of the waist region(s) can give the pull-on diaper 20 a generally hourglass shape, so long as the crotch region 37 is extended to a relatively lesser degree than the waist region(s), and can impart a tailored appearance to the pull-on diaper 20 when it is worn. In addition, the additional extensibility provided by the mechanical deformation of some or all of the elastomeric laminate may be desirable in order to minimize the cost of the pull-on diaper 20. Specifically, a lesser amount of material is needed in order to make a diaper capable of being properly fit onto a given size of a wearer when the material is mechanically deformed as described herein.

Additional extensibility in the absorbent article 100 in the lateral direction may be relatively more useful than additional extensibility in the longitudinal direction. The abdomen of the wearer may be likely to expand when the wearer changes posture from standing to sitting and the corresponding abdominal expansion increases the circumference that is encircled by the absorbent article 100, rendering lateral extension of the waist region or regions particularly advantageous.

Such an elastomeric laminate 302 can be laterally extended beyond its original dimension with the application of relatively less force than that required to extend the same material to the same extent when undeformed. In particular, the effects of an application of opposing divergent forces directed generally perpendicular to the ridges 102 and valleys 104 formed during the mechanical deformation of the laminate include an extension of such a formed web material along an axis between the opposing forces. Thus, such elastomeric laminates may exhibit an extensible behavior more closely resembling that of the elastic material itself in the range of extensibility that is useful for the type of lateral extension desired for use in absorbent articles. In addition, such elastomeric laminates can provide a given level of extensibility with less material and therefore provide an advantage in terms of the cost of materials, as well as the cost of manufacturing the absorbent articles.

The range of extensibility of a web material or an elastomeric laminate can be controlled by the degree of deformation of the altered regions and can be varied from near zero to a maximum that is dependent upon the original material. For example, the mechanically deformed materials used in the absorbent article 100 (for example a pull-on diaper 20) can typically be deformed to provide incremental extensibility above the original undeformed dimension of from about 5% to about 25% percent of the original dimension. A portion of the absorbent article 100 can have a level of incremental extensibility within a range whose lower end is between 5%, 10%, and 15%, and whose upper end is between 15%, 20%, and 25%. The requisite levels of extensibility are achieved by application of an opposing divergent force in the direction of extensibility of about 3,000 grams or about 2,000 grams. However, it should be easily appreciated that any particular value for the maximum extensibility in the range from approximately 5 percent to approximately 25 percent can be selected to suit a particular choice of the original size of the absorbent article and the range of sizes of the intended wearers. In particular, a disposable absorbent pant having a specific unextended waist opening circumference can be suitable for use on wearers having waist circumferences ranging from equal to this unextended waist opening circumference up to the maximum extensibility.

When the elastomeric laminate is subjected to an applied elongation, the laminate exhibits an elastic-like behavior as it extends in the direction of applied elongation and returns to its substantially untensioned condition once the applied elongation is removed, unless the laminate is extended beyond the point of yielding. The laminate extensibility is adjustable by varying the percentage of the laminate surface which is comprised of the ridges 102 and valleys 104. This can be achieved, for instance, by modifying the widths of the ridges 102 and valleys 104, the spacing between adjacent ridges 102 and valleys 104 and/or the depth of the ridges 102 and valleys 104. A higher percentage of area coverage of the elastomeric laminate by the ridges 102 and valleys will increase the overall extensibility of the laminate. The elastomeric laminate is able to undergo multiple cycles of applied elongation up to the yield point without losing its ability to substantially recover. Accordingly, elastomeric laminates of the present disclosure are able to return to its substantially untensioned condition once the applied elongation is removed (e.g., as the absorbent article 100 is pulled over the wearer's hips during use).

Application-Force, Sustained-Fit-Load-Force, and Sustained-Fit-Unload Force

Absorbent articles comprising traditional stranded elastics and elastomeric laminates typically require high Application-Forces to ensure adequate Sustained-Fit-Load-Forces and Sustained-Fit-Unload-Forces to maintain the article's position on the wearer. The absorbent articles comprising traditional stranded elastics do not retain elastic forces as well as articles comprising beamed elastics, especially beamed elastics in a mechanically deformed laminate and as such typically have significant consumer performance trade-offs, i.e., difficult application for the consumers and good sustained fit and gasketing or ease of application for consumers and poor sustained fit, gasketing and leakage performance.

Figure 17:
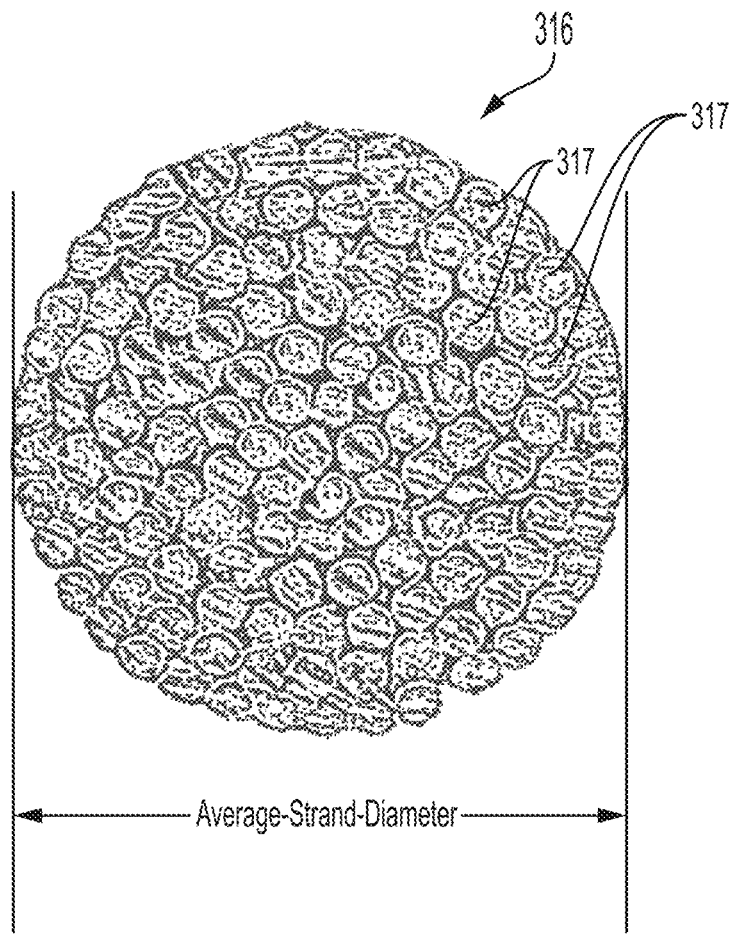
FIG. 17 illustrates the Average-Strand-Diameter of an elastic strand.

Higher decitex elastic of the traditional stranded elastic laminates have between 30 and 60 individual elastic filaments 317 (see, for example, FIG. 17) twisted together to form the elastic strand. Low decitex elastic of the beamed elastic laminate have between 3 and 7 elastic filaments. The low decitex elastic used in the beamed elastic laminate have fewer individual filaments than the higher decitex elastic. In some cases the lower decitex may have as few as $1/10^{th}$ of the number of filaments. Given the elastic filaments are twisted to form the strands, the elastic comprising more filaments will have more filament to filament interaction as the strands extend and contract. This increase in interaction may adversely impact the retention of sustained fit load and unload forces. Furthermore, the larger bundle of twisted filaments also will likely result in different filaments being bonded to the substrates of the laminate at different points along the strand introducing additional constraints on various filaments in the bundle further impacting the filaments ability to extend and contract. The lower decitex elastic strands of the beamed elastic laminate comprise significantly fewer filaments and as such the filaments can extend and contract more independently of each other providing an elastic response closer to a monofilament strand.

An absorbent article comprising a beamed elastic laminate that has not been mechanically deformed may have an Application-Force of between about 900 gf and about 1,600 gf, a Sustained-Fit-Load-Force of greater than about 30% of the Application-Force and a Sustained-Fit-Unload-Force of greater than about 25% of the Application-Force. Alternatively, an absorbent article comprising a beamed elastic laminate that has not been mechanically deformed may have an Application-Force of between about 1,500 gf and about 3,000 gf, a Sustained-Fit-Load-Force of greater than about 35% of the Application-Force and a Sustained-Fit-Unload-Force of greater than about 30% of the Application-Force. While this performance is a significant improvement over traditional stranded elastic laminates, mechanically deformed elastomeric beamed laminates perform even better without sacrificing key fit performance measures.

Figure 5A:
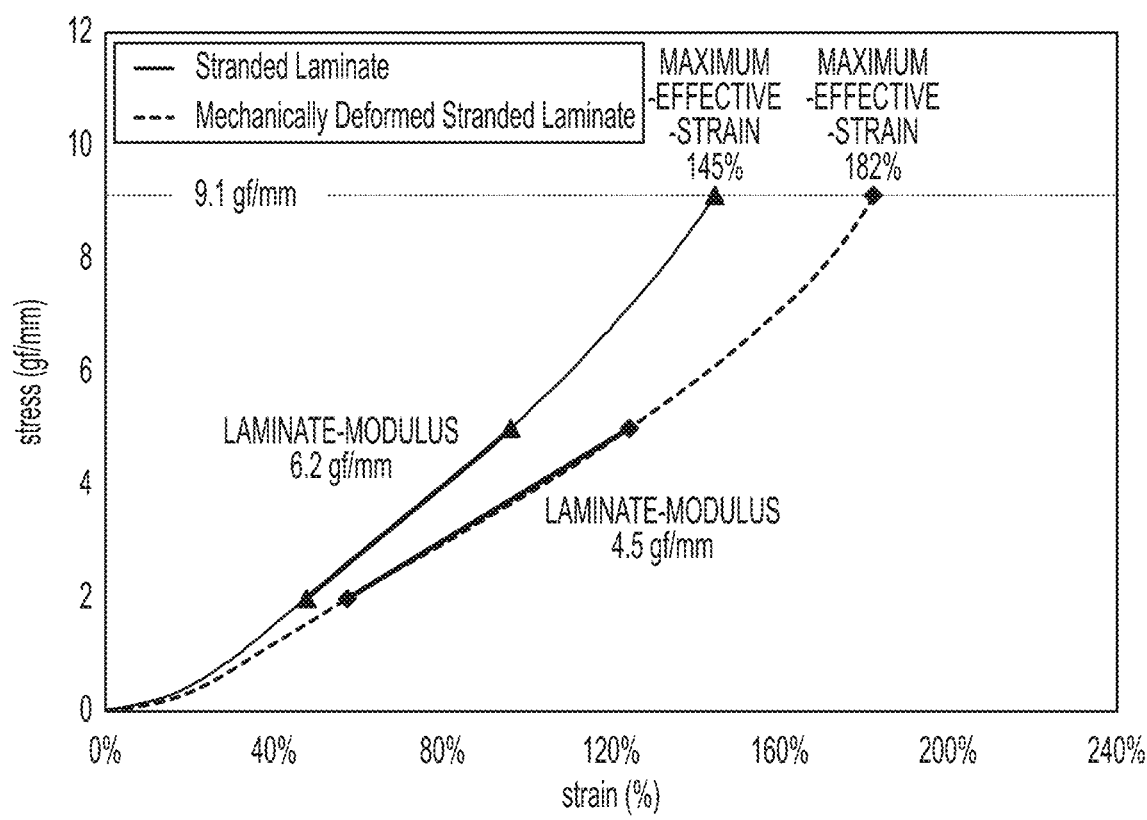
FIG. 5A illustrates the Stress-Strain curves with Maximum-Effective-Strain and Laminate-Modulus for a stranded laminate, and that same stranded laminate after mechanical deformation. The laminates of FIG. 5A are further detailed in Table A.
Figure 5B:
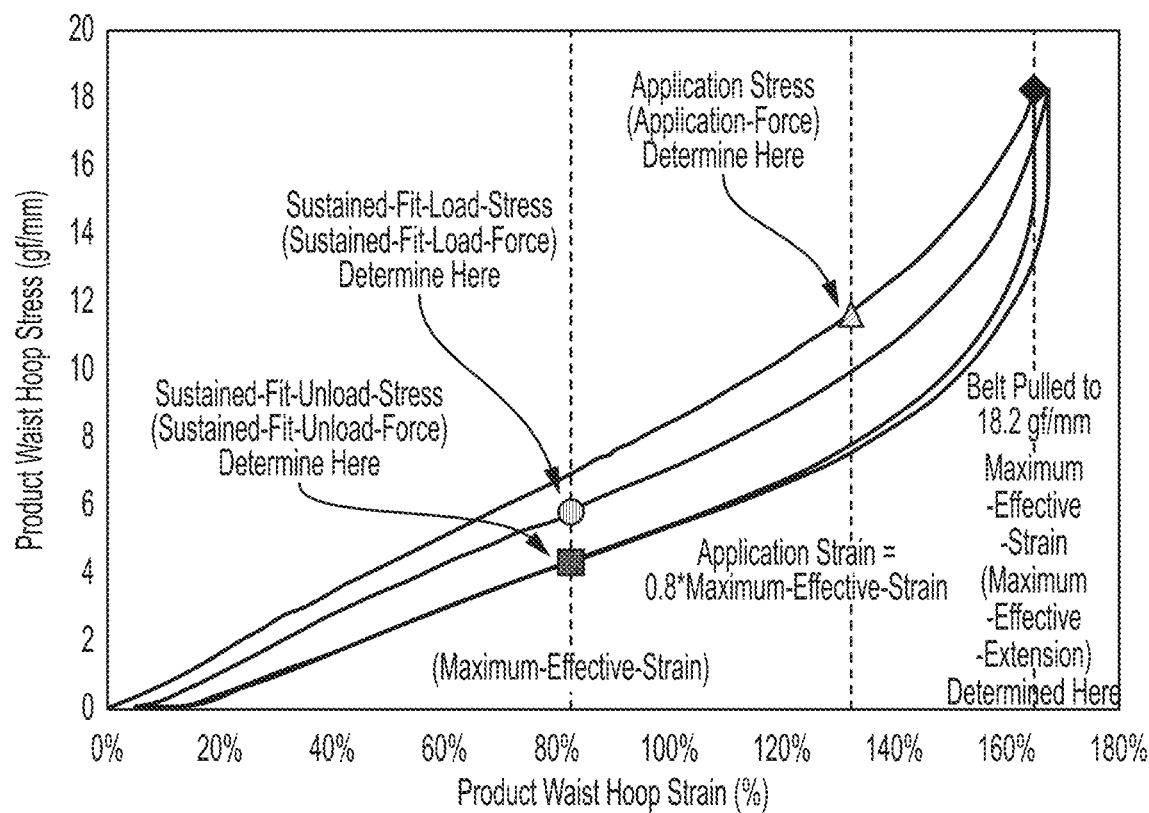
FIG. 5B illustrates the data generated in the first load of the Hip-Hoop-Test, including the stress-strain curve with Maximum-Effective-Extension, Application-Force, Sustained-Fit-Load-Force, and Sustained-Fit-Unload-Force, for the mechanically deformed stranded laminate of FIG. 5A.
Figure 5C:
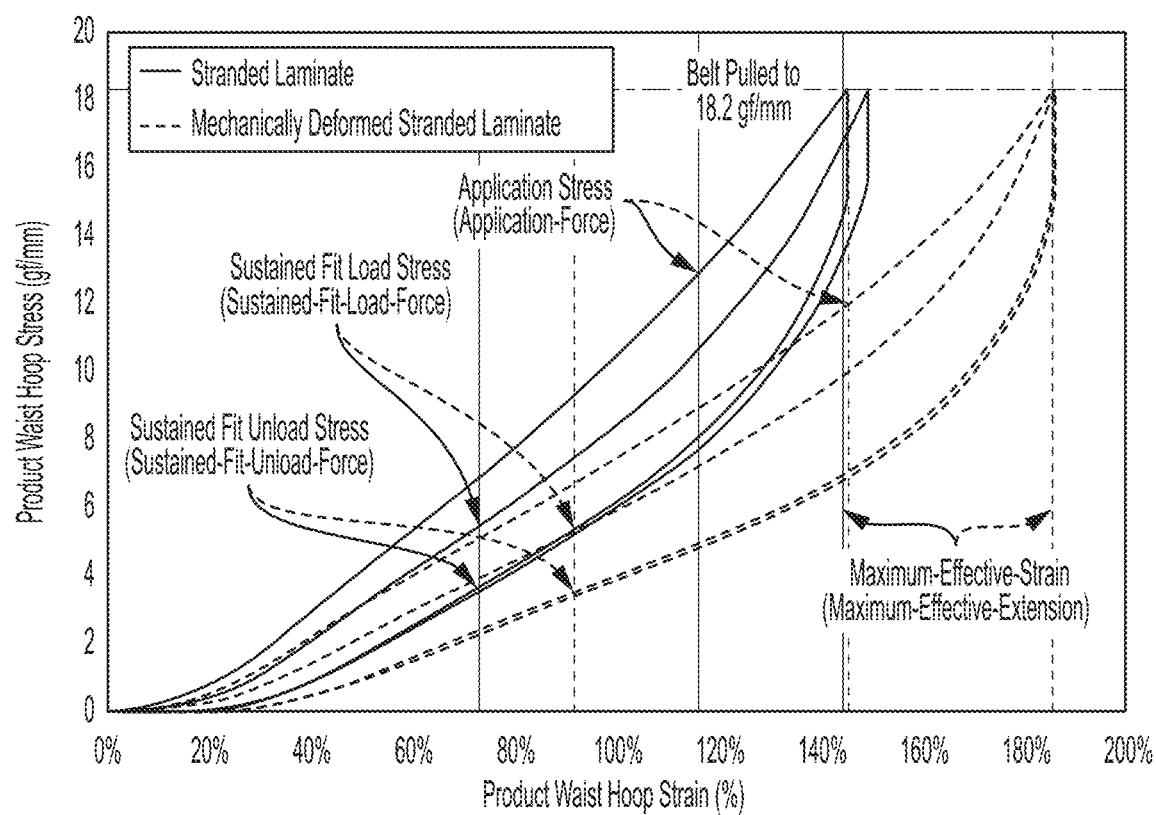
FIG. 5C illustrates the impact of MD activation on the Hip-Hoop-Test of a stranded laminate and that same laminate after mechanical deformation. The laminates of FIG. 5C are further detailed in Table A.
Figure 5H:
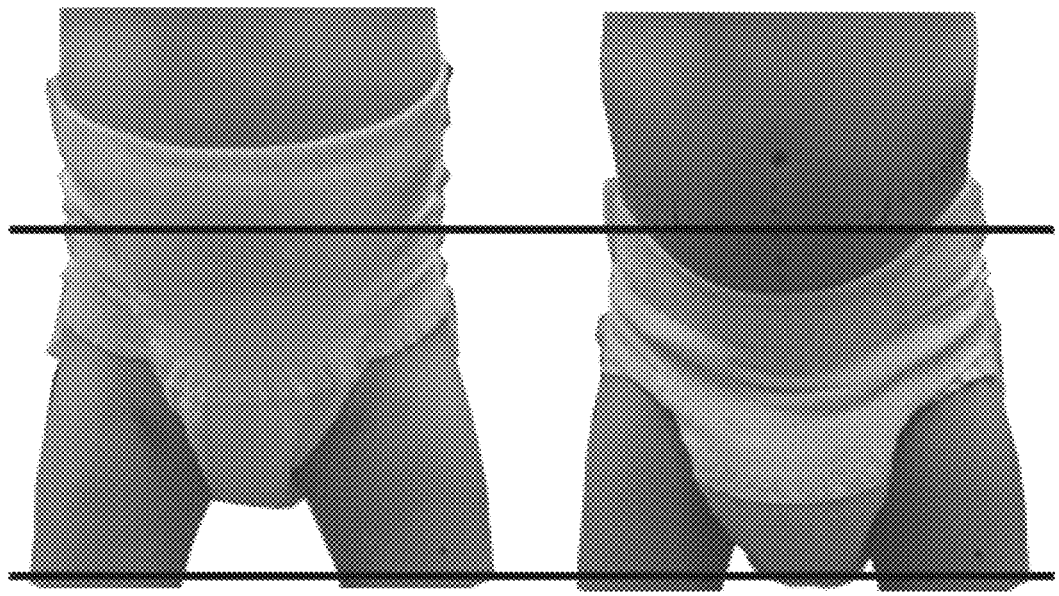
FIG. 5H is a front view illustrating the initial fit of the inventive product of FIG. 5E.
Figure 5I:
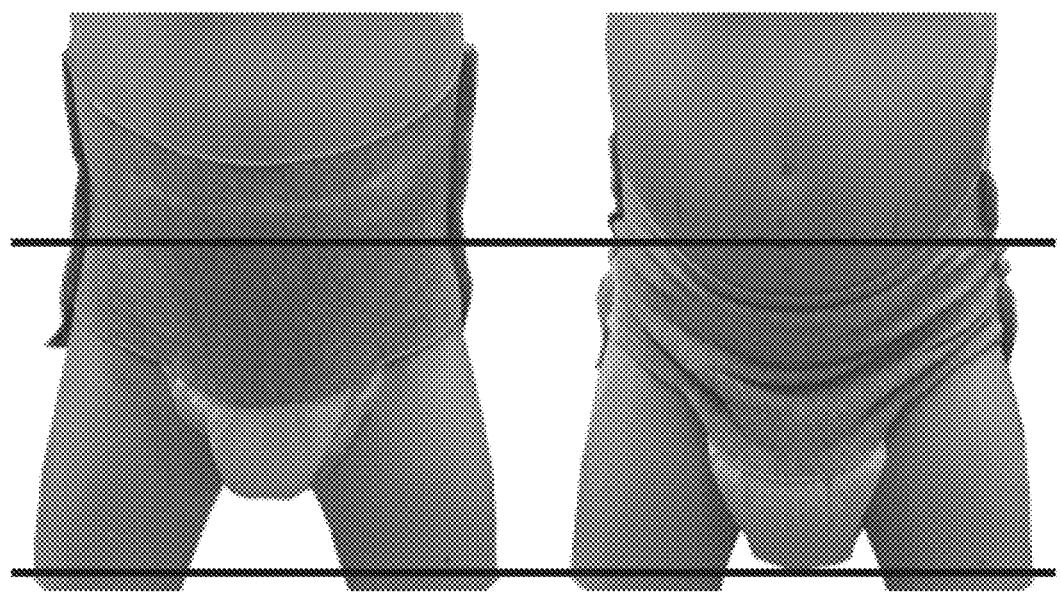
FIG. 5I is a front view illustrating the initial fit of a comparative product, the comparative product being the same as FIG. 5D, except that the belts are made from a durable yoga pant.

In order to create the optimum usage experience it is desirable to provide an absorbent article having the right balance of Application-Force, Sustained-Fit-Load-Force and Sustained-Fit-Load-Force. FIG. 5A shows a force elongation curve that illustrates where these forces are taken along the curve. The desired outcome would be to have an article comprising a mechanically deformed elastomeric laminate having an Application-Force that is equal to or lower than an article comprising a non-mechanically deformed elastomeric laminate and a Sustained-Fit-Load-Force and Sustained-Fit-Unload-Force that are comparable between an article comprising a mechanically deformed elastomeric laminate and an article comprising a non-mechanically deformed elastomeric laminate. For products having similar Application-Force the Sustained-Fit-Load-Force and Sustained-Fit-Unload-Force can also be reflected as a percentage relative to the Application-Force. Actual Application-Forces, Sustained-Fit-Load-Forces, Sustained-Fit-Unload-Forces, Laminate-Modulus and Strain-to-Modulus-Ratio of an article comprising a mechanically deformed elastomeric laminate, as well as articles comprising a non-mechanically deformed elastomeric laminate, can be found in Table A (below). FIG. 5A is an illustration of the Laminate-Modulus of the base stranded ("Stranded Laminate" in FIG. 5A and "Base Laminate" in Table A) and that same laminate after mechanical deformation ("Mechanically Deformed Stranded Laminate" in FIG. 5A and "Base Laminate (Mechanically Deformed)") shown in Table A. FIG. 5B is an illustration of the Sustained-Fit-Load-Forces and Sustained-Fit-Unload-Forces of the inventive laminate ("Mechanically Deformed Stranded Laminate" in FIG. 5A). FIG. 5C is an illustration of the Sustained-Fit-Load-Forces and Sustained-Fit-Unload-Forces of a stranded laminate (solid line in FIG. 5C) and that same laminate after mechanical deformation (dashed line in FIG. 5C).

TABLE A

Impact of Mechanical Deformation on a Beamed Elastiomeric Laminate Hip-Hoop

| Laminate | Maximum Strain (%) | Application-Stress (Application-Force) | Sustained-Fit-Load-Stress (Sustained-Fit-Load-Force) | Sustained-Fit-Unload-Stress (Sustained-Fit-Unload-Force) | Laminate-Modulus (gf/mm) | Strain-to-Modulus-Ratio | Reduction in Laminate Modulus (%) | Increase in Maximum Strain (%) | Increase in Strain-to-Modulus-Ratio (%) |
|---|---|---|---|---|---|---|---|---|---|
| Base Laminate | 145% | 12.8 gf/mm 1408 gf | 5.5 gf/mm 605 gf | 3.6 gf/mm 396 gf | 6.2 | 24% | na | na | na |
| Base Laminate (Mechanically Deformed) | 182% | 12.0 gf/mm 1320 gf | 5.4 gf/mm 594 gf | 3.5 gf/mm 385 gf | 4.5 | 41% | 27% | 26% | 73% |

Two products, Adhesively Bonded Beamed Elastic comprising a mechanically deformed elastomeric laminate (inventive) and Adhesively Bonded Beamed Elastic comprising a non-mechanically deformed elastomeric laminate (non-inventive), are illustrated in FIGS. 5D-5K' and were subjected to mannequin fit testing. During the mannequin fit test, the products were applied to a mechanically manipulated mannequin that undergoes a fixed series of motions that simulate real baby movements. After application the initial position of where the pant article rests on the mannequin was measured: 1) front waist initial position, 2) back waist initial position, and 3) initial rise (measured from a fixed point in the front through the crotch to a fixed point in the back). FIG. 5D shows the initial fit of an adhesively bonded Beamed Elastic comprising a non-mechanically deformed elastomeric laminate (non-inventive) from the front and FIG. 5F shows the initial fit of an adhesively bonded Beamed Elastic comprising a non-mechanically deformed elastomeric laminate (non-inventive) from the side/back. FIG. 5E shows the initial fit of an adhesively bonded Beamed Elastic comprising a mechanically deformed elastomeric laminate (inventive) from the front and FIG. 5G shows the initial fit of an adhesively bonded Beamed Elastic comprising a mechanically deformed elastomeric laminate (inventive) from the side/back. The article was then loaded with 75 mls of synthetic urine and then undergoes the mechanical manipulation steps. After the first cycle of mechanical manipulation the product was again loaded with another 75 mls of synthetic urine and then subjected to a second cycle of mechanical manipulation. After the second cycle, the product final position was measured, front waist final position, back waist final position, and final rise. FIG. 5D' shows the final fit of an adhesively bonded Beamed Elastic comprising a non-mechanically deformed elastomeric laminate (non-inventive) from the front and FIG. 5F' shows the final fit of an adhesively bonded Beamed Elastic comprising a non-mechanically deformed elastomeric laminate (non-inventive) from the side/back. FIG. 5E' shows the final fit of an adhesively bonded Beamed Elastic comprising a mechanically deformed elastomeric laminate (inventive) from the front and FIG. 5G' shows the final fit of an adhesively bonded Beamed Elastic comprising a mechanically deformed elastomeric laminate (inventive) from the side/back. The black lines on FIGS. 5D', 5E', 5F' and 5G' are included to provide a reference for comparison between the adhesively bonded Beamed Elastic comprising a non-mechanically deformed elastomeric laminate and the adhesively bonded Beamed Elastic comprising a mechanically deformed elastomeric laminate. From the charts, tables, and images it is clear that the sustained fit resulting from the Sustained-Fit-Load-Forces and Sustained-Fit-Unload-Forces of the beamed elastomeric belts mechanically deformed and non-mechanically deformed are substantially the same despite the significant increase in extensibility of the mechanically deformed elastomeric laminate versus that of the non-mechanically deformed elastomeric laminate.

The actual measurements from the mannequin test are shown in Table B (below). The data shows that the articles comprising adhesively bonded Beamed Elastic comprising a mechanically deformed elastomeric laminate (inventive) and the articles comprising adhesively bonded Beamed Elastic comprising a non-mechanically deformed elastomeric laminate (non-inventive) are within +/−10% for total sagging (measure of how much the product slips from the initial positions to the final positions). Compared to the marketed products the articles comprising adhesively bonded Beamed Elastic comprising a mechanically deformed elastomeric laminate have significantly less sagging. The marketed products (non-inventive) have from between 129% to 159% more sagging at the front and from 135% to 157% more total sagging than articles comprising adhesively bonded Beamed Elastic comprising a mechanically deformed elastomeric laminate (inventive).

TABLE B

Sustained Fit Measurements from Laboratory Mannequin Testing

| Laminate | Sagging at Product Front (mm) | Sagging at Product Rise (mm) | Sagging at Product Back (mm) | Sagging at Product Side (mm) | Total Sagging (mm) | Sagging at Front relative to Base (%) | Total Sagging relative to Base (%) |
|---|---|---|---|---|---|---|---|
| Base Laminate (no mechanical deformation) (FIGS. 5D, 5D', 5F, 5F') | −59 | −57 | −30 | −23 | −168 | na | na |
| Inventive Products | | | | | | | |
| Mechanically Deformed Laminate A (FIGS. 5E, 5E', 5G, 5G') | −52 | −58 | −30 | −25 | −165 | 88% | 98% |
| Mechanically Deformed Laminate B | −56 | −66 | −34 | −21 | −176 | 95% | 105% |
| Mechanically Deformed Laminate C | −52 | −63 | −30 | −18 | −164 | 88% | 98% |
| Currently Marketed Products | | | | | | | |
| Easy Ups China | −89 | −89 | −45 | −27 | −249 | 151% | 148% |
| Merries | −76 | −77 | −50 | −23 | −226 | 129% | 135% |
| Goon | −94 | −87 | −52 | −30 | −264 | 159% | 157% |
| Cruisers 360 | −85 | −86 | −49 | −28 | −248 | 144% | 148% |

Table C shows how the Laminate-Modulus and Strain-to-Modulus-Ratio of the inventive products compare to currently marketed products.

TABLE C

Comparison of Currently Marketed Products to an Inventive Mechanically Deformed Product

| Product | Maximum Strain (%) | Laminate-Modulus (gf/mm) | Strain-to-Modulus-Ratio |
|---|---|---|---|
| Easy Ups China | 161% | 5.7 | 29% |
| Goon Angel | 155% | 6.6 | 24% |
| Goon Feather | 150% | 7.1 | 21% |
| Inventive Mechanically Deformed Product | 182% | 4.5 | 41% |

Figure 11:
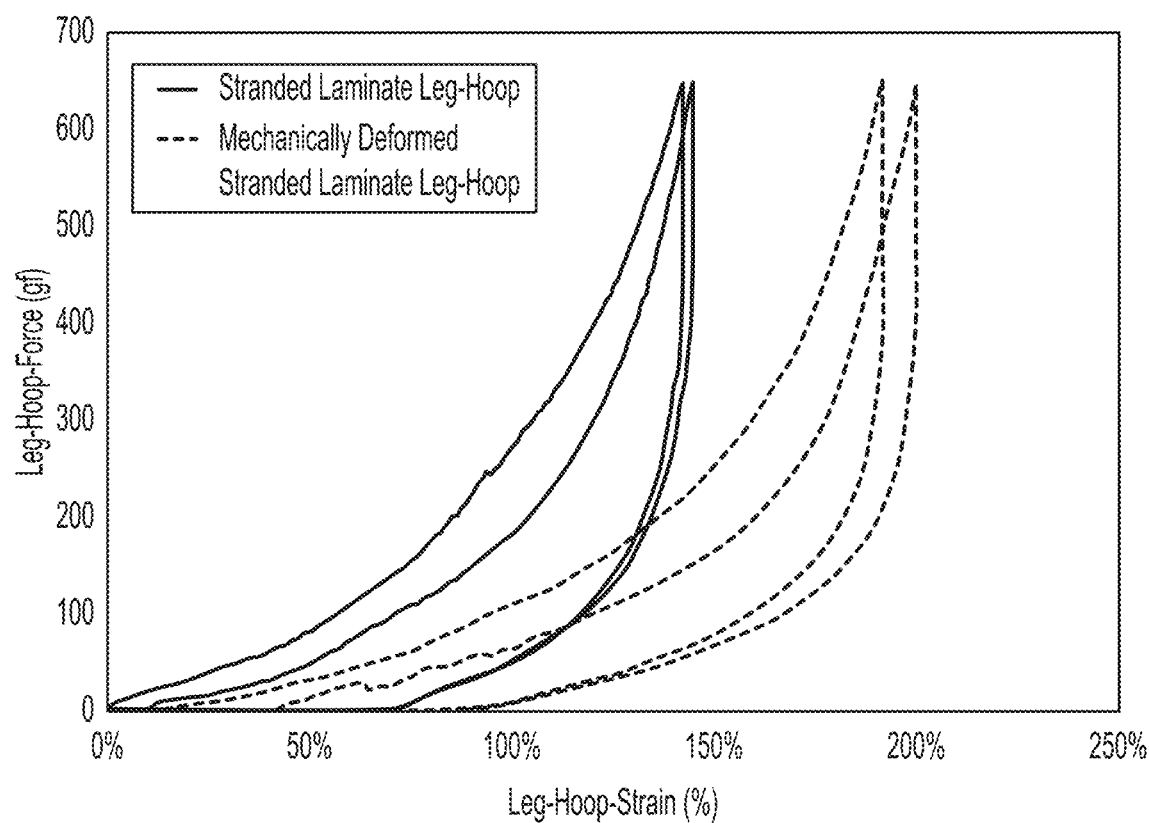
FIG. 11 shows the Leg-Hoop-Force versus Leg-Hoop-Strain curves of the laminates of FIG. 10, as generated in the Leg-Hoop-Test.

Table D shows the impact of mechanical deformation on the Leg-Hoop of a beamed elastic laminate ("Base Laminate" in Table D is the solid line "Stranded Laminate Leg Loop" in FIG. 1 land is non-inventive; and "Base Laminate (Mechanically Deformed)" in Table D is the dashed line "Mechanically Deforormed Leg Loop" in FIG. 11 and is inventive.

TABLE D

Impact of Mechanical Deformation on a Beamed Elastiomeric Laminate Leg-Hoop

| Product | Leg-Hoop-Maximum-Strain at 1st Cycle (%) | Leg-Hoop-Maximum-Strain at 2nd Cycle (%) | Leg-Hoop-Load-Force at 120% Strain (gf) | Leg-Hoop-Unload-Force at 120% Strain (gf) |
|---|---|---|---|---|
| Base Laminate | 142% | 145% | 397.3 | 116.2 |
| Base Laminate (Mechanically Deformed) | 192% | 200% | 151.8 | 33.5 |

TABLE E

Impact of Mechanical Deformation on Percent-Contact-Area

| Product | Average Filament Count | Average Strand Spacing | Average Dtex | Pressure Under-Strand | Percent-Contact-Area 100 μm | Percent-Contact-Area 200 μm | Percent-Contact-Area 300 μm | 2-98% Height (mm) |
|---|---|---|---|---|---|---|---|---|
| Easy Ups | 55.7 | 8.5 | 940 | 1.578 | 9.8% | 19.1% | 27.3% | 2.667 |
| Merries | 55.4 | 5.2 | 625 | 1.344 | 7.0% | 15.8% | 24.6% | 3.092 |
| Mooney | | 5.3 | 448 | 1.626 | 6.5% | 16.1% | 24.7% | 2.292 |
| Goon | 55.6 | 4.8 | 550 | 1.323 | 5.3% | 11.6% | 19.0% | 2.260 |
| Depends | 42.8 | 6.8 | 489 | 1.987 | 6.2% | 14.9% | 24.4% | 1.841 |
| Always Discreet | 42.8 | 3.6 | 525 | 1.001 | 7.3% | 16.2% | 26.9% | 1.619 |
| Base Laminate (no mechanical deformation) | 5.0 | 0.5 | 85 | 0.351 | 14.5% | 30.8% | 45.1% | 1.00 |
| Base Laminate (mechanically deformed) | 5.0 | 0.5 | 85 | 0.351 | 17.1% | 34.8% | 51.2% | 1.08 |

Role of Parameters

Stranded elastomeric laminates of the present disclosure outperform stranded elastomeric laminates of the art in many of the relevant parameters that measure how laminates perform, including:

Hip-Hoop is relevant because it is the measure of the elongation and contraction of the closed circumference of an absorbent article. The data generated from this test can be used to determine the Application-Force, Sustained-Fit-Load-Force and the Sustained-Fit-Unload-Force.

Application-Force is relevant because it is the measure of the force that a wearer of caretaker might encounter while donning the absorbent article.

Pants (including belts and side panels) made using elastomeric laminates 302 of the present disclosure may have an Application-Force of from about 900 gf to about 1600 gf, or may have from about 1,000 gf to about 1,400 gf.

Sustained-Fit-Load-Force is relevant because it is the measure of the force that an article applies to the wearer when the wearer's waist extends for example during respiration or during wearer movement like when a wearer goes from a standing position to a sitting position.

Pants (including belts and side panels) made using elastomeric laminates 302 of the present disclosure may have a Sustained-Fit-Load-Force greater than about 30% of the Application-Force.

Sustained-Fit-Unload-Force is relevant because it is the measure of the force that an article applies to the wearer when the wearer's waist contracts for example during respiration or during wearer movement like when a wearer goes from a sitting position to a standing position.

Pants (including belts and side panels) made using elastomeric laminates 302 of the present disclosure may have a Sustained-Fit-Unload-Force greater than about 25% of the Application-Force.

Surface Topography (Percent-Contact-Area, Rugosity-Frequency, Rugosity-Wavelength, and 2-98%-Height-Value) is relevant because it is the measure of the textural properties of the elastomeric laminates. The surface topography enables definition of Percent-Contact-Area which is the portion of the surface that may be in contact with the skin, Rugosity-Frequency, and Rugosity-Wavelength characterize the structural aspects of the texture and the 2-98%-Height-Value helps define the thickness of the elastomeric laminate.

Surface Topography

Surface Topography is the surface topology of the elastomeric laminate measured using optical profilometry. The 3D surface data are then sampled and processed to extract several parameters that describe the Percent-Contact-Area and 2-98% Height of the elastomeric laminate specimen surface as well as the Rugosity-Frequency and Rugosity-Wavelength.

Figure 6A:
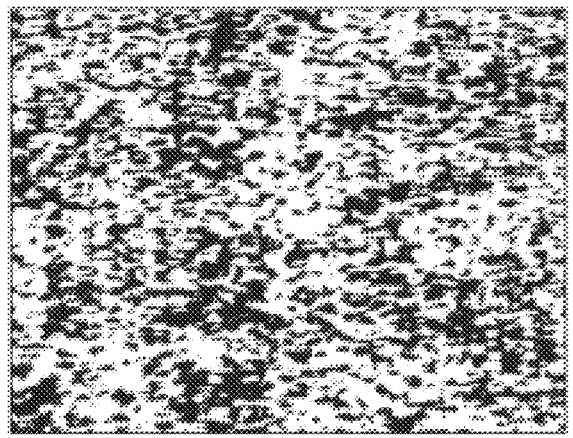
FIG. 6A is an image of comparative (non-inventive) adhesively bonded beamed laminate having an Average-Pre-Strain of 150% showing the Percent-Contact-Area taken from the Surface Topography Method.
Figure 6B:
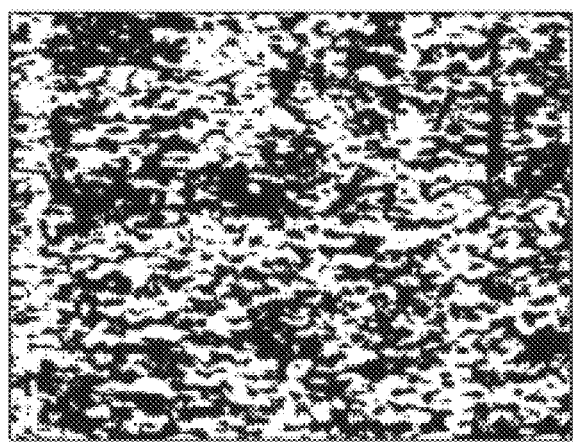
FIG. 6B is an image of an inventive adhesively beamed laminate of the present disclosure having an Average-Pre-Strain of 150% showing the Percent-Contact-Area taken from the Surface Topography Method—the laminate of FIG. 6B is the same as the laminate of FIG. 6A, except that it has been MD activated.

Referring to FIGS. 6A and B and Table E (above) for comparison of various absorbent articles, we have selected a first setting to determine the Percent-Contact-Area corresponding with the thickness of the epidermis, 100 micrometers, a second setting at 2X the epidermis or 200 micrometers and a third setting at 3X the epidermis of 300 micrometers. It is apparent from the surface topography measurements (see Table E) that the beamed elastic laminate that has been MD activated (FIG. 6B) has essentially the same Percent-Contact-Area as the non-activated (FIG. 6A) beamed elastic laminate, but also has the advantage of greater uniformity of texture (versus the non-activated beamed elastic laminate—see FIG. 1B (inventive) vs FIG. 1A (non-inventive)) and particularly, uniformity of ridges and valleys. In addition, like the non-activated beamed elastic laminate, the MD activated beamed elastic laminate also shows a significant difference in surface smoothness versus the prior art structures as shown in Table E. These differences in increased surface contact, as well as surface smoothness, will have a direct and significant impact on minimizing or eliminating skin marking of the various structures that can be created from beamed elastic laminates 302. In contrast, the data above 2% to 98% Height Value shows that the prior art product have a much rougher surface due in part to their larger decitex elastic and larger spacing which results in larger uncontrolled random rugosities. Combine the larger uncontrolled rugosities with the significantly lower Percent-Contact-Area of the prior art and one can see that the pressure on the skin and skin marking is likely to be significantly greater for the prior art product executions and significantly lower for articles comprising the beamed elastic laminates.

Elastomeric laminates 302 of the present disclosure may have a Percent-Contact-Area at 100 um of greater than about 13% and/or a Percent-Contact-Area at 200 um of greater than about 27% and/or a Percent-Contact-Area at 300 um or greater than about 39%. In addition, the elastomeric laminates 302 of the present disclosure may have a 2%-98%-Height-Value of less than about 1.6.

Pressure-Under-Strand (Average-Pressure-Under-Strand) is relevant because it is the measure of the pressure the elastic will put on the skin. Lower pressure under strand correlates with less skin indentation and marking resulting in improved skin condition and comfort.

Laminate-Modulus is relevant because it is the measure of the slope of a force elongation curve within a given section of the elastomeric laminate. Relatively, if the force increases rapidly with elongation the material is higher modulus than one in which the force increases more slowly with elongation. It may be desired to have sections with differ. The Laminate-Modulus and Section-Modulus are correlated, with the Laminate-Modulus being the linear slope of a section between 2 gf/mm and 5 gf/mm, and the Section-Modulus being defined as the linear slope of a section between 3 gf/mm and 7 gf/mm.

Figure 19:
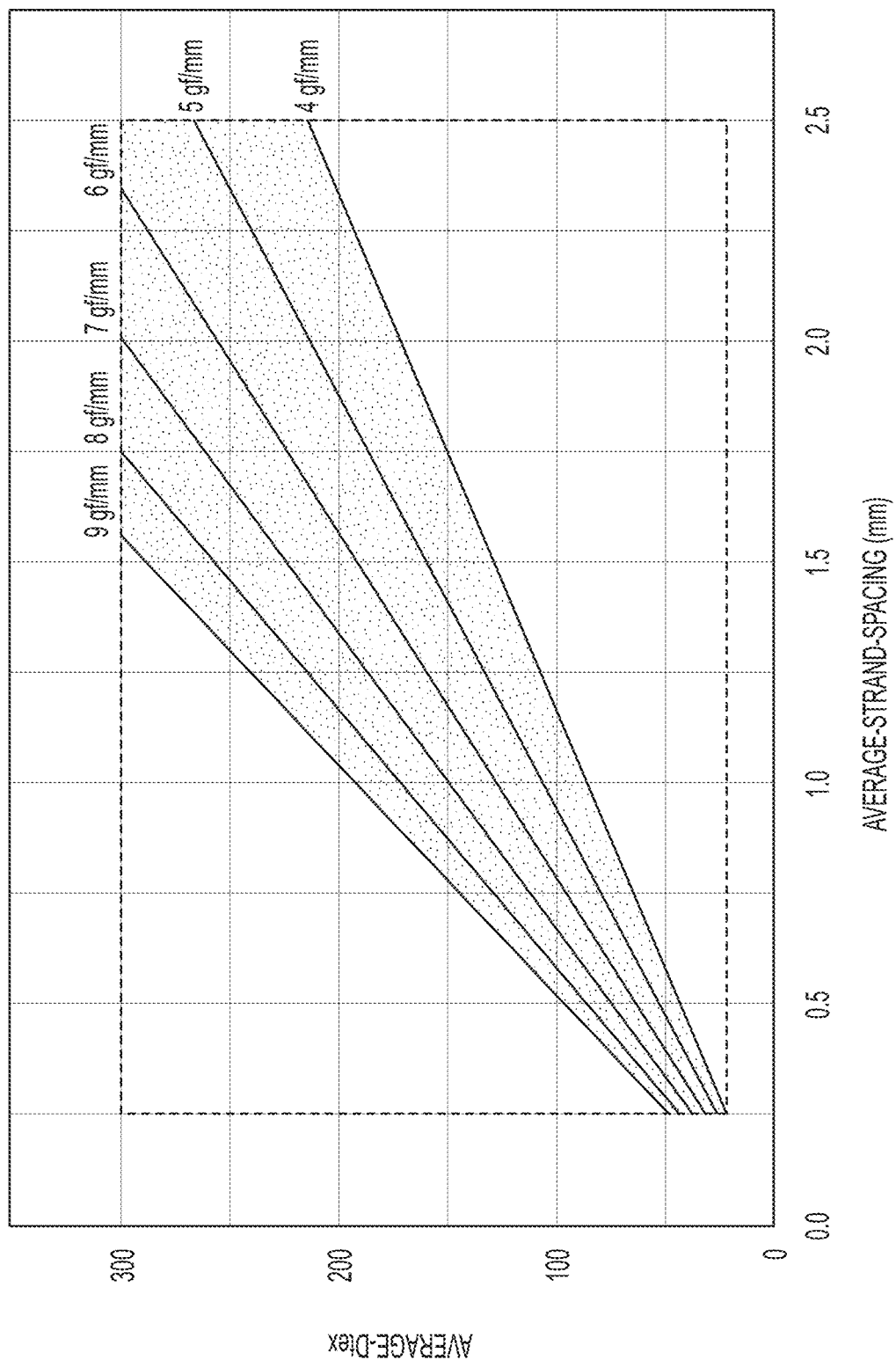
FIG. 19 is a graph illustrating the relationship linking Average-Strand-Spacing and Average-Dtex to Section-Modulus.

Referring to FIG. 19, the determination of Section-Modulus from any combination of Average-Strand-Spacing and Average-Dtex for Spandex strands is shown. The relevance of Section-Modulus to product performance and consumer perception is significant for two key reasons. First, Section-Modulus is how consumers perceive the ease of application, fit and comfort of a product. Section-Modulus conveys the ease and extent of elongation at a given applied force. Too high a Section-Modulus, and consumers perceive the product to be too small, too tight and uncomfortable with higher potential for skin marking. On the other hand, too low of a Section-Modulus and the consumer perceives the product to be too big, too loose and not able to stay in place nor able to properly gasket around the legs and waist. Consumer testing has revealed that a Section-Modulus of between from about 4 gf/mm to about 9 gf/mm are the preferred range for absorbent garments.

A second key impact of Section-Modulus is in the number of sizes that are needed within an array of products to fit a range of consumers. The higher the Section-Modulus, the more sizes that may need to be offered to achieve proper fit given the range over which consumers perceive the product to be comfortable.

Elastomeric laminates 302 of the present disclosure may have a Laminate-Modulus from about 3 gf/mm to about 12 gf/mm; or from about 4 gf/mm to about 10 gf/mm; of from about 7 gf/mm to about 14 gf/mm, or from about 3 gf/mm to about 9 gf/mm.

A first section of an elastomeric laminate 302, which may be used for an absorbent article component, may have a Section-Modulus from about 3 gf/mm to about 12 gf/mm, and a second section may have a Section-Modulus from about 4 gf/mm to about 10 gf/mm.

A first section of an elastomeric laminate 302 may have a Laminate-Modulus that is 20%, or 30%, or 50% greater than a second section of the elastomeric laminate.

Strain is a measure quantifying laminate extension in the MD as a percentage of it's original length (MD as defined herein). A strain of 100% is the equivalent of the laminate extending to twice it's original length along its MD. Stress is a measure quantifying how much force per laminate CD width is required to extend the laminate (CD as defined herein). For example, if an elastomeric laminate with relaxed dimensions of 500 mm in the MD, and 100 mm in the CD was pulled along its MD at a force of 2000 gf, and this force resulted in a laminate MD extension of 1000 mm, this is equivalent to a laminate stress of 20 gf/mm at a laminate strain of 100%. Laminate stress and strain correlate directly to product application; product fit; product sustained fit and product comfort.

Elastomeric laminates 302 of the present disclosure may have a Strain of greater than 110% at a Stress of 9.1 gf/mm, of greater than 60% at a stress of 10 gf/mm, of greater than 100% at a stress of 10 gf/mm, or greater than 120% at a Stress of 9.1 gf/mm, or greater than 150% at a Stress of 9.1 gf/mm.

Application-Stress (and Application-Force) correlate to the ease or difficulty of product application for a closed form product. During application, the waist hoop of the product is typically extended to a larger circumference than that it is intended to fit. This is necessary for pulling up the product over the hip and waist region. Lower Application-Forces (Application-Stress) at the required waist hoop strain (extension) result in easier product application.

Pants (including belts and side panels) made using elastomeric laminates 302 of the present disclosure may have an Application-Stress of from about 7.5 gf/mm to about 14 gf/mm, or from about 10 gf/mm to about 14 gf/mm, or from about 11 gf/mm to about 14 gf/mm.

Leg-Hoop-Max-Strain is a critical parameter that not only impacts the ease of application of the article but has a significant impact on comfort and marking especially for wearers with large thighs and when the wearers of the article move, sit, stand, etc. It is known that the body shape and dimensions waist, hips, thighs, etc. change when a wearer goes from a standing position to a sitting post it is important that the waist openings and especially the leg openings have sufficient extension to meet these changing shapes and dimensions. The Leg-Hoop-Max-Strain defines parametrically the maximum extension of the leg opening and thus an indication of how well it will fit the intended range of wearers.

Pants (including belts and side panels) made using elastomeric laminates 302 of the present disclosure may have a Leg-Hoop-Max-Strain of greater than about 125% at a force of less than 650 gf, or greater than about 150% at a force of less than 650 gf, or greater than about 180% at a force of less than 650 gf.

Ratios

One of they key product structure ratios is Product-Pitch-to-Belt-Spacing-Ratio. The Product-Pitch-to Belt-Spacing-Ratio is important as it defines the leg opening as a function of size of product which is important for ease of application, comfort and skin marking. The Product-Pitch is determined by measuring the product along the longitudinal centerline while the product is in its fully extended state. The Belt-Spacing is the distance between the proximal most elastic in a first waist region to the proximal most elastic in a second waist region. It has been determined that a Product-Pitch-to Belt-Spacing-Ratio of from about 2.1 to about 2.7 provides an adequately sized leg opening for ease of application and comfort throughout the wearers movement and skin marking minimization. Another key product structure ratio is the Product-Pitch-to-Seam-to-Seam-Spacing-Ratio. The Product-Pitch-to-Seam-to-Seam-Spacing-Ratio is important as it defines the size of the waist opening and the leg opening as a function of the size of product which is also important for ease of application, comfort and skin marking. The Product-Pitch is determined by measuring the product along the longitudinal centerline while the product is in its fully extended state. The Seam-to-Seam-Spacing is determined by measuring the distance between the seams with the product fully extended between the seams. It has been determined that a Product-Pitch-to-Seam-to-Seam-Spacing-Ratio of from about 0.9 to about 1.3 provides an adequately sized waist and leg openings for ease of application and comfort throughout the wearers movement and skin marking minimization. The waist opening is determined by the Seam-to-Seam-Spacing and the leg opening is determined by a combination of Seam-to-Seam-Spacing and the Belt-Spacing as the leg opening is formed in part by the proximal edges of the belts between the center chassis and the side seam and by the side edges of the chassis disposed between the proximal edges of the front and back belts. Another key product structural ratio is Product-Pitch-to-Center-Chassis-Length. The Product-Pitch-to-Center-Chassis-Length-Ratio determines the size of the waistband which is determined by the difference in the Center-Chassis-Length and the Product-Pitch. This difference may vary between sizes of products and as such a ratio assures the proper sizing of the waistband. The Product-Pitch is determined as described above. The Center-Chassis-Length is determined by measuring the center chassis along the longitudinal centerline while the center chassis is fully extended. It has been determined that a Product-Pitch-to-Seam-to-Seam-Spacing-Ratio of from about 1.0 to about 1.5 provides an adequately sized waist and leg openings for ease of application, gasketing, comfort at the waist throughout the wearers movement and skin marking minimization.

Elastomeric laminates useful in absorbent articles need to have a level of extension, dimensional change from the fully contracted state to a fully extended state that is sufficient to fit across a defined range of users having varying waist, hip and leg circumference. The level of extension can be increased for a given combination of elastics by increasing the level of pre-strain in the elastics of the elastomeric laminate prior to combining. The increase in pre-strain results in a greater level of contraction and a smaller fully contracted length. When extended the smaller contracted length relative to the fully extended length provides a higher level of extension. In such a configuration if the decitex and spacing remain constant the higher level of extension can be achieved without impacting the Laminate-Modulus. Alternatively, an elastomeric laminate of the present disclosure can be mechanically deformed as described herein to transform an elastomeric laminate having a first level of extension and a first Laminate-Modulus to a mechanically deformed elastomeric laminate having a second level of extension greater than the first level of extension and a second Laminate-Modulus lower than the first Laminate-Modulus. The increase in extension and coinciding reduction in modulus is a result of deformation of the substrate layers forming the laminate. This phenomenon is unique to the mechanical deformation of the elastomeric laminates of the present disclosure. This unexpected result of increased extension/strain and reduced Laminate-Modulus, results in Strain-to-Modulus-Ratios that are unique to the elastomeric laminates of the present disclosure. The importance of the Strain-to-Modulus-Ratio is that the article may be strained or extended to a significantly greater degree at equal or lower force which has a substantial impact on ease of application and comfort as the wearer goes through a series of movements and positions for example as the wearer breathes the waist expands and contracts. Lower modulus versus strain means lower force and greater extension which means the comfort and freedom of movement is significantly improved. Elastomeric laminates 302 of the present disclosure may have a Strain-to-Modulus-Ratio of greater than about 12 and less than about 80, or greater than about 30 and less than about 80.

Please refer to the Methods of the Present Disclosure section for details about performing tests for each of these parameters.

EXAMPLES OF ELASTOMERIC LAMINATES AND ARTICLES OF THE PRESENT DISCLOSURE

Examples 1-4

|  | Example 1 Base Laminate | Example 2 No MDA, wider belt | Example 3 Inventive 1 | Example 4 Inventive 2 |
|---|---|---|---|---|
| Outer Belt Nonwoven (Front & Back) |  |  |  |  |
| Type | Carded | Carded | Carded | Carded |
| Basis Weight (grams/square meter) | 20 | 20 | 22 | 22 |
| Lateral Length (mm) | 365 | 415 | 415 | 415 |
| Longitudinal Length (mm) - Front | 110 | 110 | 110 | 110 |
| Longitudinal Length (mm) - Back | 145 | 170 | 145 | 170 |
| Intermediate Belt Nonwoven |  |  |  |  |
| Type |  |  |  |  |
| Basis Weight (grams/square meter) |  |  |  |  |
| Lateral Length (mm) |  |  |  |  |
| Longitudinal Length (mm) - Front |  |  |  |  |
| Longitudinal Length (mm) - Back |  |  |  |  |
| Inner Belt Nonwoven |  |  |  |  |
| Type | Spunbond | Spunbond | Spunbond | Spunbond |
| Initial Basis Weight (grams/square meter) | 13 | 15 | 13 | 13 |
| Lateral Length (mm) | 365 | 415 | 415 | 415 |
| Longitudinal Length (mm) - Front | 110 | 110 | 110 | 110 |
| Longitudinal Length (mm) - Back | 145 | 170 | 145 | 170 |
| Elastic |  |  |  |  |
| Decitex | 78 | 78 | 78 | 78 |
| Pre-strain (%) | 150 | 165 | 150 | 150 |
| Spacing (mm) | 0.8 | 0.8 | 0.8 | 0.8 |
| MD Activation | na | na |  |  |
| Tooling Pitch |  |  | 100 | 100 |
| Depth of Engagement (inch) |  |  | 0.055 | 0.055 |
| Section L1 (MD = MD Activation, A = aperture) |  |  | MD | MD |
| Section L2 (MD = MD Activation, A = aperture) |  |  | MD | MD |
| Section L3 (MD = MD Activation, A = aperture) |  |  | MD | MD |
| Section L4 (MD = MD Activation, A = aperture) |  |  | MD | MD |
| Section M1 (MD = MD Activation, A = aperture) |  |  | MD | MD |
| Section M2 (MD = MD Activation, A = aperture) |  |  | MD | MD |
| Section M3 (MD = MD Activation, A = aperture) |  |  | MD/A | MD/A |
| Section M4 (MD = MD Activation, A = aperture) |  |  | MD/A | MD/A |
| Section R1 (MD = MD Activation, A = aperture) |  |  | MD | MD |
| Section R2 (MD = MD Activation, A = aperture) |  |  | MD | MD |
| Section R3 (MD = MD Activation, A = aperture) |  |  | MD | MD |
| Section R4 (MD = MD Activation, A = aperture) |  |  | MD | MD |
| Adhesive |  |  |  |  |
| Type | Hotmelt | Hotmelt | Hotmelt | Hotmelt |
| Application Type | Slot | Spray | Slot | Slot |
| Basis Weight Side 1 (grams/square meter) | 3 | 3 | 6 | 6 |

-continued

|  | Example 1 Base Laminate | Example 2 No MDA, wider belt | Example 3 Inventive 1 | Example 4 Inventive 2 |
| --- | --- | --- | --- | --- |
| Application Type | Slot | Spray | Slot | Slot |
| Basis Weight Side 2 (grams/square meter) | 3 | 3 | 6 | 6 |
| Nip Pressure (bar) | 0.3 | 0.5 | 0.5 | 0.5 |
| Product Dimensions |  |  |  |  |
| Seam to Seam (mm) | 345 | 395 | 395 | 395 |
| Seam Width (mm) | 10 | 10 | 10 | 10 |
| Seam Length (mm) | 110 | 110 | 110 | 110 |
| Product Pitch (mm) | 450 | 460 | 460 | 460 |
| Belt to Belt Spacing (mm) | 195 | 180 | 205 | 180 |
| Center Chassis Length (mm) | 405 | 405 | 405 | 405 |
| Center Chassis Width (mm) | 190 | 190 | 190 | 190 |
| Front Belt Shape | Rectangular | Rectangular | Rectangular | Rectangular |
| Back Belt Shape | Rectangular | Shaped | Rectangular | Shaped |
| Style | Belted | Belted | Belted | Belted |

Examples 5-8

|  | Example 5 Elastic Spacing & Dtex | Example 6 Elastic Spacing & Dtex | Example 7 Elastic Spacing & Dtex | Example 8 Elastic Spacing & Dtex |
| --- | --- | --- | --- | --- |
| Outer Belt Nonwoven (Front & Back) |  |  |  |  |
| Type | Carded | Carded | Carded | Carded |
| Basis Weight (grams/square meter) | 20 | 20 | 20 | 20 |
| Lateral Length (mm) | 415 | 415 | 415 | 415 |
| Longitudinal Length (mm) - Front | 110 | 110 | 110 | 110 |
| Longitudinal Length (mm) - Back | 145 | 145 | 145 | 145 |
| Intermediate Belt Nonwoven |  |  |  |  |
| Type |  |  |  |  |
| Basis Weight (grams/square meter) |  |  |  |  |
| Lateral Length (mm) |  |  |  |  |
| Longitudinal Length (mm) - Front |  |  |  |  |
| Longitudinal Length (mm) - Back |  |  |  |  |
| Inner Belt Nonwoven |  |  |  |  |
| Type | Spunbond | Spunbond | Spunbond | Spunbond |
| Initial Basis Weight (grams/square meter) | 17 | 17 | 17 | 17 |
| Lateral Length (mm) | 415 | 415 | 415 | 415 |
| Longitudinal Length (mm) - Front | 110 | 110 | 110 | 110 |
| Longitudinal Length (mm) - Back | 145 | 145 | 145 | 145 |
| Elastic |  |  |  |  |
| Decitex | 150 | 200 | 250 | 300 |
| Pre-strain (%) | 150 | 150 | 150 | 150 |
| Spacing (mm) | 1.54 | 2.05 | 2.56 | 3.08 |
| MD Activation | na |  |  |  |
| Tooling Pitch | 100 | 100 | 100 | 100 |
| Depth of Engagement (inch) | 0.055 | 0.055 | 0.055 | 0.055 |
| Section L1 (MD = MD Activation, A = aperture) | MD | MD | MD | MD |
| Section L2 (MD = MD Activation, A = aperture) |  | A | A | A |
| Section L3 (MD = MD Activation, A = aperture) |  | A | A | A |
| Section L4 (MD = MD Activation, A = aperture) | MD | MD | MD | MD |
| Section M1 (MD = MD Activation, A = aperture) | MD | MD | MD | MD |
| Section M2 (MD = MD Activation, A = aperture) |  |  |  |  |
| Section M3 (MD = MD Activation, A = aperture) |  |  |  |  |
| Section M4 (MD = MD Activation, A = aperture) | MD |  |  |  |

-continued

|  | Example 5 Elastic Spacing & Dtex | Example 6 Elastic Spacing & Dtex | Example 7 Elastic Spacing & Dtex | Example 8 Elastic Spacing & Dtex |
|---|---|---|---|---|
| Section R1 (MD = MD Activation, A = aperture) | MD | MD | MD | MD |
| Section R2 (MD = MD Activation, A = aperture) |  | A | A | A |
| Section R3 (MD = MD Activation, A = aperture) |  | A | A | A |
| Section R4 (MD = MD Activation, A = aperture) | MD | MD | MD | MD |
| Adhesive |  |  |  |  |
| Type | Hotmelt | Hotmelt | Hotmelt | Hotmelt |
| Application Type | Slot | Slot | Slot | Slot |
| Basis Weight Side 1 (grams/square meter) | 6 | 6 | 6 | 6 |
| Application Type | Slot | Slot | Slot | Slot |
| Basis Weight Side 2 (grams/square meter) | 6 | 6 | 6 | 6 |
| Nip Pressure (bar) | 0.5 | 0.5 | 0.5 | 0.5 |
| Product Dimensions |  |  |  |  |
| Seam to Seam (mm) | 395 | 395 | 395 | 395 |
| Seam Width (mm) | 10 | 10 | 10 | 10 |
| Seam Length (mm) | 110 | 110 | 110 | 110 |
| Product Pitch (mm) | 460 | 460 | 460 | 460 |
| Belt to Belt Spacing (mm) | 205 | 205 | 205 | 205 |
| Center Chassis Length (mm) | 405 | 405 | 405 | 405 |
| Center Chassis Width (mm) | 190 | 190 | 190 | 190 |
| Front Belt Shape | Rectangular | Rectangular | Rectangular | Rectangular |
| Back Belt Shape | Rectangular | Rectangular | Rectangular | Rectangular |
| Style | Belted | Belted | Belted | Belted |

Examples 9-11

|  | Example 9 Size 2 | Example 10 Size 6 | Example 11 Adult |
|---|---|---|---|
| Outer Belt Nonwoven (Front & Back) |  |  |  |
| Type | Carded | Carded | Carded |
| Basis Weight (grams/square meter) | 20 | 20 | 20 |
| Lateral Length (mm) | 335 | 445 | 750 |
| Longitudinal Length (mm) - Front | 95 | 115 | Unibody |
| Longitudinal Length (mm) - Back | 150 | 180 | 760 |
| Intermediate Belt Nonwoven |  |  |  |
| Type |  |  |  |
| Basis Weght (grams/square meter) |  |  |  |
| Lateral Length (mm) |  |  |  |
| Longitudinal Length (mm) - Front |  |  |  |
| Longitudinal Length (mm) - Back |  |  |  |
| Inner Belt Nonwoven |  |  |  |
| Type | Spunbond | Spunbond | Spunbond |
| Initial Basis Weight (grams/square meter) | 15 | 15 | 15 |
| Lateral Length (mm) | 335 | 445 | 750 |
| Longitudinal Length (mm) - Front | 95 | 115 | 185 |
| Longitudinal Length (mm) - Back | 150 | 180 | 250 |
| Elastic |  |  |  |
| Decitex | 78 | 78 | 78 |
| Pre-strain (%) | 150 | 150 | 150 |
| Spacing (mm) | 0.8 | 0.8 | 0.8 |
| MD Activation | na |  |  |
| Tooling Pitch | 100 | 100 | 100 |
| Depth of Engagement (inch) | 0.055 | 0.055 | 0.055 |
| Section L1 (MD = MD Activation, A = aperture) | MD | MD | MD |
| Section L2 (MD = MD Activation, A = aperture) | MD | MD | MD |

-continued

|  | Example 9 Size 2 | Example 10 Size 6 | Example 11 Adult |
|---|---|---|---|
| Section L3 (MD = MD Activation, A = aperture) | MD | MD | MD |
| Section L4 (MD = MD Activation, A = aperture) | MD | MD | MD |
| Section M1 (MD = MD Activation, A = aperture) | MD | MD | MD |
| Section M2 (MD = MD Activation, A = aperture) | MD | MD | MD |
| Section M3 (MD = MD Activation, A = aperture) | MD/A | MD/A | MD/A |
| Section M4 (MD = MD Activation, A = aperture) | MD/A | MD/A | MD/A |
| Section R1 (MD = MD Activation, A = aperture) | MD | MD | MD |
| Section R2 (MD = MD Activation, A = aperture) | MD | MD | MD |
| Section R3 (MD = MD Activation, A = aperture) | MD | MD | MD |
| Section R4 (MD = MD Activation, A = aperture) | MD | MD | MD |
| Adhesive |  |  |  |
| Type | Hotmelt | Hotmelt | Hotmelt |
| Application Type | Spiral | Spiral | Spiral |
| Basis Weight Side 1 (grams/square meter) | 3 | 3 | 3 |
| Application Type | Spiral | Spiral | Spiral |
| Basis Weight Side 2 (grams/square meter) | 3 | 3 | 3 |
| Nip Pressure (bar) | 0.2 | 0.2 | 0.2 |
| Product Dimensions |  |  |  |
| Seam to Seam (mm) | 335 | 445 | 725 |
| Seam Width (mm) | 10 | 10 | 12 |
| Seam Length (mm) | 95 | 115 | 180 |
| Product Pitch (mm) | 400 | 490 | 750 |
| Belt to Belt Spacing (mm) | 155 | 195 | 315 |
| Center Chassis Length (mm) | 350 | 430 | 548 |
| Center Chassis Width (mm) | 170 | 190 | 210 |
| Front Belt Shape | Rectangular | Rectangular | Shaped |
| Back Belt Shape | Shaped | Shaped | Shaped |
| Style | Belted | Belted | Unibody |

Examples 12 & 13

|  | Example 12 Gluing | Example 13 Tri-lam |
|---|---|---|
| Outer Belt Nonwoven (Front & Back) |  |  |
| Type | Carded | Carded |
| Basis Weight (grams/square meter) | 20 | 14 |
| Lateral Length (mm) | 415 | 415 |
| Longitudinal Length (mm) - Front | 110 | 110 |
| Longitudinal Length (mm) - Back | 170 | 170 |
| Intermediate Belt Nonwoven |  |  |
| Type |  | Spunbond |
| Basis Weght (grams/square meter) |  | 8 |
| Lateral Length (mm) |  | 415 |
| Longitudinal Length (mm) - Front |  | 110 |
| Longitudinal Length (mm) - Back |  | 170 |
| Inner Belt Nonwoven |  |  |
| Type | Spunbond | Spunbond |
| Initial Basis Weight (grams/square meter) | 15 | 15 |
| Lateral Length (mm) | 415 | 415 |
| Longitudinal Length (mm) - Front | 110 | 110 |
| Longitudinal Length (mm) - Back | 170 | 170 |
| Elastic |  |  |
| Decitex | 78 | 78 |
| Pre-strain (%) | 150 | 150 |
| Spacing (mm) | 0.8 | 0.8 |
| MD Activation | na |  |
| Tooling Pitch | 100 | 100 |
| Depth of Engagement (inch) | 0.055 | 0.055 |
| Section L1 (MD = MD Activation, A = aperture) | MD | MD/A |
| Section L2 (MD = MD Activation, A = aperture) | MD | MD/A |
| Section L3 (MD = MD Activation, A = aperture) | MD | MD/A |
| Section L4 (MD = MD Activation, A = aperture) | MD | MD/A |
| Section M1 (MD = MD Activation, A = aperture) | MD | MD/A |
| Section M2 (MD = MD Activation, A = aperture) | MD | MD/A |
| Section M3 (MD = MD Activation, A = aperture) | MD/A | MD/A |
| Section M4 (MD = MD Activation, A = aperture) | MD/A | MD/A |
| Section R1 (MD = MD Activation, A = aperture) | MD | MD/A |

-continued

|  | Example 12 Gluing | Example 13 Tri-lam |
|---|---|---|
| Section R2 (MD = MD Activation, A = aperture) | MD | MD/A |
| Section R3 (MD = MD Activation, A = aperture) | MD | MD/A |
| Section R4 (MD = MD Activation, A = aperture) | MD | MD/A |
| Adhesive | | |
| Type | Hotmelt | Hotmelt |
| Application Type | Spiral | Slot |
| Basis Weight Side 1 (grams/square meter) | 3 | 6 |
| Application Type | Spiral | Slot |
| Basis Weight Side 2 (grams/square meter) | 3 | 6 |
| Nip Pressure (bar) | 0.2 | 0.5 |
| Product Dimensions | | |
| Seam to Seam (mm) | 395 | 395 |
| Seam Width (mm) | 10 | 10 |
| Seam Length (mm) | 110 | 110 |
| Product Pitch (mm) | 460 | 460 |
| Belt to Belt Spacing (mm) | 180 | 180 |
| Center Chassis Length (mm) | 405 | 405 |
| Center Chassis Width (mm) | 190 | 190 |
| Front Belt Shape | Rectangular | Rectangular |
| Back Belt Shape | Shaped | Shaped |
| Style | Belted | Belted |

Methods of the Present Disclosure
General Sample Preparation

The General Sample Preparation is intended to be used for methods that do not have specific sample preparation instructions within the method itself.

When collecting a specimen for testing, the specimen must contain a plurality of elastic strands and/or an elastic material, elastic scrim, elastic ribbons, elastic strips, etc. In situations where the elastic material and/or elastic strands is not fully secured within the sample, the test specimen must be obtained in a way that elastic material and/or elastic strands within the test region of the specimen are as they were intended and not altered as a result of collection of the specimen. If the elastic material or any elastic strands release, creep or become separated within or from the laminate, the specimen is discarded and a new specimen prepared. And, depending on the method, the portion or area of the stranded elastomeric laminate that should be tested will include a plurality of elastic strands between an area of first and second nonwovens, excluding any cut window (such as an elastic-free zone or area overlapping with the core or center chassis, and excluding any seams joining multiple article components together. Certain methods, however, may require testing of the absorbent article component, including cut windows and seams (e.g., Hip-Hoop-Test).

For pants, remove the side panels where they are attached to the chassis and separate the side panels at the side seams. Identify the elastic material that transverses the entire width of the panel. Identify the longitudinally distal most edge of the elastic material or elastic strand (closest to the waist edge) and the longitudinally proximal most edge of the elastic material or elastic strand (closest to the leg edge) determine the midpoint between the distal most elastic strand or elastic material edge and the proximal most elastic strand or elastic material edge. Cut a 40 mm wide strip laterally across the entire panel centered at the midpoint. Repeat for each front and rear side panel that contains elastic material and/or elastic strands.

For taped, remove ear panels where they are attached to the chassis. Identify the elastic material that transverses the entire width of the panel. Identify the distal most elastic material edge or elastic strand (closest to the waist edge) and the proximal most elastic material edge or elastic strand (closest to the leg edge) determine the midpoint between the distal most elastic strand or elastic material edge and the proximal most elastic strand or elastic material edge. Cut a 40 mm wide strip laterally across the entire ear panel centered at the midpoint. Repeat for each front and rear ear panel that contains elastic material and/or elastic strands.

For a belted article, mark the product on the front and back by extending a line from along the side of the core to the waist edge. Remove the belt from the article, using an appropriate means (e.g. freeze spray), taking care not to delaminate the belt or release the elastics. Separate the front belt from the back belt along any seams. Identify the distal most elastic material edge or elastic strand (closest to the waist edge) and the proximal most elastic material edge or strand (closest to the leg edge) determine the midpoint between the distal most elastic strand or elastic material edge and the proximal most elastic strand or elastic material edge. Cut a 40 mm wide strip parallel to the waist edge if linear or to the elastic strands if linear and centered at the midpoint, across the entire belt portion. If the strip has a region that does not contain elastic strands or elastic material (e.g., a portion that overlapped the core, etc.) cut along the ends of the elastic strands/elastic material, to remove the non-elastic region and treat as two specimens.

For waistbands, they are tested as a single piece of material. Remove the belt from the article, using an appropriate means (e.g. freeze spray), taking care not to delaminate the belt or release the elastics.

For the leg cuffs, each of the leg cuffs are tested as a single piece of material. The inner leg cuff sample is considered to be the portion of the inner leg cuff that extends from the proximal most edge of the inner leg cuff to and including the distal most elastic of the inner leg cuff and extending longitudinally to the front and back waist edges of the chassis. The outer leg cuff sample is considered to be the portion of the outer leg cuff that extends from the distal most edge of the outer leg cuff to and including the proximal most elastic of the outer leg cuff and extending longitudinally to the front and back waist edges of the chassis.

For all specimen strips calculate a Span Corrected Width (SCW) is calculated as:

$$\text{Span Corrected Width} = d\left(\frac{n}{n-1}\right)$$

where d is the distance (mm) between the two distal strands, and n is the number of strands, when n>1. Clamp the strip at each end and measure the length between the clamps to the nearest 1 mm. Apply a weight equal to 3 g/mm SCW. After 10 seconds measure the final length to the nearest 1 mm. Calculate the elongation as (Final Length−Initial Length)/Initial length.

Average-Strand-Spacing

Using a ruler calibrated against a certified NIST ruler and accurate to 0.5 mm, measure the distance between the two distal strands within a section to the nearest 0.5 mm, and then divide by the number of strands in that section−1

$$\text{Average-Strand-Spacing} = d/(n-1) \text{ where } n>1$$

report to the nearest 0.1 mm.

Pressure-Under-Strand (Also Referred to as Average-Pressure-Under-Strand)

Figure 16:
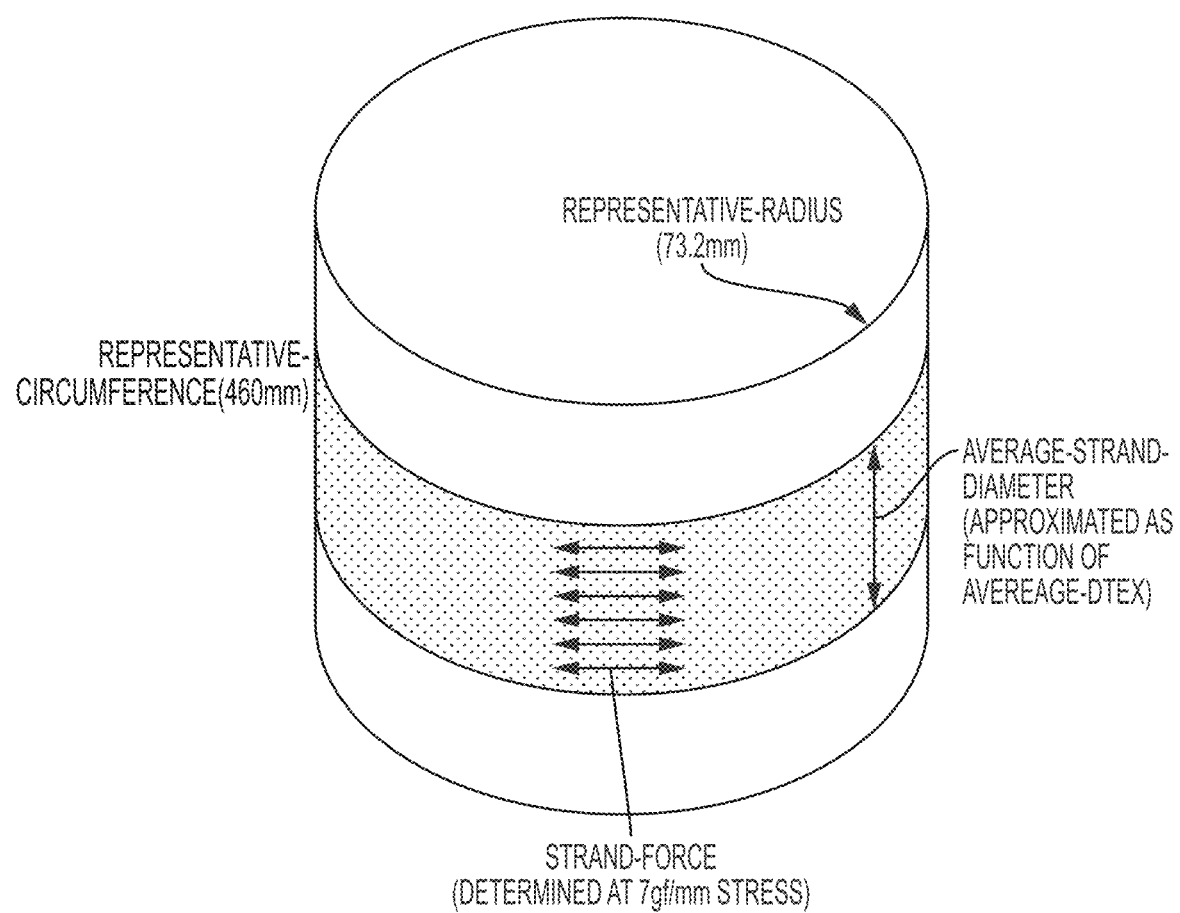
FIG. 16 illustrates Pressure-Under-Strand.

Defined as the average pressure imparted by each individual elastic strand of a section under specific conditions. These conditions are defined as (refer to FIGS. 16 and 17):

The section is pulled to a Stress of 7 gf/mm (within a consumer preferred range of stresses as determined experimentally)

The section is pulled over a cylinder whose circumference is defined as a Representative-Circumference Where:

Pressure-Under-Strand (psi)=1.422*Strand-Force/(2*Representative-Radius*Average-Strand-Diameter)

Representative-Radius (mm)=Representative-Circumference/(2*pi)

Representative-Circumference (mm)=460 mm

Stress (gf/mm)=(Summation of Strand-Forces within a section)/(Section-Width)

Section-Width (mm)=(Number of Elastics in the section)*Average-Strand-Spacing (mm)

Strand-Force (gf)=Strand-Strain (%)*0.046875*Average-Dtex

Strand-Strain (%)=strain in each elastic strand within a section

Average-Strand-Diameter (mm)=2*sqrt (Strand-Cross-Sectional-Area/pi)

Strand-Cross-Sectional-Area (mm$^2$)=Average-Dtex/Strand-Density/10,000

Strand-Density (g/cc)=1.15 g/cc (industry standard for PolyUrethaneUrea based spandex elastics)

Dtex (g/10,000 m)=Standard textile unit of measure. Dtex is weight in grams for 10,000 m of the material Average-Pre-Strain=Amount of stretch in elastic strands in a section prior to combining with substrate layer(s).

Maximum-Strain=Average-Pre-Strain. This is the maximum amount of strain each section can be pulled to. It cannot exceed the Average-Pre-Strain.

Maximum-Section-Force=Summation of each strand in the section pulled to the Maximum-Strain.

Section-Modulus

Figure 4:
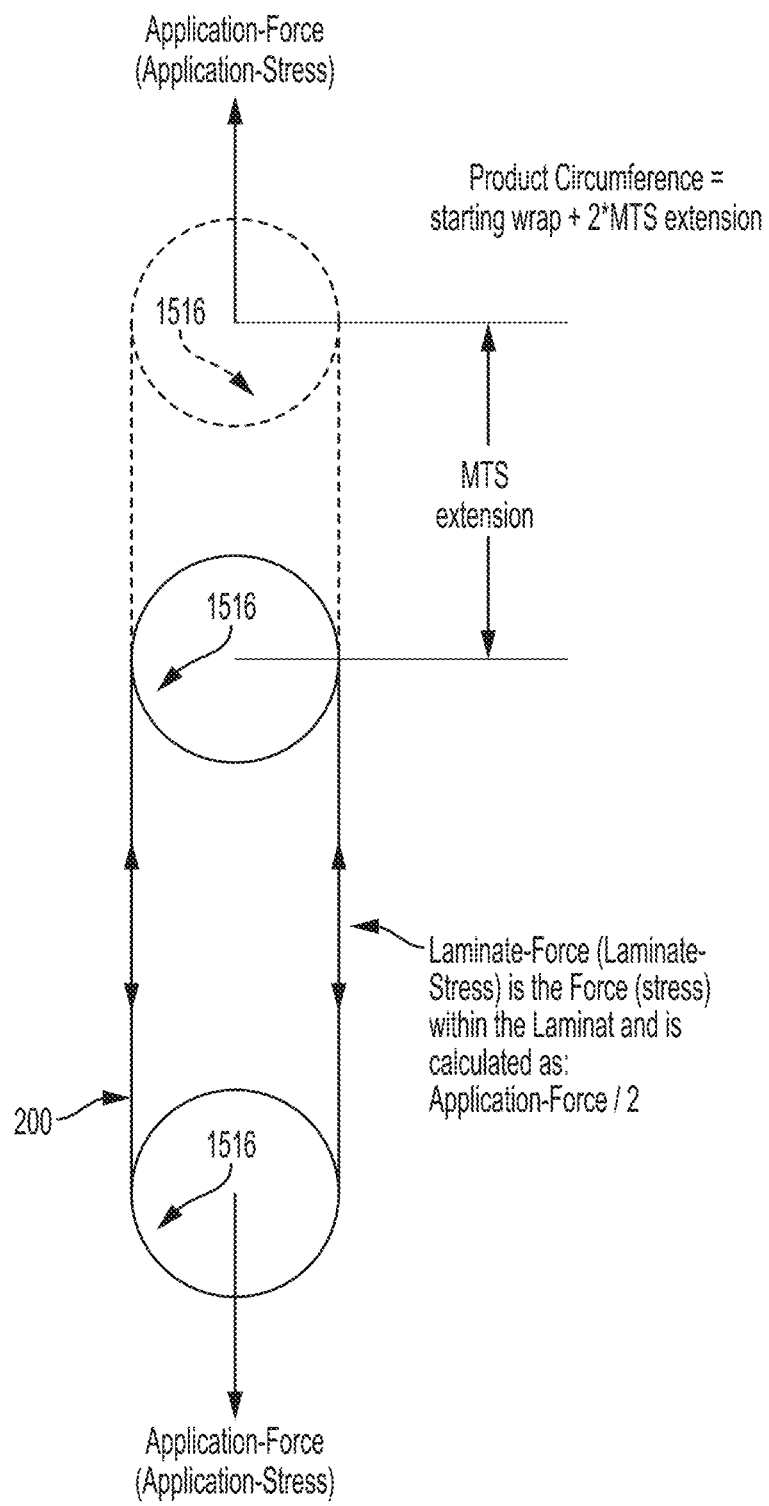
FIG. 4 is a cross-section view at 4-4 of FIG. 3 and illustrates the relationship between Application-Force and Laminate-Force.
Figure 7A:
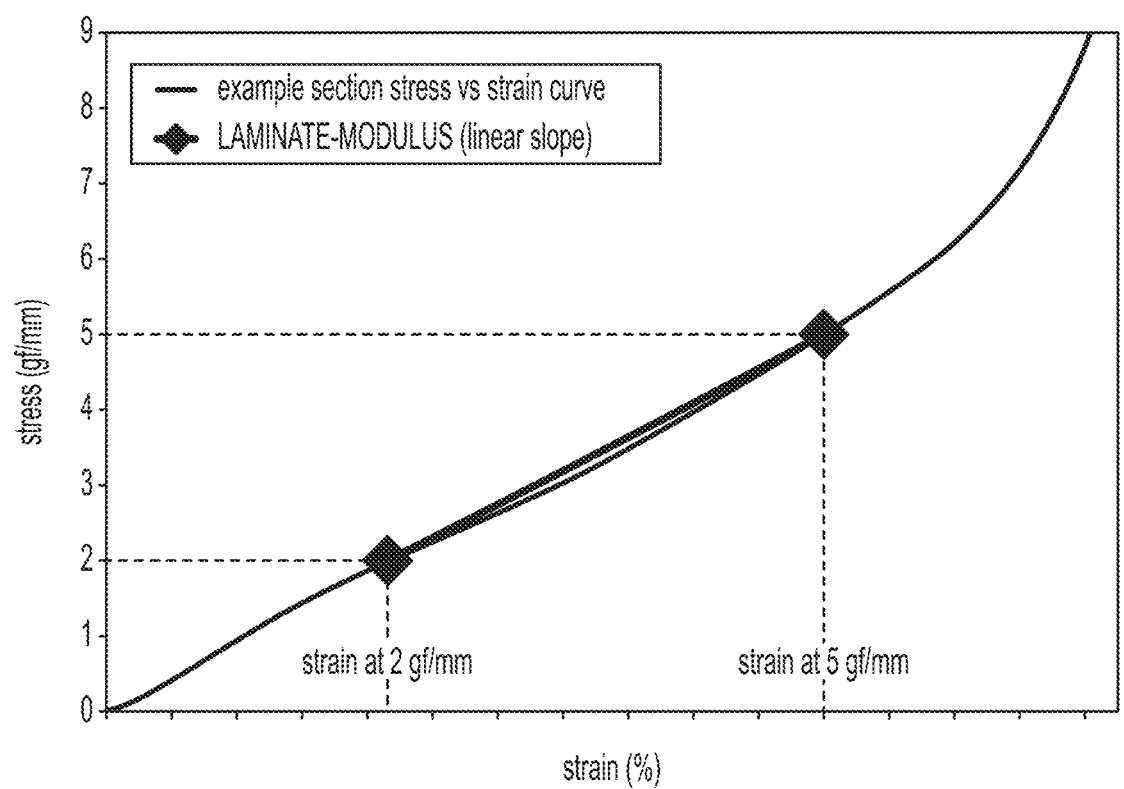
FIG. 7A illustrates the Laminate-Modulus of an inventive beamed elastomeric laminate that has been MD activated.
Figure 7B:
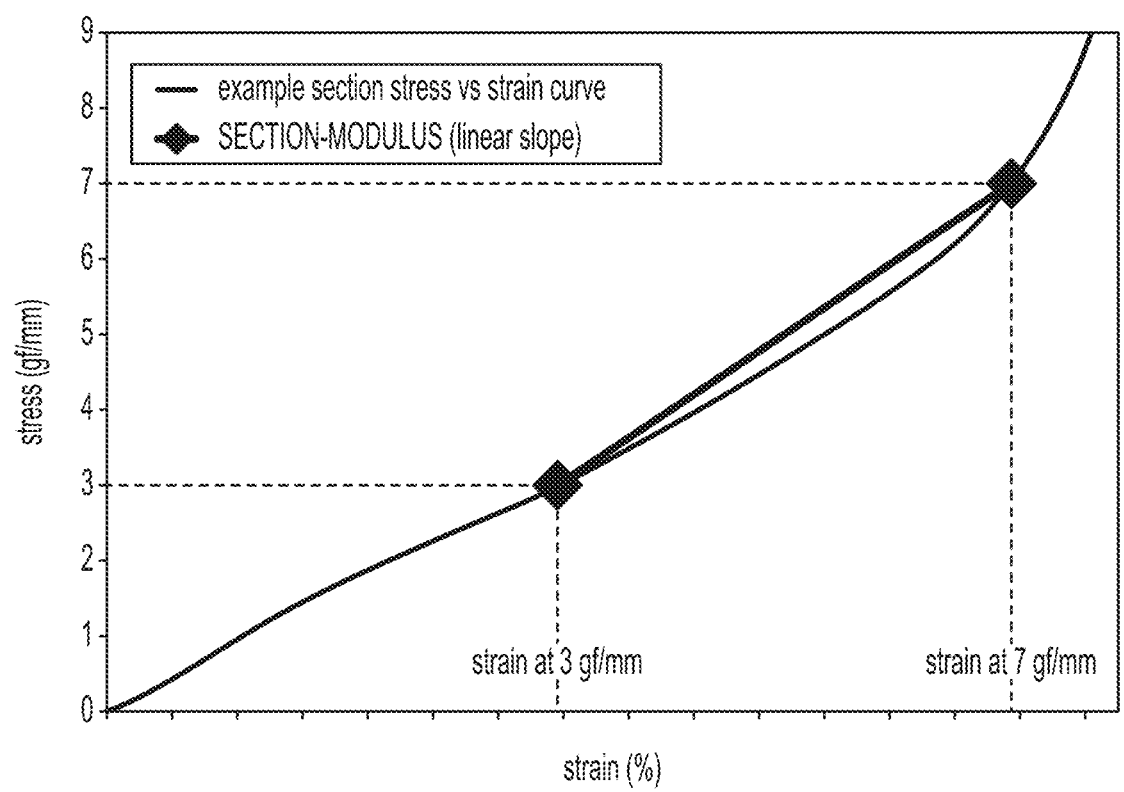
FIG. 7B illustrates the Section-Modulus of an inventive beamed elastomeric laminate that has been MD activated.
Figure 8:
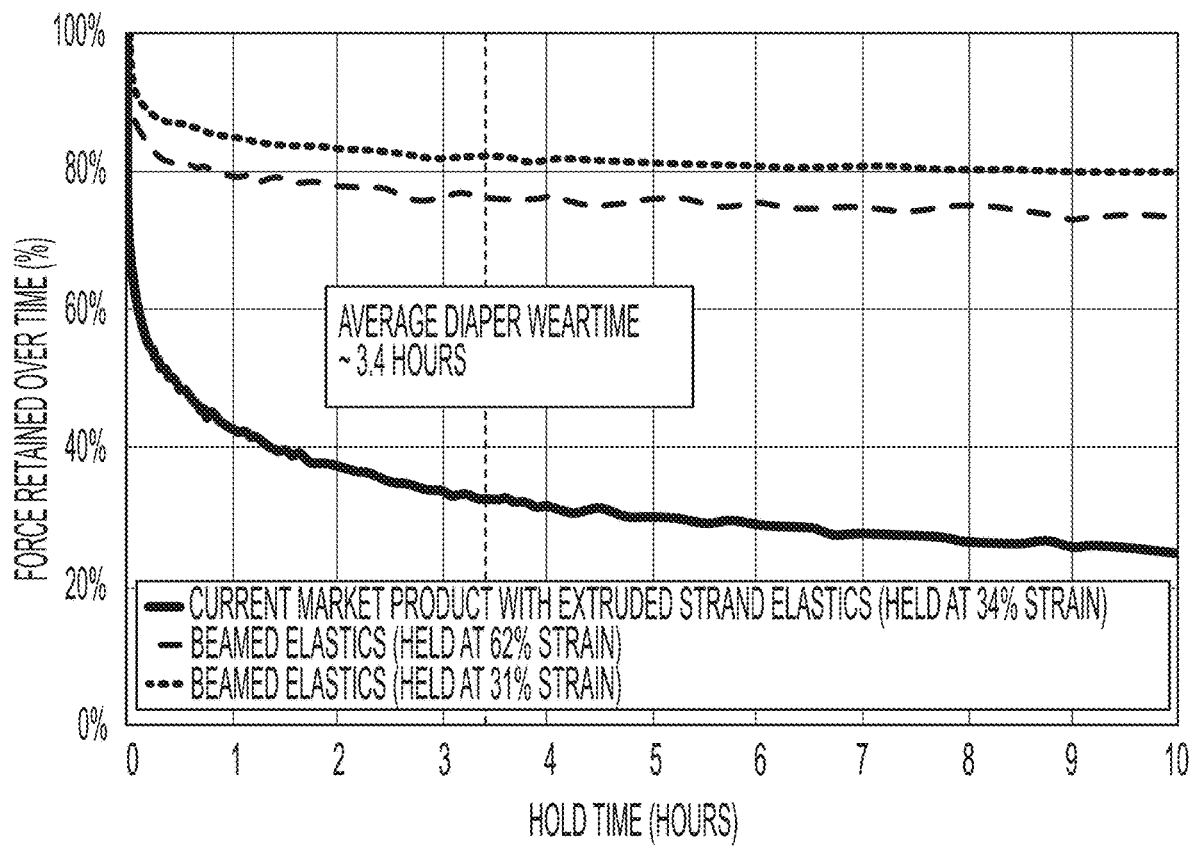
FIG. 8 is a chart showing Force-Relaxation-Over-Time (Force Retained over Time) for a laminate comprising extruded strand elastics and for an inventive MD activated elastomeric laminate of the present disclosure.

Defined as the modulus of a given section. Section-Modulus (also referred to as modulus) is the linear slope of the stress vs strain data of the section between 3 gf/mm and 7 gf/mm as determined in the 1$^{st}$ load cycle of the Hip-Hoop-Test (refer to FIG. 7B). For these calculations, the stresses used are those contained within the laminate, as illustrated in FIGS. 4 and 5A. The stresses contained within the laminate are ½ of those measured during the Hip-Hoop-Test as that test measures two sides of the closed belt. The Section-Modulus can also be calculated as:

Section-Modulus=[7 gf/mm−3 gf/mm]/[(section strain at 7 gf/mm)−(section strain at 3 gf/mm)]

Where:

section strain at 7 gf/mm=7 gf/mm*(Average-Strand-Spacing)/DTEX-FACTOR section strain at 3 gf/mm=3 gf/mm*(Average-Strand-Spacing)/DTEX-FACTOR Average-Strand-Spacing (mm)=d/(n−1)

d is the distance (mm) between the two distal strands of the section n is the number of strands, when n>1

DTEX-FACTOR=37.5*Average-Dtex/800 (dtex as measured, specified)

Section-Modulus is reported in units of (gf/mm)

Laminate-Modulus

Defined as the modulus of a given section. Laminate-Modulus is the linear slope of the stress vs strain data of the section between 2 gf/mm and 5 gf/mm as determined in the 1$^{st}$ load cycle of the Hip-Hoop-Test (refer to FIG. 7A). For these calculations, the stresses used are those contained within the laminate, as illustrated in FIGS. 4 and 5A. The stresses contained within the laminate are ½ of those measured during the Hip-Hoop-Test as that test measures two sides of the closed belt.

Strain-to-Modulus-Ratio

Strain-to-Modulus-Ratio=Strain/Laminate-Modulus

Where:

Strain=Strain at Laminate Stress of 9.1 gf/mm

Average-Decitex (Average-Dtex)

The Average-Decitex Method is used to calculate the Average-Dtex on a length-weighted basis for elastic fibers present in an entire article, or in a specimen of interest extracted from an article. The decitex value is the mass in grams of a fiber present in 10,000 meters of that material in the relaxed state. The decitex value of elastic fibers or elastomeric laminates containing elastic fibers is often reported by manufacturers as part of a specification for an elastic fiber or an elastomeric laminate including elastic fibers. The Average-Dtex is to be calculated from these specifications if available. Alternatively, if these specified values are not known, the decitex value of an individual elastic fiber is measured by determining the cross-sectional area of a fiber in a relaxed state via a suitable microscopy technique such as scanning electron microscopy (SEM), determining the composition of the fiber via Fourier Transform Infrared (FT-IR) spectroscopy, and then using a literature value for density of the composition to calculate the mass in grams of the fiber present in 10,000 meters of the fiber. The manufacturer-provided or experimentally measured decitex values for the individual elastic fibers removed from an entire article, or specimen extracted from an article, are used in the expression below in which the length-weighted average of decitex value among elastic fibers present is determined.

The lengths of elastic fibers present in an article or specimen extracted from an article is calculated from overall dimensions of and the elastic fiber pre-strain ratio associated with components of the article with these or the specimen, respectively, if known. Alternatively, dimensions and/or elastic fiber pre-strain ratios are not known, an absorbent article or specimen extracted from an absorbent article is disassembled and all elastic fibers are removed. This disassembly can be done, for example, with gentle heating to soften adhesives, with a cryogenic spray (e.g. Quick-Freeze, Miller-Stephenson Company, Danbury, Conn.), or with an appropriate solvent that will remove adhesive but not swell, alter, or destroy elastic fibers. The length of each elastic fiber in its relaxed state is measured and recorded in millimeters (mm) to the nearest mm.

Calculation of Average-Dtex

For each of the individual elastic fibers $f_i$ of relaxed length $L_i$ and fiber decitex value $d_i$ (obtained either from the manufacturer's specifications or measured experimentally) present in an absorbent article, or specimen extracted from an absorbent article, the Average-Dtex for that absorbent article or specimen extracted from an absorbent article is defined as:

$$\text{Average-Dtex} = \frac{\sum_{i=1}^{n}(L_i \times d_i)}{\sum_{i=1}^{n} L_i}$$

where n is the total number of elastic fibers present in an absorbent article or specimen extracted from an absorbent article. The Average-Dtex is reported to the nearest integer value of decitex (grams per 10 000 m).

If the decitex value of any individual fiber is not known from specifications, it is experimentally determined as described below, and the resulting fiber decitex value(s) are used in the above equation to determine Average-Dtex.

Experimental Determination of Decitex Value for a Fiber

For each of the elastic fibers removed from an absorbent article or specimen extracted from an absorbent article according to the procedure described above, the length of each elastic fiber $L_k$ in its relaxed state is measured and recorded in millimeters (mm) to the nearest mm. Each elastic fiber is analyzed via FT-IR spectroscopy to determine its composition, and its density $\rho_k$ is determined from available literature values. Finally, each fiber is analyzed via SEM. The fiber is cut in three approximately equal locations perpendicularly along its length with a sharp blade to create a clean cross-section for SEM analysis. Three fiber segments with these cross-sections exposed are mounted on an SEM sample holder in a relaxed state, sputter coated with gold, introduced into an SEM for analysis, and imaged at a resolution sufficient to clearly elucidate fiber cross-sections. Fiber cross-sections are oriented as perpendicular as possible to the detector to minimize any oblique distortion in the measured cross-sections. Fiber cross-sections may vary in shape, and some fibers may consist of a plurality of individual filaments. Regardless, the area of each of the three fiber cross-sections is determined (for example, using diameters for round fibers, major and minor axes for elliptical fibers, and image analysis for more complicated shapes), and the average of the three areas $a_k$ for the elastic fiber, in units of micrometers squared ($m^2$), is recorded to the nearest 0.1 $\mu m^2$. The decitex $d_k$ of the kth elastic fiber measured is calculated by:

$$d_k = 10{,}000 \text{ m} \times a_k \times \rho_k \times 10^{-6}$$

where $d_k$ is in units of grams (per calculated 10,000 meter length), $a_k$ is in units of $\mu m^2$, and $\rho_k$ is in units of grams per cubic centimeter (g/cm$^3$). For any elastic fiber analyzed, the experimentally determined $L_k$ and $d_k$ values are subsequently used in the expression above for Average-Dtex.

Surface Topography (Percent-Contact-Area, Rugosity-Frequency, Rugosity-Wavelength, and 2-98%-Height-Value)

In the Surface Topography Method, an elastomeric laminate specimen is removed from an absorbent article and extended across and in contact with the convex surface of a transparent horizontal cylindrical tubing segment, allowing the areal surface topology of the wearerfacing side of the laminate to be measured through the transparent tubing segment using optical profilometry. The 3D surface data are then sampled and processed to extract several parameters that describe the Percent-Contact-Area and height of the elastomeric laminate specimen surface as well as the frequency and wavelength of its associated rugosities. All sample preparation and testing is performed in a conditioned room maintained at about 23±2° C. and about 50±2% relative humidity, and samples are equilibrated in this environment for at least 24 hours prior to testing.

Sample Preparation

Each elastomeric laminate specimen extracted from an article is mounted on a horizontal tubing segment as described below. The tubing segment is cut from a sufficient length of optically clear, colorless cast acrylic cylindrical tubing having an outer diameter of 8.0 inches (203 mm) and a wall thickness of 0.1875 inches (4.76 mm). The segment has a dimension of 4.0 inches (102 mm) along an axis parallel to the central cylindrical axis of the parent tubing and a circumferential outer arc length of 5.5 inches (140 mm).

The elastomeric laminate specimen is extended in its primary stretch direction to a ratio corresponding to its extension at 3 g/mm (mass per linear width), where its width is determined by the Span Corrected Width metric as defined in the Caliper Test Method, and in which the extension is the average ratio measured under static load for the first ten seconds during which it is applied. In this extended state, the extended elastomeric laminate specimen is oriented such that its wearer-facing surface is in contact with the convex surface of the tubing segment and that the axis of extension is oriented around the circumference of the tubing segment. The extended laminate is secured at both ends to the transparent tubing segment such that the wearer-facing surface of the laminate is viewable through the concave side of the transparent tubing segment.

Five replicate elastomeric laminate specimens are isolated and prepared in this way from five equivalent absorbent articles for analysis.

3D Surface Image Acquisition

A three-dimensional (3D) surface topography image of the wearerfacing surface of the extended elastomeric laminate specimen is obtained using a DLP-based, structured-light 3D surface topography measurement system (a suitable surface topography measurement system is the MikroCAD Premium instrument commercially available from LMI Technologies Inc., Vancouver, Canada, or equivalent). The system includes the following main components: a) a Digital Light Processing (DLP) projector with direct digital controlled micro-mirrors; b) a CCD camera with at least a 1600×1200 pixel resolution; c) projection optics adapted to a measuring area of at least 60 mm×45 mm; d) recording optics adapted to a measuring area of 60 mm×45 mm; e) a table tripod based on a small hard stone plate; f) a blue LED light source; g) a measuring, control, and evaluation computer running surface texture analysis software (a suitable software is MikroCAD software with Mountains Map technology, or equivalent); and h) calibration plates for lateral (XY) and vertical (Z) calibration available from the vendor.

The optical 3D surface topography measurement system measures the surface height of a sample using the digital micro-mirror pattern fringe projection technique. The nature of this pattern projection technique allows the surface topography of a specimen to be interrogated through a transparent material. The result of the measurement is a 3D data set of surface height (defined as the Z-axis) versus displacement in the horizontal (XY) plane. This 3D data set can also be thought of as an image in which every pixel in the image there is associated an XY displacement, and the value of the pixel is the recorded Z-axis height value. The system has a field of view of 60×45 mm with an XY pixel resolution of approximately 37 microns, and a height resolution of 0.5 microns, with a total possible height range of 32 mm.

The instrument is calibrated according to manufacturer's specifications using the calibration plates for lateral (XY plane) and vertical (Z-axis) available from the vendor.

The elastomeric laminate specimen mounted on the transparent tubing segment is positioned with the concave surface of the tubing segment surface facing upward so that the wearerfacing surface is facing upward and visible through the transparent material. The tubing segment is placed on a stand such that the convex (downward-facing) specimen surface in the region to be analyzed is suspended freely and not resting on a surface. The tubing segment is oriented such that its circumferential direction (that direction or axis along which the laminate is stretched) is centered and perpendicular relative to the long axis of the camera's field of view (or either of the central axes if the field of view is square). A 3D surface topology image of the elastomeric laminate specimen is collected by following the instrument manufacturer's recommended measurement procedures, which may include focusing the measurement system and performing a brightness adjustment. No pre-filtering options are used. The collected height image file is saved to the evaluation computer running the surface texture analysis software.

If the field of view of the 3D surface topography measurement system exceeds the evaluation region on the elastomeric laminate specimen the image may be cropped to remove extraneous areas and retain a rectangular field of view of the relevant portion, while maintaining the XY resolution, prior to performing the analysis.

3D Surface Image Analysis

The 3D surface topography image is opened in the surface texture analysis software. The following filtering procedure is then performed on each image: 1) removal of invalid or non-measured points; 2) a 5×5 pixel median filter to remove noise; 3) a 5×5 pixel mean filter to smooth the surface; and 4) subtraction of a two-dimensional, second-order polynomial (determined via least-squares fit of the surface topology image) to remove the general form and flatten the surface. The second-order polynomial is defined by the following equation:

$$f(x,y)=c_1+c_2x+c_3y+c_4x^2+c_5y^2+c_6xy$$

Each data set that has been processed to this point as described above is referred to as a "preprocessed specimen data set." The highest points of the resulting topology image correspond to those areas in contact with the convex surface of the tubing segment, and the lowest points are those points most distal below the convex surface of the tubing segment.

Percent-Contact-Area and 2-98%-Height-Value

For each of the 3D surface topography images of the five replicate specimens, the following analysis is performed on preprocessed specimen data sets. The Percent-Contact-Area and 2-98% Height measurements are derived from the Areal Material Ratio (Abbott-Firestone) curve described in the ISO 13565-2:1996 standard extrapolated to surfaces. This curve is the cumulative curve of the surface height distribution histogram versus the range of surface heights measured. A material ratio is the ratio, expressed as a percent, of the area corresponding to points with heights equal to or above an intersecting plane passing through the surface at a given height, or cut depth, to the cross-sectional area of the evaluation region (field of view area). The height at a material ratio of 2% is initially identified. A cut depth of 100 μm below this height is then identified, and the material ratio at this depth is recorded as the Percent-Contact-Area at 100 p.m. This procedure is repeated at a cut depth of 200 μm and 300 μm below the identified height at a material ratio of 2%, and the material ratio at these depths are recorded as the Percent-Contact-Area at 200 μm and the Percent-Contact-Area at 300 μm respectively. All of the Percent-Contact-Area values are recorded to the nearest 0.1%.

The 2-98%-Height-Value of the specimen surface is defined as the difference in heights between two material ratios that exclude a small percentage of the highest peaks and lowest valleys. The 2-98% Height of the specimen surface is the height between the two cutting depths corresponding to a material ratio value of 2% to the material ratio of 98%, and is recorded to the nearest 0.01 mm.

Rugosity-Frequency and Rugosity-Wavelength

The preprocessed 3D surface topology images for each specimen are subjected to Fourier transform spatial frequency analysis to determine Rugosity-Frequency and Rugosity-Wavelength.

Each 3D surface topology image is deconstructed into individual line profiles by isolating each entire row of single data points that run in the dimension parallel to the elastic strands (if present and evident) of the elastomeric laminate, or, more generally, perpendicular to the rugosity exhibited by the elastomeric laminate in the relaxed state. These line profiles are therefore data sets in the form of height (in millimeters) versus distance (in millimeters).

For each replicate 3D surface topology image deconstructed, each line profile is mean centered, and a fast Fourier transform (FFT) is applied to calculate the frequency amplitude spectrum of each line profile. The Fourier transform amplitude versus spatial frequency spectra of all extracted line profiles are averaged, and the resulting average amplitude versus spatial frequency spectrum is defined as $F(1/d)$, where $1/d$ is reciprocal distance in units of $mm^{-1}$. Finally, the function $P(1/d)=d\times F^2(1/d)$, the spatial frequency power spectral density with a prefactor of distance d to correct for the expected $1/d$ noise, is plotted versus $1/d$. The value of reciprocal distance $1/d$ at which $P(1/d)$ is at a maximum is defined as the Rugosity-Frequency and is recorded in units of $mm^{-1}$ to the nearest $0.001\ mm^{-1}$. The reciprocal of the Rugosity-Frequency is defined as the Rugosity-Wavelength and is recorded in units of mm to the nearest 0.01 mm.

Reporting of Method Parameters

After the 3D surface image analysis described above is performed on 3D surface topology images of all five specimen replicates, the following output parameters are defined and reported. The arithmetic mean of all five Percent-Contact-Area at 100 μm measurements is defined as the Average Percent-Contact-Area at 100 μm and is reported to the nearest 0.1%. The arithmetic mean of all five Percent-Contact-Area at 200 μm measurements is defined as the Average Percent-Contact-Area at 200 μm and is reported to the nearest 0.1%. The arithmetic mean of all five Percent-Contact-Area at 300 μm measurements is defined as the Average Percent-Contact-Area at 300 μm and is reported to the nearest 0.1%. The arithmetic mean of all five 2-98% Height measurements is defined as the Average 2-98% Height and is reported in units of mm to the nearest 0.01 mm. The arithmetic mean of all five Rugosity-Frequency measurements is defined as the Average Rugosity-Frequency and is reported in units of mm to the nearest 0.001 $mm^{-1}$. The arithmetic mean of all five Rugosity-Wavelength measurements is defined as the Average Rugosity-Wavelength and is reported in units of mm to the nearest 0.01 mm.

Average-Pre-Strain

The Average-Pre-Strain of a specimen are measured on a constant rate of extension tensile tester (a suitable instrument is the MTS Insight using Testworks 4.0 Software, as available from MTS Systems Corp., Eden Prairie, Minn.) using a load cell for which the forces measured are within 1% to 90% of the limit of the cell. Articles are conditioned at 23° C.±2 C.° and 50%±2% relative humidity for 2 hours prior to analysis and then tested under the same environmental conditions.

Program the tensile tester to perform an elongation to break after an initial gage length adjustment. First raise the cross head at 10 mm/min up to a force of 0.05N. Set the current gage to the adjusted gage length. Raise the crosshead at a rate of 100 mm/min until the specimen breaks (force drops 20% after maximum peak force). Return the cross head to its original position. Force and extension data is acquired at a rate of 100 Hz throughout the experiment.

Set the nominal gage length to 40 mm using a calibrated caliper block and zero the crosshead. Insert the specimen into the upper grip such that the middle of the test strip is positioned 20 mm below the grip. The specimen may be folded perpendicular to the pull axis, and placed in the grip to achieve this position. After the grip is closed the excess material can be trimmed. Insert the specimen into the lower grips and close. Once again, the strip can be folded, and then trimmed after the grip is closed. Zero the load cell. The specimen should have a minimal slack but less than 0.05N of force on the load cell. Start the test program.

From the data construct a Force (N) verses Extension (mm). The Average-Pre-Strain is calculated from the bend in the curve corresponding to the extension at which the nonwovens in the elastic are engaged. Plot two lines, corresponding to the region of the curve before the bend (primarily the elastics), and the region after the bend (primarily the nonwovens). Read the extension at which these two lines intersect, and calculate the % Pre-Strain from the extension and the corrected gage length. Record as % Pre-strain 0.1%. Calculate the arithmetic mean of three replicate samples for each elastomeric laminate and Average-Pre-Strain to the nearest 0.1%.

Hip-Hoop-Test (or the Whole Outer Cover Waist Opening Circumference Extension Force Test)

This method is a 2 cycle hysteresis test, with is used for determining: the maximum extension of the product waist hoop at a stress of 18.2 gf/mm (and Maximum-Effective-Strain); the Application-Force (and Application-Stress); the Sustained-Fit-Load-Force (and Sustained-Fit-Load-Stress); and Sustained-Fit-Unload-Force (and Sustained-Fit-Unload-Stress) of a disposable article with a continuous waist. The article can be a pant or a closable article that has been pre-fastened. This method is also used for determining the Laminate-Modulus and Section-Modulus.

Whole product waist opening circumference extension forces (and stresses) are measured on a constant rate of extension tensile tester with computer interface (a suitable instrument is the MTS Insight using Testworks 4.0 Software, as available from MTS Systems Corp., Eden Prairie, Minn.) using a load cell for which the forces measured are within 10% to 90% of the limit of the cell. The Initial Circumference around engaging arms 1516 is measured using a flexible tape measure 1519. The accuracy of the tape is either traceable to NIST or other standards organization, or verified for accuracy against a traceable ruler. All testing is performed in a conditioned room maintained at about 23° C.±2 C.° and about 50%±2% relative humidity. Samples are condition under the same conditions for 2 hours prior to testing. Five replicate articles are analyzed and the results averaged.

For this test, a custom hook fixture 1510 (FIGS. 3 and 4) is used. The hook fixture 1510 comprises a pair of J-shaped hooks 1512, each with an attachment member 1514 designed to mount to the tester's stationary base and upper movable crosshead (via the load cell). Each J-shaped hook 1512 has a substantially circular cross-sectional shape with a diameter, D, of about 1 cm. The hooks 1512 have a width, W, of about 25 cm. If the elastic side panel to be tested extends past the end of the engaging arm, or bunches at the J curve of the fixture, W is lengthened to accommodate the longer side panel. The hooks 1512 exhibit a smooth curvature to form the two engaging arms 1516 that are perpendicular to the attachment member 1514. Each attachment member is fitted with a locking collar 1513 which fixes the engagement arms 1516 of the hooks parallel to one another and perpendicular to the pull axis of the tensile tester.

The stress in the product waist is calculated by first determining the narrowest longitudinal length within the closed waist hoop. For a disposable article with a continuous waist, this is typically the length of the side seam. For a pant that is prefastened, this is typically the longitudinal length of the attaching fastener. For example, a closed form product with the narrowest longitudinal length within the hoop being an 11 cm side panel, the maximum stress to pull to, 18.2 gf/mm, would be 2000 gf.

Figure 3:
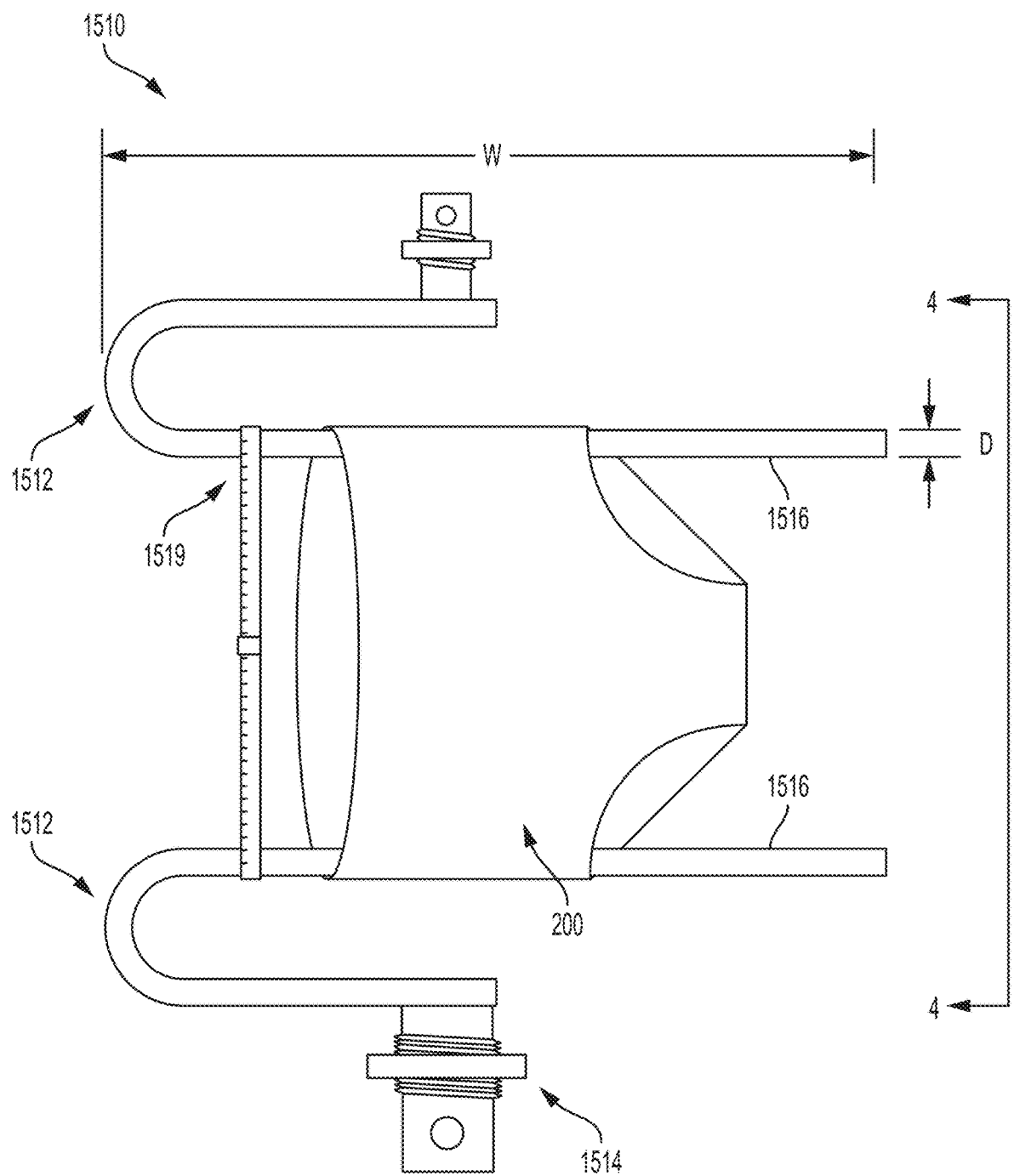
FIG. 3 is an illustration showing the hook fixture for performing the Hip-Hoop-Test and where the Application-Force is determined.

Manually move the crosshead up. Hang the article from the top engaging arm 1516 such that the article is solely supported from the top arm, and zero the load cell. Lower the top engaging arm so that the chassis 200 can be slid onto the engaging arms 1516 with the elastic sides centered along the pull axis of the tester, as illustrated in FIGS. 3 and 4. The chassis 200 should have some slack when first slid onto the engaging arms 1516. Adjust the engaging arms 1516 to remove any slack from the article, but ensure that no more than 5 grams of force is measured on the load cell. Zero the crosshead. With a flexible measuring tape, graduated in mm, measure the relaxed waist opening circumference by wrapping the tape 1519 around the engaging arms 1516 proximate to the waist opening of the article of FIGS. 3 and 4. Record the Initial Circumference to the nearest 1 mm. Remove the measuring tape from the arms 1516.

The test consists of 7 distinct steps.
1. This is called the first load. Program the tensile tester to move the crosshead up at a rate of 254 mm/min. Extend the crosshead until a stress of 18.2 gf/mm is reached. At this point, record the extension as the maximum extension. The Maximum-Effective-Strain is also calculated using the Initial Circumference. Maximum-Effective-Strain=(maximum extension)/(Initial Circumference/2).
2. Hold at this crosshead extension for 30 seconds.
3. This is called the first unload. Return the crosshead at a rate of 254 mm/min to the starting position.
4. Hold at this crosshead extension for 60 seconds.
5. This is called the second load. Move the crosshead up at a rate of 254 mm/min. Extend until a stress of 18.2 gf/mm is reached.
6. Hold at this crosshead extension for 30 seconds.
7. This is called the second unload. Return the crosshead at a rate of 254 mm/min to the starting position.

Collect data at an acquisition rate of 100 Hz throughout the experiment.

In like fashion repeat for the remaining four replicates.

Maximum-Effective-Strain (i.e., Maximum Extension)=(maximum extension at 18.2 gf/mm)/(Initial Circumference/2)

Application-Strain (i.e., Application Extension)=Maximum-Effective-Strain multiplied by 80%.

Application-Force (i.e., Application-Stress)=Force (gf/mm) (Stress) at Application-Strain in the first load (step 1 of Hip-Hoop-Test).

Sustained-Fit-Load-Force (i.e., Sustained-Fit-Load-Stress)=Force (gf/mm) (Stress) at (Maximum-Effective-Strain/2) in the second load (step 5 of Hip-Hoop-Test) cycle.

Sustained-Fit-Unload-Force (i.e., Sustained-Fit-Unload-Stress)=Force (gf/mm) (Stress) at (Maximum-Effective-Strain/2) in the second unload (step 7 of Hip-Hoop-Test) cycle.

Leg-Hoop-Test

This method is a 2 cycle hysteresis test, with is used for determining: the Leg-Hoop-Max-Strain at a force of 650 gf (1300 gf in the load cell of the MTS tester) of a disposable article with a continuous leg opening (192). The article can be a pant or a closable article that has been pre-fastened.

Leg hoop extension forces are measured on a constant rate of extension tensile tester with computer interface (a suitable instrument is the MTS Insight using Testworks 4.0 Software, as available from MTS Systems Corp., Eden Prairie, Minn.) using a load cell for which the forces measured are within 10% to 90% of the limit of the cell. The initial gap X between the fixtures 1430 is measured using a ruler. The accuracy of the ruler is either traceable to NIST or other standards organization, or verified for accuracy against a traceable ruler. All testing is performed in a conditioned room maintained at about 23° C.±2 C.° and about 50%±2% relative humidity. Samples are condition under the same conditions for 2 hours prior to testing. Five replicate articles are analyzed and the results averaged.

Figure 20A:
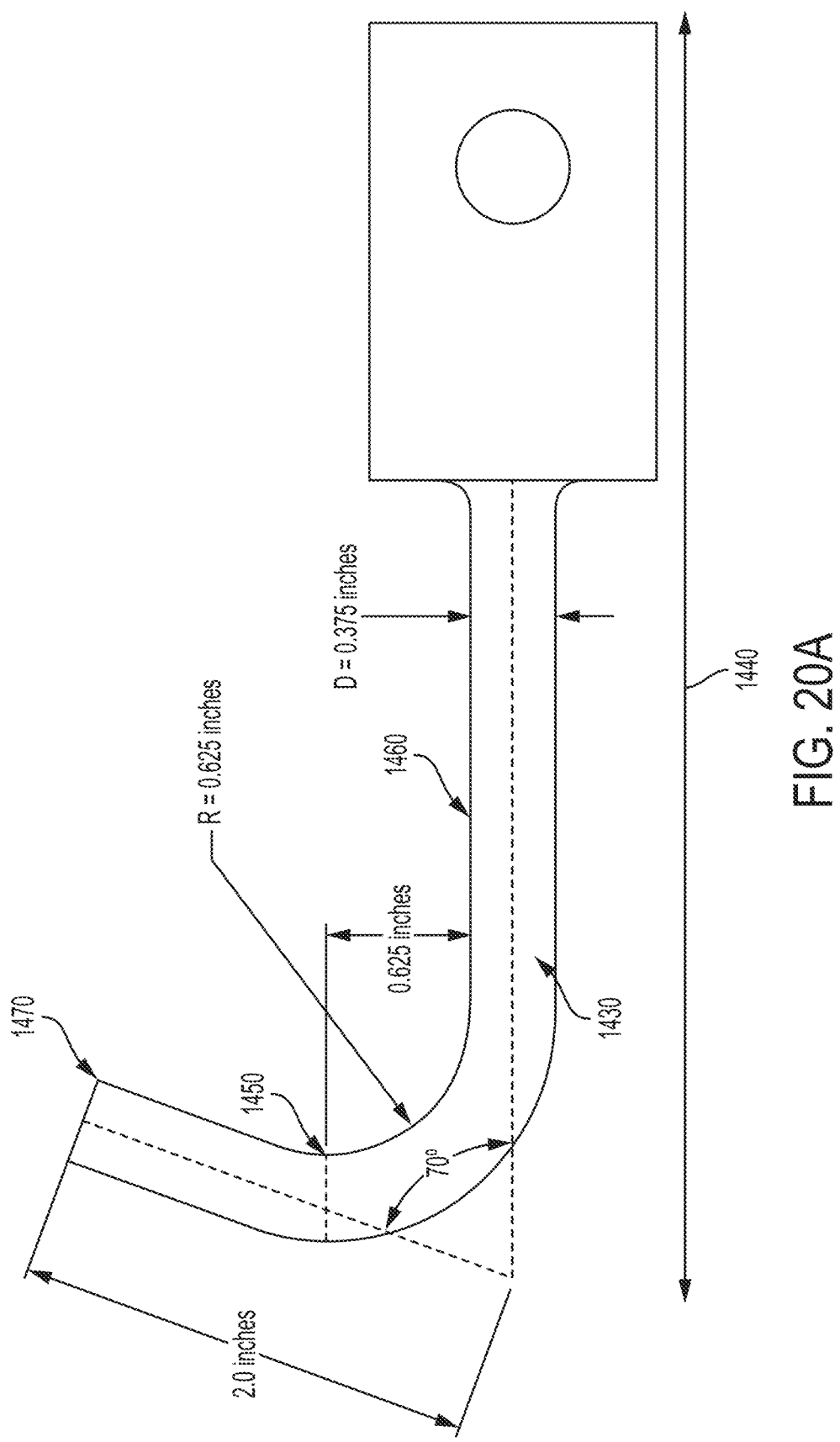
FIG. 20A illustrates the fixtures used with the tensile tester for determining the Leg-Hoop-Test of a disposable pant.
Figure 20B:
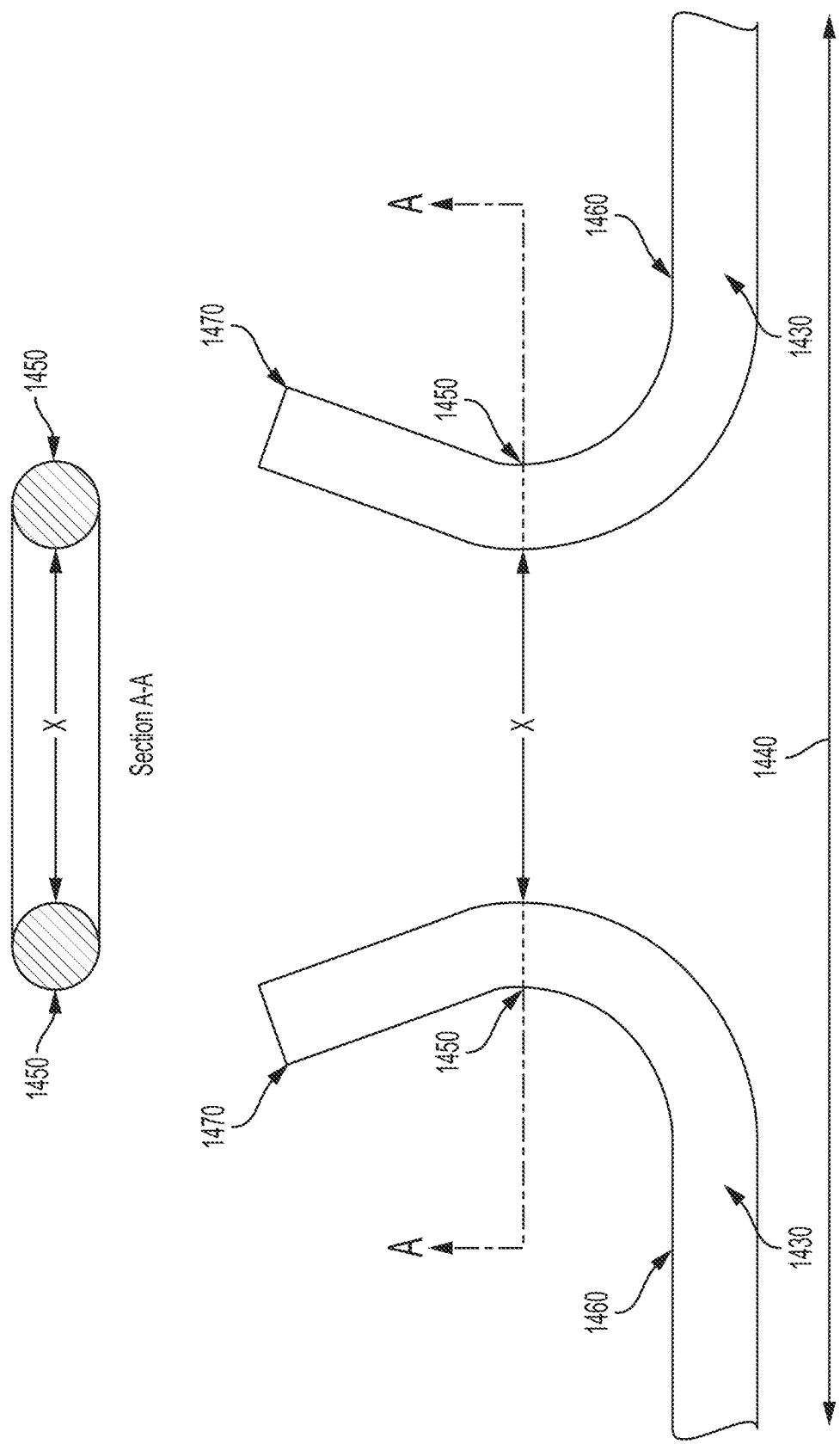
FIG. 20B illustrates the configuration of the fixtures as used in a tensile tester in the Leg-Hoop-Test for a disposable pant.
Figure 20C:
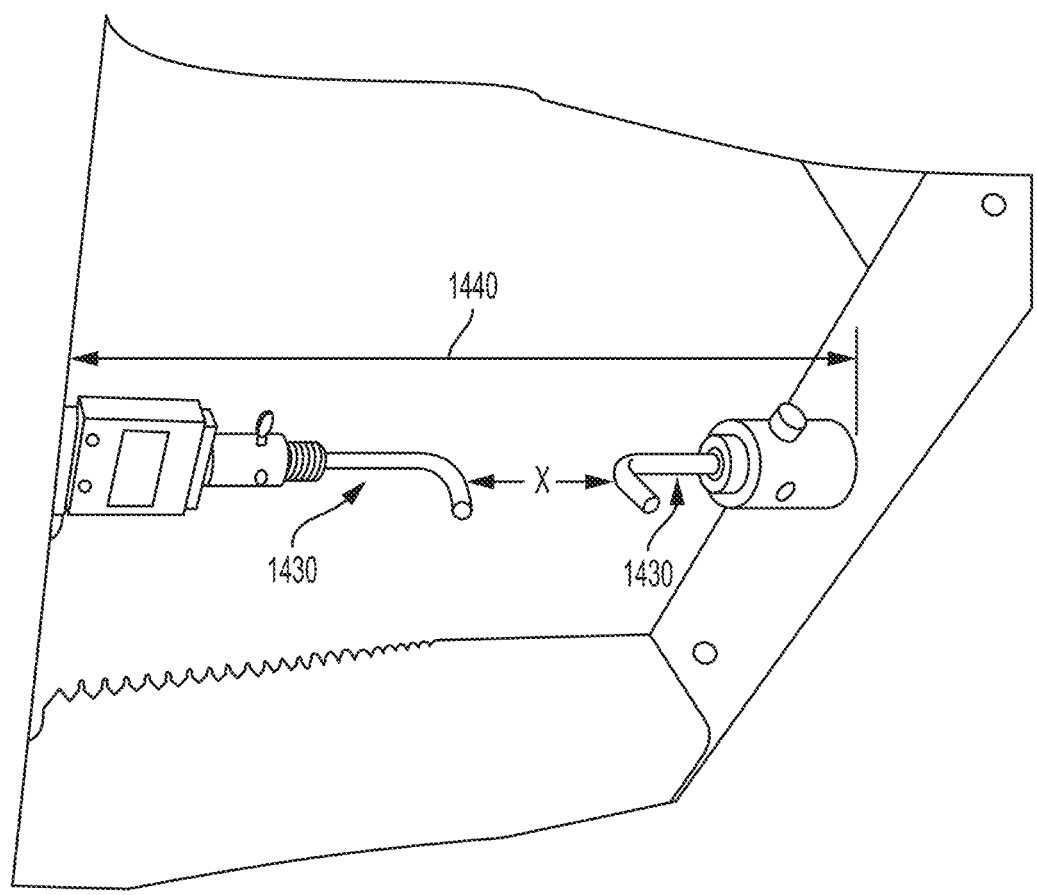
FIG. 20C illustrates how the product leg opening circumference is calculated.
Figure 20D:
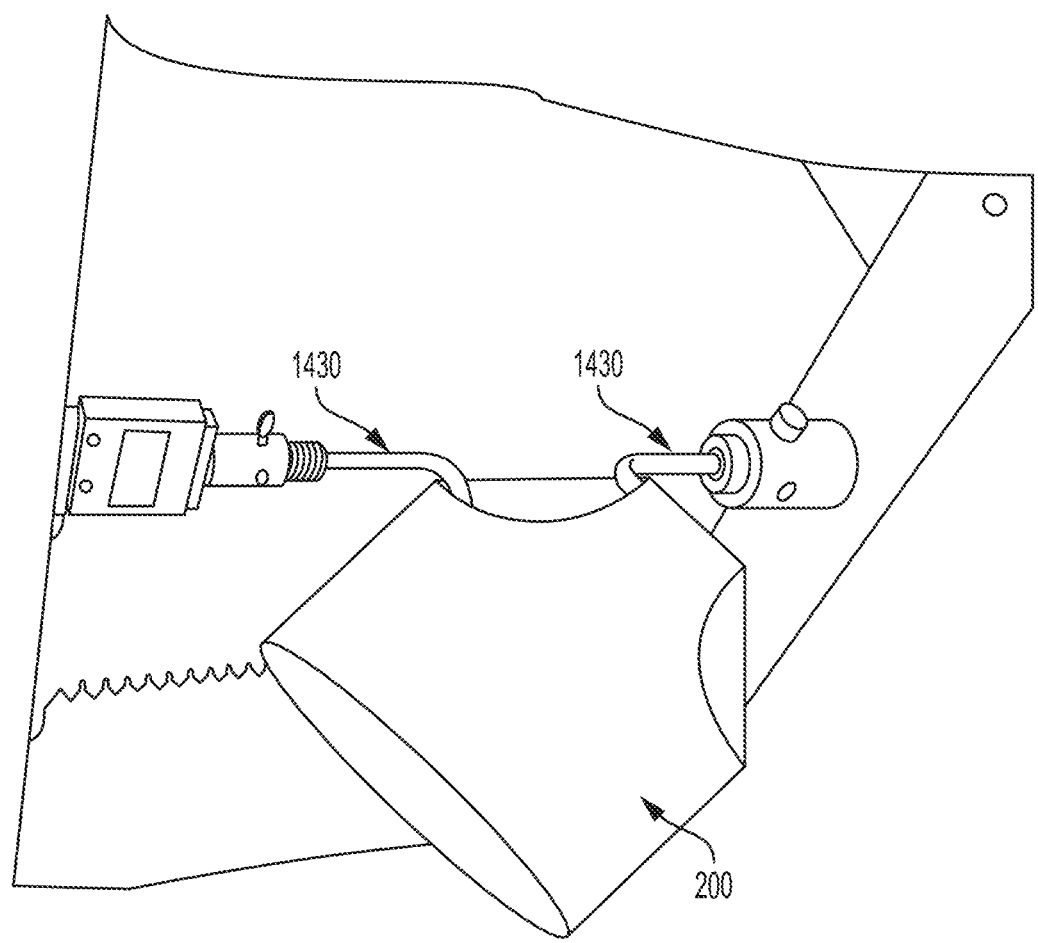
FIG. 20D illustrates a hook fixture for performing the Leg-Hoop-Test.

For this test, the instrument is equipped with two fixtures 1430 as specified in FIG. 20A. Each fixture 1430 has a 0.375 inch diameter shaft (type 303 stainless steel), bent at an angle of 70° with an inner radius of 0.625 inches, per the drawing in FIG. 20A. The fixtures 1430 are oriented 1440 in the tensile testing machine as indicated in FIG. 20C, and the machine is oriented such that the extension of the fixtures is vertical. The gap X between the fixtures 1430 (shown in FIGS. 20B, 20C and 20D) is initially set such that there is no stretch in the products leg opening 192. The product is inserted into the apparatus by inserting the leg opening 192 on the hook at the top of the fixture 1430 as shown in FIG. 20D. The leg opening 192 should come into contact with the inside bottom of the top fixture 1430 at the point denoted by 1450 as shown in FIG. 20B. This represents the deepest section of the hook, and is 0.625 inches from the inside edge 1460 of the fixture 1430 as shown in FIG. 20A. As the products leg opening 192 hangs from the top fixture 1430, the opposite side of the same leg opening hangs below the bottom edge 1470 of the bottom fixture 1430. Once the product is in the machine, the machine's force channel is set to zero (which eliminates the weight of the sample in the calculations).

The Test Length for the method is the circumference wrapped around the fixtures 1430 at points 1450 (shown in FIG. 20B). This is a calculated value.

$$\text{Test Length}=2*(X+D+pi*r)$$

Where X is gap between the fixtures (shown in FIGS. 20B and 20C), and D is the diameter of the fixture 1430 shaft and is equal to 0.375 inches. X increases as the fixtures 1430 move apart during the test.

The fixtures 1430 are slowly moved apart at 2.0 in/min (5.04 cm/min). As the fixtures slowly move apart, the test operator must ensure that the bottom fixture 1430 captures the bottom of the leg opening 192 at point 1450 of the bottom fixture (the leg opening 192 should be captured between the two fixtures 1430 at points 1450 of each). The fixtures continue to move apart until at 2.0 in/min until a tare load of 0.05N is attained. The Test Length at this position is recorded as Lo. Lo is the relaxed leg circumference at the leg opening 192 of the chassis 200.

Immediately extend the product at a rate of 10 in/min (25.4 cm/min) until either 1300 gf is reached or the sample breaks.

The Leg Force is calculated by dividing the force in the machine's load cell by 2 (since the leg opening 192 is wrapped around the fixtures 1430, the leg force is the tension in the leg opening). The Leg Strain is calculated by (Test Length−Lo)/Lo.

The test consists of 7 distinct steps.

1. This is called the first load. Program the tensile tester to move the crosshead up at a rate of 254 mm/min. Extend the crosshead until a force of 1300 gf is reached. At this point, record the extension as the maximum-extension. The Leg-Hoop-Max-Strain is calculated as.

$$\text{Leg-Hoop-Max-Strain}=(2*(\text{maximum-extension}+D+pi*r)-Lo)/Lo$$

2. Hold at this crosshead extension for 30 seconds.
3. This is called the first unload. Return the crosshead at a rate of 254 mm/min to the starting position.
4. Hold at this crosshead extension for 60 seconds.
5. This is called the second load. Move the crosshead up at a rate of 254 mm/min. Extend until a force of 1300 gf is reached.
6. Hold at this crosshead extension for 30 seconds.
7. This is called the second unload. Return the crosshead at a rate of 254 mm/min to the starting position.

Collect data at an acquisition rate of 100 Hz throughout the experiment.

In like fashion repeat for the remaining four replicates.

CONCLUSION

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent pant article, comprising:
   a chassis comprising a topsheet, a backsheet and an absorbent core disposed between the topsheet and the backsheet;
   a first plurality of elastic strands disposed in a front waist region;
   a second plurality of elastic strands disposed in a back waist region;
   wherein the front and back waist regions are joined together at laterally opposed side seams to form a waist and leg openings;

wherein the front waist region is a region between a) a proximal most front axis extending parallel to the lateral axis and passing through proximal most points of the laterally opposed side seams; and b) a distal most front axis extending parallel to the lateral axis and passing through distal most points of the laterally opposed side seams;

wherein the back waist region is a region between a) a proximal most back axis extending parallel to the lateral axis and passing through proximal most points of the laterally opposed side seams; and b) a distal most back axis extending parallel to the lateral axis and passing through distal most points of the laterally opposed side seams;

wherein the front waist region comprises a front component region disposed between and including a front distal most elastic strand of the front waist region and a proximal most elastic strand of the front waist region;

wherein the front component region is defined by a front distal component region line extending parallel to the lateral axis and passing through a distal most point of the front distal most elastic strand and a front proximal component region line extending parallel to the lateral axis and passing through a proximal most point of the front proximal most elastic strand;

wherein the front component region is then divided into 4 equal component sections, defined by first, second, and third component section lines, each disposed parallel to the lateral axis and disposed at 25%, 50% and 75% of the distance between the front distal component region line and front proximal component region line;

wherein the front component region comprises a first component section, Front Section 1, comprising the front distal most elastic strand, a fourth component section, Front Section 4, comprising the front proximal most elastic strand, a second component section, Front Section 2, adjacent to Front Section 1, and a third component section, Front Section 3, disposed between Front Sections 2 and 4;

wherein the back waist region comprises a back component region disposed between and including a back distal most elastic strand of the back waist region and a proximal most elastic strand of the back waist region;

wherein the back component region is defined by a back distal component region line extending parallel to the lateral axis and passing through a distal most point of the back distal most elastic strand and a back proximal component region line extending parallel to the lateral axis and passing through a proximal most point of the back proximal most elastic strand;

wherein the back component region is then divided into 4 equal component sections, defined by first, second, and third component section lines, each disposed parallel to the lateral axis and disposed at 25%, 50% and 75% of the distance between the back distal component region line and back proximal component region line;

wherein the back component region comprises a first component section, Back Section 1, comprising the back distal most elastic strand, a fourth component section, Back Section 4, comprising the back proximal most elastic strand, a second component section, Back Section 2, adjacent to Back Section 1, and a third component section, Back Section 3, disposed between Back Sections 2 and 4;

wherein at least one of Front Sections 1-4 comprises the first plurality of elastics and at least one of a plurality of apertures and a mechanically deformed portion forming ridges and valleys;

wherein the at least one of Front Sections 1-4 has a Laminate-Modulus from about 3 gf/mm to about 12 gf/mm, a Strain of greater than 110% at a Stress of 9.1 gf/mm, and a Strain-to-Modulus-Ratio greater than about 30 and less than about 80; and wherein the disposable absorbent pant article has an Application-Stress of from about 7.5 gf/mm to about 14 gf/mm, and a Sustained-Fit-Load-Stress greater than 30% of the Application-Stress, and a Sustained-Fit-Unload-Stress greater than 25% of the Application-Stress.

2. The disposable absorbent pant article of claim 1, wherein the at least one of Front Sections 1-4 comprises mechanically deformed portions forming ridges and valleys, an inner belt nonwoven and an outer belt nonwoven, and the first plurality of elastics, and wherein the at least one of Back Sections 1-4 comprises mechanically deformed portions forming ridges and valleys, an inner belt nonwoven and an outer belt nonwoven, and the second plurality of elastics.

3. The disposable absorbent pant article of claim 1, wherein at least two of Front Sections 1-4 comprise mechanically deformed portions forming ridges and valleys, and wherein at least two of Back Sections 1-4 comprise mechanically deformed portions forming ridges and valleys.

4. The disposable absorbent pant article of claim 1, wherein each of Front Sections 1-4 comprise mechanically deformed portions forming ridges and valleys, and wherein each of Back Sections 1-4 comprise mechanically deformed portions forming ridges and valleys.

5. The disposable absorbent pant article of claim 1, wherein the disposable absorbent pant article has a Leg-Hoop-Max-Strain of greater than 120% at a force of less than 650 gf.

6. The disposable absorbent pant article of claim 1, wherein at least one of Front Sections 1-4 comprises a plurality of apertures forming an apertured portion and wherein the apertured portion of the front component region are disposed through a garment-facing belt nonwoven, but not a wearer-facing belt nonwoven.

7. The disposable absorbent pant article of claim 6, wherein the apertured portion of a first belt nonwoven comprises a first aperture that overlaps a first strand of the first plurality of elastics and a second aperture that overlaps a second strand of the second plurality of elastics.

8. The disposable absorbent pant article of claim 1, wherein one or both of Back Sections 1, 3, and 4 have a lower Laminate-Modulus than one or both of Back Section 2.

9. The disposable absorbent pant article of claim 1, wherein one or both of Front Sections 1 and 2 have a lower Laminate-Modulus than one or both of Front Sections 3 and 4.

10. The disposable absorbent pant article of claim 1, wherein the absorbent article is divided into three article sections, Section L, Section M, and Section R, wherein the article sections are defined by a left article section line extending parallel to the longitudinal axis and passing through a left laterally distal most point of a left side edge of the chassis and by a right article section line extending parallel to the longitudinal axis and passing through a right laterally distal most point of a right side edge, which is laterally opposed from the left side edge of the chassis, wherein any portion of the article to one lateral side or the other of the Section M defines Section L and the laterally opposed Section R, and wherein Front Sections L and R comprise mechanically deformed portion forming ridges and valleys and Section M is substantially free from ridges and valleys.

* * * * *